United States Patent
Chen et al.

(10) Patent No.: US 10,045,530 B2
(45) Date of Patent: Aug. 14, 2018

(54) AGRICULTURAL PHEROMONE COMPOSITIONS COMPRISING POSITIONAL ISOMERS

(71) Applicant: PROVIVI, INC., Santa Monica, CA (US)

(72) Inventors: Mike Ming Yu Chen, Pasadena, CA (US); Pedro Coelho, Santa Monica, CA (US); Peter Meinhold, Topanga, CA (US); Toni M. Lee, Los Angeles, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 15/349,575

(22) Filed: Nov. 11, 2016

(65) Prior Publication Data
US 2017/0135343 A1    May 18, 2017

Related U.S. Application Data

(60) Provisional application No. 62/255,215, filed on Nov. 13, 2015.

(51) Int. Cl.
*A01N 35/00* (2006.01)
*A61K 31/11* (2006.01)
*A01N 35/04* (2006.01)

(52) U.S. Cl.
CPC .................... *A01N 35/04* (2013.01)

(58) Field of Classification Search
USPC .......................................................... 514/703
See application file for complete search history.

(56) References Cited

U.S. PATENT DOCUMENTS 4,216,202 A      8/1980   Klun et al.
4,219,542 A *    8/1980   Klun ...................... A01N 35/02
                                                       424/84

OTHER PUBLICATIONS

Cardé and Haynes, "Structure of the pheromone communication channel in moths." Adv. Insec. Chem. Ecol. (2004); 8: 283-332.
Cardé, R. T., "Using pheromones to disrupt mating of moth pests." Cambridge University Press, Cambridge (2007); 5: 122-169.
Carpenter, J. E., et al., "Effects of Moth Population Density and Pheromone Concentration on Mating Disruption of the Corn Earworm in Large Screened Cages." Journal of Economic Entomology (1982); 75(2): 333-336.
Cork and De Souza, "Control of yellow stem borer, Scirpophaga incertulas (Lepidoptera: Pyralidae) by mating disruption on rice in India: effect of unnatural pheromone blends and application time on efficacy." Bulletin of Entomological Research (1996); 86(5): 515-524.
Haynes, K. F., et al., "Potential for evolution of resistance to pheromones: interindividual and interpopulational variation in chemical communication system of pink bollworm." Journal of Chemical Ecology (1984); 10(11): 1551-1565.
Klun, J. . A. et al., "Sex Pheromone Chemistry of Female Corn Earworm Moth, *Heliothis zea*." Journal of Economic Entomology (1980); 6(1): 165-175.
Klun, J. A., et al., "Trace chemicals: The essence of sexual communication systems in *Heliothis* species." Science (1979); 204(4399): 1328-1330, 5 pages.
Mitchell, E. R. "Suppression of Mating and Oviposition by Fall Armyworm and Mating by Corn Earworm in Corn, Using Air Permeation Technique." Journal of Economic Entomology (1982); 75(2): 270-274.
Mitchell, E. R., et al., "Reduction of Mating Potential of Male *Heliothis* spp. and *Spodoptera frugiperda* in Field Plots Treated with Disruptants." Environ. Entomol. (1976); 5(3): 484-486.
Mitchell, E. R., et al., "*Heliothis* spp.: Disruption of Pheromonal Communication with (Z)-9-tetradecen-1-ol Formate." Environmental Entomology (1975); 4(4): 577-579.
Pope, M. M., et al., "Composition, quantification, and periodicity of sex pheromone volatiles from individual *Heliothis zea* females." Journal of Insect Physiology (1984); 30(12): 943-945.
Sekul, A.A., et al., "A natural inhibitor of the corn earworm moth sex attractant." Journal of Economic Entomology (1975); 68(5): 603-604.
Vickers, N. J., et al. "Chemical communication in heliothine moths." Journal of Comparative Physiology A: Neuroethology, Sensory, Neural, and Behavioral Physiology (1991); 169(3): 275-280.

* cited by examiner

*Primary Examiner* — Marcos L Sznaidman
(74) *Attorney, Agent, or Firm* — Cooley LLP

(57) ABSTRACT

The present disclosure provides pheromone compositions. In some aspects, the compositions taught herein comprise a pheromone chemically corresponding to the pheromone naturally produced by a given insect, along with at least one positional isomer of said pheromone. In various aspects, pheromone compositions of the present disclosure are able to modulate the response of the insect based on the ratio of natural pheromone to its positional isomer.

8 Claims, 4 Drawing Sheets

Figure 4
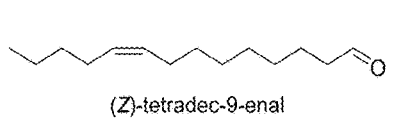
(Z)-tetradec-9-enal
(Z)-9-tetradecenal is the authentic pheromone for various lepidopteran species
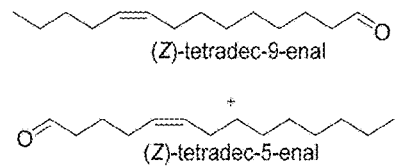
(Z)-tetradec-9-enal
+
(Z)-tetradec-5-enal
Mixture of (Z)-9-tetradecenal with (Z)-5-tetradece

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: CYP52A13 forward primer OPV 0042

<400> SEQUENCE: 1
atgacggttc atgacatcat cgc                                            23

<210> SEQ ID NO 2
<211> LENGTH: 20
<212> TYPE: DNA
<213> ORGANISM: Artificial Sequence
<220> FEATURE:
<223> OTHER INFORMATION: CYP52A13/A3 reverse primer OPV 0043

<400> SEQUENCE: 2
ctgacatcct cttgagcggc                                                20

<210> SEQ ID NO 3
<211> LENGTH: 25
<212> TYPE: DNA
<213> ORGANISM: Artificial Sequence
<220> FEATURE:
<223> OTHER INFORMATION: CYP52A3 forward primer OPV 0044

<400> SEQUENCE: 3
atggctattg agcagattat cgaag                                          25

<210> SEQ ID NO 4
<211> LENGTH: 8374
<212> TYPE: DNA
<213> ORGANISM: Artificial Sequence
<220> FEATURE:
<223> OTHER INFORMATION: DNA sequence of the linearized construct for
      expressing CYP52A3/CPR used for genome integration
```

```
<400> SEQUENCE: 4
agatccaatt cccgctttga ctgcctgaaa tctccatcgc ctacaatgat gacatttgga        60
tttggttgac tcatgttggt attgtgaaat agacgcagat cgggaacact gaaaaataca       120
cagttattat tcatttaaat aacatccaaa gacgaaaggt tgaatgaaac cttttttgcca      180 tccgacatcc acaggtccat tctcacacat aagtgccaaa cgcaacagga ggggatacac       240
tagcagcaga ccgttgcaaa cgcaggacct ccactcctct tctcctcaac acccacttt       300 gccatcgaaa aaccagccca gttattgggc ttgattggag ctcgctcatt ccaattcctt       360
ctattaggct actaacacca tgactttatt agcctgtcta tcctggcccc cctggcgagg       420
ttcatgtttg tttatttccg aatgcaacaa gctccgcatt acacccgaac atcactccag       480
atgagggctt tctgagtgtg gggtcaaata gtttcatgtt ccccaaatgg cccaaaactg       540
acagtttaaa cgctgtcttg gaacctaata tgacaaaagc gtgatctcat ccaagatgaa       600
ctaagtttgg ttcgttgaaa tgctaacggc cagttggtca aaagaaact tccaaaagtc        660 ggcataccgt ttgtcttgtt tggtattgat tgacgaatgc tcaaaaataa tctcattaat       720
gcttagcgca gtctctctat cgcttctgaa ccccggtgca cctgtgccga aacgcaaatg       780
gggaaacacc cgcttttggg atgattatgc attgtctcca cattgtatgc ttccaagatt       840
ctggtgggaa tactgctgat agcctaacgt tcatgatcaa aatttaactg ttctaacccc       900
tacttgacag caatatataa acagaaggaa gctgccctgt cttaaaccctt ttttttttatc     960 atcattatta gcttactttc ataattgcga ctggttccaa ttgacaagct tttgatttta     1020
acgactttta acgacaactt gagaagatca aaaacaact aattattgaa agaattccga      1080
aacgatggct ttgataagt tggatttgta cgtcatcatt gttcttgctg ttgctgttgc       1140
tgcctacttt gctaaaaacc agttcttgga tcaacctcag acactggtt tcttgtcaaa      1200 cgatacagct ggtggaaata gtagagatat ccttgaaact ttgaagaaaa acaataagaa     1260
cacattgctt ttgttcggat ctcaaaccgg tactgctgag gactacgcca ataagctttc     1320
aagagaaatc catagtagat tcggattgaa aactatggtt gccgatttcg cagattacga     1380
ctgggataac tttggtgaca tccctaacga tatcttggtt ttctttatcg tcgccaccta    1440
tggagaggga gaaccaactg acaacgcaga tgagtttcac acctggttga ctgacgaagc    1500
tgatacactt tccaccttga gataccacgt tttcggtttg ggaaactcaa cttacgaatt    1560
ttacaacgct atcggtagaa agttttgacag acttttggaa gagaaaggtg gagagagatt   1620
tgctgattat ggtgaaggag atgacggtac aggaacccctt gacgaggatt tcttgacatg   1680
gaaggacaac gttttcgata cccttaaaaa cgatttgaac ttcgaagaga gagagttgaa    1740
gtacgaacct aacgttaagc ttacagaaag agatgacttg accgttgatg actctgaggt   1800
ctccttggga gaaccaaata gaaaatacat ccaatctgaa gagatcgact tgacaaaggg   1860
tccttttgat catacccacc catatcttgc aaagatctct aagactagag agttgtttgc   1920
ttccaaggaa agaaactgtg ttcatgtcga gttcgatgtt tctgaatcca atcttaagta   1980
cactacagga gaccacttgg ccgtttggcc atcaaacagt gatgagaata ttgcaaagtt   2040
catcaaatgc tttggtttgg atgacaagat taacactgtt ttcgaactta agccttgga    2100 ttctacatac caaattccat tccctaatcc aatcacctat ggagcagttg tcagacatca   2160
cttggaaatt tcaggtcctg ttagtagaca gtttttttcctt gctatcgccg gattcgctcc   2220
agacgaagag actaagaaaa ctttttacaag aatcggtaac gataagcaag aatttgccaa   2280
caagatcaca agaaagaaat tgaacgttgc agacgctctt ttgtttgctt caaatggtag   2340
```

```
accttggagt gatgttccat ttgagttcat tatcgaaaac gtccctcatt tgcaaccaag    2400
atactactct atctcttcct caagtttgtc cgagaagcag actattaata tcacagctgt    2460
tgtcgaagtt gaagaggaag cagacggaag agctgtcacc ggtgttgtca ctaaccttt    2520
gaagaatatt gagatcgaac agaacaagac tggagaaaaa cctgttgtcc attacgattt    2580
gtctggtcca agaaacaagt ttaacaagtt taagttgcct gttcacgtca aagatccaa    2640
ctttaagctt cctaaaaata ccactacacc agttattttg atcggtcctg aactggtgt    2700
tgctccactt agaggtttcg tcagagagag agttcaacag gtcaagaacg gagttaacgt    2760
cggtaaaact gtttttgttt atggatgtag aaacgaacat gatgacttct tgtacaagca    2820
agagtggtct gaatatgctt ccgttttggg agagaatttt gaaatgttca ctgccttttc    2880
tagacaagac ccatccaaga aagtttacgt ccaggataag attgcagaaa actctaaagt    2940
tgtcaacgat cttttgaacg aaggagctat catctatgtt tgcggtgacg cctcaagaat    3000
ggcaagagat gttcaaagta ctattgctaa gatcgtcgcc aaacacagag agattcagga    3060
agataaagct gtcgagttgg ttaaatcctg gaaagttcag aatagatatc aagaagatgt    3120
ttggtaagcg gccgctcaag aggatgtcag aatgccattt gcctgagaga tgcaggcttc    3180
atttttgata cttttttatt tgtaacctat atagtatagg atttttttg tcattttgtt    3240
tcttctcgta cgagcttgct cctgatcagc ctatctcgca gcagatgaat atcttgtggt    3300
aggggtttgg gaaaatcatt cgagtttgat gtttttcttg gtatttccca ctcctcttca    3360
gagtacagaa gattaagtga gaccttcgtt tgtgcggatc caacatccaa agacgaaagg    3420
ttgaatgaaa cctttttgcc atccgacatc cacaggtcca ttctcacaca taagtgccaa    3480
acgcaacagg aggggataca ctagcagcag accgttgcaa acgcaggacc tccactcctc    3540
ttctcctcaa cacccacttt tgccatcgaa aaaccagccc agttattggg cttgattgga    3600
gctcgctcat tccaattcct tctattaggc tactaacacc atgactttat tagcctgtct    3660
atcctggccc ccctggcgag gttcatgttt gtttatttcc gaatgcaaca agctccgcat    3720
tacacccgaa catcactcca gatgagggct ttctgagtgt ggggtcaaat agtttcatgt    3780
tccccaaatg gcccaaaact gacagtttaa acgctgtctt ggaacctaat atgacaaaag    3840
cgtgatctca tccaagatga actaagtttg gttcgttgaa atgctaacgg ccagttggtc    3900
aaaaagaaac ttccaaaagt cggcataccg tttgtcttgt ttggtattga ttgacgaatg    3960
ctcaaaaata atctcattaa tgcttagcgc agtctctcta tcgcttctga accccggtgc    4020
acctgtgccg aaacgcaaat ggggaaacac ccgcttttg gatgattatg cattgtctcc    4080
acattgtatg cttccaagat tctggtggga atactgctga tagcctaacg ttcatgatca    4140
aaatttaact gttctaaccc ctacttgaca gcaatatata aacagaagga agctgccctg    4200
tcttaaacct ttttttttat catcattatt agcttacttt cataattgcg actggttcca    4260
attgacaagc ttttgatttt aacgactttt aacgacaact tgagaagatc aaaaaacaac    4320
taattattga agaattccg aaacgatggc tattgagcag attatcgaag aggttttgcc    4380
ttacttgact aaatggtaca ctatcctttt tggtgccgct ttcacatact ttttgtcaat    4440
cgcacttaga aacaaatact acgagtacaa gttgaagtgt gaaaacccac cttacttcaa    4500
gactgctgga ttcgttggta tccctggatt gattgatgtc atcaaggcta agaacgctgg    4560
taaattggcc gattacgcag accaaacatt tgacgaatac cctcatcaca gtttctatat    4620
gaccgttgct ggaatgttga aaattgttct tactgtcgat ccagaaaaca tcaaggctgt    4680
```

```
tcttgccaca cagtttaatg acttcgcatt gggtgctaga catgcccact ttgatccatt    4740
gcttggagac ggtattttca ccttggatgg agaaggttgg aaacattcca gagcaatgtt    4800
gagacctcaa tttgctagag agcagattgc ccatgttaag gcattggaac cacacgttca    4860
agtccttgcc aagcagatca aattgaacaa gggagagaca ttcgatttgc aagaattgtt    4920
tttcagattc accgttgaca cagctaccga gttttgttc ggagaatcag ttcacagtct    4980
ttacgatgag aaattgggtg tcccacctcc aaacaatatt cctggaagag aaaactttgc    5040
taaggccttc aatacctcac aacattattt ggctactaga acatacagtc agatgttcta    5100
tttcttgact aacccaaagg agtttagaga ctgcaatgcc aaagttcaca gcttgcaca    5160 atacttcgtc aataaggcat tggatgcttc tgaagacgag gttgctgaga agtccaaagg    5220
tggatacgtt ttcttgtatg aacttgtcaa acagactaga gatcctaagg tttgcaaga    5280 ccagttgctt aacattatgg tcgctggtag agatactaca gccggattgc tttcttttgc    5340
aatgttcgag cttgctagaa acccaaagat ctggaataag ttgagagaag agatcgaagt    5400
taattttgga cttggtgaag aggccagagt cgacgaaatc tcattcgaga cttgaagaa    5460 atgcgagtac ttgaaggcag ttcttaacga acattgaga atgtatccta gtgttccagt    5520
caattttaga accgctacta gagataccac tttgcctaga ggtggtggta aagacggtac    5580
ttctcctatt ttcgttccaa agggatcttc cgttgtctac acagtctata aaacccatag    5640
attggaagag tactatggta aagatgctta cgagtttaga cctgagagat ggttcgaacc    5700
atccactaga aaatttgggtt gggcctatgt tccttttaat ggaggtccaa gaatttgcct    5760
tggacaacag ttcgctttga ctgaggcctc ttacgttatc acaagacttg ctcaaatgtt    5820
tgaacacttg gagtccaagg atgaaactta ccctccaaac aagtgtatcc atttgactat    5880
gaatcacaac gaaggagttt ttatttctgc taagtaggcg gccgctcaag aggatgtcag    5940
aatgccattt gcctgagaga tgcaggcttc attttgata cttttttatt tgtaacctat    6000
atagtatagg attttttttg tcattttgtt tcttctcgta cgagcttgct cctgatcagc    6060
ctatctcgca gcagatgaat atcttgtggt aggggtttgg gaaaatcatt cgagtttgat    6120 gttttttcttg gtatttccca ctcctcttca gagtacagaa gattaagtga gaccttcgtt    6180
tgtgcggatc cttcagtaat gtcttgtttc ttttgttgca gtggtgagcc attttgactt    6240
cgtgaaagtt tctttagaat agttgtttcc agaggccaaa cattccaccc gtagtaaagt    6300
gcaagcgtag gaagaccaag actggcataa atcaggtata agtgtcgagc actggcaggt    6360
gatcttctga aagtttctac tagcagataa gatccagtag tcatgcatat ggcaacaatg    6420
taccgtgtgg atctaagaac gcgtcctact aaccttcgca ttcgttggtc cagtttgttg    6480
ttatcgatca acgtgacaag gttgtcgatt ccgcgtaagc atgcataccc aaggacgcct    6540
gttgcaattc caagtgagcc agttccaaca atctttgtaa tattagagca cttcattgtg    6600
ttgcgcttga aagtaaaatg cgaacaaatt aagagataat ctcgaaaccg cgacttcaaa    6660
cgccaatatg atgtgcggca cacaataagc gttcatatcc gctgggtgac tttctcgctt    6720
taaaaaatta tccgaaaaaa ttttctagag tgttgttact ttatacttcc ggctcgtata    6780
atacgacaag gtgtaaggag gactaaaacca tggctaaact cacctctgct gttccagtcc    6840
tgactgctcg tgatgttgct ggtgctgttg agttctggac tgatagactc ggtttctccc    6900
gtgacttcgt agaggacgac tttgccggtg ttgtacgtga cgacgttacc ctgttcatct    6960
ccgcagttca ggaccaggtt gtgccagaca acactctggc atgggtatgg gttcgtggtc    7020
tggacgaact gtacgctgag tggtctgagg tcgtgtctac caacttccgt gatgcatctg    7080
```

```
gtccagctat gaccgagatc ggtgaacagc cctggggtcg tgagtttgca ctgcgtgatc    7140
cagctggtaa ctgcgtgcat ttcgtcgcag aagagcagga ctaacaattg acaccttacg    7200
attatttaga gagtatttat tagttttatt gtatgtatac ggatgtttta ttatctattt    7260
atgcccttat attctgtaac tatccaaaag tcctatctta tcaagccagc aatctatgtc    7320
cgcgaacgtc aactaaaaat aagcttttta tgctcttctc tctttttttc ccttcggtat    7380
aattatacct tgcatccaca gattctcctg ccaaattttg cataatcctt tacaacatgg    7440
ctatatggga gcacttagcg ccctccaaaa cccatattgc ctacgcatgt ataggtgttt    7500
tttccacaat atttttctctg tgctctcttt ttattaaaga gaagctctat atcggagaag   7560
cttctgtggc cgttatattc ggccttatcg tgggaccaca ttgcctgaat tggtttgccc    7620
cggaagattg gggaaacttg gatctgatta ccttagctgc aggtaccact gagcgtcaga    7680
ccccgtagaa aagatcaaag gatcttcttg agatcctttt tttctgcgcg taatctgctg    7740
cttgcaaaca aaaaaccac cgctaccagc ggtggtttgt ttgccggatc aagagctacc     7800
aactcttttt ccgaaggtaa ctggcttcag cagagcgcag ataccaaata ctgttcttct    7860
agtgtagccg tagttaggcc accacttcaa gaactctgta gcaccgccta catacctcgc    7920
tctgctaatc ctgttaccag tggctgctgc cagtggcgat aagtcgtgtc ttaccgggtt    7980
ggactcaaga cgatagttac cggataaggc gcagcggtcg ggctgaacgg ggggttcgtg    8040
cacacagccc agcttggagc gaacgaccta caccgaactg agatacctac agcgtgagct    8100
atgagaaagc gccacgcttc ccgaagggag aaaggcggac aggtatccgg taagcggcag    8160
ggtcggaaca ggagagcgca cgagggagct tccaggggga aacgcctggt atctttatag    8220
tcctgtcggg tttcgccacc tctgacttga gcgtcgattt tgtgatgct cgtcaggggg     8280 gcggagccta tggaaaaacg ccagcaacgc ggcctttta cggttcctgg cctttgctg      8340 gccttttgct cacatgttct ttcctgcggt accc                                8374
```

<210> SEQ ID NO 5
<211> LENGTH: 8369
<212> TYPE: DNA
<213> ORGANISM: Artificial Sequence
<220> FEATURE:
<223> OTHER INFORMATION: DNA sequence of the linearized construct for
      expressing CYP52A13/CPR used for genome integration

<400> SEQUENCE: 5

```
agatccaatt cccgctttga ctgcctgaaa tctccatcgc ctacaatgat gacatttgga      60
tttggttgac tcatgttggt attgtgaaat agacgcagat cgggaacact gaaaaataca    120
cagttattat tcatttaaat aacatccaaa gacgaaaggt tgaatgaaac cttttttgcca   180 tccgacatcc acaggtccat tctcacacat aagtgccaaa cgcaacagga ggggatacac    240
tagcagcaga ccgttgcaaa cgcaggacct ccactcctct tctcctcaac acccactttt    300
gccatcgaaa aaccagccca gttattgggc ttgattggag ctcgctcatt ccaattcctt    360
ctattaggct actaacacca tgactttatt agcctgtcta tcctggcccc cctggcgagg    420
ttcatgtttg tttatttccg aatgcaacaa gctccgcatt acaccgaac atcactccag     480 atgagggctt tctgagtgtg gggtcaaata gtttcatgtt ccccaaatgg cccaaaactg    540
acagtttaaa cgctgtcttg gaacctaata tgacaaaagc gtgatctcat ccaagatgaa    600
ctaagtttgg ttcgttgaaa tgctaacggc cagttggtca aaaagaaact tccaaaagtc    660
ggcataccgt ttgtcttgtt tggtattgat tgacgaatgc tcaaaaataa tctcattaat    720
```

-continued

```
gcttagcgca gtctctctat cgcttctgaa ccccggtgca cctgtgccga aacgcaaatg    780
gggaaacacc cgcttttttgg atgattatgc attgtctcca cattgtatgc ttccaagatt    840
ctggtgggaa tactgctgat agcctaacgt tcatgatcaa aatttaactg ttctaacccc    900
tacttgacag caatatataa acagaaggaa gctgccctgt cttaaacctt ttttttttatc    960 atcattatta gcttactttc ataattgcga ctggttccaa ttgacaagct tttgatttta   1020
acgactttta acgacaactt gagaagatca aaaacaact aattattgaa agaattcaaa   1080
acgatggcac ttgataaact agatttgtac gtgattatca ccttagtggt tgctatcgct   1140
gcctacttcg ctaaaaacca atttctggac caacagcagg acactggatt tttgaatact   1200
gattccggtg atggtaactc cagagacatt ttacaagcac ttaagaagaa taacaaaaat   1260
actctactgt tatttggatc acaaactggt acagctgaag attacgccaa caaactgtcc   1320
cgtgaattac attcgaggtt tggattgaaa acaatggttg cagacttcgc tgattatgac   1380
ttcgagaatt tcggtgatat tacagaggac attttggtct ttttcatagt cgccacttat   1440
ggtgaaggtg aaccgactga taatgctgac gagttccaca cttggctgac cgaggaggct   1500
gatactttga gtacactgaa gtacacagtt tttggattgg gtaattctac ttacgaattt   1560
ttcaacgcta ttggtaggaa gttcgacaga ttactgggtg agaaaggtgg cgacagattt   1620
gctgaatacg gtgaaggcga cgacggtact ggaactttgg atgaagattt ccttgcttgg   1680
aaggacaacg tctttgattc attgaaaaat gatttgaatt tcgaggagaa agagcttaag   1740
tatgaaccaa acgtaaaatt gaccgaaagg gacgatttga gcggtaatga tccagatgta   1800
tctctaggtg aacctaatgt gaaatacatc aaaagtgaag gtgtggacct taccaaagga   1860
cctttcgacc atacccatcc cttttttggca aggatcgtga aaacaaaaga gttgttcaca   1920
agcgaagata gacactgtgt tcatgtagag tttgacatat ccgaatcaaa ccttaagtac   1980
acaacaggtg accatctggc aatctggcca tcaaattctg atgagaatat caagcaattt   2040
gccaagtgtt ttggactgga ggataagctc gacactgtca ttgaattgaa ggcattggac   2100
tcaacgtatt ctattccatt tccaaatcct atcacctacg gtgcagttat cagacaccat   2160
ctagaaataa gtggtcctgt ctcaagacaa tttttcctct ccatcgccgg atttgctcca   2220
gatgaggaga ctaaaaagtc cttcactaga attggtggag acaaacagga gttcgccagc   2280
aaggtaacta gacgtaagtt taacatcgct gatgcccttt tgttcgcttc caacaatcgt   2340
ccgtggtctg acgttccatt cgagtttcta attgaaaatg ttcaacactt gacaccacgt   2400
tattactcta tttcctcaag ctccctatca gaaaaacaga ccattaatgt tacagctgtg   2460
gttgaagctg aggaggaagc agacggcagg cctgttacgg gagttgtgac aaatctgctt   2520
aaaaacattg aaattgaaca aaataagacg ggagaaactc ctatggttca ctatgacttg   2580
aatggtccaa gaggtaagtt ctccaagttc agactgcccg ttcacgttag aagatccaac   2640
tttaagctcc caagaactc gactacaccc gtcatcttga ttggtccagg tacaggtgtt   2700 gccccttga gaggattcgt tagagaacgt gtacagcaag tgaaaacgg tgtcaatgtg   2760 ggtaaaacgg ttttgttttta tggatgtaga aattccgaac aagacttcct gtacaagcag   2820
gaatggtctg agtatgcttc ggtgctaggt gagaactttg atgtgttcaa tgcattcagt   2880
cgtcaagacc ctactaaaaa ggtgtacgtt caagataaaa tcttagaaaa ttctgcactt   2940
gtagatgagt tgctctcttc tggagccata atctacgtgt gcggagatgc tagtcgtatg   3000
gcaagagatg tccaagcagc tatcgctaaa atcgtcgcta agtcacgaga catccatgaa   3060
```

-continued

```
gataaggccg cagagttggt gaagagctgg aaagttcaaa atcgttatca ggaggatgtt    3120
tggtaagcgg ccgctcaaga ggatgtcaga atgccatttg cctgagagat gcaggcttca    3180
tttttgatac ttttttattt gtaacctata tagtatagga ttttttttgt catttttgttt   3240 cttctcgtac gagcttgctc ctgatcagcc tatctcgcag cagatgaata tcttgtggta    3300
ggggtttggg aaaatcattc gagtttgatg ttttctttgg tatttcccac tcctcttcag    3360
agtacagaag attaagtgag accttcgttt gtgcggatcc aacatccaaa gacgaaaggt    3420
tgaatgaaac cttttttgcca tccgacatcc acaggtccat tctcacacat aagtgccaaa   3480
cgcaacagga ggggatacac tagcagcaga ccgttgcaaa cgcaggacct ccactcctct    3540
tctcctcaac acccactttt gccatcgaaa aaccagccca gttattgggc ttgattggag    3600
ctcgctcatt ccaattcctt ctattaggct actaacacca tgactttatt agcctgtcta    3660
tcctggcccc cctggcgagg ttcatgtttg tttatttccg aatgcaacaa gctccgcatt    3720
acacccgaac atcactccag atgagggctt tctgagtgtg gggtcaaata gtttcatgtt    3780
ccccaaatgg cccaaaactg acagtttaaa cgctgtcttg gaacctaata tgacaaaagc    3840
gtgatctcat ccaagatgaa ctaagtttgg ttcgttgaaa tgctaacggc cagttggtca    3900 aaagaaact tccaaaagtc ggcataccgt ttgtcttgtt tggtattgat tgacgaatgc     3960
tcaaaaataa tctcattaat gcttagcgca gtctctctat cgcttctgaa ccccggtgca    4020
cctgtgccga aacgcaaatg gggaaacacc cgcttttttgg atgattatgc attgtctcca   4080
cattgtatgc ttccaagatt ctggtgggaa tactgctgat agcctaacgt tcatgatcaa    4140
aatttaactg ttctaacccc tacttgacag caatatataa acagaaggaa gctgccctgt    4200
cttaaacctt tttttttatc atcattatta gcttactttc ataattgcga ctggttccaa    4260
ttgacaagct tttgatttta acgacttta acgacaactt gagaagatca aaaacaact     4320 aattattgaa agaattcaaa acgatgacgg ttcatgacat catcgctact tacttcacaa    4380
agtggtacgt tatcgttcct ttagcccctta ttgcatacag agtgctggat tacttctatg   4440
gtaggtactt aatgtataag ttgggtgcaa aaccattttt ccagaaacag accgacggtt    4500
gtttcggttt taaggctcct ttggaattgc ttaaaaagaa atcagacggt actctgatcg    4560
actttacatt gcaaaggata cacgatctgg atagacctga cattcccact tttactttc    4620 cagtattcag cattaatctt gttaacactc tcgaaccaga gaacataaaa gctattttgg   4680
caacgcaatt caatgatttc tccttgggta ccagacactc ccactttgct ccactcctcg    4740
gtgatggtat tttcacactg gacggtgcag gatggaagca ttctagatcc atgctaaggc    4800
cacaatttgc aagagagcag atttcccatg tgaagctgtt ggagccacat gtgcaggtct    4860
ttttcaagca cgtccgtaag gctcaaggaa aaacttttga tattcaggag ttgttttttca    4920 gattgactgt tgattcagcc accgaatttt tgttcggaga aagtgttgaa tcgctgcgtg    4980
acgaatcaat tggaatgagc atcaacgcac ttgatttcga tggtaaagca ggttttgctg    5040
atgcttttaa ctactctcaa aactaccttg cttcaagagc tgtgatgcaa caactgtact    5100
gggttttgaa tggtaaaaag tttaaggaat gcaatgccaa ggtacacaag ttcgctgact    5160
attatgttaa caaagctctt gatctaacac ctgagcaatt ggaaaaacaa gacggctacg    5220
ttttcctata tgagttggtt aaacaaacta gagacaaaca agtttttacgt gatcagttgt    5280 tgaatatcat ggtagctggc cgagatacaa cagcaggact gttgtcgttc gtcttttttcg   5340 aactggccag aaatcccgaa gtcacaaaca aactgagaga agagatcgag gacaagtttg    5400
gtttaggtga gaatgctagt gttgaggaca tcagctttga atctttaaag tcctgtgagt    5460
```

```
acttgaaggc tgtgctgaat gaaactttgc gtttatatcc atctgttcct caaaatttcc   5520
gtgtcgctac caaaaatacg acattgccaa gaggaggagg caaagacggt ctgagtcctg   5580
tactagtcag aaaaggtcag actgtgatct acggagttta tgcagcccat agaaatcctg   5640
ccgtatatgg aaaagatgct ttggagtttc gtccggagag atggtttgaa ccagaaacca   5700
aaaagctcgg atgggctttc cttccattca atggtggtcc caggatatgt ttaggtcaac   5760
aattcgcttt aactgaagca tcctacgtga cagtgcgttt gttacaagag tttgcacatc   5820
tttccatgga cccagacact gagtatcctc ctaaaaagat gtctcatttg actatgtctt   5880
tgttcgatgg tgcaaacatt gaaatgtatt aagcggccgc tcaagaggat gtcagaatgc   5940
catttgcctg agagatgcag gcttcatttt tgatactttt ttatttgtaa cctatatagt   6000
ataggatttt ttttgtcatt ttgtttcttc tcgtacgagc ttgctcctga tcagcctatc   6060
tcgcagcaga tgaatatctt gtggtagggg tttgggaaaa tcattcgagt ttgatgtttt   6120
tcttggtatt tcccactcct cttcagagta cagaagatta agtgagacct tcgtttgtgc   6180
ggatccttca gtaatgtctt gtttcttttg ttgcagtggt gagccatttt gacttcgtga   6240
aagtttcttt agaatagttg tttccagagg ccaaacattc cacccgtagt aaagtgcaag   6300
cgtaggaaga ccaagactgg cataaatcag gtataagtgt cgagcactgg caggtgatct   6360
tctgaaagtt tctactagca gataagatcc agtagtcatg catatggcaa caatgtaccg   6420
tgtggatcta agaacgcgtc ctactaacct tcgcattcgt tggtccagtt tgttgttatc   6480
gatcaacgtg acaaggttgt cgattccgcg taagcatgca tacccaagga cgcctgttgc   6540
aattccaagt gagccagttc caacaatctt tgtaatatta gagcacttca ttgtgttgcg   6600
cttgaaagta aaatgcgaac aaattaagag ataatctcga aaccgcgact tcaaacgcca   6660
atatgatgtg cggcacacaa taagcgttca tatccgctgg gtgactttct cgctttaaaa   6720
aattatccga aaaattttc tagagtgttg ttactttata cttccggctc gtataatacg   6780
acaaggtgta aggaggacta aaccatggct aaactcacct ctgctgttcc agtcctgact   6840
gctcgtgatg ttgctggtgc tgttgagttc tggactgata gactcggttt ctcccgtgac   6900
ttcgtagagg acgactttgc cggtgttgta cgtgacgacg ttaccctgtt catctccgca   6960
gttcaggacc aggttgtgcc agacaacact ctggcatggg tatgggttcg tggtctggac   7020
gaactgtacg ctgagtggtc tgaggtcgtg tctaccaact tccgtgatgc atctggtcca   7080
gctatgaccg agatcggtga acagccctgg ggtcgtgagt ttgcactgcg tgatccagct   7140
ggtaactgcg tgcatttcgt cgcagaagag caggactaac aattgacacc ttacgattat   7200
ttagagagta tttattagtt ttattgtatg tatacggatg ttttattatc tatttatgcc   7260
cttatattct gtaactatcc aaaagtccta tcttatcaag ccagcaatct atgtccgcga   7320
acgtcaacta aaaataagct ttttatgctc ttctctcttt ttttcccttc ggtataatta   7380
taccttgcat ccacagattc tcctgccaaa ttttgcataa tcctttacaa catggctata   7440
tgggagcact tagcgccctc caaaacccat attgcctacg catgtatagg tgtttttcc    7500
acaatatttt ctctgtgctc tcttttatt aaagagaagc tctatatcgg agaagcttct   7560
gtggccgtta tattcggcct tatcgtggga ccacattgcc tgaattggtt tgccccggaa   7620
gattggggaa acttggatct gattacctta gctgcaggta ccactgagcg tcagaccccg   7680
tagaaaagat caaaggatct tcttgagatc ctttttttct gcgcgtaatc tgctgcttgc   7740
aaacaaaaaa accaccgcta ccagcggtgg tttgtttgcc ggatcaagag ctaccaactc   7800
```

```
tttttccgaa ggtaactggc ttcagcagag cgcagatacc aaatactgtt cttctagtgt    7860
agccgtagtt aggccaccac ttcaagaact ctgtagcacc gcctacatac ctcgctctgc    7920
taatcctgtt accagtggct gctgccagtg gcgataagtc gtgtcttacc gggttggact    7980
caagacgata gttaccggat aaggcgcagc ggtcgggctg aacgggggt tcgtgcacac    8040 agcccagctt ggagcgaacg acctacaccg aactgagata cctacagcgt gagctatgag    8100
aaagcgccac gcttcccgaa gggagaaagg cggacaggta tccggtaagc ggcagggtcg    8160
gaacaggaga gcgcacgagg gagcttccag ggggaaacgc ctggtatctt tatagtcctg    8220
tcgggtttcg ccacctctga cttgagcgtc gatttttgtg atgctcgtca gggggcgga    8280 gcctatggaa aaacgccagc aacgcggcct ttttacggtt cctggccttt tgctggcctt    8340
ttgctcacat gttctttcct gcggtaccc                                      8369
```

US 10,045,530 B2

AGRICULTURAL PHEROMONE COMPOSITIONS COMPRISING POSITIONAL ISOMERS

CROSS-REFERENCE TO RELATED APPLICATIONS

The present application claims the benefit of priority to U.S. Provisional Application No. 62/255,215, filed on Nov. 13, 2015, the disclosure of which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVI_010_01US_SeqList_ST25.txt, date created: Nov. 11, 2016, file size≈24 kilobytes).

BACKGROUND

Insects are estimated to cause global crop losses of approximately $250Bn—equivalent to 15% of global crop yield. Broad-spectrum insecticides, such as pyrethroid, organophosphate, and carbamate insecticide sprays, are currently used to combat such losses. However, these insecticides are harmful to both humans and the environment. In addition, the widespread use of insecticides has resulted in the evolution of resistant insects. For example, small-plot insecticide evaluations and scattered control failures in commercial sweet corn fields suggest that corn earworm populations in the Midwestern United States and southeastern Canada are gaining widespread resistance to pythrethroid-based insecticides. The rising frequency of resistant insects and the greater ease with which such insects migrate in a global economy have led to super-bugs that are causing multi-billion dollar losses. The cotton bollworm (*Helicoverpa armigera*) in Brazil and the corn rootworm (*Diabrotica virgifera virgifera*) in the United States are also contemporary illustrations of this trend. Furthermore, controlling infestations with broad-spectrum insecticides also reduces populations of beneficial insects, which leads to an outbreak of secondary pests, such as mites.

Thus, there exists a need for an insect management practice which prevents crop damage but does not have the harmful consequences of broad-spectrum insecticides.

BRIEF SUMMARY OF THE DISCLOSURE

In a first aspect, the disclosure provides for an insect pheromone composition for modifying the behavior of a target member of the order Lepidoptera. In some embodiments the pheromone composition comprises: (a) a first synthetically derived insect pheromone, having a chemical structure corresponding to that of a natural insect pheromone produced by a given target member of the order Lepidoptera; and (b) a positional isomer of said first synthetically derived insect pheromone, wherein said positional isomer is not naturally produced by the target member of the order Lepidoptera.

In some embodiments, the positional isomer is not produced by a member of the order Lepidoptera. In some embodiments, the first synthetically derived insect pheromone has a chemical structure corresponding to that of a natural insect sex pheromone produced by a member of the family Noctuidae or Plutellidae. In some embodiments, the first synthetically derived insect pheromone has a chemical structure corresponding to that of a natural insect sex pheromone produced by a member of the genus *Helicoverpa*, *Plutella*, *Spodoptera*, or *Chrysodeixis*. In some embodiments, the first synthetically derived insect pheromone has a chemical structure corresponding to that of a natural insect sex pheromone produced by *Helicoverpa zea*. In other embodiments, the first synthetically derived insect pheromone has a chemical structure corresponding to that of a natural insect sex pheromone produced by *Helicoverpa armigera*. In still other embodiments, the first synthetically derived insect pheromone has a chemical structure corresponding to that of a natural insect sex pheromone produced by *Plutella xylostella*. In yet other embodiments, the first synthetically derived insect pheromone has a chemical structure corresponding to that of a natural insect sex pheromone produced by *Spodoptera frugiperda*. In other embodiments, the first synthetically derived insect pheromone has a chemical structure corresponding to that of a natural insect sex pheromone produced by *Chrysodeixis includens*.

In some embodiments, the first synthetically derived insect pheromone is present in the composition in a ratio of from about 99% to about 1%, relative to the positional isomer, which is present in the composition in a ratio of from about 1% to about 99%. In other embodiments, the first synthetically derived insect pheromone is present in the composition in an amount of from about 99% to about 1% w/w. In yet other embodiments, the positional isomer is present in the composition in an amount of from about 99% to about 1% w/w.

In some embodiments, the first synthetically derived insect pheromone is Z-11-hexadecenal. In some embodiments, the first synthetically derived insect pheromone is Z-11-hexadecenal and the positional isomer is Z-5-hexadecenal.

In another aspect, the insect pheromone composition further comprising: (c) a second synthetically derived insect pheromone, having a chemical structure corresponding to that of a natural insect pheromone produced by a given target member of the order Lepidoptera; and (d) optionally, a positional isomer of said second synthetically derived insect pheromone, wherein said positional isomer is not naturally produced by the target member of the order Lepidoptera. In some embodiments, the second synthetically derived insect pheromone is Z-9-hexadecenal. In some embodiments, the second synthetically derived insect pheromone is Z-9-hexadecenal and the positional isomer of the second synthetically derived insect pheromone is present and is Z-7-hexadecenal. In some embodiments, the first synthetically derived insect pheromone is Z-11-hexadecenal and the positional isomer of the first synthetically derived insect pheromone is Z-5-hexadecenal, and wherein the second synthetically derived insect pheromone is Z-9-hexadecenal and the positional isomer of the second synthetically derived insect pheromone is present and is Z-7-hexadecenal.

In some embodiments, the pheromone composition further comprises at least one additional synthetically derived insect pheromone. In some embodiments, the insect pheromone composition further comprises an agriculturally acceptable adjuvant or carrier.

In some embodiments, an insect pheromone composition for modifying the behavior of male *Helicoverpa* sp., is disclosed herein which comprises: (a) Z-11-hexadecenal and Z-5-hexadecenal; and (b) an agriculturally acceptable adjuvant or carrier. In some such embodiments, the Z-11-hexadecenal is present in the composition in a ratio of from about 99% to about 1%, relative to the Z-5-hexadecenal, which is present in the composition in a ratio of from about 1% to about 99%. In other embodiments, the Z-11-hexadecenal is present in the composition in an amount of from about 99% to about 1% w/w and the Z-5-hexadecenal is present in the composition in an amount of from about 99% to about 1% w/w. In further embodiments, the insect pheromone composition further comprises: Z-9-hexadecenal. In still further embodiments, the insect pheromone composition further comprises: Z-9-hexadecenal and Z-7-hexadecenal.

In some embodiments, the Z-11-hexadecenal is present in the composition in an amount of from about 99% to about 1% w/w, the Z-5-hexadecenal is present in the composition in an amount of from about 99% to about 1% w/w, the Z-9-hexadecenal is present in the composition in an amount of from about 99% to about 1% w/w, and the Z-7-hexadecenal is present in the composition in an amount of from about 99% to about 1% w/w.

In some embodiments, a method of attracting an adult male *Helicoverpa* sp. to a locus, comprises: presenting an effective amount of the insect pheromone composition of described herein to a locus. In some embodiments, a method of attracting and killing an adult male *Helicoverpa* sp., comprises: presenting an effective amount of the insect pheromone composition described herein to a locus, wherein said locus also comprises a mechanism to kill the *Helicoverpa* sp. In some embodiments, a method of suppressing a population of *Helicoverpa* sp. in a given area, comprises: applying an effective amount of the insect pheromone composition disclosed herein to a locus within said area. In some embodiments, a method of suppressing a population of *Helicoverpa* sp. in a given area, comprises: permeating the atmosphere within said area with an effective amount of the insect pheromone composition of disclosed herein. In some embodiments, the effective amount of the insect pheromone composition is sufficient to at least partially disrupt mating within the *Helicoverpa* sp. population.

In some embodiments, an insect pheromone composition for modifying the behavior of a target insect, comprises: (a) a first synthetically derived insect pheromone having a chemical structure corresponding to the chemical structure of a naturally occurring insect pheromone produced by the target insect, said structure comprising formula (1),

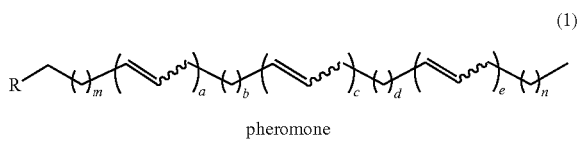

pheromone (1)

wherein R is located on a terminal carbon of an m-end of a carbon-carbon double bond in an unsaturated hydrocarbon substrate; and (b) positional isomer of said first synthetically derived insect pheromone, said positional isomer having a chemical structure of formula (2),

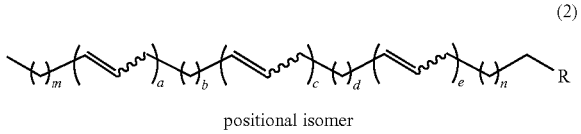

positional isomer (2)

wherein the positional isomer has an R located on a terminal carbon of an n-end of the carbon-carbon double bond in the unsaturated hydrocarbon substrate; wherein m and n are independently integers from 0 to 15, wherein a, c, and e are independently integers from 0 to 1, provided that at least one of a, c, or e is 1, wherein b and d are independently integers from 0 to 10, the m-end and the n-end are located on opposing sides of the carbon-carbon double bond in the unsaturated hydrocarbon substrate; and each R is independently —OH, =O, or —OAc.

In some embodiments, the insect pheromone composition further comprises an analog of said first synthetically derived insect pheromone, said analog having a chemical structure of formula (3)

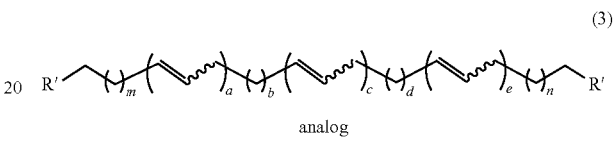

analog (3)

wherein the analog has an R' located on the n-end and the m-end of the carbon-carbon double bond in the unsaturated hydrocarbon substrate; wherein m and n are independently integers from 0 to 15, wherein a, c, and e are independently integers from 0 to 1, provided that at least one of a, c, or e is 1, wherein b and d are independently integers from 0 to 10, the m-end and the n-end are located on opposing sides of the carbon-carbon double bond in the unsaturated hydrocarbon substrate; and each R' is independently H, —OH, =O, —OAc, or —OOH.

In some embodiments, the insect pheromone composition further comprises:
a positional isomer of said first synthetically derived insect pheromone, said positional isomer having a chemical structure of formula (4),

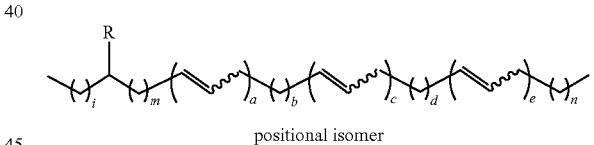

positional isomer (4)

wherein the positional isomer has an R located on a subterminal carbon on the m-end of the carbon-carbon double bond in the unsaturated hydrocarbon substrate thereby forming an i-end, wherein the i-end comprises a terminal carbon of the unsaturated hydrocarbon substrate; or a positional isomer of said first synthetically derived insect pheromone, said positional isomer having a chemical structure of formula 5,

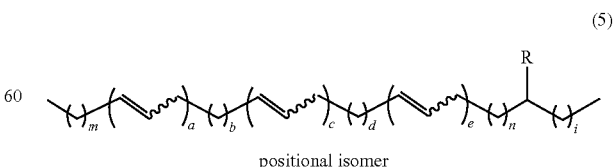

positional isomer (5)

wherein the positional isomer has an R located on a subterminal carbon on the n-end of the carbon-carbon double bond in the unsaturated hydrocarbon substrate, thereby forming an i-end, wherein the i-end comprises a terminal carbon of the unsaturated hydrocarbon substrate; wherein m, n, and i are independently integers from 0 to 15, wherein a, c, and e are independently integers from 0 to 1, provided that at least one of a, c, or e is 1, wherein b and d are independently integers from 0 to 10, the m-end and the n-end are located on opposing sides of the carbon-carbon double bond in the unsaturated hydrocarbon substrate; and R is —OH, =O, or —OAc.

In some embodiments, the sum of a, b, c, d, e, m, and n is an integer from 6 to 20. In some embodiments, the sum of a, b, c, d, e, i, m, and n is an integer from 6 to 20.

In some embodiments, the first synthetically derived pheromone has the following chemical structure:
a)

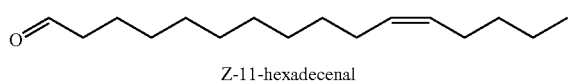 [SMILES: CCCC/C=C\CCCCCCCCCC=O]

Z-11-hexadecenal

The insect pheromone composition of claim 32, wherein the first synthetically derived insect pheromone has the following chemical structure:
a)

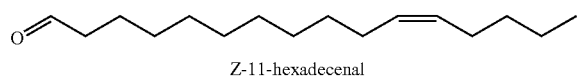

Z-11-hexadecenal and, wherein the positional isomer has the following chemical structure:
b)

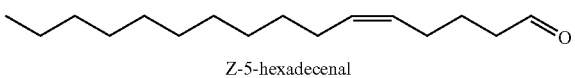

Z-5-hexadecenal

In some embodiments, the insect pheromone composition further comprises a second synthetically derived insect pheromone having a chemical structure corresponding to the chemical structure of a naturally occurring insect pheromone produced by the target insect, wherein said second synthetically derived insect pheromone has the following chemical structure:
c)

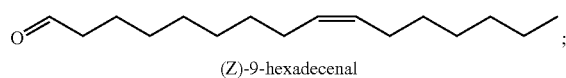

(Z)-9-hexadecenal and d) optionally, a positional isomer of said second synthetically derived insect pheromone, wherein said positional isomer is not naturally produced by the target insect.

In some embodiments, the positional isomer is present and has the following chemical structure:

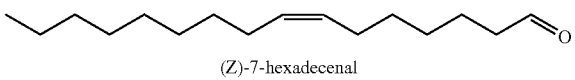

(Z)-7-hexadecenal

The insect pheromone composition of claim 40, wherein the first synthetically derived insect pheromone has the following chemical structure:
a)

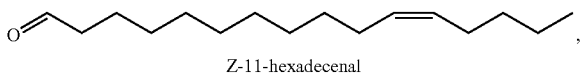 [SMILES: CCCC/C=C\CCCCCCCCCC=O]

Z-11-hexadecenal and, the positional isomer of the first synthetically derived insect pheromone has the following chemical structure:
b)

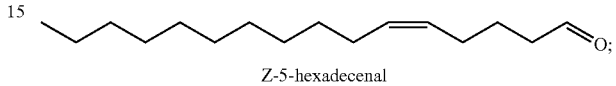

Z-5-hexadecenal and wherein the second synthetically derived insect pheromone has the following chemical structure
c)

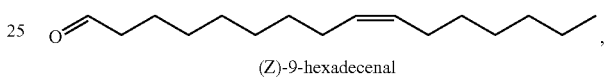

(Z)-9-hexadecenal and
the positional isomer of the second synthetically derived insect pheromone is present and has the following chemical structure:
d)

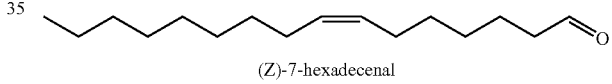

(Z)-7-hexadecenal

In some embodiments, the positional isomer is not produced by the target insect. In some embodiments, the first synthetically derived insect pheromone has a chemical structure corresponding to that of a natural insect sex pheromone produced by a member of the order Lepidoptera. In some embodiments, the first synthetically derived insect pheromone has a chemical structure corresponding to that of a natural insect sex pheromone produced by a member of the family Noctuidae or Plutellidae. In some such embodiments, the first synthetically derived insect pheromone has a chemical structure corresponding to that of a natural insect sex pheromone produced by a member of the genus *Helicoverpa, Plutella, Spodoptera*, or *Chrysodeixis*. In further embodiments, the first synthetically derived insect pheromone has a chemical structure corresponding to that of a natural insect sex pheromone produced by an insect selected from the group consisting of *Helicoverpa zea, Helicoverpa armigera, Plutella xylostella, Spodoptera frugiperda*, and *Chrysodeixis includens*.

BRIEF DESCRIPTION OF THE DRAWINGS

FIG. 4 shows Z-9-tetradecenyl acetate, the sex pheromone of *Spodoptera frugiperda* (Fall armyworm) and the positional isomer Z-5-tetradecenyl acetate.

DETAILED DESCRIPTION OF THE DISCLOSURE

I. Definitions

Figure 1:
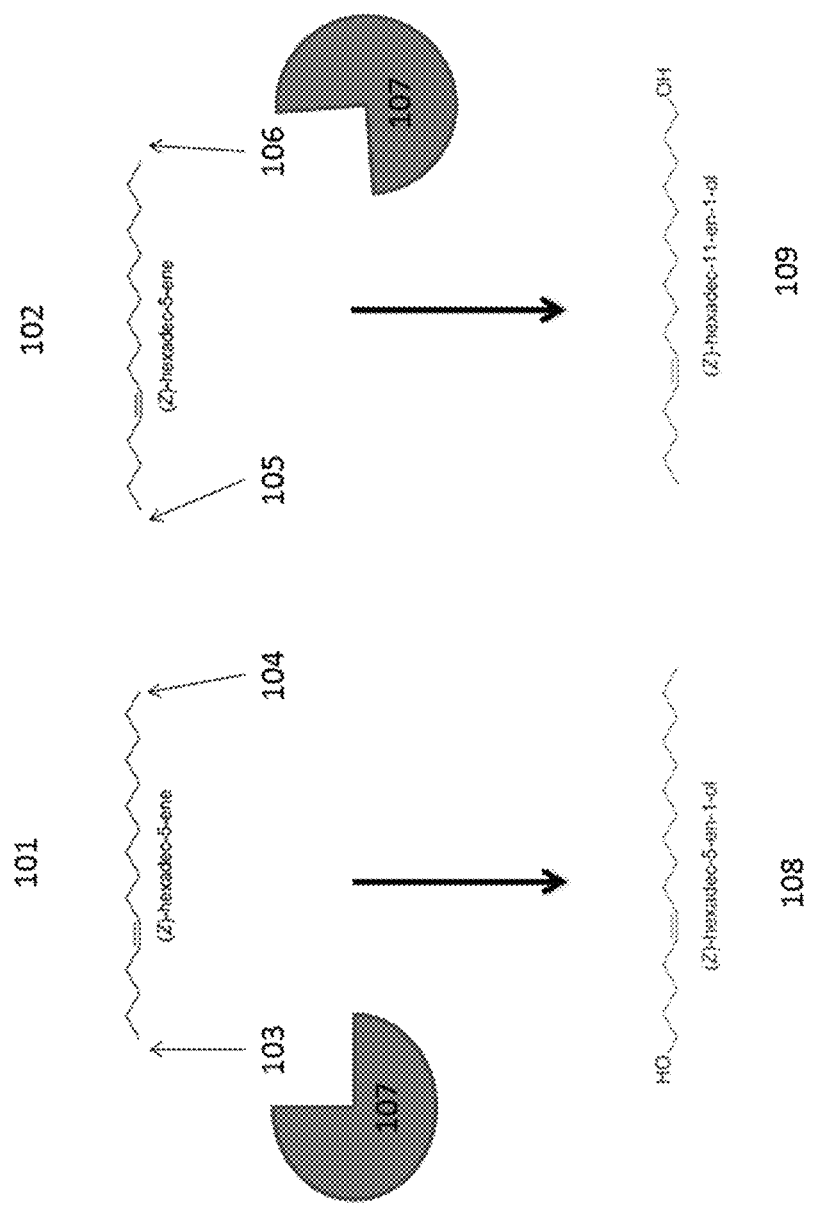
FIG. 1 shows the bioconversion of an unsaturated hydrocarbon substrate to an insect pheromone and a positional isomer.

The following definitions and abbreviations are to be used for the interpretation of the disclosure.

As used herein, the term "a" as used herein to refer to noun can refer to the singular or the plural version. Thus, a reference to a pheromone can refer to one pheromone or a more than one pheromones.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

"About" in reference to a numerical value refers to the range of values somewhat less or greater than the stated value, as understood by one of skill in the art. For example, the term "about" could mean a value ranging from plus or minus a percentage (e.g., ±1%, ±2%, ±5%, or ±10%) of the stated value. Furthermore, since all numbers, values, and expressions referring to quantities used herein are subject to the various uncertainties of measurement encountered in the art, then unless otherwise indicated, all presented values may be understood as modified by the term "about."

The terms "engineered enzyme" and "enzyme variant" include any enzyme comprising at least one amino acid mutation with respect to wild-type and also include any chimeric protein comprising recombed sequences or blocks of amino acids from two, three, or more different enzymes.

The terms "engineered heme enzyme" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The terms "engineered cytochrome P450" and "cytochrome P450 variant" include any cytochrome P450 enzyme comprising at least one amino acid mutation with respect to wild-type and also include any chimeric protein comprising recombed sequences or blocks of amino acids from two, three, or more different cytochrome P450 enzymes.

The term "whole cell catalyst" includes microbial cells expressing hydroxylase enzymes, wherein the whole cell catalyst displays hydroxylation activity.

As used herein, the term "metathesis reaction" refers to a catalytic reaction which involves the interchange of alkylidene units (i.e., $R_2C=$ units) among compounds containing one or more carbon-carbon double bonds (e.g., olefinic compounds) via the formation and cleavage of the carbon-carbon double bonds. Metathesis can occur between two like molecules (often referred to as self-metathesis) and/or between two different molecules (often referred to as cross-metathesis). The product of a "metathesis reaction" can be referred to herein as a "metathesis product," "olefinic substrate," "unsaturated hydrocarbon" and derviation and variations thereof.

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction.

As used herein, the term "metathesis product" refers to an olefin containing at least one double bond, the bond being formed via a metathesis reaction.

As used herein, the terms "microbial," "microbial organism," and "microorganism" include any organism that exists as a microscopic cell that is included within the domains of archaea, bacteria or eukarya. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As used herein, the term "non-naturally occurring," when used in reference to a microbial organism or enzyme activity of the disclosure, is intended to mean that the microbial organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microbial organism or enzyme activity includes the hydroxylation activity described above.

As used herein, the term "natural pheromone" is intended to mean the volatile chemical or particular volatile chemical blend having a chemical structure corresponding to the chemical structure of a pheromone that is released by a particular insect for the function of chemical communication within the species. As used herein, the term "non-natural" or "non-naturally occurring," when used in reference to a synthetic pheromone, is intended to mean a volatile chemical that is not produced by the particular insect species whose behavior is modified using said volatile chemical.

As used herein, the term "synthetically derived" when used in reference to a chemical compound is intended to indicate that the referenced chemical compound is transformed from starting material to product by human intervention. In some embodiments, a synthetically derived chemical compound can have a chemical structure corresponding an insect pheromone which is produced an insect species.

As used herein, the term "exogenous" is intended to mean that the referenced molecule or the referenced activity is introduced into the host microbial organism. The term as it is used in reference to expression of an encoding nucleic acid refers to the introduction of the encoding nucleic acid in an expressible form into the microbial organism. When used in reference to a biosynthetic activity, the term refers to an activity that is introduced into the host reference organism.

The term "heterologous" as used herein with reference to molecules, and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the terms "native" and/or "endogenous" as used herein with reference to molecules, and in particular enzymes and polynucleotides, indicate molecules that are expressed in the organism in which they originated or are found in nature, independently of the level of expression that can be lower equal or higher than the level of expression of the molecule in the native microorganism. It is to be understood that expression of native enzymes or polynucleotides may be modified in recombinant microorganisms.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The terms "analog" and "analogous," when used in reference to a nucleic acid or protein, include nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

As used herein, the term "alkane" refers to a straight or branched, saturated, aliphatic hydrocarbon having the number of carbon atoms indicated. The term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkanes and alkyl groups can be optionally substituted with one or more moieties selected from halo, alkenyl, and alkynyl.

As used herein, the term "alkene" and "olefin" refers to a straight chain or branched hydrocarbon having at least 2 carbon atoms and at least one double bond. The term "olefinic" refers to a composition derived from or including a straight chain or branched hydrocarbon having at least 2 carbon atoms and at least one double bond. A "terminal" alkene refers to an alkene wherein the double bond is between two carbon atoms at the end of the hydrocarbon chain (e.g., hex-1-ene). An "internal" alkene refers to an alkene wherein the double bond is between two carbon atoms that are not at the end of the hydrocarbon chain (e.g., (E)-hex-3-ene and (Z)-hex-3-ene). An "α,ω-alkenol" refers to a hydroxy-substituted terminal alkene having the formula $(CH_2=CH)(CH_2)_mOH$, wherein m is an integer ranging from 1-30, such as 2-18. The term "alkenyl" refers to a straight chain or branched hydrocarbon radical having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenes and alkenyl groups can be optionally substituted with one or more moieties selected from halo, alkyl, and alkynyl.

As used herein, the term "selective" refers to preferential reaction of one site on a chemical compound over another site on the compound. As a non-limiting example, selectively hydroxylating hept-3-ene (an asymmetric alkene) refers to preferentially hydroxylating one end of the hept-3-ene to form more hept-3-en-1-ol than hept-4-en-1-ol (or forming exclusively hept-3-en-1-ol without forming hept-4-en-1-ol). Selectively hydroxylating the other end of hept-3-ene would result in the formation of more hept-4-en-1-ol than hept-3-en-1-ol (or the exclusive formation of hept-4-en-1-ol without formation of hept-3-en-1-ol).

As used herein, the term "alkyne" refers to either a straight chain or branched hydrocarbon having at least 2 carbon atoms and at least one triple bond. A "terminal" alkyne refers to an alkyne wherein the triple bond is between two carbon atoms at the end of the hydrocarbon chain (e.g., hex-1-yne). An "internal" alkyne refers to an alkyne wherein the triple bond is between two carbon atoms that are not at the end of the hydrocarbon chain (e.g., hex-3-yne). The term "alkynyl" refers to either a straight chain or branched hydrocarbon radical having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynes and alkynyl groups can be optionally substituted with one or more moieties selected from halo, alkyl, and alkenyl.

As used herein, the term "isomer" refers to a molecule having the same chemical formula as another molecule, but with a different chemical structure. That is, isomers contain the same number of atoms of each element, but have different arrangements of their atoms. Isomers include "structural isomers" and "stereoisomers." In "structural isomers" (also referred to as "constitutional isomers"), the atoms have a different bond-sequence. Structural isomers have different IUPAC names and may or may not belong to the same functional group. This type of isomer includes skeletal isomers wherein hydrocarbon chains have variable amounts of branching, and positional isomers, which deals with the position of a functional group on a chain; and functional group isomerism, in which the molecular formula is the same but the functional group is different.

Figure 3:
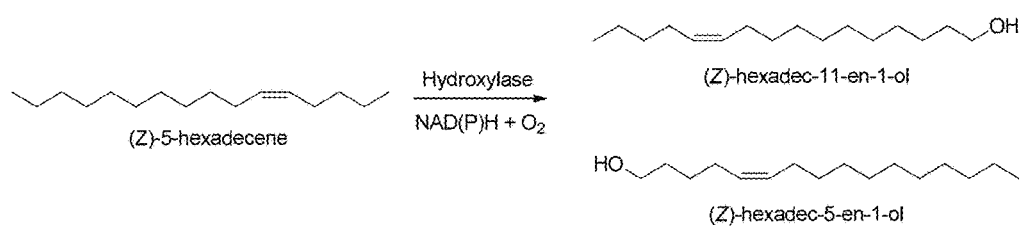
FIG. 3 shows a reaction scheme for hydroxylation of asymmetric alkenes using the methods of the disclosure.

As used herein, the term "positional isomer" refers to a first compound which has the same carbon skeleton and functional group as a second compound, but differs in the location of the functional group on or in the carbon skeleton. In a particular embodiment, a positional isomer can have a functional group (e.g., hydroxyl, aldehyde, and acetyl, etc.) located on the opposite terminus of a carbon skeleton compared to a naturally occurring compound. Thus, as used herein, a positional isomer of Z-hexadec-11-en-1-al is a Z-hexadec-5-en-1-al, because the Z-hexadec-11-en-1-al and Z-hexadec-5-en-1-al are produced via hydroxylation/oxidation of opposite termini on the Z-11-hexadecene carbon skeleton as shown in FIG. 3.

In stereoisomers, the bond structure is the same, but the geometrical positioning of atoms and functional groups in space differs. This class of isomers includes enantiomers, which are isomers that are non-superimposable mirror-images of each other, and diastereomers, which are stereoisomers that are not mirror-images. Geometric isomers or cis/trans isomers are diastereomers that with a different stereochemical orientation at a bond. E/Z isomer, which are a subset of geometric isomers, are isomers with a different geometric arrangement at a double bond. Another type of isomer, conformational isomers (conformers), may be rotamers, diastereomers, or enantiomers depending on the exact compound.

The term "analog," as used herein in reference to a chemical structure is intended to refer to compounds having a similar structure, but having a different molecular formula, e.g., a different or additional atom and/or functional group. By way of example, and not limitation, an analog of an insect pheromone can refer to molecule with two hydroxyl groups (as opposed to a single hydroxyl group required for a natural pheromone or precursor thereof) and/or an over-oxidized molecules with a carboxylic acid functional group (as opposed to an aldehyde functional group required for a natural pheromone).

An "effective amount" means that amount of the disclosed pheromone composition that is sufficient to affect desired results. An effective amount can be administered in one or more administrations. For example, an effective amount of the composition may refer to an amount of the pheromone composition that is sufficient to attract a given insect to a given locus. Further, an effective amount of the composition may refer to an amount of the pheromone composition that is sufficient to disrupt mating of a particular insect population of interest in a given locality.

II. Introduction

The present disclosure addresses a need for a safe alternative to conventional insecticides. The present disclosure provides compositions and methods for modifying the behavior of an insect using a composition comprising a pheromone.

In some aspects, the composition comprises a pheromone chemically corresponding to the pheromone naturally produced by a given insect. In some aspects, the composition comprises a pheromone chemically corresponding to the pheromone naturally produced by a given insect, along with at least one isomer of said pheromone. In various aspects, the isomer of the naturally produced insect pheromone may be a positional isomer.

In some embodiments, the insect is a pest. As used herein, the term "pest" can refer to insects that cause damage to plants, other organisms or otherwise causes a nuisance. In some embodiments, an insect pest can be attracted to a pheromone composition, e.g., by flying toward the pheromone composition or interacting with an article treated with the pheromone composition.

In various aspects, the insect that is "attracted" to the compositions taught herein may, or may not, physically contact a locus containing said pheromone composition. That is, in some aspects, the compositions taught herein are able to attract a given insect within a close proximity to a locus containing the disclosed pheromone compositions, but do not entice said insect to physically contact the locus. However, in other aspects, the compositions taught herein do entice and/or attract an insect to physically come into contact with a locus containing said pheromone compositions. In this way, inter alia, the pheromone compositions taught herein are highly "tunable" and are able to modulate the behavior (e.g., degree of attracting an insect) of an insect to a high degree, which is not associated with pheromone compositions of the prior art. Thus, the pheromone compositions taught herein, which may contain a natural insect pheromone and at least one positional isomer of said pheromone, do not merely provoke a binary "attract or not attract" response in a given insect. Rather, the pheromone compositions of the present disclosure are able to modulate the degree to which an insect is attracted along a continuous scale, depending upon, among other things, the ratio of natural pheromone to its positional isomer.

Embodiments of the present disclosure are based on the inventors' discovery of a novel methodology for the synthesis of a pheromone. The novel method includes (1) metathesis of alpha olefins to form alkenes with an internal C=C bond, (2) biohydroxylation of the product alkene via an enzymatic reaction to generate an alkenol, and (3) modification of the alkenol to an aldehyde by oxidation (MBO) or to an acetate by esterification (MBE). This method is referred to herein as MBO and MBE. The inventors' discovered synthesis, performed according to the methodology disclosed herein, yields an isomeric mixture which includes the natural pheromone and at least one isomer, e.g., a positional isomer. An unexpected and surprising result of the application of pheromone compositions comprising a synthetically derived, natural pheromone and a non-natural positional isomer was that the presence of the non-natural positional isomer in the pheromone composition modulated the behavior of the target insect. That is, while long-range attraction was maintained (i.e., upwind orienting flight), close-range attraction was eliminated. This indicates a novel partial mimic/partial antagonist response to the non-natural position isomer. Thus, the disclosure provides for pheromone compositions that comprise a natural insect pheromone, which a given target insect has evolved to recognize, along with a positional isomer of said pheromone. The combination of a natural pheromone, which would be produced by a target male insect's female counterpart—along with a positional isomer of said pheromone leads to a composition with markedly different behavioral modification properties, as compared to the naturally produced pheromone composition of a female insect.

Thus, in some embodiments, the pheromone compositions taught herein, can elicit a markedly different response from a natural pheromone blend, as they possess functional attributes not found in natural pheromone compositions produced by female insects of a given target species.

Furthermore, the pheromone compositions taught herein, are structurally different than any naturally occurring pheromone composition produced by a female insect of a given target species, as the pheromone compositions taught herein provide for a combination of a natural pheromone along with its positional isomer. This combination of an insect pheromone and a positional isomer of said pheromone does not occur in nature.

Pheromone

As described above, one aspect of the disclosure is a pheromone composition which can modify the behavior of an insect. A pheromone is a secreted or excreted chemical factor that triggers a social response in members of the same species. Thus, pheromones are chemicals capable of acting outside the body of the secreting individual to impact the behavior of the receiving individual. There are, inter alia, alarm pheromones, food trail pheromones, sex pheromones, aggregation pheromones, epideictic pheromones, releaser pheromones, primer pheromones, and territorial pheromones, that affect behavior or physiology.

As used herein, a pheromone can be a chemical, or a set of chemicals, that attract at least one species of insect. In some embodiments, the pheromone is a sex pheromone which attracts one sex of at least one insect. A pheromone synthesized as disclosed herein can be chemically identical to the natural substance for the target insect or it can be an isomer (e.g., a positional isomer, a constitutional isomer, or a stereoisomer, e.g, conformational isomer, geometric isomer, diastereomer, or enantiomer, etc.) or an analog of the natural pheromone. As used herein, the term "positional isomer" refers to a first compound which has the same carbon skeleton and functional group as a second compound, but differs in the location of the functional group on or in the carbon skeleton. For example, a positional isomer can have an aldehyde functional group located on the opposite terminus of the carbon skeleton compared to a naturally occurring compound. Thus, as used herein, a positional isomer of Z-hexadec-11-en-1-al is a Z-hexadec-5-en-1-al, because the Z-hexadec-5-en-1-al and Z-hexadec-5-en-1-al are produced via hydroxylation/oxidation of the opposite terminus of the Z-5-hexadecene carbon skeleton as shown in FIG. 3.

Pheromones described herein can be referred to using IUPAC nomenclature or various abbreviations and derivations. For example, (Z)-hexadec-11-en-1-al, can also be written as Z-11-hexadecen-1-al, Z-11-hexadecenal, or Z-x-y:Ald, wherein x represents the position of the double bond, and y represents the number of carbons in the hydrocarbon skeleton. Abbreviations used herein and known to those skilled art to identify functional groups on the hydrocarbon skeleton include "Ald," indicating an aldehyde, "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Non-limiting examples of C6-C20 linear insect pheromones that can be synthesized using the methodology disclosed herein are included in Table 1 below. Accordingly, a pheromone composition as described herein can include at least one of the pheromones listed in Table 1. Further, in some embodiments, the compositions taught herein comprise at least one of the pheromones listed in Table 1, along with at least one isomer thereof. In a particular embodiment, the compositions taught herein comprise at least one of the pheromones listed in Table 1, along with a positional isomer of at least one of the pheromones as listed in Table 1. In still further aspects of the disclosure, a composition may comprise only a positional isomer of a pheromone as listed in Table 1.

TABLE 1

C6-C20 Linear Pheromones

| Name | Name |
|---|---|
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-10-Pentadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (E)-2-Dodecenal | (E)-7-Hexadecenyl acetate |
| (Z)-3-Dodecen-1-ol | (E)-7-Hexadecenal |
| (E)-3-Dodecenyl acetate | (Z)-7-Hexadecen-1-ol |
| (Z)-3-Dodecenyl acetate | (Z)-7-Hexadecenyl acetate |
| (E)-4-Dodecenyl acetate | (Z)-7-Hexadecenal |
| (E)-5-Dodecen-1-ol | (E)-8-Hexadecenyl acetate |
| (E)-5-Dodecenyl acetate | (E)-9-Hexadecen-1-ol |
| (Z)-5-Dodecen-1-ol | (E)-9-Hexadecenyl acetate |
| (Z)-5-Dodecenyl acetate | (E)-9-Hexadecenal |
| (Z)-5-Dodecenal | (Z)-9-Hexadecen-1-ol |
| (E)-6-Dodecen-1-ol | (Z)-9-Hexadecenyl acetate |
| (Z)-6-Dodecenyl acetate | (Z)-9-Hexadecenal |
| (E)-6-Dodecenal | (E)-10-Hexadecen-1-ol |
| (E)-7-Dodecen-1-ol | (E)-10-Hexadecenal |
| (E)-7-Dodecenyl acetate | (Z)-10-Hexadecenyl acetate |
| (E)-7-Dodecenal | (Z)-10-Hexadecenal |
| (Z)-7-Dodecen-1-ol | (E)-11-Hexadecen-1-ol |
| (Z)-7-Dodecenyl acetate | (E)-11-Hexadecenyl acetate |
| (Z)-7-Dodecenal | (E)-11-Hexadecenal |
| (E)-8-Dodecen-1-ol | (Z)-11-Hexadecen-1-ol |
| (E)-8-Dodecenyl acetate | (Z)-11-Hexadecenyl acetate |
| (E)-8-Dodecenal | (Z)-11-Hexadecenal |
| (Z)-8-Dodecen-1-ol | (Z)-12-Hexadecenyl acetate |
| (Z)-8-Dodecenyl acetate | (Z)-12-Hexadecenal |
| (E)-9-Dodecen-1-ol | (E)-14-Hexadecenal |
| (E)-9-Dodecenyl acetate | (Z)-14-Hexadecenyl acetate |
| (E)-9-Dodecenal | (E,E)-1,3-Hexadecadien-1-ol |
| (Z)-9-Dodecen-1-ol | (E,Z)-4,6-Hexadecadien-1-ol |
| (Z)-9-Dodecenyl acetate | (E,Z)-4,6-Hexadecadienyl acetate |
| (Z)-9-Dodecenal | |

TABLE 1-continued

C6-C20 Linear Pheromones

| Name | Name |
|---|---|
| (E)-10-Dodecen-1-ol | (E,Z)-4,6-Hexadecadienal |
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (Z,E)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |
| (E,Z)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,Z)-7,9-Dodecadien-1-ol | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadienal | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z,Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (Z)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (Z,Z)-4,7-Tridecadienyl acetate | (Z)-8-Heptadecen-1-ol |
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadien-1-ol |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecenyl acetate | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9,12,15-Octadecatrien-1-ol |
| (E,E)-5,8-Tetradecadienal | (Z,Z,Z)-9,12,15-Octadecatrienyl acetate |
| (Z,Z)-5,8-Tetradecadien-1-ol | (Z,Z,Z)-9,12,15-Octadecatrienal |
| (Z,Z)-5,8-Tetradecadienyl acetate | |
| (Z,Z)-5,8-Tetradecadienal | |
| (E,E)-8,10-Tetradecadien-1-ol | |
| (E,E)-8,10-Tetradecadienyl acetate | |
| (E,E)-8,10-Tetradecadienal | |
| (E,Z)-8,10-Tetradecadienyl acetate | |
| (E,Z)-8,10-Tetradecadienal | |
| (Z,E)-8,10-Tetradecadien-1-ol | |
| (Z,E)-8,10-Tetradecadienyl acetate | |
| (Z,Z)-8,10-Tetradecadienal | |
| (E,E)-9,11-Tetradecadienyl acetate | |
| (E,Z)-9,11-Tetradecadienyl acetate | |
| (Z,E)-9,11-Tetradecadien-1-ol | |
| (Z,E)-9,11-Tetradecadienyl acetate | |
| (Z,E)-9,11-Tetradecadienal | |
| (Z,Z)-9,11-Tetradecadien-1-ol | |
| (Z,Z)-9,11-Tetradecadienyl acetate | |
| (Z,Z)-9,11-Tetradecadienal | |
| (E,E)-9,12-Tetradecadienyl acetate | |
| (Z,E)-9,12-Tetradecadien-1-ol | |
| (E,Z)-9,12-Tetradecadienyl acetate | |
| (Z,E)-9,12-Tetradecadienal | |
| (Z,Z)-9,12-Tetradecadien-1-ol | |
| (Z,Z)-9,12-Tetradecadienyl acetate | |

In some aspects, pheromone compositions taught in this disclosure comprise at least one pheromone listed in Table 2 and a positional isomer thereof to modulate the behavior of an insect listed in Table 2. By changing the ratios of a pheromone as listed in Table 2 and a positional isomer thereof in a given composition, the disclosure provides for a highly tunable insect behavior modifying composition.

TABLE 2

Exemplary compounds that can be synthesized, combined into compositions, and used according to methods described in the present disclosure.

| Name | Structure | Example of Biological importance |
| --- | --- | --- |
| (Z)-3-hexanol | 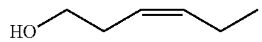 | See, Sugimoto etal. (2014) |
| (Z)-3-nonen-1-ol | 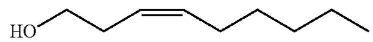 | West Indian Fruity Fly male sex pheromone |
| (Z)-5-decen-1-ol | 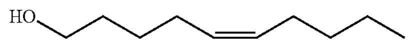 | |
| (Z)-5-decenyl acetate | 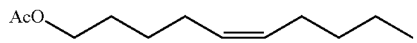 | Agrotis segetum sex pheromone component |
| (E)-5-decen-1-ol | 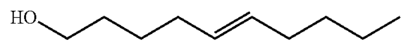 | Anarsia lineatella sex pheromone component |
| (E)-5-decenyl acetate | 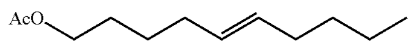 | Anarsia lineatella sex pheromone component |
| (Z)-7-dodecen-1-ol | 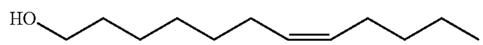 | |
| (Z)-7-dodecenyl acetate | 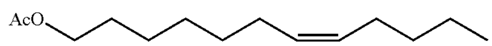 [SMILES: CCCC/C=C\CCCCCCOC(C)=O] | Pseudoplusia includens sex pheromone<br>Agrotis segetum sex pheromone component |
| (E)-8-dodecen-1-ol | 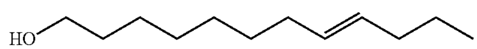 | Citrus Fruit Moth sex pheromone |
| (E)-8-dodecenyl acetate | 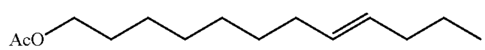 [SMILES: CCC/C=C/CCCCCCCOC(C)=O] | Grapholitha molesta, Ecdytolopha aurantiana sex pheromone component |
| (Z)-8-dodecen-1-ol | 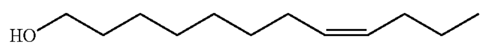 | Grapholitha molesta, Ecdytolopha aurantiana sex pheromone component |
| (Z)-8-dodecenyl acetate | 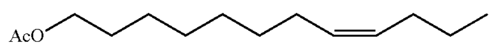 [SMILES: CCC/C=C\CCCCCCCOC(C)=O] | Grapholitha molesta sex pheromone component |
| (Z)-9-dodecen-1-01 | 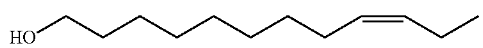 | |
| (Z)-9-dodecenyl acetate | 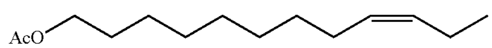 [SMILES: CC/C=C\CCCCCCCCOC(C)=O] | Eupoecilia ambiguella sex pheromone |
| (Z)-9-tetradecen-1-01 | 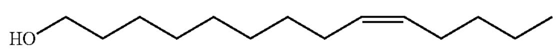 | |
| (Z)-9-tetradecenyl acetate | 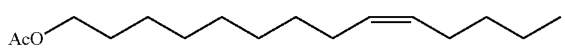 [SMILES: CCCC/C=C\CCCCCCCCOC(C)=O] | Pandemis pyrusana, Naranga aenescens, Agrotis segetum sex pheromone component |
| (Z)-11-tetraceden-1-ol | 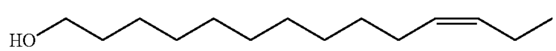 | |
| (Z)-11-tetracedenyl acetate | 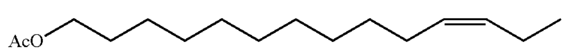 [SMILES: CC/C=C\CCCCCCCCCCOC(C)=O] | Pandemis pyrusana, Choristoneura roseceana sex pheromone component |
| (E)-11-tetradecen-1-ol | 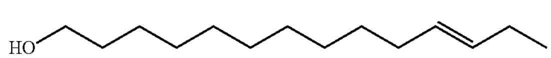 | |
| (E)-11-tetradecenyl acetate | 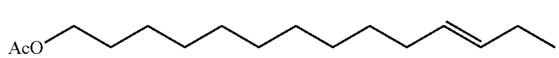 [SMILES: CC/C=C/CCCCCCCCCCOC(C)=O] | Choristoneura roseceana, Crocidolomia pavonana sex pheromone component |
| (Z)-7-hexadecen-1-ol | 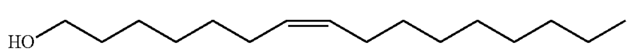 [SMILES: CCCCCCCC/C=C\CCCCCCO] | |
| (Z)-7-hexadecenal | 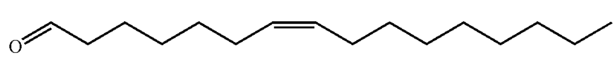 [SMILES: CCCCCCCC/C=C\CCCCCC=O] | Diatraea considerata sex pheromone component |
| (Z)-9-hexadecen-1-ol | 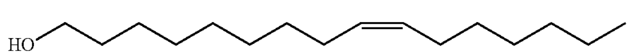 [SMILES: CCCCCC/C=C\CCCCCCCCO] | |

TABLE 2-continued

Exemplary compounds that can be synthesized, combined into compositions, and used according to methods described in the present disclosure.

| Name | Structure | Example of Biological importance |
|---|---|---|
| (Z)-9-hexadecenal | 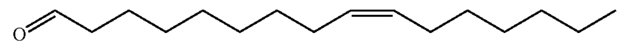 [SMILES: CCCCCC/C=C\CCCCCCCC=O] | Helicoverpa zea, Helicoverpa armigera, Heliothis virescens sex pheromone component |
| (Z)-9-hexadecenyl acetate | 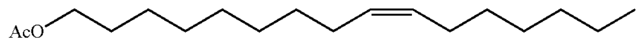 [SMILES: CCCCCC/C=C\CCCCCCCCOC(C)=O] | Naranga aenescens sex pheromone component |
| (Z)-11-hexadecen-1-ol | 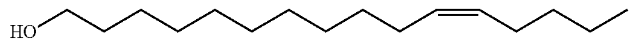 | |
| (Z)-11-hexadecenal | 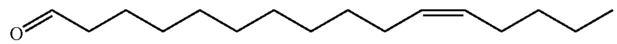 [SMILES: CCCC/C=C\CCCCCCCCCC=O] | Platyptila carduidactyla, Heliothis virescens sex pheromone Helicoverpa zea, Helicoverpa armigera, Plutella xylostella, Diatraea considerate, Diatraea grandiosella, Diatraea saccharalis, Acrolepiopsis assectella sex pheromone component |
| (Z)-11-hexadecenyl acetate | 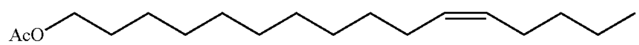 | Discestra trifolii sex pheromone Heliothis virescens, Plutella xylostella, Acrolepiopsis assectella, Crocidolomia pavonana, Naranga aenescens sex pheromone component |
| (Z)-13-octadecen-1-ol | 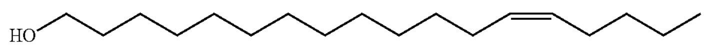 [SMILES: CCCC/C=C\CCCCCCCCCCCCO] | |
| (Z)-13-octadecenal | 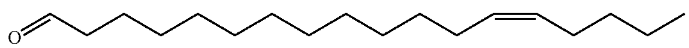 | Diatraea considerata, Diatraea grandiosella sex pheromone component |

Ac = —(CO)CH$_3$

Pheromones have the potential to challenge conventional approaches to agricultural insect control. Since their discovery in the late 1950s, these molecules have shown efficacy in reducing insect populations through sensory disruption and a subsequent reduction in mating frequency via a non-toxic mode of action.

Insect pheromones can be used in a variety of insect control strategies, including mating disruption, attract-and-kill, and mass trapping. These strategies have proven to be effective, selective (e.g., they do not harm beneficial insects, such as bees and lady bugs), and safe (e.g., the compounds are generally biodegradable and do not accumulate in the food chain).

The selectivity of pheromones allows farmers to control the population of the target pest causing minimal disruption to the ecology in the field. Because pheromones act via non-toxic mating disruption, they can be used to manage pests that have evolved resistance to chemical or transgenic insecticides.

This organic form of insect control has enjoyed success in permanent crops worldwide, particularly in Washington State apple orchards where adoption rates are greater than 90%. However, only <20 insect pests worldwide are currently controlled using pheromone solutions (e.g., mating disruption, attract-and-kill, mass trapping), and only 0.05% of global agricultural land employs pheromones. The limited use of pheromones is an unfortunate result of the high cost of synthesizing pheromones is very high, with industrial scale active ingredient (AI) prices ranging from $500 to $15,000 per kg, which prohibits widespread use of this sustainable technology beyond high-value crops.

Described herein are pheromone compositions synthesized using a novel enzymatic biohydroxylation step, which yields a pheromone at a fraction of the cost of conventional methodology. In some embodiments, the pheromone synthesized according to this methodology is a positional isomer of the natural pheromone. In one such embodiment, the positional isomer is not naturally produced by a female insect, but a male insect of the same species surprisingly responds to a composition which includes the positional isomer. This is surprising, given the fact that male insects are highly evolved to sense and respond to pheromone produced by their potential female mate. Accordingly, in some embodiments, a pheromone composition comprising: (a) an insect pheromone having a chemical structure identical to that of a pheromone produced by an insect pest, and (b) a positional isomer of said insect pheromone, can be used to modify the behavior of an insect pest.

The inclusion of a positional isomer in a pheromone composition comprising a synthetically derived natural pheromone can have at least four possible outcomes: (1) Inert—the isomer acts as a diluent, and the behavior of the target insect is not influenced; (2) Antagonist—the isomer acts as an inhibitor and blocks the response of the target insect to the natural pheromone; (3) Mimic—the isomer provides the same biological activity as the natural pheromone; and (4) Partial Mimic/Partial Antagonist—the isomer elicits an upwind flight response from the target insect, but the insect does not contact or land on a lure coated with the positional isomer.

In one embodiment, the target insect is member of the order Lepidoptera. In some embodiments, the composition is utilized to bring about mating disruption in the lepidopteran population, which subsequently leads to a decline in the population.

Lepidoptera

Lepidoptera is the second largest order in the class Insecta. The order Lepidoptera include the following families of butterflies: Nymphalidae, Danaidae, Pieridae, Papilionidae, Lycaenidae, Hesperiidae (e.g., *Epargyreus clarus*). The order also includes the following families of moths: Tineidae (e.g., (*Tineola bisselliella*, and *Tinea pellionella*), Gelechiidae (e.g., *Sitotroga cerealella* and *Pectinophora gossypiella*), Sesiidae (e.g., *Synanthedon exitiosa* and *Melittia cucurbitae*), Tortricidae (e.g., *Cydia pomonella* and *Grapholita molesta*). Pyralidae (e.g., *Ostrinia nubilalis, Plodia interpunctella*, and *Galleria mellonella*), Geometridae (e.g., *Operophtera brumata* and *Alsophila pometaria*), Lasiocampidae (e.g., *Malacosoma* Americana and *Malacosoma distria*). Satumiidae (e.g., *Hyalophora cecropiaa* and *Actias luna*), Sphingidae (e.g., *Manduca sexta* and *Manduca quinquemaculata*), Arctiidae (e.g., *Hyphantria cunea*), Lymantriidae (e.g., *Lymantria dispar* and *Euproctis chrysorrhoea*), Noctuidae (e.g., *Spodoptera frugiperda, Agrotis Ipsilon, Trichoplusia ni, Chrysodeixis includes, Helicoverpa zea,* and *Helicoverpa armigera*), and Plutellidae (e.g., *Plutella xylostella*).

The larvae of many lepidopteran species, which are commonly referred to as caterpillars, are major pests in agriculture. In many lepidopteran species, the female may produce anywhere from 200 to 600 eggs; and some species produce up to 30,000 eggs in one day. Unmitigated, the larvae can affect acres of vegetation. In fact, the larvae of Lepidoptera are probably more destructive to agricultural crops and forest trees than any other group of insects.

Some of the major pests of the order Lepidoptera include members of the families Noctuidae and Plutellidae. The larvae of the Noctuidae genus *Spodoptera* (including armyworm), *Helicoverpa* (including corn earworm and cotton bollworm), *Chrysodeixis* (including soybean looper) and larvae of the Plutellidae genus *Plutella* (including diamondback moth) can cause extensive damage to valuable crops.

*Helicoverpa zea* is known as the corn earworm; the polyphagous larva are known to cause damage to a variety of crops, including: corn, tomato, artichoke, asparagus, cabbage, cantaloupe, collards, cowpea, cucumber, eggplant, lettuce, lime bean, melon, okra, pea, pepper, potato, pumpkin, snap bean, spinach, squash, sweet potato, watermelon, soybean, as non-limiting examples.

*Helicoverpa armigera* is commonly referred to as the cotton bollworm; the polyphagous larva are known to cause damage to a variety of crops, including: tomato, cotton, pigeon pea, chickpea, sorghum, cowpea, groundnut, okra, peas, field beans, soybeans, lucerne, a variety of legumes, tobacco, potatoes, maize, flax, *Dianthus, Rosa, Pelargonium, Chrysanthemum, Lavandula angustifolia,* fruit trees, forest trees, and a range of vegetable crops, as non-limiting examples.

*Plutella xylostella* is known as the diamondback moth and is a worldwide pest; it is known to feed on cruciferous vegetables, including: broccoli, Brussels sprouts, cabbage, Chinese cabbage, cauliflower, collard, kale, kohlrabi, mustard, radish, turnip, and watercress.

*Spodoptera frugiperda*, known as the fall armyworm, has been reported to damage field crops, including: alfalfa, barley, Bermuda grass, buckwheat, cotton, clover, corn, oat, millet, peanut, rice, ryegrass, sorghum, sugarbeet, sudangrass, soybean, sugarcane, timothy, tobacco, and wheat, sweet corn, apple, grape, orange, papaya, peach, strawberry and a number of flowers.

*Chrysodeixis includens* is a type of moth whose larva is known to damage crops, including: soybeans, goldenrod, lettuce, sweet potato, peanut, cotton, tomato, brassicas (cabbage, kale, broccoli), pea, tobacco, and cocklebur.

Today, lepidopteran pests are predominantly controlled by pyrethroid, organophosphate, and carbamate insecticide sprays. Organophosphates and carbamates have demonstrated carcinogenic and neurotoxic effects in humans, while pyrethroids and organophosphates may unintentionally harm beneficial insects or sensitive vertebrates like amphibians, and fish. Conversely, lepidopteran pheromones present no known risks to humans or the environment. These non-toxic compounds may serve as a substitute for conventional pesticides, reducing the amount of chemical exposure to consumers, farm laborers, and the environment.

Insects of the order Lepidoptera produce pheromones which generally consist of unbranched, oxyfunctionalized long-chain olefins containing one to three double bonds. Lepidopteran pheromones, which are naturally occurring compounds, or identical or substantially similar synthetic compounds, are designated by an unbranched aliphatic chain (between 9 and 18 carbons) ending in an alcohol, aldehyde, or acetate functional group and containing up to 3 double bonds in the aliphatic backbone. For examples, the sex pheromones of *Helicoverpa zea, Helicoverpa armigera, Plutella xylostella*, and *Chrysodeixis* includes insects typically include one or more aliphatic aldehyde compounds having from 10 to 16 carbon atoms (e.g., 7-hexadecenal, 11-hexadecenal, 13-octadecenal, and the like). Other insects, such as *Spodoptera frugiperda*, recognize pheromones that are aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like).

Variation in the location, cis/trans selectivity, level of unsaturation along the chain, and chain length results in a diverse set of pheromones that facilitate species specific communication. These pheromones are used to attract a mate, sometimes at long distances.

The generally accepted natural pheromones produced by female *Helicoverpa zea, Helicoverpa armigera, Plutella xylostella* and *Chrysodeixis includens* are shown in the table below. Thus, aspects of the disclosure provide for pheromone compositions comprised of synthetically derived natural pheromone blends according to the table below along with various ratios of positional isomers. However, it should be noted that there can be other minor components produced by these insects as well. The below table merely lists the pheromone compositions produced by these insects, as they are commonly understood in the scientific literature. See, e.g., http://www.pherobase.com/database/species/species-*Helicoverpa-zea*.php; Halfhill, J. E. and McDonough, L. M. *Southwest Entomol.*, 1985. 10; 176-180; Pope M M, Gaston L K, and Baker T C. (1984) Composition, quantification, and periodicity of sex pheromone volatiles from individual *Heliothis zea* females. *J Insect Physiol* 30:943-945; http://www.pherobase.com/database/species/species-*Helicoverpa-armigera*.php; Zhang, J. P., et al. *J. Insect Physiol.* (2012) 58:1209-1216; http://www.pherobase.com/database/species/species-*Plutella-xylostella*.php; Lin, Y. M., et al., Bull. Inst. Sool. Acad. Sin. 21:121-127; Chisholm M D, Underhill E W, and Steck W F. (1979) Field trapping of the diamondback moth *Plutella xylostella* using synthetic sex attractants. *Environmental Entomology* 8:516-518; http://www.pherobase.com/database/species/species-*Spodoptera-frugiperda*.php; Meagher, R. L. and Mitchell, E. R. Fla. Entomol., 1998. 81:556-559; Tumlinson J H, Mitchell E R, Teal P E A, Heath R R, and Mengelkoch L J (1986) Sex pheromone of fall armyworm, *Spodoptera frugiperda* (J. E. Smith). *J Chem Ecol* 12:1909-1926; http://www.pherobase.com/database/species/species-*Pseudoplusia-includens*.php; Tumlinson, J. H, et al., *Environ. Entomol.*, 1972. 1:466-468; Linn C E, Du J, Hammond A, and Roelofs W L. (1987) Identification of unique pheromone components for soybean looper moth *Pseudoplusia includens*. *J Chem Ecol* 13:1351-1360; Cork A, Beevor P S, Hall D R, Nesbitt B F, Arida G S, and Mochida O. (1985). Components of the female sex pheromone of the yellow stem borer, *Scirpophaga incertulas*. *Entomol. Exp. Appl.* 37:149-153. Jiao X-G, Xuan W-J, Sheng C-F (2005) Mass trapping of the overwintering generation stripped stem borer, *Chilo suppressalis* (Walker) (Lepidoptera: Pyralidae) with the synthetic sex pheromone in northeastern China. *Acta Entomologica Sinica* 48:370-374; McLaughlin J and R Heath (1989) Field trapping and observations of male Velvetbean caterpillar moths and trapping of *Mocis* spp. (Lepidoptera: Noctuidae: Catacolinae) with calibrated formulations of sex pheromone. *Environmental Entomology* 18:933-938

| Pest (Latin Name(s)) | Pest (English Name(s)) | Natural Pheromone Blend | %[†] |
|---|---|---|---|
| Helicoverpa zea | Corn earworm | Z11-hexadecenal | 98 |
|  |  | Z9-hexadecenal[1] | 2 |
| Helicoverpa armigera | Cotton bollworm | Z11-hexadecenal | 98.3 |
|  | Corn earworm | Z9-hexadecenal | 1.4 |
|  | Old world bollworm | Z9-tetradecenal[2] | 0.3 |
| Plutella xylostella | Diamondback moth | Z11-hexadecenal | 70 |
|  |  | Z11-hexadecenyl acetate[3] | 30 |
| Spodoptera frugiperda | Fall armyworm | Z9-tetradecenyl acetate | 96.6 |
|  |  | Z7-dodecenyl acetate[4] | 3.4 |
| Chrysodeixis includens (Pseudoplusia includens) | Soybean looper | Z7-dodecenyl acetate[5] | 100 |
| Scirpophaga incertulas | Yellow stem borer Rice stem borer | Z11-hexadecenal Z9-hexadecenal[6] | 75 25 |
| Chilo suppressalis | Asiatic (or Striped) rice stem borer | Z11-hexadecenal Z13-octadecenal Z9-hexadecenal[7] | 82 10 8 |
| Anticarsia gemmatalis | Velvetbean caterpillar Velvetbean moth | Z3,6,9-eicosatriene Z3,6,9-heneicosatriene[8] | 62.5 37.5 |

[†]Ratios vary between regional populations and studies. The ratios reported here are based on either recent citations, more commonly cited blends, or historically accepted blends.

It is common for an individual pheromone to appear in multiple insects. For example, (Z)-11-hexadecenal is the main pheromone component for not only the corn earworm, but also the tobacco budworm, diamondback moth, and the rice stem borer.

As discussed above, pheromones can be used to manage pests. Accordingly, described herein are pheromone compositions and methods of use thereof to modulate the behavior of pests, e.g., by disrupting mating behavior.

In some embodiments, a pheromone described in Table 1 or Table 2 can be synthesized using the methods and synthetic schemes described herein. In aspects, positional isomers of the pheromones listed in Table 1 or Table 2 are produced by the synthetic schemes disclosed herein. Accordingly, a pheromone composition as described herein can include at least one of the pheromones listed in Table 1 or Table 2, along with at least one isomer thereof. In a particular embodiment, the compositions taught herein comprise at least one of the pheromones listed in Table 1 or Table 2, along with a positional isomer of at least one of the pheromones as listed in Table 1 or Table 2.

In exemplary embodiments, isomers of hexadecen-1-al can be synthesized for use in pheromone compositions. In the present disclosure, Z-hexadac-11-en-1-al, Z-11hexadacen-1-al, Z-11-hexadacenal, Z-hexadac-11-enal and Z-11-16:AL, are used synonymously, and similar variations can be used for other phenomes described herein. In exemplary embodiments, a Z-hexadac-11-en-1-al and a positional can be synthesized for use in pheromone compositions to modify the behavior of insect of the order Lepidoptera (e.g., *Helicoverpa. zea*,). In one such exemplary embodiment, the positional isomer of Z-hexadac-11-en-1-al is Z-hexadac-5-en-1-al (FIG. 1). In some embodiments, Z-hexadac-11-en-1-yl acetate can and a positional isomer can synthesized for use in pheromone compositions to modulate the behavior of an insect of the order Lepidoptera (e.g., *Plutella xylostella* and *Spodoptera frugiperda*). In one such embodiment, the positional isomer of Z-hexadac-11-en-1-yl acetate is Z-hexadac-5-en-1-yl acetate. In another embodiment, Z-hexadac-9-en-1-al and a positional isomer can be synthesized for use in pheromone compositions to modify the behavior of an insect of the order Lepidoptera (e.g., *Helicoverpa armigera* and *Helicoverpa. zea*). In one such exemplary embodiment, the positional isomer of Z-hexadac-9-en-1-al is Z-hexadac-7-en-1-al. In yet another embodiment, Z-tetradec-9-en-1-al and a positional isomer can by synthesized for use in pheromone compositions to modulate the behavior of an insect of the order Lepidoptera (e.g., *Spodoptera frugiperda*). In one such exemplary embodiment, the positional isomer of Z-tetradec-9-en-1-al is Z-hexadac-5-en-1-al. In still another embodiments, Z-tetradec-9-en-1-yl acetate and its positional isomer can by synthesized for use in pheromone compositions to modify the behavior of an insect of the order Lepidoptera (e.g., *Spodoptera frugiperda*). In one such exemplary embodiment, the positional isomer of Z-tetradec-9-en-1-yl acetate is Z-hexadac-5-en-1-yl acetate (FIG. 4). In an even further embodiment, Z-dodec-7-en-1-yl acetate and positional isomer can by synthesized for use in pheromone compositions to modify the behavior of an insect of the order Lepidoptera (e.g., *Chrysodeixis includens*). In one such exemplary embodiment, the positional isomer of Z-dodec-7-en-1-yl acetate is Z-dodec-5-en-1-yl acetate.

The present disclosure is based in part on the inventors' unexpected discovery that a pheromone composition including a synthetically derived natural pheromone and a positional isomer thereof can be used to modulate the response of a target insect relative to the response of the target insect elicited by a natural pheromone or natural pheromone blend.

III. Compositions

General Synthetic Route to Produce Pheromone Compositions

The present disclosure describes several methods for the synthesis of terminally oxyfunctionalized alkenes. Said methods are described in detail below and are generally applicable to the synthesis of various compounds, including but not limited to those shown in Table 1.

Some embodiments of the disclosure provide methods for synthesizing olefinic alcohol products wherein the olefinic alcohol product is a pheromone. In some embodiments, the olefinic alcohol product is selected from the alcohols in Table 1. Pheromones containing aldehyde functional groups can also be prepared using the olefinic alcohol products as intermediates. In such cases, the methods of the disclosure generally include oxidizing the olefin alcohol product to form an alcohol product. In some embodiments, the olefinic aldehyde product is selected from the aldehydes in Table 1.

Pheromones containing ester functional groups can also be prepared using the olefinic alcohol products as intermediates. In such cases, the methods of the disclosure generally include esterifying the olefinic alcohol product to form an olefinic ester product. In some embodiments, the olefinic ester product is an acetate ester. In some embodiments, the olefinic ester product is selected from the esters in Table 1 or Table 2.

Useful unsaturated fatty acids and related compounds can also be prepared using the olefinic alcohol products as intermediates. In such cases, the methods of the disclosure generally include oxidizing the olefinic alcohol product to form an olefinic acid product.

The synthetic strategies disclosed herein chiefly rely on the ability of hydroxylases to terminally hydroxylate hydrocarbon substrates such as linear alkenes. Linear alkenes and other hydrocarbon substrates can be synthesized via any route, including but not limited to olefin metathesis, Wittig olefination, or alkyne substitution followed by partial hydrogenation. The hydroxylation products can further be modified via any method, including—but not limited to—oxidation, esterification, and olefin metathesis, to produce the desired end products (Scheme 1). Deviations from this general scheme are also disclosed.

Scheme 1. General synthesis strategy disclosed herein.

Cheap Starting materials

Any Method, including
- olefin metathesis
- Wittig olefination
- alkyne substitution followed by partial hydrogenation
- etc.

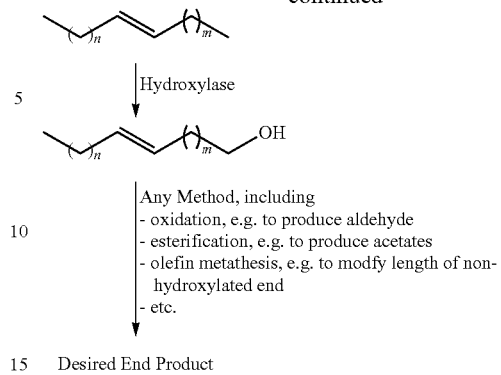

Hydroxylase

Any Method, including
- oxidation, e.g. to produce aldehyde
- esterification, e.g. to produce acetates
- olefin metathesis, e.g. to modfy length of non-hydroxylated end
- etc.

Desired End Product

MBO or MBE Synthesis

In an exemplary embodiment, the synthesis route (Scheme 2) consists of (1) metathesis of alpha olefins to form alkenes with an internal C=C bond, (2) biohydroxylation of the product alkene via an enzymatic reaction to generate an alkenol, and (3) modification of the alkenol to an aldehyde by oxidation (MBO) or to an acetate by esterification (MBE). This short and concise route can potentially capture a large segment of all lepidopteran pheromones. Further, synthesis of any insect pheromone and its positional isomer can be achieved through altering the length of the alpha olefins used in the metathesis step and finding an enzyme catalyst capable of acting on a range of alkenes. Biohydroxylation of different terminal carbons on an olefinic substrate (and subsequent oxidation/esterification if necessary) will generate a mixture of pheromones having a chemical structure of an insect sex pheromone produced by an insect and positional isomers of said sex pheromone. Thus, the disclosure is not limited to producing compositions comprising lepidopteran pheromones and positional isomers thereof; rather, the methods of the disclosure can produce any insect pheromone and any positional isomers thereof, for utilization in the disclosed compositions.

Scheme 2. Novel MBO synthesis strategy disclosed herein.

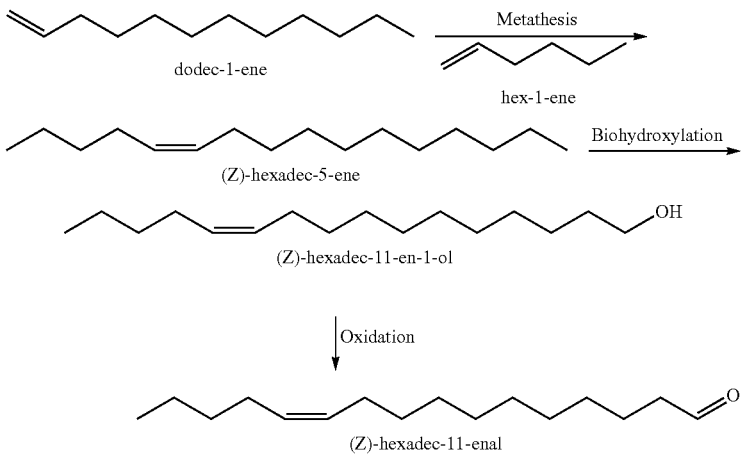

Synthesis of Terminal Alkenols Via Metathesis and Hydroxylation

In one aspect, the disclosure provides a method for synthesizing an olefinic alcohol product that includes incubating an unsaturated hydrocarbon substrate with an enzyme capable of independently hydroxylating a first terminal carbon of a first unsaturated hydrocarbon substrate and a second terminal carbon of a second unsaturated hydrocarbon substrate to form a mixture of an unsaturated hydrocarbon alcohol. The hydrocarbon alcohol can be further converted via oxidation, acetylation, or esterification as disclosed herein or according to methods known to those skilled in the art.

FIG. 1 shows a first unsaturated hydrocarbon 101 having a first end 103 and a second end 104, and a second unsaturated hydrocarbon 102 having a first end 105 and a second end 106. Biohydroxylation is performed by an enzyme catalyst 107, which independently oxidizes the second end 106 of the second substrate 102 to produce a naturally occurring sex pheromone 109 (or precursor thereof), and the first end 103 of the first substrate 101 to produce a positional isomer 108 of the sex pheromone (or precursor thereof).

Synthesis of Unsaturated Hydrocarbon Substrate for Subsequent Biohydroxylation to Produce Pheromone Composition Hydroxylation of Asymmetric Alkenes In some embodiments, the method for synthesizing an oxyfunctionalized alkene includes a combination of metathesis and terminal hydroxylation as shown in Scheme 3. In this process, terminal alkenes of different lengths are combined to generate asymmetric alkenes, which are then subjected to biohydroxylation conditions to afford the desired alkenol products.

In some embodiments, for example, m is 0 and n is 4; or m is 1 and n is 3; or m is 3 and n is 1; or m is 4 and n is 0; or m is 0 and n is 5; or m is 1 and n is 4; or m is 2 and n is 3; or m is 3 and n is 2; or m is 4 and n is 1; or m is 5 and n is 0; or m is 0 and n is 6; or m is 1 and n is 5; or m is 2 and n is 4; or m is 4 and n is 2; or m is 5 and n is 1; or m is 6 and n is 0; or m is 0 and n is 7; or m is 1 and n is 6; or m is 2 and n is 5; or m is 3 and n is 4; or m is 4 and n is 3; or m is 5 and n is 2; or m is 6 and n is 1; or m is 7 and n is 0; or m is 0 and n is 8; or m is 1 and n is 7; or m is 2 and n is 6; or m is 3 and n is 5; or m is 5 and n is 3; or m is 6 and n is 2; or m is 7 and n is 1; or m is 8 and n is 0; or m is 0 and n is 9; or m is 1 and n is 8; or m is 2 and n is 7; or m is 3 and n is 6; or m is 4 and n is 5; or m is 5 and n is 4; or m is 6 and n is 3; or m is 7 and n is 2; or m is 8 and n is 1; or m is 9 and n is 0; or m is 0 and n is 10; or m is 1 and n is 9; or m is 2 and n is 8; or m is 3 and n is 7; or m is 4 and n is 6; or m is 6 and n is 4; or m is 7 and n is 3; or m is 8 and n is 2; or m is 9 and n is 1; or m is 10 and n is 0; or m is 0 and n is 11; or m is 1 and n is 10; or m is 2 and n is 9; or m is 3 and n is 8; or m is 4 and n is 7; or m is 5 and n is 6; or m is 6 and n is 5; or m is 7 and n is 4; or m is 8 and n is 3; or m is 9 and n is 2; or m is 10 and n is 1; or m is 11 and n is 0; or m is 0 and n is 12; or m is 1 and n is 11; or m is 2 and n is 10; or m is 3 and n is 9; or m is 4 and n is 8; or m is 5 and n is 7; or m is 7 and n is 5; or m is 8 and n is 4; or m is 9 and n is 3; or m is 10 and n is 2; or m is 11 and n is 1; or m is 12 and n is 0; or m is 0 and n is 13; or m is 1 and n is 12; or m is 2 and n is 11; or m is 3 and n is 10; or m is 4 and n is 9; or m is 5 and n is 8; or m is 6 and n is 7; or m is 7 and n is 6; or m is 8 and n is 5; or m is 9 and n is 4; or m is 10 and n is 3; or m is 11 and n is 2; or m is 12 and n is 1; or m is 13 and n is 0; or m is 0 and n is 14; or m is 1 and n is 13; or m is 2 and n is Scheme 3

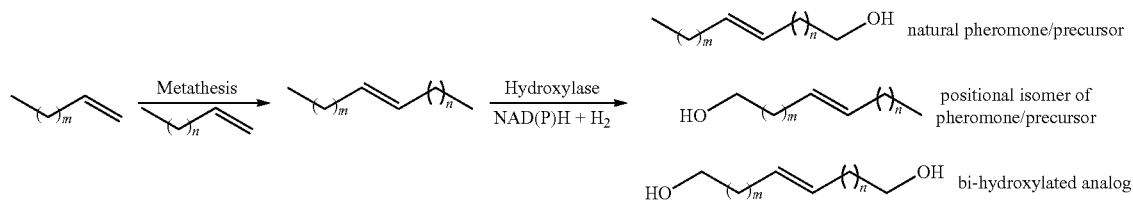

Methods including hydroxylation of asymmetric alkenes can be conducted with alkenes of any suitable length. In some embodiments, the asymmetric olefinic alcohol product is a C4-C30 olefinic alcohol product. In such embodiments, the sum of the subscripts m and n shown in Scheme 3 will bring the total number of carbon atoms in a particular asymmetric olefinic alcohol product to 4-30, when added to the number of the non-subscripted carbon atoms shown in the structure for the asymmetric olefinic alcohol product. In such embodiments, for example, subscript m in Scheme 5 can be an integer from 8-18 and subscript n in Scheme 3 can be a different integer from 0-8, bringing the total number of the carbons in the asymmetric olefinic substrate to 4-30. When m is 9 and n is 3, the route depicted in Scheme 3 provides (E/Z)-hexadec-11-en-1-ol as the target product. In some embodiments, the asymmetric olefinic alcohol product is a C4-C20 olefinic alcohol product. The asymmetric olefinic alcohol can contain, for example, 4-20 carbon atoms, or 8-20 carbon atoms, or 12-20 carbon atoms, or 16-20 carbon atoms.

12; or m is 3 and n is 11; or m is 4 and n is 10; or m is 5 and n is 9; or m is 6 and n is 8; or m is 8 and n is 6; or m is 9 and n is 5; or m is 10 and n is 4; or m is 11 and n is 3; or m is 12 and n is 2; or m is 13 and n is 1; or m is 14 and n is 0; or m is 0 and n is 15; or m is 1 and n is 14; or m is 2 and n is 13; or m is 3 and n is 12; or m is 4 and n is 11; or m is 5 and n is 10; or m is 6 and n is 9; or m is 7 and n is 8; or m is 8 and n is 7; or m is 9 and n is 6; or m is 10 and n is 5; or m is 11 and n is 4; or m is 12 and n is 3; or m is 13 and n is 2; or m is 14 and n is 1; or m is 15 and n is 0; or m is 0 and n is 16; or m is 1 and n is 15; or m is 2 and n is 14; or m is 3 and n is 13; or m is 4 and n is 12; or m is 5 and n is 11; or m is 6 and n is 10; or m is 7 and n is 9; or m is 9 and n is 7; or m is 10 and n is 6; or m is 11 and n is 5; or m is 12 and n is 4; or m is 13 and n is 3; or m is 14 and n is 2; or m is 15 and n is 1; or m is 16 and n is 0; or m is 1 and n is 16; or m is 2 and n is 15; or m is 3 and n is 14; or m is 4 and n is 13; or m is 5 and n is 12; or m is 6 and n is 11; or m is 7 and n is 10; or m is 8 and n is 9; or m is 9 and n is 8; or m is 10 and n is 7; or m is 11 and n is 6; or m is 12 and n is 5; or m is 13 and n is 4; or m is 14 and n is 3; or m is 15 and n is 2; or m is 16 and n is 1; or m is 17 and n is 0; or m is 0 and n is 18; or m is 1 and n is 17; or m is 2 and n is 16; or m is 3 and n is 15; or m is 4 and n is 14; or m is 5 and n is 13; or m is 6 and n is 12; or m is 7 and n is 11; or m is 8 and n is 10; or m is 10 and n is 8; or m is 11 and n is 7; or m is 12 and n is 6; or m is 13 and n is 5; or m is 14 and n is 4; or m is 15 and n is 3; or m is 16 and n is 2; or m is 17 and n is 1; or m is 18 and n is 0

Accordingly, some embodiments of the disclosure provide methods for preparing an olefinic alcohol product as described above, wherein the olefinic substrate is a metathesis product, and wherein the method includes: a) cross-metathesizing a first terminal olefin and a second different terminal olefin in the presence of a metathesis catalyst to form the metathesis product; and b) incubating the metathesis product with an enzyme capable of selectively hydroxylating one terminal carbon of the metathesis product to form an olefinic alcohol product.

In some embodiments, the first terminal olefin has the formula $(CH_2=CH)(CH_2)_mH$, the second different terminal olefin has the formula $(CH_2=CH)(CH_2)_nH$, the metathesis product has the formula $H(CH_2)_m(CH=CH)(CH_2)_nH$, the olefinic alcohol product has the formula $HO(CH_2)_m(CH=CH)(CH_2)_nH$, and m and n are different integers between 1 and 18. In some embodiments, the olefinic alcohol product has a chemical structure corresponding to an insect pheromone. In other embodiments, the olefinic alcohol product has a chemical structure corresponding to a precursor of a pheromone, wherein the precursor undergoes subsequent synthetic transformation, e.g., oxidation and/or acetylation, to produce a synthetically derived pheromone. In some embodiments, m and n are different integers between 1 and 9.

In some embodiments, methods described herein can be used to synthetically derive an olefinic alcohol which is an isomer of the olefinic alcohol product having a chemical structure corresponding to a pheromone or to a precursor of a pheromone. In some such embodiments, the pheromone isomer can be used in a pheromone composition.

In some embodiments, the olefinic alcohol product is a positional isomer of a pheromone which results from biohydroxylation of the terminal carbon on the n-end of the metathesis product, wherein the isomeric olefinic alcohol product has the formula $H(CH_2)_m(CH=CH)(CH_2)_nOH$, and m and n are different integers between 1 and 18. In some embodiments, m and n are different integers between 1 and 9. In other embodiments, the isomeric olefinic alcohol product can undergo a subsequent synthetic transformation, e.g., oxidation and/or acetylation, to produce a positional isomer of a pheromone.

In some embodiments, the olefinic alcohol product is a diol which results from biohydroxylation of the terminal carbon on the n-end and biohydroxylation of the terminal carbon on the m-end, the isomeric olefinic diol product has the formula $HO(CH_2)_m(CH=CH)(CH_2)_nOH$, and m and n are different integers between 1 and 18. In some embodiments, m and n are different integers between 1 and 9. In other embodiments, the olefinic diol product can undergo a subsequent synthetic transformation, e.g., oxidation and/or acetylation, to produce an analogue of a pheromone.

In some embodiments, the olefinic alcohol product is a positional isomer of a pheromone which results from biohydroxylation of a subterminal carbon on m-end of the metathesis produced, wherein the isomeric olefinic alcohol has the formula $H(CH_2)_iCHOH(CH_2)_{m-i-1}(CH=CH)(CH_2)_nH$. In some embodiments, the olefinic alcohol product is a positional isomer of a pheromone which results from biohydroxylation of a subterminal carbon on n-end of the metathesis produced, wherein the isomeric olefinic alcohol has the formula $H(CH_2)_m(CH=CH)(CH_2)_{n-i-1}CHOH(CH_2)_iH$. In some embodiment, m, n and i are different integers between 1 and 17. In some embodiments, m, n, and i are different integers between 1 and 9.

The methods of the disclosure can also be conducted such that the biohydroxylation step is conducted prior to the metathesis step and/or other synthetic transformation steps. Accordingly, some embodiments of the disclosure provide methods wherein the olefinic substrate is a first terminal olefin, and wherein the method includes: a) incubating the first terminal olefin with an enzyme capable of selectively hydroxylating the terminal carbon of the terminal olefin to form an α,ω-alkenol; and b) metathesizing the α,ω-alkenol and a second terminal olefin in the presence of a metathesis catalyst to form the olefinic alcohol product.

The alcohol can be protected with a suitable protecting group if necessary. In some embodiments, the methods of the disclosure include: a) incubating the first terminal olefin with an enzyme capable of selectively hydroxylating the terminal carbon of the terminal olefin to form an α,ω-alkenol; b) protecting the α,ω-alkenol to form a protected α,ω-alkenol; c) metathesizing the protected α,ω-alkenol and a second terminal olefin in the presence of a metathesis catalyst to form a protected olefinic alcohol product; and d) deprotecting the protected olefinic alcohol product to form the olefinic alcohol product.

Any suitable alcohol protecting group can be used in the methods of the disclosure. Such protecting groups are well known to one of ordinary skill in the art, including those that are disclosed in *Protective Groups in Organic Synthesis,* 4th edition, T. W. Greene and P. G. M. Wuts, John Wiley & Sons, New York, 2006, which is incorporated herein by reference in its entirety. In some embodiments, the α,ω-alkenol is protected via esterification and the protected olefinic alcohol product is deprotected via hydrolysis. In some embodiments, the α,ω-alkenol is protected via esterification with an acid selected from the group consisting of formate and acetate.

Any suitable olefinic substrate can be used in methods where the biohydroxylation step is conducted prior to the metathesis step and/or other synthetic transformation steps. In some embodiments, the first terminal olefin has the formula $(CH_2=CH)(CH_2)_mH$, the α,ω-alkenol has the formula $(CH_2=CH)(CH_2)_mOH$, the second terminal olefin has the formula $(CH_2=CH)(CH_2)_nH$, the olefinic alcohol product has the formula $H(CH_2)_n(CH=CH)(CH_2)_mOH$, and m and n are each independently selected from an integer between 1 and 17. In some embodiments, m and n are each independently selected from an integer between 1 and 9.

Hydroxylation of Asymmetric Alkenes Using Alkyne Starting Material

In some embodiments, the alkene is produced according to Scheme 4 (see, Oprean et al. (2006) for the acetylation step and Buck and Chong (2001) for the alkyne alkylation step), Scheme 5 (see, Buck and Chong (2001) regarding the alkyne alkylation step), Scheme 6a, or Scheme 6b. Scheme 6b shows Wittig reaction conditions that favor the formation of the Z-isomer according to Smith et al. (2000).

Scheme 4

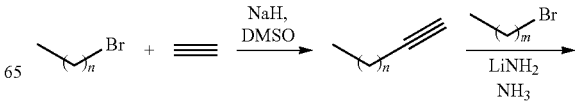

-continued

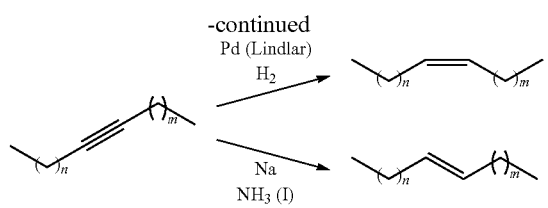

Scheme 5

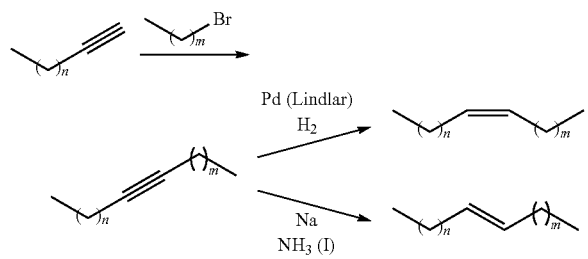

Scheme 6

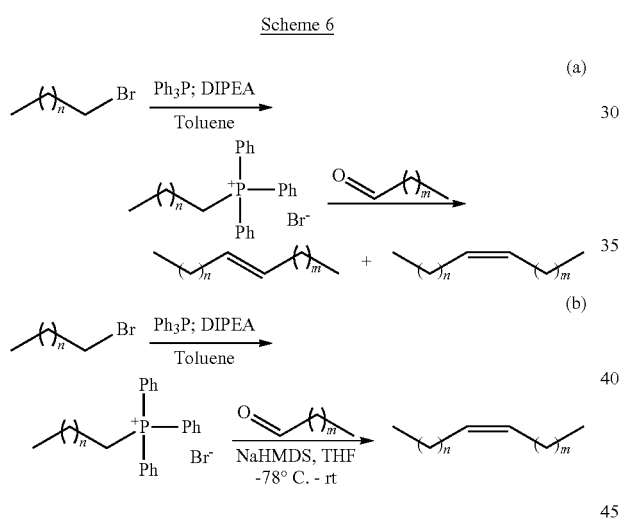

Accordingly, some embodiments of the disclosure provide a method for synthesizing an olefinic alcohol product wherein the method includes:

a) forming a reaction mixture comprising a terminal alkyne according to formula I

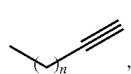   (I)

wherein n is an integer from 0 to 16,
and an alkyl halide according to formula II

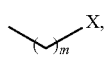   (II)

wherein X is a halogen and m is an integer from 0 to 16, under conditions sufficient to form a disubstituted alkyne according to formula III

   (III)

b) reducing the disubstituted alkyne to form an olefin according to formula IVa or IVb

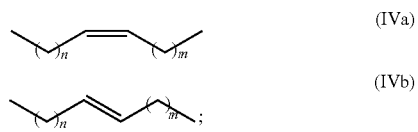

(IVa)

(IVb)

and c) incubating the olefin with an enzyme capable of selectively hydroxylating one terminal carbon of the olefin to form the olefinic alcohol product.

The terminal alkyne, the alkyl halide, the disubstituted alkyne, the olefin, and the olefinic alcohol product can have any suitable combination of subscripts m and n, as described above. In some embodiments, m and n are independently selected integers between 1 and 9. In some embodiments, m and n are different integers between 1 and 9.

In some embodiments, the disclosure includes:

a) forming a reaction mixture comprising a phosphonium salt according to formula XVI

   (XVI)

wherein
each R is independently selected from $C_{1-6}$ alkyl and $C_{6-10}$ aryl,
X is a halogen, and
n is an integer from 0 to 16,
and an aldehyde according to formula XVII (XVII)

wherein m is an integer from 0 to 16,
under conditions sufficient to form an olefin according to formula XVIIIa or formula XVIIIb

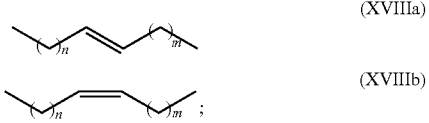

(XVIIIa)

(XVIIIb)

and b) incubating the olefin with an enzyme capable of selectively hydroxylating one terminal carbon of the olefin to form the olefinic alcohol product.

The phosphonium salt, the aldehyde, the olefin, and the olefinic alcohol product can have any suitable combination of subscripts m and n, as described above. In some embodiments, m and n are independently selected integers between 1 and 9. In some embodiments, m and n are different integers between 1 and 9.

Metathesis Catalysts

In general, any metathesis catalyst stable under the reaction conditions and nonreactive with the functional groups present on the reactant shown in Schemes 3-6 may be used with the present disclosure. Such catalysts are, for example, those described by Grubbs (Grubbs, R. H., "Synthesis of large and small molecules using olefin metathesis catalysts." PMSE Prepr., 2012), herein incorporated by reference in its entirety. Depending on the desired isomer of the olefin, as cis-selective metathesis catalyst may be used, for example one of those described by Shahane et al. (Shahane, S., et al. ChemCatChem, 2013. 5(12): p. 3436-3459), herein incorporated by reference in its entirety. Specific catalysts 1-5 exhibiting cis-selectivity are shown below (Scheme 7) and have been described previously (Khan, R. K., et al. J. Am. Chem. Soc., 2013. 135(28): p. 10258-61; Hartung, J. et al. J. Am. Chem. Soc., 2013. 135(28): p. 10183-5; Rosebrugh, L. E., et al. J. Am. Chem. Soc., 2013. 135(4): p. 1276-9; Marx, V. M., et al. J. Am. Chem. Soc., 2013. 135(1): p. 94-7; Herbert, M. B., et al. Angew. Chem. Int. Ed. Engl., 2013. 52(1): p. 310-4; Keitz, B. K., et al. J. Am. Chem. Soc., 2012. 134(4): p. 2040-3; Keitz, B. K., et al. J. Am. Chem. Soc., 2012. 134(1): p. 693-9; Endo, K. et al. J. Am. Chem. Soc., 2011. 133(22): p. 8525-7).

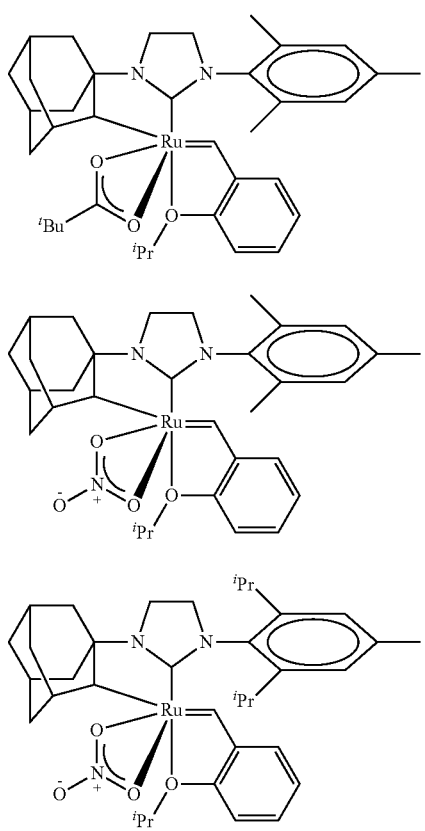

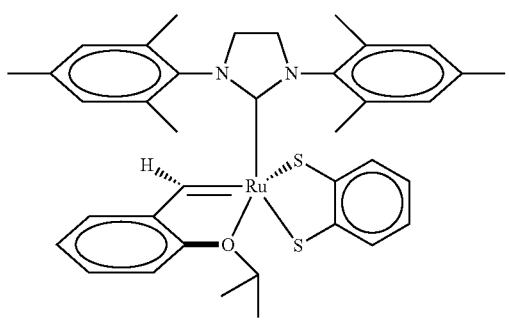

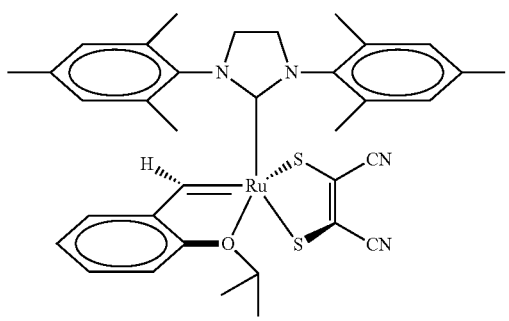

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Due to their excellent stability and functional group tolerance, in some embodiments metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis(hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the disclosure also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.*, 2012, 134: 2788-2799; Halford. *Chem. Eng. News*, 2011, 89 (45): 11; Yu, et al. *Nature*, 2011, 479: 88-93; Lee. *Nature*, 2011, 471: 452-453; Meek, et al. *Nature*, 2011: 471, 461-466; Flook, et al. *J. Am. Chem. Soc.* 2011, 133: 1784-1786; Zhao, et al. *Org Lett.*, 2011, 13(4): 784-787; Ondi, et al. "High activity, stabilized formulations, efficient synthesis and industrial use of Mo- and W-based metathesis catalysts" *XiMo Technology Updates*, 2015: http://www.ximo-inc.com/files/ximo/uploads/download/Summary_3.11.15.pdf; Schrock, et al. *Macromolecules*, 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the disclosure also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the disclosure also include those described in U.S. Pat. No. 4,231,947; U.S. Pat. No. 4,245,131; U.S. Pat. No. 4,427,595; U.S. Pat. No. 4,681,956; U.S. Pat. No. 4,727,215; International Pub. No. WO 1991/009825; U.S. Pat. No. 5,087,710; U.S. Pat. No. 5,142,073; U.S. Pat. No. 5,146,033; International Pub. No. WO 1992/019631; U.S. Pat. No. 6,121,473; U.S. Pat. No. 6,346,652; U.S. Pat. No. 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the disclosure also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the disclosure also include those set forth in the following table:

| Structure | Name |
|---|---|
| 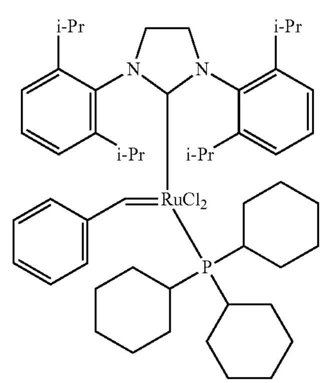 | dichloro[1,3-bis(2,6-isopropylphenyl)-2-imidazolidinylidene](benzylidene)(tricyclohexylphosphine)ruthenium(II) |
| 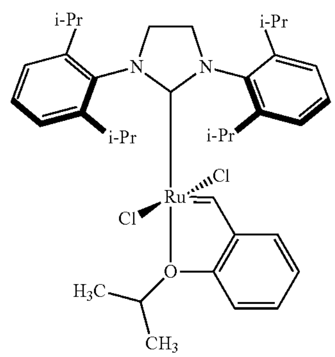 | dichloro[1,3-bis(2,6-isopropylphenyl)-2-imidazolidinylidene](2-isopropoxyphenylmethylene)ruthenium(II) |

-continued

| Structure | Name |
|---|---|
| 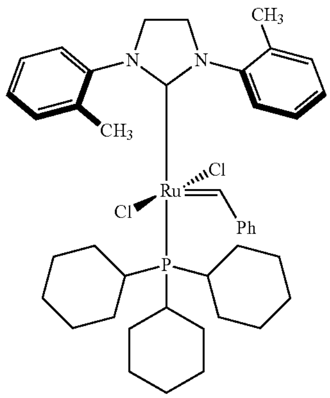 | dichloro[1,3-Bis(2-methylphenyl)-2-imidazolidinylidene](benzylidene)(tricyclohexylphosphine)ruthenium(II) |
| 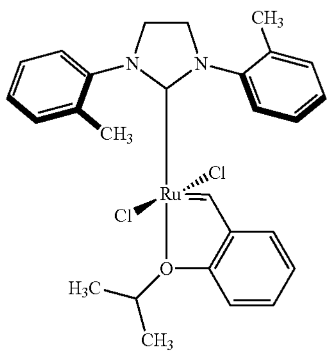 | dichloro[1,3-bis(2-methylphenyl)-2-imidazolidinylidene](2-isopropoxyphenylmethylene)ruthenium(II) |
| 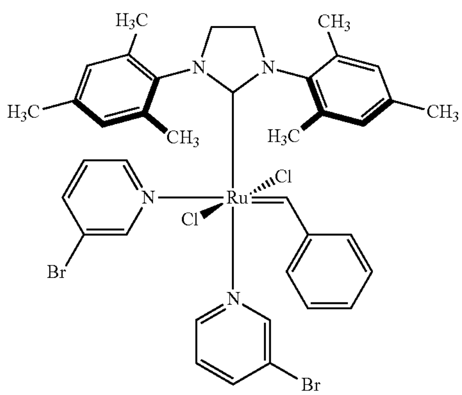 | dichloro[1,3-bis(2,4,6-trimethylphenyl)-2-imidazolidinylidene](benzylidene)bis(3-bromopyridine)ruthenium(II) |
| 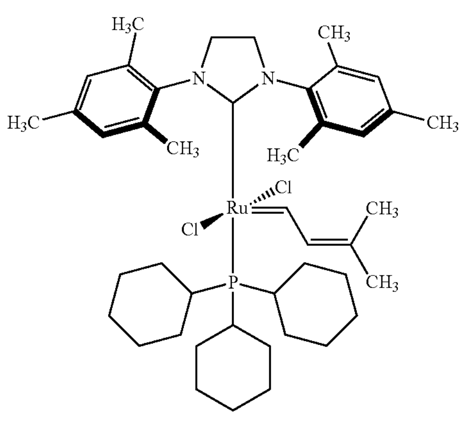 | dichloro[1,3-bis(2,4,6-trimethylphenyl)-2-imidazolidinylidene](3-methyl-2-butenylidene) (tricyclohexylphosphine) ruthenium(II) |

| Structure | Name |
|---|---|
| 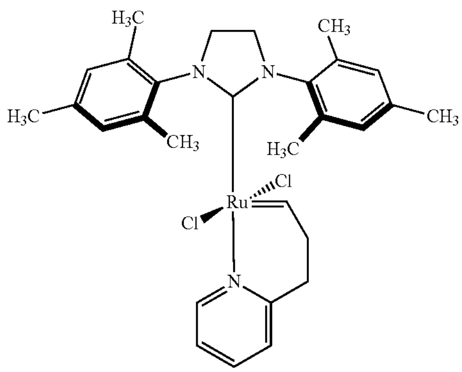 | dichloro[1,3-bis(2,4,6-trimethylphenyl)-2-imidazolidinylidene][3-(2-pyridinyl)propylidene]ruthenium(II) |
| 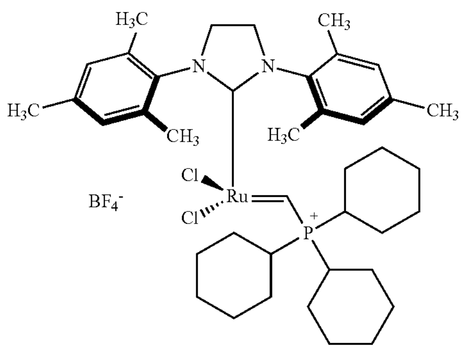 | dichloro[1,3-bis(2,4,6-trimethylphenyl)-2-imidazolidinylidene][(tricyclohexylphosphoranyl)methylidene]ruthenium(II) tetrafluoroborate |
| 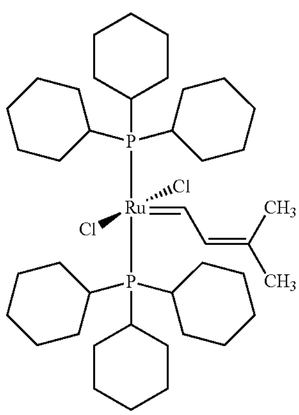 | dichloro(3-methyl-2-butenylidene)bis(tricyclohexylphosphine)ruthenium(II) |
| 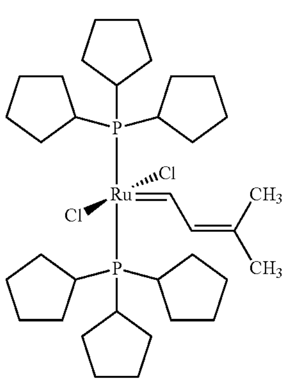 | dichloro(3-methyl-2-butenylidene)bis(tricyclopentylphosphine)ruthenium(II) |

| Structure | Name |
|---|---|
| 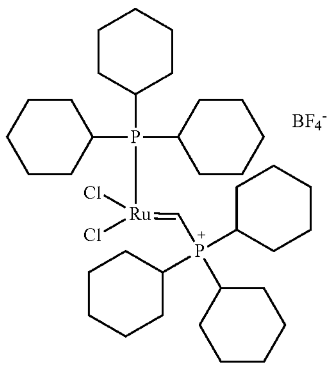 | dichloro(tricyclohexylphosphine)[(tricyclohexyl-phosphoranyl)methylidene]ruthenium(II) tetrafluoroborate |
| 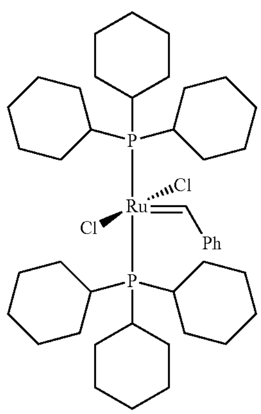 | bis(tricyclohexylphosphine) benzylidine ruthenium(IV) dichloride |
| 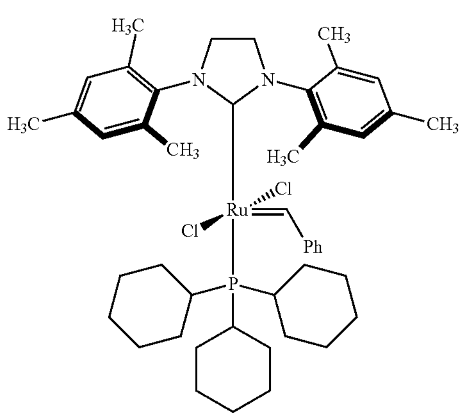 | [1,3-bis-(2,4,6-trimethylphenyl)-2-imidazolidinylidene]dichloro(phenylmethylene)(tricyclohexylphosphine)ruthenium |
| 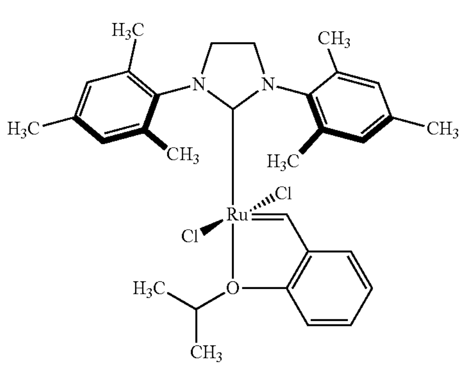 | (1,3-bis-(2,4,6-trimethylphenyl)-2-imidazolidinylidene)dichloro(o-isopropoxyphenylmethylene)ruthenium |

| Structure | Name |
| --- | --- |
| (structure) | dichloro(o-isopropoxyphenylmethylene)(tricyclohexylphosphine)ruthenium(II) |
| (structure) | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium |

Catalysts useful in the methods of the disclosure also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the disclosure include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the disclosure include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, better than 50%, better than 75%, or better than 90%. In addition, the reactants and products are chosen to provide at least a 5° C. difference, a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, less than 12 hours, less than 8 hours, or less than 4 hours.

One of skill in the art will appreciate that the time, temperature and solvent can depend on each other, and that changing one can require changing the others to prepare the pyrethroid products and intermediates in the methods of the disclosure. The metathesis steps can proceed at a variety of temperatures and times. In general, reactions in the methods of the disclosure are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the disclosure are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

Biohydroxylation to Produce a Pheromone and its Positional Isomer

As discussed above, an unsaturated hydrocarbon substrate can be subjected to biohydroxylation via an enzyme catalyst to thereby generate a mixture of a pheromone having a structure of an insect pheromone produced by a female insect and a positional isomer of the pheromone, which is not naturally produced by the female insect. The mixture of a pheromone and a positional isomer occurs through the enzyme catalyzing the hydrolysis of different carbons on the substrate, as shown in FIG. 1. In some embodiments, enzymes can be selected which catalyze hydroxylation of terminal carbons to produce unsaturated hydrocarbon products at the desired ratios. In some embodiments, an enzyme can be engineered to generate a mixture of unsaturated hydrocarbon products at desired ratios. Thus, in some embodiments, the ratio of the natural sex pheromone to the positional isomer can varied by selecting and/or engineering the biohydroxylation catalyst. In other embodiments, an enzyme can be selected and/or engineered to catalyze hydroxylation of an subterminal carbon.

Biohydroxylation Catalysts

Various enzymes and/or whole cells comprising enzymes can be used to catalyze hydroxylation reactions described above.

Known enzyme families with terminal hydroxylation activity for medium and long chain alkanes and fatty acids include AlkB, CYP52, CYP153, and LadA (Bordeaux et al., 2012, *Angew. Chem.-Int. Edit.* 51: 10712-10723; Ji et al., 2013, *Front. Microbiol.* 4). For example, Malca et al. describe terminal hydroxylation of mono-unsaturated fatty acid by cytochromes P450 of the CYP153 family (Malca et al., 2012, *Chemical Communications* 48: 5115-5117). Weissbart et al. describe the terminal hydroxylation of various cis and trans unsaturated lauric acid analogs (Weissbart et al., 1992, *Biochimica et Biophysica Acta, Lipids and Lipid Metabolism* 1124: 135-142). However, to date, none of these enzymes has been demonstrated to perform terminal hydroxylation of alkenes with internal olefins such as (E)-dec-5-ene. The presence of C═C bonds present competing sites of oxygen insertion and alters the 3-dimensional orientation of the molecule. The regioselectivity of these enzymes for the terminal C—H bond of alkanes and fatty acid substrate may not extend to alkenes with internal olefins for these reasons. For asymmetric substrates, obtaining hydroxylation at the desired terminal C—H bond presents additional challenges compared to symmetric substrates. Finally, controlling the reaction selectivity to produce a single terminal alcohol instead of α-ω diols, acids, or diacids is also a major concern.

In particular embodiments, the search for a terminal hydroxylase with activity for alkene with internal olefins starts with known terminal alkane and fatty acid hydroxylases. There are four families of enzymes with reported terminal alkane and fatty acid hydroxylation activity: (1) methane monooxygenases; (2) integral membrane diiron non-heme alkane hydroxylases (AlkB); (3) Cytochrome P450s (P450s); and (4) long chain alkane monooxygenases (LadA) (Bordeaux et al., 2012, *Angew. Chem.-Int. Edit.* 51: 10712-10723; Ji et al., 2013, *Front. Microbiol.* 4). Methane monooxygenases are difficult to express in heterologous non-methanotrophic hosts and generally prefer small substrate (<C4). Of the remaining three families, the substrate specificity based on substrate chain length of representative members is summarized below in Table 3.

TABLE 3

Relative activities of terminal hydroxylases for alkanes and fatty acids with various chain lengths.

| Alkane/FA chain length | CYP153A 6 (Funhoff et al., 2006, *J. Bacteriol.* 188: 5220-5227) | CYP153A1 6 (Scheps et al., 2011, *Org. Biomol. Chem.* 9: 6727-6733) | CYP153A P. sp. (Scheps et al., 2011, *Org. Biomol. Chem.* 9: 6727-6733) | AlkB *P. putida* GPo1 (Vanbeilen et al., 1994, *Enzyme Microb. Technol.* 16: 904-911) | alkB2 *Gordonia* sp TF6* (Fujii et al., 2004, *Biosci. Biotechnol. Biochem.* 68: 2171-2177) |
|---|---|---|---|---|---|
| C8 | 100 | 100 | 100 | 95 | 72 |
| C9 | 82 | 29 | 69 | 100 | 63 |
| C10 | 23 | 13 | 60 | 60 | 66 |
| C11 | 1 | <8 | <6 | 6 | 48 |
| C12 | | | | | 34 |
| C12 FA (lauric) | | | | | |
| C14 | | | | | |
| C14 FA (Myristic) | | | | | |
| C15 | | | | | |
| C16 | | | | | |
| C16 FA (Palmetic) | | | | | |
| C18 | | | | | |
| C18 FA (Stearic) | | | | | |
| C22 | | | | | |
| C24 | | | | | |

| Alkane/FA chain length | LadA (Feng et al., 2007, *Proc. Natl. Acad. Sci. U.S.A.* 104: 5602-5607) | CYP52A3 (Scheller et al., 1996, *Arch. Biochem Biophys.* 328: 245-254) | CYP52 A4 (Scheller et al., 1996, *Arch. Biochem Biophys.* 328: 245-254) | CYP52 A21 (Kim et al., 2007, *Arch. Biochem. Biophys.* 464: 213-220) |
|---|---|---|---|---|
| C8 | | | | |
| C9 | | | | |
| C10 | | | | |
| C11 | | | | |
| C12 | | 41 | 37 | |
| C12 FA (lauric) | | 20 | 100 | 100 |
| C14 | | | | |
| C14 FA (Myristic) | | | | 86 |
| C15 | 83 | | | |
| C16 | 100 | 100 | 33 | |
| C16 FA (Palmetic) | | 35 | 18 | 29 |
| C18 | 78 | 48 | 20 | |
| C18 FA (Stearic) | | 30 | 1 | |
| C22 | 74 | | | |
| C24 | 65 | | | |

*100% relative activity obtained with hexane

In certain embodiments, depending on the chain length of the desired substrate, some members of these four enzyme families are better suited than others as candidates for evaluation. For C-10 substrates such as (E)-dec-5-ene, the substrate specificity of characterized CYP153 and AlkB enzymes makes them candidate enzymes. Likewise, for longer substrates such as (Z)-hexadec-11-ene, members of the LadA and CYP52 families appear to have the closest substrate profile.

The most widely characterized member of the AlkB family is obtained from the Alk system of *Pseudomonas putida* GPo1 (van Beilen and Funhoff, 2005, *Curr. Opin. Biotechnol.* 16: 308-314). In addition to the integral membrane diiron non-heme hydroxylase AlkB, a rubredoxin (AlkG) and a rubredoxin reductase (AlkT) are required for hydroxylation function. The entire Alk system of *P. putida* GPo1, alkBFGHJKL and alkST genes, which allows the strain to grown on alkanes as its sole carbon source, has been cloned into the broad host range vector pLAFR1 (pGEc47) and is available from DSMZ in the host *E. Coli* K12 Gec137 (Smits et al., 2001, Plasmid 46: 16-24). The other alk genes alkF, alkJ, alkH, alkK, alkL, and alkS encode an inactive rubredoxin, an alcohol dehydrogenase, an aldehyde dehydrogenase, an acyl-CoA synthase, an alkane transporter and a global pathway regulator, respectively (Smits et al., 2003, *Antonie Van Leeuwenhoek* 84: 193-200). These genes facilitate the use of the alcohol product from the AlkB reaction to generate the fatty acyl-CoA that is substrate for β-oxidation. To accumulate the alcohol product, a knockout strain of alkJ, *E. coli* GEC137 pGEc47ΔJ has been used in a whole-cell biotransformation to produce 1-dodecanol (Grant et al., 2011, *Enzyme Microb. Technol.* 48: 480-486). The presence of alkL appears to enhance substrate uptake and consequently improve the whole-cell activity for both *Pseudomonas* and *E. coli* (Cornelissen et al., 2013, *Biotechnology and Bioengineering* 110: 1282-1292; Julsing et al., 2012, *Appl. Environ. Microbiol.* 78: 5724-5733; Scheps et al., 2013, *Microb. Biotechnol.* 6: 694-707). A simplified version of pGEc47 containing only alkBFGST in the broad-host range vector pCOM10, pBT10, has also been used for the conversion of fatty-acid methyl esters to w-hydroxy fatty acid methyl esters in *E. coli* W3110 (Schrewe et al., 2011, *Advanced Synthesis & Catalysis* 353: 3485-3495).

CYP52 family members are membrane bound cytochrome P450s that require electron delivery from a reductase for function. CYP52 members have mainly been identified from alkane-degrading *Candida* species (Scheller et al., 1996, *Arch. Biochem. Biophys.* 328: 245-254; Craft et al., 2003, *Appl. Environ. Microbiol.* 69: 5983-5991; Scheller et al., 1998, *J. Biol. Chem.* 273: 32528-32534; Seghezzi et al., 1992, *DNA Cell Biol.* 11: 767-780; Zimmer et al., 1996, *Biochem. Biophys. Res. Commun.* 224: 784-789). Thus far, expression and characterization of CYP52 enzymes have been performed in the native *Candida* host and other yeast hosts. Gene knockouts of (1) the β-oxidation pathways, (2) alcohol dehydrogenases and (3) select native CYP52s has resulted in strains that can accumulate ω-hydroxy fatty acids when fatty acids are fed to the culture (Lu et al., 2010, *J. Am. Chem. Soc.* 132: 15451-15455). Of particular interest, DP428, DP522 and DP526 are *C. tropicalis* strains expressing a single CYP52 with the appropriate knockouts for catalyzing terminal hydroxylation of fatty acids (Lu et al., 2010, *J. Am. Chem. Soc.* 132: 15451-15455).

CYP153 family members are soluble and membrane associated cytochrome P450s that also depend on electron transfer from ferredoxin and ferredoxin reductase for function (Funhoff et al., 2007, *Enzyme and Microbial Technology* 40: 806-812). CYP153 members have been isolated from a range of alkane-degrading microorganisms. There are currently 56 annotated CYP153 sequences available from the Nelson P450 database, a BLAST search of CYP153A6 resulted in 221 identified homologs with >70% sequence identity. The use of CYP153 enzymes for terminal hydroxylation of octane and dodecanoic acid has been demonstrated with heterologous expression in *E. coli*. For the conversion of octane to octanol, the CYP153 operon from *Mycobacterium* sp. HXN-1500 was cloned into pET28b(+) and the biotransformation was performed in *E. coli* BL21(DE3) (Gudiminchi et al., 2012, *Appl. Microbiol. Biotechnol.* 96: 1507-1516). For the conversion of dodecanoic acid, an *E. coli* HMS174 strain containing a fusion of a CYP153A$_{M.aq.}$ mutant with the CYP102A1 reductase domain in pCola-Duet-1 along with alkL was used for the transformation (Scheps et al., 2013, *Microb. Biotechnol.* 6: 694-707).

Long chain alkane monooxygenase, LadA, isolated from *G. thermodenitrificans* NG80-2 catalyzes the terminal hydroxylation of C15 to C36 alkanes with a metal-free flavoprotein mechanism that differs from AlkB and CYP enzymes (Dong et al., 2012, *Appl. Microbiol. Biotechnol.* 94: 1019-1029). The LadA reaction requires FMNH$_2$ or NADPH and the native reductase partner has yet to be identified. Expression of the LadA gene in *E. coli* BL21 (DE3) using the pET-28a(+) plasmid yielded cell extracts with terminal hydroxylation activity for hexadecane (Dong et al., 2012, *Appl. Microbiol. Biotechnol.* 94: 1019-1029). Literature reports of LadA hydroxylation reactions have been performed using purified enzymes and examples of whole-cell biotransformation is lacking.

Coding sequences for enzymes that may be used herein may be derived from bacterial, fungal, or plant sources. Tables 3, 4, and 5 list enzymes for coding regions of representative non-heme diiron alkane monooxygenases, long-chain alkane hydroxylases, and cytochromes P450, respectively. Additional enzymes and their coding sequences may be identified by BLAST searching of public databases. Typically, BLAST searching of publicly available databases with known non-heme diiron alkane monooxygenases, cytochromes P450, and long-chain alkane hydroxylase sequences, such as those provided herein, is used to identify enzymes and their encoding sequences that may be used in the present disclosure. For example, enzymes having amino acid sequence identities of at least about 80-85%, 85%-90%, 90%-95%, or about 90%, 91%, 92%, 93%, 94%, 95%, 96%, 97%, 98%, or 99% sequence identity to any of the enzymes listed in Tables 3, 4, and 5 may be used. Hydroxylase enzymes can be codon-optimized for expression in certain desirable host organisms, such as yeast and *E. coli*.

In other embodiments, the sequences of the enzymes provided herein may be used to identify other homologs in nature. For example, each of the encoding nucleic acid fragments described herein may be used to isolate genes encoding homologous proteins. Isolation of homologous genes using sequence-dependent protocols is well known in the art. Examples of sequence-dependent protocols include, but are not limited to, (1) methods of nucleic acid hybridization, (2) methods of DNA and RNA amplification, as exemplified by various uses of nucleic acid amplification technologies (e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker et al., *Proc. Natl. Acad. Sci. USA*, 89:392 (1992)), and (3) methods of library construction and screening by complementation.

Hydroxylase enzymes or whole cells expressing hydroxylase enzymes can be further engineered for use in the methods of the disclosure. Enzymes can be engineered for improved hydroxylation activity, improved Z:E selectivity, improved regioselectivity, improved selectivity for hydroxylation over epoxidation and/or improved selectivity for hydroxylation over dehalogenation. The term "improved hydroxylation activity" as used herein with respect to a particular enzymatic activity refers to a higher level of enzymatic activity than that measured in a comparable non-engineered hydroxylase enzyme of whole cells comprising a hydroxylase enzyme. For example, overexpression of a specific enzyme can lead to an increased level of activity in the cells for that enzyme. Mutations can be introduced into a hydroxylase enzyme resulting in engineered enzymes with improved hydroxylation activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the KM for the substrate, or by directed evolution. See, e.g., *Methods in Molecular Biology* (vol. 231), ed. Arnold and Georgiou, Humana Press (2003).

Accordingly, some embodiments of the disclosure provide methods for synthesizing olefinic alcohol products as described above, wherein the enzyme is a non-heme diiron monooxygenase. In some embodiments, the non-heme diiron monooxygenase is selected from Table 4 or a variant thereof having at least 90% identity thereto.

TABLE 4

Non-heme diiron monooxygenase enzymes capable of catalyzing selective terminal alkene hydroxylation.

| Species Origin | Gene Name | Accession No |
|---|---|---|
| *Pseudomonas oleovorans* | alkB | P12691 |
| *Pseudomonas mendocina* (strain ymp) | Pmen_0443 | A4XPE8 |
| *Pseudomonas aeruginosa* | alkB | Q932R7 |
| Enterobacteriaceae bacterium 58 | alkB | B5TVB4 |
| *Bacillus* sp. BTRH40 | alkB | B5TVB3 |
| uncultured bacterium | alkB | B6Z2G6 |
| *Pseudomonas aeruginosa* | alk | B7U6M1 |
| uncultured bacterium | alkB | U3PXQ1 |
| uncultured bacterium | alkB | U3Q1X4 |
| *Pseudomonas stutzeri* (*Pseudomonas perfectomarina*) | alkB | Q7X4G8 |
| uncultured organism | alkB | G3EBX4 |
| uncultured bacterium | alkB | U3PXQ7 |
| *Pseudomonas aeruginosa* | alk | B7U6M0 |
| *Pseudomonas chlororaphis* subsp. aureofaciens | alkB | Q9RLI5 |
| *Arthrobacter* sp. ITRH48 | alkB | B5TVB7 |
| *Streptomyces* sp. ITRH51 | alkB | B5TVB6 |
| *Arthrobacter* sp. ITRH49 | alkB | B5TVC0 |
| *Dietzia* sp. ITRH56 | alkB | B5TVB8 |
| *Microbacterium* sp. ITRH47 | alkB | B5TVB5 |
| *Pantoea* sp. BTRH11 | alkB | B5TVB2 |
| *Pseudomonas* sp. ITRI53 | alkB | B5TVB1 |
| *Pseudomonas* sp. ITRI73 | alkB | B5TVB0 |
| *Pseudomonas* sp. ITRH25 | alkB | B5TVA9 |
| *Pseudomonas* sp. MIXRI75 | alkB | B5TVA8 |
| *Pseudomonas* sp. MIXRI74 | alkB | B5TVA7 |
| *Rhodococcus* sp. ITRH43 | alkB | B5TVA4 |
| *Ochrobactrum* sp. ITRH1 | alkB | B5TVA3 |
| *Alcaligenaceae* bacterium BTRH5 | alkB | B5TVA6 |
| *Pseudomonas* sp. ITRH76 | alkB | B5TVA5 |
| *Pseudomonas* sp. 7/156 | alkB | Q93LR8 |
| uncultured Rhizobiales bacterium | alkB | D6NSH3 |
| uncultured soil bacterium | | S5DSW0 |
| uncultured bacterium | alkB | U3PYH2 |
| uncultured prokaryote | alkB | C7EAT4 |
| uncultured Rhizobiales bacterium | alkB | D6NSL1 |
| uncultured Rhizobiales bacterium | alkB | D6NSJ4 |
| uncultured prokaryote | alkB | C7EAZ5 |
| uncultured Rhizobiales bacterium | alkB | D6NSK5 |
| uncultured Rhizobiales bacterium | alkB | D6NSK3 |
| uncultured Rhizobiales bacterium | alkB | D6NSJ7 |
| uncultured Rhizobiales bacterium | alkB | D6NSK1 |
| uncultured Rhizobiales bacterium | alkB | D6NSH4 |
| uncultured Rhizobiales bacterium | alkB | D6NSJ2 |
| uncultured Rhizobiales bacterium | alkB | D6NSI2 |
| uncultured Rhizobiales bacterium | alkB | D6NSJ3 |
| uncultured Rhizobiales bacterium | alkB | D6NSJ6 |
| *Pseudomonas* sp. ITRI22 | alkB | B5TVB9 |
| uncultured Rhizobiales bacterium | alkB | D6NSK7 |
| uncultured soil bacterium | | S5DTG4 |
| *Pseudomonas putida* (*Arthrobacter siderocapsulatus*) | alkB | Q9WWW6 |

TABLE 4-continued

Non-heme diiron monooxygenase enzymes capable of catalyzing selective terminal alkene hydroxylation.

| Species Origin | Gene Name | Accession No |
|---|---|---|
| uncultured Rhizobiales bacterium | alkB | D6NSI6 |
| uncultured bacterium | alkB | B6Z2E6 |
| uncultured bacterium | alkB | B1P6K4 |
| Pseudomonas sp. G5(2012) | PG5_40690 | S2EW96 |
| Alcanivorax dieselolei | alkB | B6Z2B7 |
| Alcanivorax borkumensis | alkB | B6Z2B4 |
| uncultured bacterium | alkB | B6Z2G9 |
| Marinobacter sp. S17-4 | alkB | C7DLJ8 |
| uncultured bacterium | alkB | B6Z2H0 |
| Alcanivorax sp. S17-16 | alkB | B6Z2D8 |
| uncultured organism | alkB | G3EBX7 |
| uncultured bacterium | alkB | H9NJ23 |
| uncultured bacterium | alkB | C8AYB7 |
| uncultured bacterium | alkB | W0UB63 |
| uncultured bacterium | alkB | U3Q1V0 |
| Alcanivorax borkumensis | alkB | T1WPB9 |
| uncultured organism | alkB | G3EBX5 |
| uncultured Rhizobiales bacterium | alkB | D6NSK6 |
| uncultured bacterium | alkB | U3Q5C8 |
| uncultured bacterium | alkB | Q3HXE5 |
| Xanthobacter flavus | alkane-1-monooxygenase | Q934J9 |
| uncultured bacterium | alkB | Q3HXD6 |
| Acidisphaera sp. C197 | alkB | Q5RLH8 |
| uncultured bacterium | alkB | M9T624 |
| uncultured bacterium | alkB | M9T8D1 |
| uncultured bacterium | alkB | H9B8U8 |
| Kordiimonas gwangyangensis | alkB | B6Z2E4 |
| uncultured soil bacterium | | S5DPL2 |
| uncultured bacterium | alkB | F0X332 |
| uncultured bacterium | alkB | F0X324 |
| uncultured bacterium | alkB | F0X334 |
| uncultured organism | alkB | G3EBX2 |
| uncultured bacterium | alkB | F0X328 |
| uncultured soil bacterium | | S5DTI7 |
| uncultured bacterium | alkB | Q3HXF7 |
| uncultured bacterium | alkB | F0X327 |
| uncultured bacterium | alkB | F0X335 |
| uncultured bacterium | alkB | F0X329 |
| uncultured bacterium | alkB | F0X342 |
| uncultured bacterium | alkB | F0X300 |
| uncultured bacterium | alkB | Q3HXE8 |
| uncultured bacterium | alkB | U3Q1X0 |
| uncultured bacterium | alkB | Q3HXD7 |
| Ralstonia sp. PT11 | alkB | Q3HXC9 |
| uncultured bacterium | alkB | Q3HXE6 |
| uncultured bacterium | alkB | F0X305 |
| uncultured bacterium | alkB | U3Q5A0 |
| uncultured bacterium | alkB | F0X306 |
| Marinobacter sp. P1-14D | alkB1 | C6KEH4 |
| uncultured Rhizobiales bacterium | alkB | D6NSI7 |
| uncultured bacterium | alkB | F0X346 |
| uncultured bacterium | alkB | F0X346 |
| uncultured bacterium | alkB | F0X343 |
| uncultured bacterium | alkB | F0X339 |
| uncultured bacterium | alkB | F0X309 |
| uncultured bacterium | alkB | F0X333 |
| uncultured bacterium | alkB | F0X321 |
| uncultured bacterium | alkB | Q3HXF0 |
| uncultured bacterium | alkB | F0X312 |
| uncultured bacterium | alkB | F0X303 |
| uncultured bacterium | alkB | F0X331 |
| uncultured bacterium | alkB | F0X302 |
| uncultured bacterium | alkB | Q3HXE9 |
| uncultured bacterium | alkB | F0X313 |
| uncultured bacterium | alkB | F0X316 |
| uncultured bacterium | alkB | M9TDK6 |
| uncultured bacterium | alkB | H9B8V5 |
| uncultured Rhizobiales bacterium | alkB | D6NSF4 |
| uncultured Rhizobiales bacterium | alkB | D6NSF2 |
| uncultured bacterium | alkB | B6Z2G8 |
| uncultured Rhizobiales bacterium | alkB | D6NSF1 |
| uncultured Rhizobiales bacterium | alkB | D6NSG4 |
| uncultured Rhizobiales bacterium | alkB | D6NSG3 |
| uncultured Rhizobiales bacterium | alkB | D6NSF3 |

TABLE 4-continued

Non-heme diiron monooxygenase enzymes capable of catalyzing selective terminal alkene hydroxylation.

| Species Origin | Gene Name | Accession No |
|---|---|---|
| uncultured Rhizobiales bacterium | alkB | D6NSI4 |
| uncultured Rhizobiales bacterium | alkB | D6NSH9 |
| uncultured Rhizobiales bacterium | alkB | D6NSG1 |
| uncultured Rhizobiales bacterium | alkB | D6NSJ9 |
| uncultured Rhizobiales bacterium | alkB | D6NSG6 |
| uncultured soil bacterium | | S5DP42 |
| uncultured bacterium | alkB | F0X323 |
| uncultured bacterium | alkB | F0X318 |
| uncultured bacterium | alkB | F0X317 |
| uncultured bacterium | alkB | F0X325 |
| uncultured bacterium | alkB | F0X308 |
| uncultured bacterium | alkB | F0X336 |
| uncultured soil bacterium | | S5E0W0 |
| uncultured bacterium | alkB | F0X304 |
| *Bradyrhizobium* sp. DFCI-1 | C207_00091 | U1HQ84 |
| uncultured Rhizobiales bacterium | alkB | D6NSF9 |
| uncultured Rhizobiales bacterium | alkB | D6NSH2 |
| uncultured Rhizobiales bacterium | alkB | D6NSF6 |
| uncultured Rhizobiales bacterium | alkB | D6NSG2 |
| uncultured Rhizobiales bacterium | alkB | D6NSH7 |
| uncultured bacterium | alkB | F0X322 |
| uncultured soil bacterium | | S5DPY4 |
| uncultured bacterium | alkB | F0X349 |
| uncultured bacterium | alkB | F0X310 |
| uncultured bacterium | alkB | F0X315 |
| uncultured bacterium | alkB | F0X344 |
| uncultured bacterium | alkB | F0X326 |
| uncultured bacterium | alkB | W0UB94 |
| uncultured bacterium | alkB | W0UAL7 |
| uncultured soil bacterium | | S5DP84 |
| uncultured soil bacterium | | S5E064 |
| uncultured soil bacterium | | S5E0M5 |
| uncultured bacterium | alkB | M9T7Y4 |
| uncultured prokaryote | alkB | C7EAZ7 |
| *Thalassolituus oleivorans* | alkB | Q8RSS6 |
| uncultured prokaryote | alkB | C7EAZ8 |
| *Marinobacter* sp. EVN1 | Q672_13115 | U7NVU4 |
| uncultured Rhizobiales bacterium | alkB | D6NSF8 |
| *Marinobacter aquaeolei* (strain ATCC 700491/DSM 11845/VT8) (*Marinobacter hydrocarbonoclasticus* (strain DSM 11845)) | Maqu_0610 | A1TY92 |
| *Marinobacter hydrocarbonoclasticus* ATCC 49840 | alkB MARHY2847 | H8WCU7 |
| uncultured Rhizobiales bacterium | alkB | D6NSG8 |
| *Alcanivorax borkumensis* | alkB1 | Q93UQ1 |
| *Alcanivorax borkumensis* (strain SK2/ATCC 700651/DSM 11573) | alkB1 ABO_2707 | Q0VKZ3 |
| *Marinobacter aquaeolei* (strain ATCC 700491/DSM 11845/VT8) (*Marinobacter hydrocarbonoclasticus* (strain DSM 11845)) | Maqu_0440 | A1TXS2 |
| *Alcanivorax* sp. 97CO-5 | Y017_07510 | W7AC06 |
| *Marinobacter* sp. C1S70 | Q667_13505 | U7P171 |
| *Marinobacter* sp. EVN1 | Q672_13130 | U7NYF9 |
| *Pseudoxanthomonas spadix* (strain BD-a59) | DSC_08960 | G7UVX3 |
| *Marinobacter* sp. EN3 | Q673_04890 | U7H9M7 |
| *Marinobacter* sp. ES-1 | Q666_09550 | U7G9A6 |
| *Oceanicaulis* sp. HTCC2633 | OA2633_08724 | A3UHL2 |
| *Citreicella* sp. 357 | C357_19621 | I1AS33 |
| *Caulobacter* sp. (strain K31) | Caul_5439 | B0TA04 |
| *Thalassolituus oleivorans* MIL-1 | TOL_1423 | M5DQR5 |
| uncultured bacterium | alkB | W0UAQ4 |
| uncultured bacterium | alkB | W0UAL9 |
| uncultured bacterium | alkB | W0UAQ9 |
| gamma proteobacterium NOR5-3 | NOR53_3428 | B8KLY6 |
| uncultured marine microorganism | 21G8-5 | A5CFX9 |
| uncultured marine microorganism | 9E7-8 | A5CFU5 |
| *Alcanivorax pacificus* W11-5 | S7S_02132 | K2GLA3 |
| *Alcanivorax dieselolei* | | C3W4W7 |
| *Alcanivorax* sp. PN-3 | Q668_06955 | U7I1M1 |
| *Alcanivorax dieselolei* (strain DSM 16502/CGMCC 1.3690/B-5) | B5T_00721 | K0C8Z6 |

TABLE 4-continued

Non-heme diiron monooxygenase enzymes capable of catalyzing selective terminal alkene hydroxylation.

| Species Origin | Gene Name | Accession No |
|---|---|---|
| *Alcanivorax dieselolei* | alkB2 | D2JNY2 |
| bacterium enrichment culture clone US3-MTBE | mdpA | L7T214 |
| bacterium enrichment culture clone US2-MTBE | mdpA | L7SZY0 |
| *Marinobacter* sp. ELB17 | MELB17_10558 | A3JHB9 |
| *Marinobacter* sp. BSs20148 | alkB1 MRBBS_1602 | M1FBW8 |
| *Pseudomonas alcaligenes* NBRC 14159 | alkB PA6_005_01830 | U3AUD1 |
| *Simiduia agarivorans* (strain DSM 21679/JCM 13881/BCRC 17597/SA1) | M5M_18065 | K4KP06 |
| gamma proteobacterium HTCC2207 | GB2207_03060 | Q1YPC4 |
| *Limnobacter* sp. MED105 | LMED105_14555 | A6GTF8 |
| *Alcanivorax* sp. R8-12 | alkB2 | R9R6I2 |
| Gammaproteobacteria bacterium MOLA455 | alkB1 U062_00014 | W2UFM4 |
| *Alcanivorax hongdengensis* A-11-3 | A11A3_01150 | L0WGR7 |
| *Acidovorax* sp. KKS102 | C380_12125 | K0IAD8 |
| *Moritella* sp. PE36 | PE36_11657 | A6FHH9 |
| *Moritella* sp. PE36 | PE36_11657 | A6FHH9 |
| *Ahrensia* sp. R2A130 | alkB R2A130_3229 | E0MP68 |
| *Hoeflea phototrophica* DFL-43 | HPDFL43_04645 | A9D3P4 |
| *Curvibacter putative* symbiont of *Hydra magnipapillata* | alkB Csp_A02180 | C9Y7W7 |
| *Pseudovibrio* sp. JE062 | PJE062_1512 | B6QXF8 |
| Oxalobacteraceae bacterium IMCC9480 | IMCC9480_2292 | F1W4Y4 |
| *Methylibium petroleiphilum* (strain PM1) | alkB Mpe_B0606 | A2SP81 |
| *Ralstonia* sp. AU12-08 | C404_01360 | S9TME3 |
| *Burkholderia phytofirmans* (strain DSM 17436/PsJN) | Bphyt_5401 | B2TBV7 |
| gamma proteobacterium BDW918 | DOK_05250 | I2JMD3 |
| *Pseudovibrio* sp. (strain FO-BEG1) | alkB PSE_3490 | G8PKM2 |
| *Bradyrhizobium* sp. DFCI-1 | C207_06028 | U1H8I8 |
| *Alcanivorax dieselolei* (strain DSM 16502/CGMCC 1.3690/B-5) | B5T_04393 | K0CLJ4 |
| *Alcanivorax* sp. PN-3 | Q668_04650 | U7HLN0 |
| *Alcanivorax dieselolei* | alkB1 | Q6B431 |
| *Burkholderia thailandensis* E444 | BTJ_212 | W6C501 |
| *Burkholderia thailandensis* 2002721723 | BTQ_2100 | W6BLA1 |
| *Burkholderia thailandensis* H0587 | BTL_1506 | W6BA85 |
| *Burkholderia thailandensis* (strain E264/ATCC 700388/DSM 13276/CIP 106301) | BTH_I1814 | Q2SXK3 |
| *Burkholderia pseudomallei* 1026b | BP1026B_I0975 | I1WH83 |
| *Burkholderia pseudomallei* 1026a | BP1026A_4019 | I2KNJ5 |
| *Burkholderia pseudomallei* MSHR305 | BDL_3139 | S5P5X7 |
| *Burkholderia pseudomallei* 305 | alkB BURPS305_7408 | A4LDP5 |
| *Burkholderia pseudomallei* Pasteur 52237 | alkB BURPSPAST_R0133 | A8KVJ2 |
| *Burkholderia pseudomallei* (strain K96243) | BPSL2350 | Q63SH1 |
| *Burkholderia pseudomallei* (strain 1710b) | BURPS1710b_2801 | Q3JQG8 |
| *Burkholderia pseudomallei* BPC006 | BPC006_I2776 | K7Q7Y2 |
| *Burkholderia pseudomallei* 1710a | alkB BURPS1710A_3234 | C6TUD4 |
| *Burkholderia pseudomallei* 1106b | alkB_2BURPS1106B_A1957 | C5ZKC8 |
| *Burkholderia pseudomallei* (strain 1106a) | alkB BURPS1106A_2735 | A3NXB5 |
| *Burkholderia pseudomallei* (strain 668) | BURPS668_2678 | A3NBI1 |
| *Burkholderia pseudomallei* NCTC 13178 | BBJ_481 | V9Y591 |
| *Burkholderia pseudomallei* MSHR1043 | D512_14116 | M7EHA3 |
| *Burkholderia pseudomallei* 354a | BP354A_0895 | I2MQ94 |
| *Burkholderia pseudomallei* 354e | BP354E_0708 | I2MD23 |
| *Burkholderia pseudomallei* 1258b | BP1258B_0905 | I2LQQ4 |
| *Burkholderia pseudomallei* 1258a | BP1258A_0812 | I2LKD3 |
| *Burkholderia pseudomallei* 576 | alkB BUC_2998 | B7CM79 |
| *Burkholderia pseudomallei* 1655 | alkB BURPS1655_H0133 | B2HAC8 |
| *Burkholderia pseudomallei* S13 | alkB BURPSS13_V0139 | B1HDJ2 |
| *Burkholderia pseudomallei* 406e | alkB BURPS406E_H0229 | A8EBS1 |
| *Burkholderia pseudomallei* MSHR146 | BBN_1088 | W0PXC8 |
| *Burkholderia pseudomallei* MSHR511 | BBQ_961 | W0MCN0 |
| *Burkholderia pseudomallei* NAU20B-16 | BBS_2570 | V9YGA1 |
| *Burkholderia pseudomallei* MSHR346 | GBP346_A2857 | C4KQU6 |
| *Burkholderia pseudomallei* MSHR338 | M218_13015 | W1M8G5 |
| Burkholderia xenovorans (strain LB400) | Bxe_B1208 | Q13ME1 |
| *Burkholderia thailandensis* MSMB43 | A33K_14899 | I6AHY8 |
| *Burkholderia* sp. Ch1-1 | BCh11DRAFT_02054 | I2IU52 |
| *Alcanivorax* sp. R8-12 | alkB3 | R9R6Q8 |

TABLE 4-continued

Non-heme diiron monooxygenase enzymes capable of catalyzing selective terminal alkene hydroxylation.

| Species Origin | Gene Name | Accession No |
| --- | --- | --- |
| gamma proteobacterium HTCC5015 | GP5015_636 | B5JV27 |
| *Alcanivorax pacificus* W11-5 | S7S_03034 | K2GFU4 |
| *Actinoplanes* sp. (strain ATCC 31044/ CBS 674.73/SE50/110) | alkB ACPL_4910 | G8SLX8 |
| *Alcanivorax* sp. DG881 | ADG881_1174 | B4X426 |
| *Methylibium* sp. T29-B | alkB1 Y694_03823 | W7WAG2 |
| *Methylibium* sp. T29 | mdpA X551_03232 | W7VT91 |
| *Burkholderia thailandensis* MSMB121 | BTI_1284 | N0AI18 |
| *Burkholderia* sp. TJI49 | B1M_44170 | F0GKQ0 |
| *Burkholderia mallei* (strain ATCC 23344) | alkB BMA0635 | Q62LK2 |
| *Burkholderia mallei* (strain NCTC 10247) | alkB BMA10247_1692 | A3MLU7 |
| *Burkholderia mallei* (strain NCTC 10229) | alkB BMA10229_A2910 | A2SA87 |
| *Burkholderia mallei* (strain SAVP1) | alkB BMASAVP1_A2377 | A1V630 |
| *Burkholderia mallei* PRL-20 | alkB BMAPRL20_A0647 | C5NLY3 |
| *Burkholderia mallei* GB8 horse 4 | BMAGB8_0674 | C4AYJ3 |
| *Burkholderia mallei* ATCC 10399 | alkB BMA10399_E0136 | A9KA35 |
| *Burkholderia mallei* JHU | alkB BMAJHU_C0140 | A5XN41 |
| *Burkholderia mallei* FMH | alkB BMAFMH_C0136 | A5XJ42 |
| *Burkholderia mallei* 2002721280 | alkB BMA721280_A1345 | A5TJ65 |
| *Burkholderia pseudomallei* Pakistan 9 | alkB BUH_2787 | C0YFB6 |
| *Burkholderia* sp. (strain 383) (*Burkholderia cepacia* (strain ATCC 17760/NCIB 9086/R18194)) | Bcep18194_A4085 | Q39IN4 |
| *Ralstonia* sp. 5_2_56FAA | HMPREF0989_00681 | U3G9A8 |
| *Ralstonia* sp. 5_7_47FAA | HMPREF1004_00261 | E2ST40 |
| *Burkholderia cenocepacia* (strain AU 1054) | Bcen_0501 | Q1BY92 |
| *Burkholderia cenocepacia* (strain HI2424) | Bcen2424_0980 | A0K5F6 |
| *Burkholderia* sp. KJ006 | MYA_0870 | I2DKR1 |
| *Burkholderia vietnamiensis* (strain G4/LMG 22486) (*Burkholderia cepacia* (strain R1808)) | Bcep1808_0897 | A4JCA5 |
| *Burkholderia cenocepacia* KC-01 | P355_2107 | V5A0K9 |
| *Ralstonia pickettii* (strain 12D) | Rpic12D_4221 | C6BN09 |
| *Ralstonia pickettii* (strain 12J) | Rpic_4109 | B2UI09 |
| *Ralstonia pickettii* OR214 | OR214_00862 | R0CSD0 |
| *Mycobacterium thermoresistibile* ATCC 19527 | KEK_22639 | G7CND0 |
| *Burkholderia cenocepacia* PC184 | BCPG_00786 | A2VS55 |
| *Parvularcula bermudensis* (strain ATCC BAA-594/HTCC2503/KCTC 12087) | PB2503_09204 | E0TD71 |
| *Rhodococcus triatomae* BKS 15-14 | G419_20650 | M2WXQ1 |
| *Alcanivorax hongdengensis* A-11-3 | A11A3_01155 | L0WH65 |
| *Alcanivorax hongdengensis* | | G1C7G7 |
| *Micromonospora* sp. ATCC 39149 | MCAG_04553 | C4REI2 |
| *Micromonospora lupini* str. Lupac 08 | alkB MILUP08_41795 | I0KZ81 |
| *Patulibacter medicamentivorans* | PAI11_23570 | H0E6A7 |
| *Burkholderia cenocepacia* (strain ATCC BAA-245/DSM 16553/LMG 16656/NCTC 13227/J2315/CF5610) (*Burkholderia cepacia* (strain J2315)) | BCAL3029 | B4EBR3 |
| *Burkholderia cenocepacia* BC7 | BURCENBC7_AP5666 | U1ZCU6 |
| *Burkholderia cenocepacia* K56-2Valvano | BURCENK562V_C5856 | T0E860 |
| *Burkholderia cenocepacia* H111 | I35_3695 | G7HIJ0 |
| *Burkholderia cepacia* GG4 | GEM_2548 | J7J4L5 |
| *Burkholderia ambifaria* IOP40-10 | BamIOP4010DRAFT_1629 | B1FC70 |
| *Burkholderia vietnamiensis* AU4i | L810_3738 | U2H0D0 |
| *Burkholderia ambifaria* MEX-5 | BamMEX5DRAFT_0109 | B1SX43 |
| *Burkholderia cenocepacia* (strain MC0-3) | Bcenmc03_0941 | B1JX99 |
| *Burkholderia cepacia* (*Pseudomonas cepacia*) | alkB | Q9AEN3 |
| *Burkholderia multivorans* CGD1 | BURMUCGD1_2488 | B9BAK1 |
| *Burkholderia multivorans* (strain ATCC 17616/249) | alkB BMULJ_00816 | B3CYB3 |
| *Burkholderia multivorans* (strain ATCC 17616/249) | alkB BMULJ_00816 | B3CYB3 |
| *Burkholderia multivorans* CGD2M | BURMUCGD2M_2894 | B9CFY2 |
| *Burkholderia multivorans* CGD2 | BURMUCGD2_2807 | B9BSN6 |
| *Burkholderia glumae* (strain BGR1) | bglu_1g25240 | C5AA12 |
| *Burkholderia multivorans* CF2 | BURMUCF2_0698 | J5AST2 |
| *Burkholderia multivorans* ATCC BAA-247 | BURMUCF1_0763 | J4JJ2 |
| *Mycobacterium xenopi* RIVM700367 | MXEN_06581 | I0RWI2 |
| *Alcanivorax* sp. P2S70 | Q670_07625 | U7G3V1 |
| *Rhodococcus* sp. p52 | alkB | U5S015 |

TABLE 4-continued

Non-heme diiron monooxygenase enzymes capable of catalyzing selective terminal alkene hydroxylation.

| Species Origin | Gene Name | Accession No |
|---|---|---|
| *Rhodococcus pyridinivorans* AK37 | AK37_15478 | H0JTS8 |
| *Micromonospora* sp. M42 | MCBG_00051 | W7V9N0 |
| Nocardia nova SH22a | NONO_c63170 | W5TPA6 |
| *Actinoplanes missouriensis* (strain ATCC 14538/DSM 43046/CBS 188.64/JCM 3121/NCIMB 12654/NBRC 102363/431) | AMIS_28610 | I0H4Z4 |
| *Mycobacterium thermoresistibile* ATCC 19527 | KEK_04707 | G7CD93 |
| *Streptomyces collinus* Tu 365 | B446_00650 B446_34640 | S5VEV9 |
| *Mycobacterium smegmatis* MKD8 | alkB D806_1894 | L8FH78 |
| *Mycobacterium smegmatis* (strain ATCC 700084/mc(2)155) | alkB MSMEG_1839 MSMEI_1797 | A0QTH1 |
| *Burkholderia gladioli* (strain BSR3) | bgla_1g28520 | F2LCU4 |
| *Nocardia cyriacigeorgica* (strain GUH-2) | alkB NOCYR_2725 | H6R6Y1 |
| *Mycobacterium* sp. (strain Spyr1) | Mspyr1_40540 | E6TPD9 |
| *Mycobacterium gilvum* (strain PYR-GCK) (*Mycobacterium flavescens* (strain ATCC 700033/PYR-GCK)) | Mflv_4721 | A4TF88 |
| *Mycobacterium hassiacum* DSM 44199 | C731_1322 | K5BKD8 |
| *Mycobacterium phlei* RIVM601174 | MPHLEI_02293 | I0S2Q3 |
| *Burkholderia ambifaria* (strain MC40-6) | BamMC406_0853 | B1YUL7 |
| *Conexibacter woesei* (strain DSM 14684/JCM 11494/NBRC 100937/ID131577) | Cwoe_5739 | D3F1V9 |
| *Burkholderia ambifaria* (strain ATCC BAA-244/AMMD) (*Burkholderia cepacia* (strain AMMD)) | Bamb_0841 | Q0BHH3 |
| *Mycobacterium vaccae* ATCC 25954 | MVAC_06502 | K0V939 |
| *Streptomyces* sp. AA4 | SSMG_06597 | D9UYP9 |
| *Nocardia asteroides* NBRC 15531 | alkB NCAST_33_00580 | U5EK43 |
| *Hydrocarboniphaga effusa* AP103 | WQQ_35830 | I8T3V4 |
| *Mycobacterium* sp. (strain Spyr1) | Mspyr1_27000 | E6TM45 |
| *Rhodococcus* sp. EsD8 | EBESD8_14280 | N1M251 |
| *Rhodococcus pyridinivorans* SB3094 | Y013_10875 Y013_14995 | V9XCI1 |
| uncultured bacterium | alk | A7XY59 |
| *Dietzia* sp. D5 | | W0C8S6 |
| *Gordonia amarae* NBRC 15530 | alkB GOAMR_34_00200 | G7GP29 |
| gamma proteobacterium BDW918 | DOK_15269 | I2JH75 |
| *Marinobacter* sp. EVN1 | Q672_03155 | U7NQ32 |
| *Marinobacter santoriniensis* NKSG1 | MSNKSG1_09613 | M7CV98 |
| *Marinobacter* sp. ES-1 | Q666_05770 | U7GFG6 |
| gamma proteobacterium HdN1 | alkM HDN1F_04190 | E1VGR0 |
| *Nocardia farcinica* (strain IFM 10152) | NFA_33210 | Q5YUH3 |
| *Mycobacterium chubuense* (strain NBB4) | Mycch_2783 | I4BJT7 |
| *Acinetobacter towneri* DSM 14962 = CIP 107472 | F947_01315 | N9CH84 |
| *Rhodococcus erythropolis* CCM2595 | O5Y_10330 | T1VNI2 |
| *Rhodococcus erythropolis* (strain PR4/NBRC 100887) | alkB RER_21620 | C0ZWY5 |
| *Rhodococcus* sp. P27 | N806_20680 | U0E9X4 |
| *Rhodococcus erythropolis* DN1 | N601_09550 | T5IBP7 |
| *Rhodococcus erythropolis* (*Arthrobacter picolinophilus*) | alkB | A4ZZL2 |
| *Mycobacterium fortuitum* subsp. fortuitum DSM 46621 | MFORT_07571 | K0VIS2 |
| *Rhodococcus qingshengii* BKS 20-40 | G418_14624 | M2XAS5 |
| *Rhodococcus erythropolis* (*Arthrobacter picolinophilus*) | alkB2 | Q9AE68 |
| *Rhodococcus* sp. (strain RHA1) | alkB RHA1_ro02534 | Q0SDP7 |
| *Rhodococcus* sp. JVH1 | JVH1_3134 | J1RMD5 |
| *Rhodococcus wratislaviensis* IFP 2016 | Rwratislav_18854 | L2TK91 |
| *Rhodococcus wratislaviensis* | alkB1 | K7WI49 |
| *Rhodococcus* sp. (strain Q15) | alkB2 | Q93DM7 |
| *Rhodococcus opacus* M213 | WSS_A20069 | K8XV97 |
| *Rhodococcus erythropolis* (*Arthrobacter picolinophilus*) | alkB | V5LET8 |
| *Streptomyces* sp. AA4 | SSMG_06805 | D9V1L5 |
| *Geobacillus* sp. MH-1 | alkB-geo6 | C5J0F7 |
| *Mycobacterium neoaurum* VKM Ac-1815D | D174_08465 | V5X9E7 |
| *Rhodococcus imtechensis* RKJ300 = JCM 13270 | W59_13161 | I0WSJ7 |
| *Prauserella rugosa* | alkB | Q9XBM1 |
| *Rhodococcus erythropolis* SK121 | RHOER0001_4201 | C3JG64 |

TABLE 4-continued

Non-heme diiron monooxygenase enzymes capable of catalyzing selective terminal alkene hydroxylation.

| Species Origin | Gene Name | Accession No |
|---|---|---|
| *Amycolatopsis azurea* DSM 43854 | C791_5134 | M2PZK0 |
| *Mycobacterium rhodesiae* (strain NBB3) | MycrhN_0412 | G8RK27 |
| *Rhodococcus* ruber | alkB7 | D3U1I1 |
| *Rhodococcus* ruber BKS 20-38 | G352_25762 | M2XQQ3 |
| *Mycobacterium chubuense* (strain NBB4) |  | D2JYT1 |
| *Mycobacterium chubuense* (strain NBB4) | Mycch_1351 | I4BFU6 |
| *Mycobacterium smegmatis* JS623 | Mycsm_01384 | L0IUF4 |
| *Nocardia nova* SH22a | alkB NONO_c46180 | W5TJL9 |
| *Rhodococcus* sp. BCP1 | alkB | E5G6V9 |
| *Saccharomonospora marina* XMU15 | SacmaDRAFT_4417 | H5X9W5 |
| *Mycobacterium* sp. (strain JLS) | Mjls_1369 | A3PW94 |
| *Rhodococcus* ruber | alkB7 | D3U1I9 |
| Mycobacterium tuberculosis BT1 | alkB HKBT1_3428 | W6HJ76 |
| *Mycobacterium tuberculosis* BT2 | alkB HKBT2_3435 | W6H3Z6 |
| *Mycobacterium tuberculosis* HKBS1 | alkB HKBS1_3438 | W6GVB7 |
| *Mycobacterium tuberculosis* EAI5 | M943_16800 | S5F023 |
| *Mycobacterium tuberculosis* EAI5/NITR206 | J114_17435 | R4MLW1 |
| *Mycobacterium tuberculosis* CAS/NITR204 | J113_22685 | R4MIF7 |
| *Mycobacterium bovis* (strain ATCC BAA-935/AF2122/97) | alkB Mb3280c | Q7TWW3 |
| *Mycobacterium tuberculosis* (strain ATCC 25618/H37Rv) | alkB Rv3252c RVBD_3252c | O05895 |
| *Mycobacterium tuberculosis* str. Beijing/NITR203 | J112_17475 | M9UX97 |
| *Mycobacterium bovis* BCG str. Korea 1168P | K60_033810 | M1IQ04 |
| *Mycobacterium liflandii* (strain 128FXT) | alkB MULP_01451 | L7V4G7 |
| *Mycobacterium tuberculosis* (strain CDC 1551/Oshkosh) | alkB MT3350 | L7N540 |
| *Mycobacterium canettii* CIPT 140070017 | alkB BN45_60281 | L0QZH1 |
| *Mycobacterium canettii* CIPT 140070008 | alkB BN43_60261 | L0QC77 |
| *Mycobacterium canettii* CIPT 140060008 | alkB BN44_70036 | L0Q026 |
| *Mycobacterium tuberculosis* 7199-99 | MT7199_3294 | L0NZI4 |
| *Mycobacterium tuberculosis* KZN 605 | TBXG_003280 | I6RJV1 |
| *Mycobacterium tuberculosis* KZN 4207 | TBSG_03323 | I1SDS8 |
| *Mycobacterium tuberculosis* RGTB327 | MRGA327_20020 | H8HLB9 |
| *Mycobacterium tuberculosis* (strain ATCC 35801/TMC 107/Erdman) | alkB ERDMAN_3566 | H8EY95 |
| *Mycobacterium tuberculosis* UT205 | alkB UDA_3252c | H6S7Q5 |
| *Mycobacterium bovis* BCG str. Mexico | alkB BCGMEX_3279c | G7QY42 |
| *Mycobacterium tuberculosis* CTRI-2 | alkB MTCTRI2_3319 | G2N7Q9 |
| *Mycobacterium canettii* (strain CIPT 140010059) | alkB MCAN_32711 | G0THM9 |
| *Mycobacterium canettii* (strain CIPT 140010059) | alkB MCAN_32711 | G0THM9 |
| *Mycobacterium africanum* (strain GM041182) | alkB MAF_32630 | F8M6G6 |
| *Mycobacterium tuberculosis* (strain CCDC5180) | alkB CCDC5180_2963 CFBR_3446 | F7WQM1 |
| *Mycobacterium tuberculosis* (strain CCDC5079) | alkB CCDC5079_3000 CFBS_3441 | F7WLN9 |
| *Mycobacterium tuberculosis* (strain KZN 1435/MDR) | TBMG_03300 | C6DXJ8 |
| *Mycobacterium bovis* (strain BCG/Tokyo 172/ATCC 35737/TMC 1019) | alkB JTY_3277 | C1AH26 |
| *Mycobacterium marinum* (strain ATCC BAA-535/M) | alkB MMAR_1291 | B2HEP2 |
| *Mycobacterium tuberculosis* (strain F11) | TBFG_13281 | A5WSG7 |
| *Mycobacterium tuberculosis* (strain ATCC 25177/H37Ra) | alkB MRA_3293 | A5U7S6 |
| *Mycobacterium tuberculosis* str. Haarlem | TBHG_03188 | A4KLE9 |
| *Mycobacterium bovis* (strain BCG/Pasteur 1173P2) | alkB BCG_3281c | A1KNQ4 |
| *Mycobacterium bovis* 04-303 | O216_17560 | V2W1E0 |
| *Mycobacterium bovis* AN5 | O217_17270 | V2VQT4 |
| *Mycobacterium tuberculosis* GuangZ0019 | alkB GuangZ0019_1145 | T5HDB1 |
| *Mycobacterium tuberculosis* FJ05194 | alkB FJ05194_2026 | T5H4I2 |
| *Mycobacterium tuberculosis* '98-R604 INH-RIF-EM' | TBKG_02259 | T0EL87 |
| *Mycobacterium marinum* str. Europe | MMEU_4939 | S7S303 |
| *Mycobacterium marinum* MB2 | MMMB2_4134 | S7QZY6 |
| *Mycobacterium orygis* 112400015 | MORY_17288 | M8DBT2 |

TABLE 4-continued

Non-heme diiron monooxygenase enzymes capable of catalyzing selective terminal alkene hydroxylation.

| Species Origin | Gene Name | Accession No |
|---|---|---|
| *Mycobacterium tuberculosis* NCGM2209 | alkB NCGM2209_3538 | G2UTS8 |
| *Mycobacterium bovis* BCG str. Moreau RDJ | alkB BCGM_3265c | F9UZB9 |
| *Mycobacterium tuberculosis* W-148 | TBPG_00365 | F2VCH4 |
| *Mycobacterium tuberculosis* CDC1551A | TMMG_02400 | E9ZP16 |
| *Mycobacterium tuberculosis* SUMu012 | TMLG_02024 | E2WM40 |
| *Mycobacterium tuberculosis* SUMu011 | TMKG_02511 | E2WA16 |
| *Mycobacterium tuberculosis* SUMu010 | TMJG_03436 | E2VYW3 |
| *Mycobacterium tuberculosis* SUMu009 | TMIG_02769 | E2VMD7 |
| *Mycobacterium tuberculosis* SUMu006 | TMFG_00461 | E2UQS7 |
| *Mycobacterium tuberculosis* SUMu005 | TMEG_03649 | E2UEQ4 |
| *Mycobacterium tuberculosis* SUMu004 | TMDG_02087 | E2U2V2 |
| *Mycobacterium tuberculosis* SUMu003 | TMCG_01675 | E2TRB4 |
| *Mycobacterium tuberculosis* SUMu002 | TMBG_01947 | E2TG69 |
| *Mycobacterium tuberculosis* SUMu001 | TMAG_02705 | E1HE07 |
| *Mycobacterium africanum* K85 | TBOG_03815 | D6FRF3 |
| Mycobacterium tuberculosis CPHL_A | TBNG_02887 | D6FLF8 |
| *Mycobacterium tuberculosis* T46 | TBLG_03890 | D6F9Q1 |
| *Mycobacterium tuberculosis* T17 | TBJG_02010 | D5ZLD1 |
| *Mycobacterium tuberculosis* GM 1503 | TBIG_02964 | D5Z897 |
| *Mycobacterium tuberculosis* 02_1987 | TBBG_01719 | D5YWK4 |
| *Mycobacterium tuberculosis* EAS054 | TBGG_02463 | D5YJM0 |
| *Mycobacterium tuberculosis* T85 | TBEG_02389 | D5Y8I4 |
| *Mycobacterium tuberculosis* T92 | TBDG_02114 | D5XYS2 |
| *Mycobacterium tuberculosis* C | TBCG_03191 | A2VP49 |
| *Rhodococcus* sp. EsD8 | EBESD8_35530 | N1M6K3 |
| *Amycolatopsis orientalis* HCCB10007 | AORI_4274 | R4SU00 |
| *Mycobacterium tuberculosis* SUMu008 | TMHG_02473 | E2VD73 |
| *Mycobacterium tuberculosis* SUMu007 | TMGG_02800 | E2V1Z1 |
| *Mycobacterium tuberculosis* 94_M4241A | TBAG_02148 | D7EUC2 |
| *Gordonia amarae* NBRC 15530 | alkB GOAMR_02_00080 | G7GIN7 |
| *Rhodococcus rhodochrous* ATCC 21198 | RR21198_2302 | W4A7D8 |
| *Amycolatopsis decaplanina* DSM 44594 | H074_07696 | M2XNH0 |
| *Mycobacterium* sp. 012931 | MMSP_4721 | S7R3L1 |
| *Rhodococcus erythropolis* (strain PR4/ NBRC 100887) | alkB RER_07460 | C0ZPX6 |
| *Rhodococcus* sp. (strain Q15) | alkB1 | Q93DN3 |
| *Rhodococcus erythropolis* CCM2595 | O5Y_03630 | T1VI31 |
| *Rhodococcus* sp. P27 | N806_28900 | U0EPX3 |
| *Rhodococcus erythropolis* (*Arthrobacter picolinophilus*) | alkB1 | Q9XAU0 |
| *Rhodococcus qingshengii* BKS 20-40 | G418_23516 | M2V230 |
| *Rhodococcus erythropolis* SK121 | RHOER0001_0742 | C3JUT8 |
| *Rhodococcus erythropolis* DN1 | N601_07180 | T5HYU5 |
| *Nocardia farcinica* (strain IFM 10152) | NFA_46180 | Q5YQS2 |
| *Rhodococcus equi* NBRC 101255 = C 7 | H849_17115 | U5DRE7 |
| *Shewanella* sp. NJ49 | alkB1 | E3VRS8 |
| *Mycobacterium canettii* CIPT 140070010 | alkB BN42_41302 | L0QPN9 |
| *Nocardia nova* SH22a | NONO_c63220 | W5TPB1 |
| *Rhodococcus equi* (strain 103S) (*Corynebacterium equi*) | alkB REQ_33430 | E4WK80 |
| *Gordonia terrae* C-6 | GTC6_09699 | R7YA99 |
| *Nocardioides* sp. (strain BAA-499/JS614) | Noca_0122 | A1SCY2 |
| *Gordonia* sp. TF6 | alkB2 | Q5WA49 |
| *Hydrocarboniphaga effusa* AP103 | WQQ_18760 | I7ZII6 |
| *Gordonia terrae* NBRC 100016 | alkB GOTRE_037_00320 | H5UBE8 |
| *Nocardia brasiliensis* ATCC 700358 | O3I_035145 | K0FBU4 |
| *Amycolatopsis mediterranei* RB | B737_6308 | T1V895 |
| *Amycolatopsis mediterranei* (strain S699) (*Nocardia mediterranei*) | AMES_6308 RAM_32810 | G0FN68 |
| *Amycolatopsis mediterranei* (strain U-32) | AMED_6400 | D8HXC8 |
| *Rhodococcus* sp. p52 | alkB | U5S065 |
| *Rhodococcus pyridinivorans* AK37 | AK37_01067 | H0JKW2 |
| *Rhodococcus pyridinivorans* SB3094 | Y013_07620 | V9XAS5 |
| *Janibacter* sp. HTCC2649 | JNB_17248 | A3TPZ2 |
| *Gordonia* sp. KTR9 | KTR9_2914 | J9SIP3 |
| *Aeromicrobium marinum* DSM 15272 | HMPREF0063_10220 | E2S863 |
| *Dietzia cinnamea* P4 | ES5_02159 | E6J5E4 |
| *Micromonospora aurantiaca* (strain ATCC 27029/DSM 43813/JCM 10878/NBRC 16125/INA 9442) | Micau_3940 | D9T1D7 |
| *Dietzia* sp. E1 | alkB/rub fusion | C0LMW6 |
| *Rhodococcus ruber* BKS 20-38 | G352_24171 | M2YYB5 |
| *Mycobacterium gilvum* (strain PYR-GCK) | Mflv_3369 | A4TAB7 |

TABLE 4-continued

Non-heme diiron monooxygenase enzymes capable of catalyzing selective terminal alkene hydroxylation.

| Species Origin | Gene Name | Accession No |
|---|---|---|
| (Mycobacterium flavescens (strain ATCC 700033/PYR-GCK)) | | |
| Nocardioidaceae bacterium Broad-1 | NBCG_03866 | E9UYJ8 |
| Rhodococcus rhodochrous ATCC 21198 | RR21198_2485 | W4A610 |
| Salinisphaera shabanensis E1L3A | SSPSH_001855 | U2E637 |
| Rhodococcus erythropolis (strain PR4/NBRC 100887) | alkB RER_54580 | C0ZSH4 |
| Corynebacterium falsenii DSM 44353 | CFAL_02965 | W5WPK1 |
| Rhodococcus erythropolis CCM2595 | O5Y_25995 | T1VVR3 |
| gamma proteobacterium BDW918 | DOK_04793 | I2JMI2 |
| Rhodococcus sp. P27 | N806_02390 | U0DZR9 |
| Rhodococcus erythropolis DN1 | N601_00885 | T5IAL6 |
| Rhodococcus erythropolis SK121 | RHOER0001_2104 | C3JNE0 |
| Rhodococcus qingshengii BKS 20-40 | G418_13569 | M2WBK9 |

In some embodiments, the disclosure provides methods for synthesizing olefinic alcohol products as described above, wherein the enzyme is a long-chain alkane hydroxylase. In some embodiments, the long-chain alkane hydroxylase is selected from Table 5 or a variant thereof having at least 90% identity thereto.

TABLE 5

Long chain alkane hydroxylase enzymes capable of catalyzing selective terminal alkene hydroxylation.

| Species Origin | Gene names | Accession No |
|---|---|---|
| Geobacillus thermodenitrificans (strain NG80-2) | ladA GTNG_3499 | A4IU28 |
| Geobacillus stearothermophilus (Bacillus stearothermophilus) | | A8DC15 |
| Paenibacillus sp. JCM 10914 | JCM10914_4324 | V9GEW8 |
| Bacillus methanolicus MGA3 | MGA3_06970 | I3E8X7 |
| Geobacillus sp. (strain Y4.1MC1) | GY4MC1_0235 | E3IA76 |
| Geobacillus thermoglucosidans TNO-09.020 | GT20_0226 | I0U377 |
| Geobacillus thermoglucosidasius (strain C56-YS93) | Geoth_0249 | F8CWH6 |
| Bacillus methanolicus PB1 | PB1_11994 | I3DVL0 |
| Alicyclobacillus acidoterrestris ATCC 49025 | N007_16655 | T0BMR6 |
| Bhargavaea cecembensis DSE10 | ntaA_1 C772_00943 | M7P9Z6 |
| Bacillus sp. 1NLA3E | B1NLA3E_02955 | N0AV94 |
| Burkholderia graminis C4D1M | BgramDRAFT_6080 | B1G9N8 |
| Burkholderia thailandensis H0587 | BTL_4503 | W6BDT9 |
| Planomicrobium glaciei CHR43 | G159_18855 | W3A818 |
| Burkholderia thailandensis E444 | BTJ_3656 | W6C8D0 |
| Burkholderia thailandensis 2002721723 | BTQ_5029 | W6BNA4 |
| Burkholderia pseudomallei (strain K96243) | BPSS0686 | Q63MH2 |
| Burkholderia mallei (strain ATCC 23344) | BMAA1146 | Q62BX8 |
| Burkholderia thailandensis (strain E264/ATCC 700388/DSM 13276/CIP 106301) | BTH_II1741 | Q2T4G4 |
| Burkholderia pseudomallei BPC006 | BPC006_II0968 | K7QBE8 |
| Burkholderia pseudomallei 1106b | BURPS1106B_1056 | C5ZS78 |
| Burkholderia pseudomallei MSHR346 | GBP346_B0209 | C4I1H5 |
| Burkholderia pseudomallei (strain 1106a) | BURPS1106A_A0931 | A3P3Q7 |
| Burkholderia mallei (strain NCTC 10247) | BMA10247_A1520 | A3MEL8 |
| Burkholderia mallei (strain NCTC 10229) | BMA10229_0093 | A2RW50 |
| Burkholderia pseudomallei MSHR338 | M218_32405 | W1LX20 |
| Burkholderia mallei PRL-20 | BMAPRL20_0872 | C5N9G7 |
| Burkholderia mallei GB8 horse 4 | BMAGB8_A1284 | C4B2F1 |
| Burkholderia pseudomallei Pakistan 9 | BUH_5241 | C0Y1N2 |
| Burkholderia pseudomallei 576 | BUC_5105 | B7CGH3 |
| Burkholderia pseudomallei S13 | BURPSS13_T0065 | B1H503 |
| Burkholderia mallei ATCC 10399 | BMA10399_L0048 | A9LC22 |
| Burkholderia pseudomallei Pasteur 52237 | BURPSPAST_J0304 | A8KQQ8 |
| Burkholderia pseudomallei 406e | BURPS406E_G0092 | A8EKE5 |
| Burkholderia mallei JHU | BMAJHU_I0303 | A5XK99 |
| Burkholderia mallei 2002721280 | BMA721280_L0585 | A5TFQ0 |
| Alicyclobacillus acidoterrestris ATCC 49025 | N007_09450 | T0BMI0 |
| Burkholderia pseudomallei MSHR305 | BDL_3916 | S5NPF6 |
| Burkholderia pseudomallei MSHR146 | BBN_4086 | W0Q1C4 |
| Burkholderia pseudomallei MSHR511 | BBQ_5508 | W0MJC7 |
| Burkholderia pseudomallei NAU20B-16 | BBS_5466 | V9YUR9 |
| Burkholderia pseudomallei NCTC 13178 | BBJ_4354 | V9YFT0 |
| Burkholderia pseudomallei NCTC 13179 | BBK_3804 | U5V4E4 |

TABLE 5-continued

Long chain alkane hydroxylase enzymes capable of catalyzing selective terminal alkene hydroxylation.

| Species Origin | Gene names | Accession No |
| --- | --- | --- |
| *Burkholderia pseudomallei* MSHR1043 | D512_19607 | M7EBY4 |
| *Burkholderia pseudomallei* 1655 | BURPS1655_I0183 | B2H6F2 |
| *Burkholderia pseudomallei* 305 | BURPS305_5546 | A4LI20 |
| *Segniliparus rugosus* ATCC BAA-974 | HMPREF9336_02889 | E5XTR7 |
| *Burkholderia pseudomallei* 1026b | BP1026B_II0759 | I1WRX2 |
| *Burkholderia pseudomallei* 354a | BP354A_4019 | I2MG65 |
| *Burkholderia pseudomallei* 354e | BP354E_3240 | I2M2Q7 |
| *Burkholderia pseudomallei* 1026a | BP1026A_2436 | I2L127 |
| *Burkholderia pseudomallei* 1258b | BP1258B_3899 | I2KY00 |
| *Burkholderia pseudomallei* 1258a | BP1258A_3523 | I2KWT0 |
| *Pseudomonas putida* (strain DOT-T1E) | T1E_2746 | I7B0Q5 |
| *Pseudomonas putida* ND6 | YSA_09788 | I3V2W3 |
| *Pseudomonas putida* TRO1 | C206_18269 | N9VYA0 |
| *Pseudomonas putida* LS46 | PPUTLS46_018911 | M7RI48 |
| *Burkholderia graminis* C4D1M | BgramDRAFT_6182 | B1G9Y6 |
| *Burkholderia phytofirmans* (strain DSM 17436/PsJN) | Bphyt_4538 | B2TDZ4 |
| *Bhargavaea cecembensis* DSE10 | moxC_3 C772_02411 | M7NEH3 |
| *Burkholderia thailandensis* MSMB121 | BTI_5494 | N0APC1 |
| *Burkholderia pseudomallei* (strain 668) | BURPS668_A1016 | A3NI44 |
| *Burkholderia pseudomallei* (strain 1710b) | BURPS1710b_A2257 | Q3JG95 |
| *Burkholderia pseudomallei* 1710a | BURPS1710A_A0072 | C6U1I8 |
| *Planomicrobium glaciei* CHR43 | G159_14295 | W3AA87 |
| *Burkholderia thailandensis* MSMB43 | A33K_16732 | I6AD68 |
| *Pseudomonas* sp. GM50 | PMI30_04278 | J3GFD6 |
| *Pseudomonas fluorescens* BBc6R8 | MHB_001910 | V7EA47 |
| *Pseudomonas* sp. Ag1 | A462_06954 | J0YEG1 |
| *Pseudomonas* sp. GM102 | PMI18_00569 | J2VSE5 |
| *Pseudomonas fluorescens* (strain SBW25) | PFLU_3858 | C3JYC1 |
| *Pseudomonas* sp. (strain M1) | PM1_0212365 | W5IVB1 |
| *Pseudomonas* sp. TKP | U771_20325 | V9R055 |
| *Pseudomonas putida* (strain F1/ATCC 700007) | Pput_3007 | A5W4S5 |
| *Pseudomonas putida* (strain GB-1) | PputGB1_1120 | B0KS73 |
| *Azotobacter vinelandii* CA6 | seuA AvCA6_43810 | M9YDA5 |
| *Azotobacter vinelandii* CA | seuA AvCA_43810 | M9Y6B1 |
| *Azotobacter vinelandii* (strain DJ/ATCC BAA-1303) | seuA Avin_43810 | C1DGK6 |
| *Pseudomonas brassicacearum* (strain NFM421) | PSEBR_a2282 | F2KFH4 |
| *Pseudomonas fluorescens* Q8r1-96 | PflQ8_2313 | I4KKG5 |
| *Klebsiella oxytoca* E718 | A225_4709 | I6X485 |
| *Pseudomonas putida* (strain KT2440) | PP_2746 | Q88JA3 |
| *Pseudomonas fluorescens* BBc6R8 | MHB_002244 | V7E7E4 |
| *Pseudomonas fluorescens* Q2-87 | PflQ2_2259 | J2EFB8 |
| *Pseudomonas* sp. Ag1 | A462_04671 | J0PSS9 |
| *Klebsiella oxytoca* MGH 42 | L388_04093 | V3KYZ2 |
| *Klebsiella oxytoca* 10-5245 | HMPREF9689_03721 | H3M9T3 |
| *Klebsiella oxytoca* 10-5243 | HMPREF9687_03258 | H3LSS6 |
| *Klebsiella oxytoca* (strain ATCC 8724/DSM 4798/JCM 20051/NBRC 3318/NRRL B-199/KCTC 1686) | KOX_01240 | G8WD25 |
| *Streptomyces himastatinicus* ATCC 53653 | SSOG_01846 | D9WSJ3 |
| *Klebsiella oxytoca* MGH 28 | L374_04760 | V3PRZ9 |
| *Klebsiella oxytoca* 10-5250 | HMPREF9694_02187 | H3N1Z4 |
| *Klebsiella* sp. OBRC7 | HMPREF1144_4230 | J8VYP0 |
| *Klebsiella oxytoca* 10-5242 | HMPREF9686_03185 | H3LCA0 |
| *Pantoea ananatis* LMG 5342 | soxA PANA5342_1855 | G9ARF4 |
| *Pantoea ananatis* PA13 | PAGR_g1792 | G7UD55 |
| *Pantoea ananatis* (strain AJ13355) | soxA PAJ_1557 | F2EW92 |
| *Pantoea ananatis* (strain LMG 20103) | soxA PANA_2246 | D4GGW6 |
| *Pantoea ananatis* BRT175 | L585_00145 | U4W7P0 |
| *Segniliparus rotundus* (strain ATCC BAA-972/CDC 1076/CIP 108378/DSM 44985/JCM 13578) | Srot_2598 | D6ZC64 |
| *Pantoea stewartii* subsp. *stewartii* DC283 | CKS_1871 | H3RFH9 |
| *Pantoea stewartii* subsp. *stewartii* DC283 | CKS_1871 | H3RFH9 |
| *Rhodococcus opacus* M213 | WSS_A14179 | K8XV73 |
| *Klebsiella pneumoniae* DMC0799 | H217_2899 | S7AJY1 |
| *Klebsiella pneumoniae* 700603 | KP700603_18582 | M7P910 |
| *Klebsiella* sp. MS 92-3 | HMPREF9538_02211 | F3Q553 |
| *Klebsiella pneumoniae* CG43 | D364_16040 | U5MF64 |
| *Klebsiella pneumoniae* subsp. *pneumoniae* 1084 | A79E_0950 | K4HBM3 |
| *Klebsiella pneumoniae* subsp. *pneumoniae* (strain HS11286) | KPHS_42240 | G8VT84 |
| *Klebsiella pneumoniae* KCTC 2242 | KPN2242_18760 | G0GTG2 |
| *Klebsiella pneumoniae* NB60 | X657_3893 | W7K535 |
| *Klebsiella pneumoniae* EGD-HP19-C | N035_09715 | W1LTN4 |
| *Escherichia coli* ISC56 | | W1HC22 |
| *Klebsiella pneumoniae* IS33 | | W1CX87 |
| *Klebsiella pneumoniae* subsp. *pneumoniae* BJ1-GA | KPST380_90022 | W0YH64 |

TABLE 5-continued

Long chain alkane hydroxylase enzymes capable of catalyzing selective terminal alkene hydroxylation.

| Species Origin | Gene names | Accession No |
|---|---|---|
| *Klebsiella pneumoniae* subsp. *pneumoniae* SA1 | KPST86_100232 | W0XPM0 |
| *Klebsiella pneumoniae* subsp. *pneumoniae* T69 | SB4536_310004 | W0XIP7 |
| *Klebsiella pneumoniae* MGH 18 | L364_01157 | V3UHS5 |
| *Klebsiella pneumoniae* MGH 17 | L363_03338 | V3SPP7 |
| *Klebsiella pneumoniae* MGH 21 | L367_03372 | V3RJW0 |
| *Klebsiella pneumoniae* MGH 19 | L365_03262 | V3RDD9 |
| *Klebsiella pneumoniae* MGH 32 | L378_01018 | V3P5E6 |
| *Klebsiella pneumoniae* MGH 30 | L376_01094 | V3NNG8 |
| *Klebsiella pneumoniae* MGH 40 | L386_03550 | V3MB44 |
| *Klebsiella pneumoniae* MGH 36 | L382_03249 | V3M7N6 |
| *Klebsiella pneumoniae* BWH 28 | L399_01071 | V3JYS4 |
| *Klebsiella pneumoniae* BWH 30 | L401_03358 | V3IHX3 |
| *Klebsiella pneumoniae* UCICRE 2 | L413_01241 | V3H9M1 |
| *Klebsiella pneumoniae* UCICRE 7 | L418_00976 | V3FW02 |
| *Klebsiella pneumoniae* UCICRE 6 | L417_03180 | V3FI89 |
| *Klebsiella pneumoniae* BIDMC 21 | L457_03247 | V3DWM2 |
| *Klebsiella pneumoniae* BIDMC 22 | L458_03227 | V3DGZ8 |
| *Klebsiella pneumoniae* BIDMC 24 | L460_03188 | V3BDU6 |
| *Klebsiella pneumoniae* BIDMC 25 | L461_03214 | V3B499 |
| *Klebsiella pneumoniae* BIDMC 40 | L477_03188 | V3A962 |
| *Klebsiella pneumoniae* BIDMC 36 | L473_03258 | V3A6I8 |
| *Klebsiella pneumoniae* BIDMC 41 | L478_00374 | V2Z7W2 |
| *Klebsiella pneumoniae* BIDMC 12C | L441_03468 | U7BFN1 |
| *Klebsiella pneumoniae* BIDMC 18C | L450_03424 | U7AVL5 |
| *Klebsiella pneumoniae* BIDMC 16 | L445_03710 | U7AGB1 |
| *Enterococcus gallinarum* EGD-AAK12 | N036_14515 | U1CX13 |
| *Klebsiella pneumoniae* subsp. *pneumoniae* MP14 | KKPNMP14_39700 | S8A752 |
| *Klebsiella pneumoniae* subsp. *pneumoniae* UKKV901664 | UKKV901664_39580 | S7YC36 |
| *Klebsiella pneumoniae* 120_1020 | J048_0227 | S7I734 |
| *Klebsiella pneumoniae* 140_1040 | J046_0551 | S7HZ61 |
| *Klebsiella pneumoniae* 280_1220 | J049_0615 | S7H6G5 |
| *Klebsiella pneumoniae* 160_1080 | J047_06104 | S7FI27 |
| *Klebsiella pneumoniae* UHKPC06 | H228_0695 | S7F6A3 |
| *Klebsiella pneumoniae* UHKPC67 | H212_0084 | S7EIH5 |
| *Klebsiella pneumoniae* UHKPC02 | H229_0083 | S7EFH7 |
| *Klebsiella pneumoniae* UHKPC17 | H225_0083 | S7E3F9 |
| *Klebsiella pneumoniae* UHKPC31 | H227_0223 | S7E0F6 |
| *Klebsiella pneumoniae* UHKPC59 | H223_2084 | S7DJY5 |
| *Klebsiella pneumoniae* UHKPC18 | H226_0627 | S7CZN2 |
| *Klebsiella pneumoniae* UHKPC61 | H220_0228 | S7CKP4 |
| *Klebsiella pneumoniae* UHKPC07 | H224_0554 | S7C1T8 |
| *Klebsiella pneumoniae* DMC1316 | H219_1515 | S7C0U0 |
| *Klebsiella pneumoniae* UHKPC33 | H222_0227 | S7BH54 |
| *Klebsiella pneumoniae* DMC1097 | H218_2245 | S7A1J0 |
| *Klebsiella pneumoniae* UHKPC96 | H215_0710 | S6YYA8 |
| *Klebsiella pneumoniae* UHKPC77 | H214_0083 | S6YU31 |
| *Klebsiella pneumoniae* UHKPC28 | H209_0679 | S6YQS7 |
| *Klebsiella pneumoniae* UHKPC69 | H213_0083 | S6YBZ0 |
| *Klebsiella pneumoniae* UHKPC47 | H211_0128 | S6XBP3 |
| *Klebsiella pneumoniae* UHKPC32 | H242_0078 | S2J6Y7 |
| *Klebsiella pneumoniae* UHKPC48 | H221_0076 | S2I2J3 |
| *Klebsiella pneumoniae* DMC0526 | H216_2445 | S2I0S2 |
| *Klebsiella pneumoniae* VAKPC278 | H247_0907 | S2H7F7 |
| *Klebsiella pneumoniae* UHKPC29 | H241_0227 | S2GQ63 |
| *Klebsiella pneumoniae* UHKPC05 | H210_0554 | S2G118 |
| *Klebsiella pneumoniae* UHKPC45 | H239_0077 | S2FVN7 |
| *Klebsiella pneumoniae* UHKPC 52 | H234_0218 | S2FQ55 |
| *Klebsiella pneumoniae* 646_1568 | J054_0227 | S2E5R5 |
| *Klebsiella pneumoniae* 540_1460 | J053_0083 | S2E2M9 |
| *Klebsiella pneumoniae* 440_1540 | J051_2140 | S2CWI6 |
| *Klebsiella pneumoniae* 500_1420 | J052_0542 | S2CKG8 |
| *Klebsiella pneumoniae* VAKPC309 | H252_1202 | S2C6A5 |
| *Klebsiella pneumoniae* KP-11 | H254_0775 | S2BTB1 |
| *Klebsiella pneumoniae* 361_1301 | J050_2658 | S2B565 |
| *Klebsiella pneumoniae* VAKPC297 | H251_0083 | S2ACA5 |
| *Klebsiella pneumoniae* VAKPC270 | H249_0897 | S1ZBB5 |
| *Klebsiella pneumoniae* VAKPC280 | H248_0984 | S1Z9L1 |
| *Klebsiella pneumoniae* VAKPC276 | H250_1158 | S1Z4C6 |
| *Klebsiella pneumoniae* VAKPC269 | H246_1198 | S1YJN2 |
| *Klebsiella pneumoniae* VAKPC254 | H245_0083 | S1XZP2 |
| *Klebsiella pneumoniae* UHKPC22 | H240_0083 | S1XYX9 |
| *Klebsiella pneumoniae* UHKPC04 | H243_0549 | S1X5H6 |
| *Klebsiella pneumoniae* VAKPC252 | H244_3523 | S1WWW4 |
| *Klebsiella pneumoniae* UHKPC26 | H236_0227 | S1W5H8 |

TABLE 5-continued

Long chain alkane hydroxylase enzymes capable of catalyzing selective terminal alkene hydroxylation.

| Species Origin | Gene names | Accession No |
|---|---|---|
| *Klebsiella pneumoniae* UHKPC27 | H233_0552 | S1VUY3 |
| *Klebsiella pneumoniae* UHKPC24 | H235_0228 | S1V9Y4 |
| *Klebsiella pneumoniae* UHKPC01 | H231_1154 | S1V1B9 |
| *Klebsiella pneumoniae* UHKPC81 | H232_2378 | S1TWU9 |
| *Klebsiella pneumoniae* UHKPC40 | H207_0083 | S1TR15 |
| *Klebsiella pneumoniae* UHKPC09 | H230_0227 | S1TQU1 |
| *Klebsiella pneumoniae* KP-7 | H253_1042 | S1T453 |
| *Klebsiella pneumoniae* UHKPC23 | H208_0755 | R9BIA6 |
| *Klebsiella pneumoniae* subsp. *pneumoniae* KpMDU1 | C210_21528 | N9SXP2 |
| *Klebsiella pneumoniae* ATCC BAA-1705 | KPBAA1705_02256 | M7QWX8 |
| *Klebsiella pneumoniae* ATCC BAA-2146 | G000_17665 Kpn2146_4394 | M7PZV3 |
| *Klebsiella pneumoniae* VA360 | MTE2 213 | M5T2W9 |
| *Klebsiella pneumoniae* RYC492 | KPRYC492_05065 | M5Q5H7 |
| *Klebsiella pneumoniae* RYC492 | KPRYC492_05065 | M5Q5H7 |
| *Klebsiella pneumoniae* subsp. *pneumoniae* KpQ3 | B819_29014 | M5GIZ6 |
| *Klebsiella pneumoniae* subsp. *pneumoniae* Ecl8 | BN373_37921 | K4UK89 |
| *Klebsiella pneumoniae* subsp. *pneumoniae* WGLW5 | HMPREF1308_03340 | K1NXD5 |
| *Klebsiella pneumoniae* subsp. *pneumoniae* WGLW3 | HMPREF1307_01233 | K1NCK1 |
| *Klebsiella pneumoniae* subsp. *pneumoniae* WGLW1 | HMPREF1305_01058 | K1MMN7 |
| *Klebsiella pneumoniae* subsp. *pneumoniae* KPNIH23 | KPNIH23_01714 | J2W4N5 |
| *Klebsiella pneumoniae* subsp. *pneumoniae* KPNIH21 | KPNIH21_18909 | J2UUP0 |
| *Klebsiella pneumoniae* subsp. *pneumoniae* KPNIH18 | KPNIH18_04648 | J2TP42 |
| *Klebsiella pneumoniae* subsp. *pneumoniae* KPNIH17 | KPNIH17_07852 | J2SZ94 |
| *Klebsiella pneumoniae* subsp. *pneumoniae* KPNIH9 | KPNIH9_07912 | J2PY88 |
| *Klebsiella pneumoniae* subsp. *pneumoniae* KPNIH6 | KPNIH6_12977 | J2NIU0 |
| *Klebsiella pneumoniae* subsp. *pneumoniae* KPNIH1 | KPNIH1_04615 | J2MHH3 |
| *Klebsiella pneumoniae* subsp. *pneumoniae* KPNIH22 | KPNIH22_01396 | J2KA06 |
| *Klebsiella pneumoniae* subsp. *pneumoniae* KPNIH19 | KPNIH19_02887 | J2JA47 |
| *Klebsiella pneumoniae* subsp. *pneumoniae* KPNIH16 | KPNIH16_07898 | J2HIQ1 |
| *Klebsiella pneumoniae* subsp. *pneumoniae* KPNIH14 | KPNIH14_01932 | J2GTK1 |
| *Klebsiella pneumoniae* subsp. *pneumoniae* KPNIH11 | KPNIH11_05794 | J2G1J7 |
| *Klebsiella pneumoniae* subsp. *pneumoniae* KPNIH2 | KPNIH2_14379 | J2BUC4 |
| *Klebsiella pneumoniae* subsp. *pneumoniae* KPNIH20 | KPNIH20_08348 | J2BFJ4 |
| *Klebsiella pneumoniae* subsp. *pneumoniae* KPNIH12 | KPNIH12_01874 | J1YXJ0 |
| *Klebsiella pneumoniae* subsp. *pneumoniae* KPNIH10 | KPNIH10_07382 | J1X9E8 |
| *Klebsiella pneumoniae* subsp. *pneumoniae* KPNIH8 | KPNIH8_09376 | J1WTX7 |
| *Klebsiella pneumoniae* subsp. *pneumoniae* KPNIH7 | KPNIH7_03054 | J1WDZ3 |
| *Klebsiella pneumoniae* subsp. *pneumoniae* KPNIH5 | KPNIH5_11286 | J1V7M9 |
| *Klebsiella pneumoniae* subsp. *pneumoniae* KPNIH4 | KPNIH4_01334 | J1UFY7 |
| *Klebsiella* sp. 4_1_44FAA | HMPREF1024_02306 | G9REB7 |
| *Klebsiella* JM45 | N559_1083 | S5YDY6 |
| *Klebsiella pneumoniae* subsp. *pneumoniae* Kp13 | KP13_02362 | V9ZFM9 |
| *Klebsiella pneumoniae* subsp. *rhinoscleromatis* ATCC 13884 | HMPREF0484_1763 | C8T2C2 |
| *Klebsiella pneumoniae* subsp. *pneumoniae* ST258-K26BO | BN426_1797 | K4RX40 |
| *Klebsiella variicola* (strain At-22) | Kvar_0908 | D3RIP8 |
| *Klebsiella pneumoniae* (strain 342) | KPK_0975 | B5XUZ5 |
| *Klebsiella pneumoniae* MGH 20 | L366_04030 | V3R3V0 |
| *Klebsiella pneumoniae* UCICRE 10 | L421_04096 | V3DSZ3 |
| *Klebsiella* sp. KTE92 | A1WC_04002 | R8X357 |
| *Klebsiella pneumoniae* hvKP1 | G057_03698 | M2A8M6 |
| *Mycobacterium hassiacum* DSM 44199 | C731_0966 | K5B980 |
| *Klebsiella pneumoniae* MGH 48 | L394_03318 | V3J564 |
| *Pantoea vagans* (strain C9-1) (*Pantoea agglomerans* (strain C9-1)) | Pvag_pPag10056 | E1PKF9 |
| *Klebsiella pneumoniae* IS22 | | W1BJB8 |
| *Klebsiella pneumoniae* subsp. *pneumoniae* NTUH-K2044 | KP1_4424 | C4XCS7 |
| *Burkholderia* sp. CCGE1001 | BC1001_4137 | E8YTA8 |
| *Microvirga lotononidis* | MicloDRAFT_00046760 | I4YVV6 |
| *Burkholderia phenoliruptrix* BR3459a | BUPH_00719 | K0DVZ1 |
| *Pseudomonas cichorii* JBC1 | PCH70_03420 | W0H3V5 |
| *Burkholderia* sp. (strain CCGE1003) | BC1003_5279 | E1TDZ6 |
| *Pseudomonas protegens* CHA0 | soxA1 PFLCHA0_c02440 | R4QZ42 |
| *Herbaspirillum* sp. CF444 | PMI16_04881 | J2L7C4 |
| *Pseudomonas fluorescens* (strain Pf-5/ATCC BAA-477) | PFL_0243 | Q4KK44 |
| *Bacillus megaterium* WSH-002 | BMWSH_4371 | G2RTT4 |
| *Pseudomonas* sp. GM30 | PMI25_001642 | W6W1D9 |
| *Pseudomonas* sp. GM78 | PMI35_05139 | J3D9L9 |
| *Pseudomonas* sp. GM60 | PMI32_02771 | J2U6I1 |
| *Pseudomonas* sp. FH1 | H096_21398 | W2DLN3 |
| *Pseudomonas* sp. GM41(2012) | PMI27_000125 | W6VAV2 |
| *Pseudomonas* sp. GM67 | PMI33_04861 | J2TPB1 |
| *Pseudomonas fluorescens* EGD-AQ6 | O204_08695 | U1U9U7 |
| *Pseudomonas* sp. CF161 | CF161_31485 | S6JVW1 |
| *Pseudomonas fluorescens* BRIP34879 | A986_05371 | L7HKJ7 |

TABLE 5-continued

Long chain alkane hydroxylase enzymes capable of catalyzing
selective terminal alkene hydroxylation.

| Species Origin | Gene names | Accession No |
|---|---|---|
| *Pseudomonas* sp. Lz4W | B195_18896 | M5QDB7 |
| *Collimonas fungivorans* (strain Ter331) | CFU_2748 | G0A9F2 |
| *Pseudomonas poae* RE*1-1-14 | H045_11420 | M4K052 |
| *Pseudomonas fluorescens* BBc6R8 | MHB_005864 | V7DXC0 |
| *Pseudomonas* sp. Lz4W | B195_14957 | M5QFC1 |
| *Pseudomonas* sp. GM24 | PMI23_03232 | J2QII9 |
| *Pseudomonas* sp. GM16 | PMI19_05169 | J2MFI6 |
| *Rhizobium* sp. CF080 | PMI07_000401 | W6W3M6 |
| *Pseudomonas* sp. FH1 | H096_13584 | W2DVJ0 |
| *Pseudomonas* sp. GM25 | PMI24_00141 | J2Q9Q8 |
| *Rhizobium leguminosarum* bv. *trifolii* (strain WSM2304) | Rleg2_6510 | B6A4D5 |
| *Pseudomonas* sp. G5(2012) | PG5_63250 | S2FDS8 |
| *Pseudomonas chlororaphis* O6 | PchlO6_2640 | I4XU61 |
| *Pseudomonas protegens* CHA0 | soxA3 PFLCHA0_c26840 | R4R5M1 |
| *Pseudomonas fluorescens* (strain Pf-5/ATCC BAA-477) | PFL_2617 | Q4KDF9 |
| *Rhizobium leguminosarum* bv. *trifolii* WSM597 | Rleg9DRAFT_0832 | I9N5T8 |
| *Bacillus megaterium* (strain DSM 319) | BMD_1582 | D5DC52 |
| *Pseudomonas fluorescens* WH6 | PFWH6_3643 | E2XUD7 |
| *Rhizobium* sp. Pop5 | RCCGEPOP_16608 | K0VYN0 |
| *Bacillus megaterium* (strain ATCC 12872/QMB1551) | BMQ_0870 | D5E197 |
| *Pseudomonas cichorii* JBC1 | PCH70_26220 | W0HAE8 |
| *Pseudomonas* sp. TKP | U771_03925 | V9QRK7 |
| *Pseudomonas aeruginosa* C41 | Q088_02376 | U8DE40 |
| *Pseudomonas aeruginosa* 62 | P997_00130 | U9DU73 |
| *Pseudomonas aeruginosa* BL19 | Q073_02117 | U8H8T3 |
| *Pseudomonas aeruginosa* YL84 | AI22_19865 | W5VAE7 |
| *Pseudomonas aeruginosa* SCV20265 | SCV20265_2995 | V9U1K6 |
| *Pseudomonas aeruginosa* LES431 | T223_15220 | V9T819 |
| *Pseudomonas aeruginosa* MTB-1 | U769_13585 | V5SWN7 |
| *Pseudomonas aeruginosa* PA1R | PA1R_gp0125 | U6AQA7 |
| *Pseudomonas aeruginosa* PA1 | PA1S_gp0125 | U6A6M8 |
| *Pseudomonas aeruginosa* PAO1-VE13 | N297_2400 | U5RPB5 |
| *Pseudomonas aeruginosa* PAO1-VE2 | N296_2400 | U5R2L8 |
| *Pseudomonas aeruginosa* c7447m | M802_2397 | T2EJL9 |
| *Pseudomonas aeruginosa* RP73 | M062_12135 | R9ZF43 |
| *Pseudomonas aeruginosa* (strain ATCC 15692/PAO1/1C/PRS 101/LMG 12228) | PA2326 | Q9I1F2 |
| *Pseudomonas aeruginosa* (strain UCBPP-PA14) | PA14_34540 | Q02MC3 |
| *Pseudomonas aeruginosa* B136-33 | G655_13420 | M9S636 |
| *Pseudomonas aeruginosa* DK2 | PADK2_13640 | I6SJ32 |
| *Pseudomonas aeruginosa* (strain LESB58) | PLES_29781 | B7V8Z7 |
| *Pseudomonas aeruginosa* (strain PA7) | PSPA7_2933 | A6V5F8 |
| *Pseudomonas aeruginosa* (strain PA7) | PSPA7_2933 | A6V5F8 |
| *Pseudomonas aeruginosa* DHS29 | V441_13990 | W1QXR3 |
| *Pseudomonas aeruginosa* MH38 | P38_3412 | W0WGT3 |
| *Pseudomonas aeruginosa* VRFPA06 | V527_13850 | V8HJN2 |
| *Pseudomonas aeruginosa* VRFPA08 | X922_29130 | V8DQV8 |
| *Pseudomonas aeruginosa* DHS01 | DPADHS01_13190 | V4WR77 |
| *Pseudomonas aeruginosa* VRFPA01 | G039_0203575 | V4QMQ4 |
| *Pseudomonas aeruginosa* HB15 | PA15_0330520 | V4MN40 |
| *Pseudomonas aeruginosa* M8A.3 | Q082_00075 | U9SHI5 |
| *Pseudomonas aeruginosa* CF27 | Q003_00104 | U9RU06 |
| *Pseudomonas aeruginosa* MSH10 | Q000_02112 | U9RT23 |
| *Pseudomonas aeruginosa* CF127 | Q001_02232 | U9RQB8 |
| *Pseudomonas aeruginosa* CF5 | Q004_02036 | U9R042 |
| *Pseudomonas aeruginosa* S54485 | Q007_00776 | U9QQE4 |
| *Pseudomonas aeruginosa* BWHPSA007 | Q020_00157 | U9PK67 |
| *Pseudomonas aeruginosa* BWHPSA009 | Q022_02698 | U9NGB4 |
| *Pseudomonas aeruginosa* BWHPSA008 | Q021_00149 | U9NF67 |
| *Pseudomonas aeruginosa* BWHPSA010 | Q023_01638 | U9MXZ6 |
| *Pseudomonas aeruginosa* BWHPSA015 | Q028_00447 | U9MBW2 |
| *Pseudomonas aeruginosa* BWHPSA016 | Q029_01714 | U9LQK4 |
| *Pseudomonas aeruginosa* BL03 | Q057_00105 | U9LB58 |
| *Pseudomonas aeruginosa* BL01 | Q055_02736 | U9KLQ0 |
| *Pseudomonas aeruginosa* BL02 | Q056_06394 | U9JUP8 |
| *Pseudomonas aeruginosa* BL05 | Q059_02100 | U9JF28 |
| *Pseudomonas aeruginosa* BL06 | Q060_06378 | U9IJ92 |
| *Pseudomonas aeruginosa* BL21 | Q075_03038 | U9GQQ1 |
| *Pseudomonas aeruginosa* BL23 | Q077_03073 | U9FQH5 |
| *Pseudomonas aeruginosa* BL24 | Q078_06288 | U9EQY5 |
| *Pseudomonas aeruginosa* M8A.4 | Q083_01720 | U9ECA2 |
| *Pseudomonas aeruginosa* MSH3 | P999_02290 | U9D2B6 |
| *Pseudomonas aeruginosa* X24509 | Q005_02076 | U9CCX5 |
| *Pseudomonas aeruginosa* UDL | Q006_01725 | U9C927 |
| *Pseudomonas aeruginosa* CF18 | Q002_02068 | U9BVH8 |

TABLE 5-continued

Long chain alkane hydroxylase enzymes capable of catalyzing
selective terminal alkene hydroxylation.

| Species Origin | Gene names | Accession No |
| --- | --- | --- |
| *Pseudomonas aeruginosa* 19660 | Q010_02159 | U9AF43 |
| *Pseudomonas aeruginosa* X13273 | Q013_02044 | U8Z334 |
| *Pseudomonas aeruginosa* S35004 | Q012_06204 | U8YF61 |
| *Pseudomonas aeruginosa* BWHPSA001 | Q014_02765 | U8YAB2 |
| *Pseudomonas aeruginosa* BWHPSA003 | Q016_02194 | U8XR83 |
| *Pseudomonas aeruginosa* BWHPSA002 | Q015_02292 | U8XP62 |
| *Pseudomonas aeruginosa* BWHPSA004 | Q017_02030 | U8X7A0 |
| *Pseudomonas aeruginosa* BWHPSA005 | Q018_03069 | U8W6E8 |
| *Pseudomonas aeruginosa* BWHPSA011 | Q024_01957 | U8VA48 |
| *Pseudomonas aeruginosa* BWHPSA013 | Q026_03028 | U8URW4 |
| *Pseudomonas aeruginosa* BWHPSA012 | Q025_02769 | U8UQP2 |
| *Pseudomonas aeruginosa* BWHPSA014 | Q027_01719 | U8TK96 |
| *Pseudomonas aeruginosa* BWHPSA017 | Q030_05589 | U8SKH8 |
| *Pseudomonas aeruginosa* BWHPSA020 | Q033_02593 | U8S609 |
| *Pseudomonas aeruginosa* BWHPSA019 | Q032_03133 | U8RPR9 |
| *Pseudomonas aeruginosa* BWHPSA022 | Q035_01895 | U8R8U4 |
| *Pseudomonas aeruginosa* BWHPSA023 | Q036_00320 | U8R6B4 |
| *Pseudomonas aeruginosa* BWHPSA021 | Q034_02035 | U8R1N4 |
| *Pseudomonas aeruginosa* BWHPSA025 | Q038_01757 | U8PR31 |
| *Pseudomonas aeruginosa* BWHPSA024 | Q037_02761 | U8PP93 |
| *Pseudomonas aeruginosa* BWHPSA027 | Q040_02049 | U8N8N1 |
| *Pseudomonas aeruginosa* BL07 | Q061_01439 | U8LYS6 |
| *Pseudomonas aeruginosa* BL04 | Q058_06192 | U8LL05 |
| *Pseudomonas aeruginosa* BL11 | Q065_03099 | U8K8S5 |
| *Pseudomonas aeruginosa* BL10 | Q064_02801 | U8JQ84 |
| *Pseudomonas aeruginosa* BL15 | Q069_01997 | U8IMR3 |
| *Pseudomonas aeruginosa* BL16 | Q070_01957 | U8IID0 |
| *Pseudomonas aeruginosa* BL18 | Q072_02105 | U8H8J8 |
| *Pseudomonas aeruginosa* M8A.2 | Q081_01961 | U8FTG3 |
| *Pseudomonas aeruginosa* M8A.1 | Q080_04721 | U8FHJ8 |
| *Pseudomonas aeruginosa* M9A.1 | Q084_05530 | U8EPH5 |
| *Pseudomonas aeruginosa* C20 | Q085_03119 | U8EML6 |
| *Pseudomonas aeruginosa* C23 | Q086_03122 | U8EJ68 |
| *Pseudomonas aeruginosa* C40 | Q087_02201 | U8DKJ1 |
| *Pseudomonas aeruginosa* C48 | Q089_02700 | U8CPW7 |
| *Pseudomonas aeruginosa* C51 | Q090_05806 | U8BVH7 |
| *Pseudomonas aeruginosa* CF77 | Q092_01904 | U8BA80 |
| *Pseudomonas aeruginosa* C52 | Q091_05688 | U8AZD2 |
| *Pseudomonas aeruginosa* CF614 | Q093_06204 | U8ACM4 |
| *Pseudomonas aeruginosa* VRFPA04 | P797_30195 | U5AHY5 |
| *Pseudomonas aeruginosa* HB13 | PA13_1029315 | U1E3A4 |
| *Pseudomonas aeruginosa* MSH-10 | L346_02111 | S0IJJ1 |
| *Pseudomonas aeruginosa* PA14 | CIA_02266 | S0I9C6 |
| *Pseudomonas aeruginosa* PAK | PAK_02986 | S0I695 |
| *Pseudomonas* sp. P179 | HMPREF1224_05539 | N2DDM6 |
| *Pseudomonas aeruginosa* str. Stone 130 | HMPREF1223_07114 | N2D7D2 |
| *Pseudomonas aeruginosa* PA21_ST175 | H123_24636 | M3AW72 |
| *Pseudomonas aeruginosa* E2 | P998_02032 PAE2_2544 | K1DHT6 |
| *Pseudomonas aeruginosa* ATCC 25324 | PABE173_3188 | K1DD82 |
| *Pseudomonas aeruginosa* CI27 | PACI27_2786 | K1CTB3 |
| *Pseudomonas aeruginosa* ATCC 700888 | PABE177_2660 | K1CGR7 |
| *Pseudomonas aeruginosa* ATCC 14886 | PABE171_3115 | K1BXJ5 |
| *Pseudomonas aeruginosa* PADK2_CF510 | CF510_22344 | I1ACS3 |
| *Pseudomonas aeruginosa* MPAO1/P2 | O1Q_15090 | H3TFC3 |
| *Pseudomonas aeruginosa* MPAO1/P1 | O1O_28545 | H3T6G4 |
| *Pseudomonas* sp. 2_1_26 | HMPREF1030_05556 | G5G1F3 |
| *Pseudomonas aeruginosa* 2192 | PA2G_01431 | A3LB74 |
| *Pseudomonas aeruginosa* C3719 | PACG_01235 | A3KU95 |
| *Erwinia billingiae* (strain Eb661) | EbC_20720 | D8MRZ6 |
| *Xanthomonas axonopodis* pv. *citri* (strain 306) | XAC0855 | Q8PP33 |
| *Xanthomonas citri* subsp. *citri* Aw12879 | XCAW_03724 | M4W2T5 |
| *Xanthomonas axonopodis* Xac29-1 | XAC29_04355 | M4U7K3 |
| *Xanthomonas citri* pv. *mangiferaeindicae* LMG 941 | ladA XMIN_2789 | H8FHG1 |
| *Xanthomonas axonopodis* pv. *punicae* str. LMG 859 | ladA XAPC_728 | H1XCV7 |
| *Leifsonia aquatica* ATCC 14665 | N136_01626 | U2TBF7 |
| *Serratia marcescens* subsp. *marcescens* Db11 | SMDB11_2421 | V6A0D9 |
| *Pseudomonas aeruginosa* VRFPA05 | T266_33830 | V4WJP9 |
| *Pseudomonas aeruginosa* BL22 | Q076_01761 | U9GCW5 |
| *Pseudomonas aeruginosa* BL22 | Q076_01761 | U9GCW5 |
| *Xanthomonas axonopodis* pv. *malvacearum* str. GSPB1386 | MOU_00060 | K8GBN4 |
| *Pseudomonas aeruginosa* VRFPA07 | X778_28580 | V8E3G0 |
| *Pseudomonas aeruginosa* BL20 | Q074_02826 | U9HSV9 |
| *Pseudomonas aeruginosa* BL25 | Q079_01143 | U9F0W8 |
| *Pseudomonas aeruginosa* BL09 | Q063_00187 | U8L2Y0 |

TABLE 5-continued

Long chain alkane hydroxylase enzymes capable of catalyzing selective terminal alkene hydroxylation.

| Species Origin | Gene names | Accession No |
|---|---|---|
| *Serratia marcescens* WW4 | SMWW4_v1c31920 | L7ZQQ5 |
| *Serratia marcescens* VGH107 | F518_24469 | M3BTM0 |
| *Pseudomonas aeruginosa* BWHPSA018 | Q031_00379 | U8TSK3 |
| *Pseudomonas aeruginosa* M18 | PAM18_2715 | G2L1H6 |
| *Pseudomonas aeruginosa* BL12 | Q066_03852 | U9I855 |
| *Pseudomonas aeruginosa* BWHPSA028 | Q041_02218 | U8NES6 |
| *Pseudomonas aeruginosa* WC55 | L683_26830 | T5KSU5 |
| *Pseudomonas aeruginosa* NCGM1179 | NCGM1179_2739 | G2U5R3 |
| *Rhodococcus erythropolis* SK121 | RHOER0001_2299 | C3JDL9 |
| *Pseudomonas aeruginosa* VRFPA03 | M770_16185 | W1MK34 |
| *Pseudomonas aeruginosa* BL13 | Q067_03184 | U9I925 |
| *Serratia marcescens* EGD-HP20 | N040_11055 | U1TLQ0 |
| *Pseudomonas aeruginosa* NCGM2.S1 | NCGM2_3338 | G4LI50 |
| *Pseudomonas aeruginosa* 39016 | PA39016_002700003 | E3A2U8 |
| *Pseudomonas aeruginosa* MH27 | PAMH27_2887 | V6AFD9 |
| *Pseudomonas aeruginosa* JJ692 | Q008_02805 | U9PMT7 |
| *Pseudomonas aeruginosa* 6077 | Q011_02150 | U9ATK4 |
| *Pseudomonas aeruginosa* U2504 | Q009_02593 | U9AAM5 |
| *Pseudomonas aeruginosa* BWHPSA006 | Q019_02936 | U8VL16 |
| *Pseudomonas aeruginosa* BL08 | Q062_04340 | U8KSZ8 |
| *Pseudomonas aeruginosa* BL14 | Q068_02182 | U8JUF2 |
| *Pseudomonas aeruginosa* BL17 | Q071_02971 | U8H8J5 |
| *Pseudomonas aeruginosa* PA45 | H734_07342 | N4W202 |
| *Rhodococcus erythropolis* CCM2595 | O5Y_21155 | T1VSG7 |
| *Rhodococcus* sp. P27 | N806_09240 | U0ED84 |
| *Kosakonia radicincitans* DSM 16656 | Y71_0158 | J1QW00 |
| *Rhodococcus erythropolis* (strain PR4/NBRC 100887) | RER_45000 | C0ZMF0 |
| *Klebsiella pneumoniae* MGH 46 | L392_03264 | V3LZ98 |
| *Klebsiella pneumoniae* MGH 44 | L390_02205 | V3JUR2 |
| *Klebsiella pneumoniae* UCICRE 4 | L415_03363 | V3FXF6 |
| *Klebsiella pneumoniae* 303K | N598_24365 | U6T101 |
| *Klebsiella pneumoniae* UHKPC179 | H238_2267 | S7F9A7 |
| *Klebsiella pneumoniae* UHKPC57 | H237_2247 | S2EDB5 |
| *Klebsiella pneumoniae* JHCK1 | MTE1_213 | M3U9Q5 |
| *Klebsiella pneumoniae* subsp. *pneumoniae* WGLW2 | HMPREF1306_03733 | K1NBI6 |
| *Klebsiella pneumoniae* UCICRE 14 | L425_03054 | V3CJD9 |
| *Rhodococcus qingshengii* BKS 20-40 | G418_04858 | M2XMT9 |
| *Pantoea* sp. Sc1 | S7A_19914 | H8DUB8 |
| *Klebsiella* sp. 1_1_55 | HMPREF0485_02899 | D6GIG4 |
| *Pantoea agglomerans* Tx10 | L584_13665 | U4VW62 |
| *Escherichia coli* 909957 | HMPREF1619_02817 | V0B421 |
| *Klebsiella pneumoniae* KP-1 | KLP1_1662 | U2ABR1 |
| *Rhodococcus erythropolis* DN1 | N601_05680 | T5I9L8 |
| *Klebsiella pneumoniae* UCICRE 8 | L419_03300 | V3F3T1 |
| *Brenneria* sp. EniD312 | BrE312_1717 | G7LVX2 |
| *Klebsiella pneumoniae* BIDMC 23 | L459_03205 | V3BAE8 |
| *Raoultella ornithinolytica* B6 | RORB6_23555 | M9W8P0 |
| *Klebsiella oxytoca* 10-5246 | HMPREF9690_03902 | H3MRJ7 |
| *Pantoea agglomerans* 299R | F385_1445 | L7BV82 |
| *Pantoea* sp. aB | PanABDRAFT_3926 | E0M3F8 |
| *Pseudomonas* sp. CFII64 | CFII64_23274 | S6GXI3 |
| *Pseudomonas synxantha* BG33R | PseBG33_0275 | I4KV50 |
| *Pseudomonas syringae* pv. *actinidiae* ICMP 18801 | A221_07756 | S6XYV3 |
| *Pseudomonas syringae* pv. *actinidiae* ICMP 19072 | A3SO_07400 | S6PNP2 |
| *Pseudomonas syringae* pv. *actinidiae* ICMP 19073 | A262_20054 | S6MLA8 |
| *Pseudomonas syringae* pv. *actinidiae* ICMP 19071 | A264_07551 | S6M2E1 |
| *Pseudomonas syringae* pv. *actinidiae* ICMP 19104 | A258_19792 | S6QSB5 |
| *Pseudomonas syringae* pv. *actinidiae* ICMP 9855 | A252_19596 | S6QRN6 |
| *Pseudomonas syringae* pv. *actinidiae* ICMP 19102 | A253_19857 | S6Q6B9 |
| *Pseudomonas syringae* pv. *actinidiae* ICMP 19068 | A260_20086 | S6Q126 |
| *Pseudomonas syringae* pv. *theae* ICMP 3923 | A584_21008 | S6MKD2 |
| *Pseudomonas syringae* pv. *actinidiae* ICMP 19103 | A256_19800 | S6M4P1 |
| *Rhizobium leguminosarum* bv. *viciae* (strain 3841) | pRL90300 | Q1M8E2 |
| *Pseudomonas* sp. GM25 | PMI24_01694 | J2PHH1 |
| *Herbaspirillum* sp. YR522 | PMI40_00700 | J3HY53 |
| *Pseudomonas syringae* pv. *morsprunorum* str. M302280 | PSYMP_05599 | F3DS65 |
| *Pseudomonas fluorescens* (strain Pf0-1) | Pfl01_0238 | Q3KJS4 |
| *Pseudomonas avellanae* BPIC 631 | Pav631_4731 | K2RRZ8 |
| *Pseudomonas fluorescens* R124 | I1A_000262 | K0W8U4 |
| *Pseudomonas syringae* pv. *syringae* (strain B728a) | Psyr_2869 | Q4ZSG7 |
| *Pseudomonas syringae* CC1557 | N018_12850 | W0MW63 |
| *Pseudomonas* sp. GM80 | PMI37_03766 | J3DKC5 |
| *Pseudomonas syringae* pv. *syringae* SM | PssSM_2902 | S3MKC4 |
| *Pseudomonas syringae* pv. *avellanae* str. ISPaVe037 | Pav037_2494 | K2T3F9 |
| *Pseudomonas syringae* pv. *aceris* str. M302273 | PSYAR_06142 | F3JE47 |

TABLE 5-continued

Long chain alkane hydroxylase enzymes capable of catalyzing selective terminal alkene hydroxylation.

| Species Origin | Gene names | Accession No |
|---|---|---|
| *Pseudomonas syringae* pv. *maculicola* str. ES4326 | PMA4326_07981 | F3HHE2 |
| *Pseudomonas syringae* BRIP39023 | A988_19986 | L7GSY0 |
| *Pseudomonas syringae* pv. *aptata* str. DSM 50252 | PSYAP_18083 | F3J2D2 |
| *Pseudomonas savastanoi* pv. *savastanoi* NCPPB 3335 | PSA3335_0550 | D7HUP0 |
| *Pseudomonas syringae* pv. *aesculi* str. 0893_23 | PSYAE_00125 | F3D7S6 |
| *Pseudomonas syringae* BRIP34881 | A987_17762 | L7G2P2 |
| *Pseudomonas syringae* BRIP34876 | A979_21556 | L7FTL3 |
| *Rhizobium leguminosarum* bv. *viciae* WSM1455 | Rleg5DRAFT_0033 | J0URT9 |
| *Pseudomonas syringae* Cit 7 | PSYCIT7_07619 | F3GWQ5 |
| *Acinetobacter baumannii* NIPH 410 | F910_02332 | S3TEC4 |
| *Acinetobacter baumannii* OIFC110 | ACIN5110_2029 | K5S1X4 |
| *Acinetobacter baumannii* WC-692 | ACINWC692_1619 | K1ER91 |
| *Pseudomonas* sp. TKP | U771_01460 | V9QPN2 |
| *Pseudomonas syringae* pv. *syringae* B64 | PssB64_3039 | L8NFP3 |
| *Pseudomonas syringae* pv. *actinidiae* ICMP 19094 | A241_11585 | S6VCM5 |
| *Pseudomonas syringae* pv. *actinidiae* ICMP 18883 | A243_23241 | S6TZP7 |
| *Pseudomonas syringae* pv. *actinidiae* ICMP 19095 | A242_23680 | S6TDL4 |
| *Pseudomonas syringae* pv. *actinidiae* ICMP 19099 | A247_15969 | S6S3V9 |
| *Pseudomonas syringae* pv. *actinidiae* ICMP 19100 | A248_23237 | S6R962 |
| *Pseudomonas syringae* pv. *actinidiae* ICMP 19098 | A246_16023 | S6LVQ8 |

In some embodiments, the disclosure provides methods for synthesizing olefinic alcohol products as described above, wherein the enzyme is a cytochrome P450. In some embodiments, the cytochrome P450 is selected from Table 6 or a variant thereof having at least 90% identity thereto. In some embodiments, the cytochrome P450 is a member of the CYP52 or CYP153 family. In some embodiments, the CYP52 enzyme is selected from CYP52A17, CYP52A13, and CYP52A12.

TABLE 6

Cytochrome P450 enzymes capable of catalyzing selective terminal alkene hydroxylation.

| Species Origin | Gene names | Accession No |
|---|---|---|
| *Candida tropicalis* (Yeast) | CYP52A12 | Q874J5 |
| *Candida tropicalis* (strain ATCC MYA-3404/T1) (Yeast) | CTRG_02725 | C5M8K3 |
| *Candida tropicalis* (Yeast) | CYP52A6 | P30608 |
| *Candida albicans* (Yeast) | | Q9C2X5 |
| *Candida maltosa* (Yeast) | CYP52A3-B | P24458 |
| *Candida dubliniensis* (strain CD36/ATCC MYA-646/CBS 7987/NCPF 3949/NRRL Y-17841) (Yeast) | CYP52A5 CD36_64140 | B9WJ64 |
| *Candida albicans* (strain SC5314/ATCC MYA-2876) (Yeast) | ALK1 CaO19.13150 orf19.13150 | Q5A8M1 |
| *Candida albicans* (strain SC5314/ATCC MYA-2876) (Yeast) | ALK1 CaO19.5728 orf19.5728 | Q5A8U5 |
| *Candida maltosa* (strain Xu316) (Yeast) | G210_4862 | M3HRI7 |
| *Candida maltosa* (Yeast) | CYP52A3-A | P16496 |
| *Candida orthopsilosis* (strain 90-125) (Yeast) | CORT_0F01930 | H8X8E5 |
| *Candida parapsilosis* (strain CDC 317/ATCC MYA-4646) (Yeast) (*Monilia parapsilosis*) | CPAR2_600870 | G8B4X9 |
| *Lodderomyces elongisporus* (strain ATCC 11503/CBS 2605/JCM 1781/NBRC 1676/NRRL YB-4239) (Yeast) (*Saccharomyces elongisporus*) | LELG_04957 | A5E5R8 |
| *Candida maltosa* (Yeast) | ALK3-B (CYP52A4) | B0VX53 |
| *Candida maltosa* (Yeast) | ALK8-B | Q12584 |
| *Candida tropicalis* (Yeast) | CYP52A8 | P30610 |
| *Debaryomyces hansenii* (strain ATCC 36239/CBS 767/JCM 1990/NBRC 0083/IGC 2968) (Yeast) (*Torulaspora hansenii*) | DEHA2E18634g | Q6BNV8 |
| *Candida tropicalis* (Yeast) | CYP52A17 | Q874I9 |
| *Candida maltosa* (strain Xu316) (Yeast) | G210_3820 | M3II00 |
| *Spathaspora passalidarum* (strain NRRL Y-27907/11-Y1) | SPAPADRAFT_59378 | G3AJR6 |
| *Scheffersomyces stipitis* (strain ATCC 58785/CBS 6054/NBRC 10063/NRRL Y-11545) (Yeast) (*Pichia stipitis*) | CP52M PICST_58031 | A3LRT5 |
| *Candida parapsilosis* (strain CDC 317/ATCC MYA-4646) (Yeast) (*Monilia parapsilosis*) | CPAR2_503950 | G8BH23 |
| *Candida parapsilosis* (strain CDC 317/ATCC MYA-4646) (Yeast) (*Monilia parapsilosis*) | CPAR2_800510 | G8BBI4 |

TABLE 6-continued

Cytochrome P450 enzymes capable of catalyzing selective terminal alkene hydroxylation.

| Species Origin | Gene names | Accession No |
|---|---|---|
| *Candida tropicalis* (Yeast) | CYP52A18 | Q874I8 |
| *Candida maltosa* (strain Xu316) (Yeast) | G210_4812 | M3K5V3 |
| *Debaryomyces hansenii* (Yeast) (*Torulaspora hansenii*) | CYP52A13 ALK2 | Q9Y758 |
| *Meyerozyma guilliermondii* (strain ATCC 6260/ CBS 566/DSM 6381/JCM 1539/NBRC 10279/NRRL Y-324) (Yeast) (*Candida guilliermondii*) | PGUG_05855 | A5DRF4 |
| *Debaryomyces hansenii* (strain ATCC 36239/ CBS 767/JCM 1990/NBRC 0083/IGC 2968) (Yeast) (*Torulaspora hansenii*) | DEHA2C02596g | Q6BVH7 |
| *Candida maltosa* (Yeast) | CYP52A5 | Q12581 |
| *Meyerozyma guilliermondii* (strain ATCC 6260/ CBS 566/DSM 6381/JCM 1539/NBRC 10279/NRRL Y-324) (Yeast) (*Candida guilliermondii*) | PGUG_01238 | A5DD87 |
| *Debaryomyces hansenii* (Yeast) (*Torulaspora hansenii*) | CYP52A12 ALK1 | Q9Y757 |
| *Candida dubliniensis* (strain CD36/ATCC MYA-646/CBS 7987/NCPF 3949/NRRL Y-17841) (Yeast) | CYP52A14 CD36_25250 | B9WKL6 |
| *Meyerozyma guilliermondii* (strain ATCC 6260/ CBS 566/DSM 6381/JCM 1539/NBRC 10279/NRRL Y-324) (Yeast) (*Candida guilliermondii*) | PGUG_05670 | A5DQW9 |
| *Candida albicans* (strain SC5314/ATCC MYA-2876) (Yeast) | ALK2 CaO19.7513 orf19.7513 | Q5AAH6 |
| *Candida albicans* (strain WO-1) (Yeast) | CAWG_01382 | C4YNC3 |
| *Candida tropicalis* (Yeast) | CYP52A14 CYP14 | Q874J3 |
| *Candida tropicalis* (Yeast) | CYP52A13 | Q874J4 |
| *Pichia sorbitophila* (strain ATCC MYA-4447/ BCRC 22081/CBS 7064/NBRC 10061/ NRRL Y-12695) (Hybrid yeast) | Piso0_002820 GNLVRS 01_PISO0I18532g | G8YG24 |
| *Candida parapsilosis* (strain CDC 317/ATCC MYA-4646) (Yeast) (*Monilia parapsilosis*) | CPAR2_204220 | G8BFZ5 |
| *Candida tropicalis* (Yeast) | CYP52A20 | Q874I6 |
| *Candida tropicalis* (Yeast) | CYP52A19 | Q874I7 |
| *Lodderomyces elongisporus* (strain ATCC 11503/CBS 2605/JCM 1781/NBRC 1676/ NRRL YB-4239) (Yeast) (*Saccharomyces elongisporus*) | LELG_00044 | A5DRQ8 |
| *Candida albicans* (strain WO-1) (Yeast) | CAWG_02011 | C4YMD2 |
| *Candida albicans* (strain SC5314/ATCC MYA-2876) (Yeast) | ALK8 CaO19.10 CaO19.7683 | Q59K96 |
| *Candida albicans* (Yeast) | alk8 | O74626 |
| *Candida maltosa* (strain Xu316) (Yeast) | G210_4811 | M3JDC1 |
| *Scheffersomyces stipitis* (strain ATCC 58785/ CBS 6054/NBRC 10063/NRRL Y-11545) (Yeast) (*Pichia stipitis*) | CP52C PICST_56580 | A3LR60 |
| *Lodderomyces elongisporus* (strain ATCC 11503/CBS 2605/JCM 1781/NBRC 1676/ NRRL YB-4239) (Yeast) (*Saccharomyces elongisporus*) | LELG_03506 | A5E1L9 |
| *Candida tropicalis* (strain ATCC MYA-3404/ T1) (Yeast) | CTRG_03115 | C5MAM3 |
| *Pichia sorbitophila* (strain ATCC MYA-4447/ BCRC 22081/CBS 7064/NBRC 10061/ NRRL Y-12695) (Hybrid yeast) | Piso0_002820 GNLVRS 01_PISO0J20293g | G8YDL5 |
| *Candida parapsilosis* (strain CDC 317/ATCC MYA-4646) (Yeast) (*Monilia parapsilosis*) | CPAR2_204210 | G8BFZ4 |
| *Spathaspora passalidarum* (strain NRRL Y-27907/11-Y1) | SPAPADRAFT_134963 | G3AJD3 |
| *Candida tropicalis* (strain ATCC MYA-3404/T1) (Yeast) | CTRG_01061 | C5M4S1 |
| *Candida tropicalis* (Yeast) | CYP52A2 | P30607 |
| *Candida parapsilosis* (strain CDC 317/ATCC MYA-4646) (Yeast) (*Monilia parapsilosis*) | CPAR2_800520 | G8BBI5 |
| *Scheffersomyces stipitis* (strain ATCC 58785/ CBS 6054/NBRC 10063/NRRL Y-11545) (Yeast) (*Pichia stipitis*) | CP52L PICST_56638 | A3LSP0 |
| *Candida parapsilosis* (strain CDC 317/ATCC MYA-4646) (Yeast) (*Monilia parapsilosis*) | CPAR2_203780 | G8BFV1 |
| *Candida maltosa* (strain Xu316) (Yeast) | G210_4902 | M3IU34 |
| *Candida orthopsilosis* (strain 90-125) (Yeast) | CORT_0D03890 | H8X5Y1 |
| *Candida dubliniensis* (strain CD36/ATCC MYA-646/CBS 7987/NCPF 3949/NRRL Y-17841) (Yeast) | CD36_32710 | B9WMB3 |
| *Pichia sorbitophila* (strain ATCC MYA-4447/ BCRC 22081/CBS 7064/NBRC 10061/ NRRL Y-12695) (Hybrid yeast) |  | G8YJP0 |
| *Debaryomyces hansenii* (strain ATCC 36239/ CBS 767/JCM 1990/NBRC 0083/IGC 2968) (Yeast) (*Torulaspora hansenii*) | DEHA2E18590g | Q6BNW0 |
| *Candida maltosa* (Yeast) | CYP52A9 | Q12586 |

TABLE 6-continued

Cytochrome P450 enzymes capable of catalyzing selective terminal alkene hydroxylation.

| Species Origin | Gene names | Accession No |
|---|---|---|
| Scheffersomyces stipitis (strain ATCC 58785/CBS 6054/NBRC 10063/NRRL Y-11545) (Yeast) (Pichia stipitis) | ALK2 PICST_35590 | A3LS01 |
| Spathaspora passalidarum (strain NRRL Y-27907/11-Y1) | SPAPADRAFT_67265 | G3APG2 |
| Candida tropicalis (strain ATCC MYA-3404/T1) (Yeast) | CTRG_03120 | C5MAM8 |
| Candida maltosa (Yeast) | CYP52A11 | Q12589 |
| Candida albicans (strain WO-1) (Yeast) | CAWG_01383 | C4YNC4 |
| Candida tropicalis (strain ATCC MYA-3404/T1) (Yeast) | CTRG_01060 | C5M4S0 |
| Candida albicans (strain SC5314/ATCC MYA-2876) (Yeast) | ALK3 CaO19.7512 orf19.7512 | Q5AAH7 |
| Candida tropicalis (Yeast) | CYP52A1 | P10615 |
| Scheffersomyces stipitis (strain ATCC 58785/CBS 6054/NBRC 10063/NRRL Y-11545) (Yeast) (Pichia stipitis) | CYP52 PICST_37142 | A3LZV9 |
| Debaryomyces hansenii (strain ATCC 36239/CBS 767/JCM 1990/NBRC 0083/IGC 2968) (Yeast) (Torulaspora hansenii) | DEHA2E18612g | Q6BNV9 |
| Candida tenuis (strain ATCC 10573/BCRC 21748/CBS 615/JCM 9827/NBRC 10315/NRRL Y-1498/VKM Y-70) (Yeast) | CANTEDRAFT_115474 | G3BA51 |
| Lodderomyces elongisporus (strain ATCC 11503/CBS 2605/JCM 1781/NBRC 1676/NRRL YB-4239) (Yeast) (Saccharomyces elongisporus) | LELG_03309 | A5E122 |
| Lodderomyces elongisporus (strain ATCC 11503/CBS 2605/JCM 1781/NBRC 1676/NRRL YB-4239) (Yeast) (Saccharomyces elongisporus) | LELG_03505 | A5E1L8 |
| Candida tropicalis (Yeast) | CYP52A16 CYP16 | Q874J1 |
| Candida tropicalis (Yeast) | CYP52A15 | Q874J2 |
| Candida maltosa (Yeast) | CYP52A10 | Q12588 |
| Candida dubliniensis (strain CD36/ATCC MYA-646/CBS 7987/NCPF 3949/NRRL Y-17841) (Yeast) | ALK3-A CD36_25260 | B9WKL7 |
| Candida maltosa (Yeast) | CYP52A4 | P16141 |
| Candida tenuis (strain ATCC 10573/BCRC 21748/CBS 615/JCM 9827/NBRC 10315/NRRL Y-1498/VKM Y-70) (Yeast) | CANTEDRAFT_113909 | G3B3X3 |
| Meyerozyma guilliermondii (Yeast) (Candida guilliermondii) | CYP52 | I6UGD5 |
| Spathaspora passalidarum (strain NRRL Y-27907/11-Y1) | SPAPADRAFT_153278 | G3AMY8 |
| Candida tenuis (strain ATCC 10573/BCRC 21748/CBS 615/JCM 9827/NBRC 10315/NRRL Y-1498/VKM Y-70) (Yeast) | CANTEDRAFT_116673 | G3BEU9 |
| Candida maltosa (strain Xu316) (Yeast) | G210_3821 | M3J257 |
| Candida tropicalis (Yeast) | CYP52A7 | P30609 |
| Clavispora lusitaniae (strain ATCC 42720) (Yeast) (Candida lusitaniae) | CLUG_03984 | C4Y750 |
| Debaryomyces hansenii (strain ATCC 36239/CBS 767/JCM 1990/NBRC 0083/IGC 2968) (Yeast) (Torulaspora hansenii) | DEHA2C01100g | Q6BVP2 |
| Candida tropicalis (Yeast) | CYP52D2 | Q874J0 |
| Clavispora lusitaniae (strain ATCC 42720) (Yeast) (Candida lusitaniae) | CLUG_04851 | C4Y9G1 |
| Meyerozyma guilliermondii (strain ATCC 6260/CBS 566/DSM 6381/JCM 1539/NBRC 10279/NRRL Y-324) (Yeast) (Candida guilliermondii) | PGUG_04005 | A5DL54 |
| Yarrowia lipolytica (Candida lipolytica) | ALK6 | O74132 |
| Yarrowia lipolytica (strain CLIB 122/E 150) (Yeast) (Candida lipolytica) | YALI0_B01848g | F2Z623 |
| Yarrowia lipolytica (strain CLIB 122/E 150) (Yeast) (Candida lipolytica) | YALI0_E25982g | Q6C4K6 |
| Yarrowia lipolytica (Candida lipolytica) | ALK1 | O74127 |
| Yarrowia lipolytica (Candida lipolytica) | ALK2 | O74128 |
| Yarrowia lipolytica (strain CLIB 122/E 150) (Yeast) (Candida lipolytica) | YALI0_F01320g | F2Z6J3 |
| Candida maltosa (Yeast) | CYP52D1 | Q12585 |
| Yarrowia lipolytica (strain CLIB 122/E 150) (Yeast) (Candida lipolytica) | YALI0_B20702g | Q6CDW4 |
| Byssochlamys spectabilis (strain No. 5/NBRC 109023) (Paecilomyces variotii) | PVAR5_4403 | V5G4E7 |
| Byssochlamys spectabilis (strain No. 5/NBRC 109023) (Paecilomyces variotii) | PVAR5_4403 | V5G4E7 |
| Aspergillus terreus (strain NIH 2624/FGSC A1156) | ATEG_02198 | Q0CVT6 |

TABLE 6-continued

Cytochrome P450 enzymes capable of catalyzing selective terminal alkene hydroxylation.

| Species Origin | Gene names | Accession No |
|---|---|---|
| *Neosartorya fischeri* (strain ATCC 1020/DSM 3700/FGSC A1164/NRRL 181) (*Aspergillus fischerianus*) | NFIA_029600 | A1D9P7 |
| *Yarrowia lipolytica* (*Candida lipolytica*) | ALK4 | O74130 |
| *Yarrowia lipolytica* (strain CLIB 122/E 150) (Yeast) (*Candida lipolytica*) | YALI0_B13816g | F2Z6H3 |
| *Penicillium digitatum* (strain PHI26/CECT 20796) (Green mold) | PDIG_58170 | K9G9Y0 |
| *Penicillium digitatum* (strain Pd1/CECT 20795) (Green mold) | PDIP_67660 | K9FGZ9 |
| *Aspergillus niger* (strain ATCC 1015/CBS 113.46/FGSC A1144/LSHB Ac4/NCTC 3858a/NRRL 328/USDA 3528.7) | ASPNIDRAFT_210944 | G3XNK4 |
| *Aspergillus niger* (strain CBS 513.88/FGSC A1513) | An14g01110 | A2R2K9 |
| *Tuber melanosporum* (strain Mel28) (Perigord black truffle) | GSTUM_00009186001 | D5GJT6 |
| *Yarrowia lipolytica* (*Candida lipolytica*) | ALK7 | O74133 |
| *Yarrowia lipolytica* (strain CLIB 122/E 150) (Yeast) (*Candida lipolytica*) | YALI0_A15488g | F2Z6A4 |
| *Arthrobotrys oligospora* (strain ATCC 24927/CBS 115.81/DSM 1491) (Nematode-trapping fungus) (*Didymozoophaga oligospora*) | AOL_s00109g132 | G1XKA3 |
| *Dactylellina haptotyla* (strain CBS 200.50) (Nematode-trapping fungus) (*Monacrosporium haptotylum*) | H072_6900 | S8ADY3 |
| *Yarrowia lipolytica* (strain CLIB 122/E 150) (Yeast) (*Candida lipolytica*) | YALI0_B06248g | Q6CFK2 |
| *Aspergillus clavatus* (strain ATCC 1007/CBS 513.65/DSM 816/NCTC 3887/NRRL 1) | ACLA_054640 | A1C993 |
| *Byssochlamys spectabilis* (strain No. 5/NBRC 109023) (*Paecilomyces variotii*) | PVAR5_0196 | V5FIS1 |
| *Aspergillus kawachii* (strain NBRC 4308) (White koji mold) (*Aspergillus awamori* var. *kawachi*) | AKAW_05280 | G7XJE1 |
| *Aspergillus oryzae* (strain 3.042) (Yellow koji mold) | Ao3042_00039 | I8AC74 |
| *Aspergillus flavus* (strain ATCC 200026/FGSC A1120/NRRL 3357/JCM 12722/SRRC 167) | AFLA_041790 | B8NCU4 |
| *Aspergillus oryzae* (strain ATCC 42149/RIB 40) (Yellow koji mold) | AO090011000346 | Q2U0Q3 |
| *Aspergillus oryzae* (Yellow koji mold) | CYP52H3 | D4QC14 |
| *Candida tenuis* (strain ATCC 10573/BCRC 21748/CBS 615/JCM 9827/NBRC 10315/NRRL Y-1498/VKM Y-70) (Yeast) | CANTEDRAFT_130130 | G3B1J0 |
| *Emericella nidulans* (strain FGSC A4/ATCC 38163/CBS 112.46/NRRL 194/M139) (*Aspergillus nidulans*) | AN7131.2 ANIA_07131 | Q5AX49 |
| *Talaromyces stipitatus* (strain ATCC 10500/CBS 375.48/QM 6759/NRRL 1006) (*Penicillium stipitatum*) | TSTA_012000 | B8ME14 |
| *Starmerella bombicola* |  | B8QHP3 |
| *Hordeum vulgare* var. *distichum* (Two-rowed barley) |  | F2E8C2 |
| *Mycosphaerella graminicola* (strain CBS 115943/IPO323) (Speckled leaf blotch fungus) (*Septoria tritici*) | CYP-27 MYCGRDRAFT_70822 | F9X9F0 |
| *Neosartorya fumigata* (strain ATCC MYA-4609/Af293/CBS 101355/FGSC A1100) (*Aspergillus fumigatus*) | AFUA_4G03800 | Q4W9T4 |
| *Neosartorya fumigata* (strain CEA10/CBS 144.89/FGSC A1163) (*Aspergillus fumigatus*) | AFUB_099220 | B0YEH7 |
| *Penicillium chrysogenum* (strain ATCC 28089/DSM 1075/Wisconsin 54-1255) (*Penicillium notatum*) | Pc14g00320 PCH_Pc14g00320 | B6H5K4 |
| *Clavispora lusitaniae* (strain ATCC 42720) (Yeast) (*Candida lusitaniae*) | CLUG_04098 | C4Y4W0 |
| *Penicillium roqueforti* | CYP52A12PROQFM164_S03g001613 | W6QFZ4 |
| *Yarrowia lipolytica* (*Candida lipolytica*) | ALK5 | O74131 |
| *Yarrowia lipolytica* (strain CLIB 122/E 150) (Yeast) (*Candida lipolytica*) | YALI0_B13838g | F2Z5W7 |
| *Candida tenuis* (strain ATCC 10573/BCRC 21748/CBS 615/JCM 9827/NBRC 10315/NRRL Y-1498/VKM Y-70) (Yeast) | CANTEDRAFT_107892 | G3B8A7 |
| *Penicillium marneffei* (strain ATCC 18224/CBS 334.59/QM 7333) | PMAA_059650 | B6QM59 |
| *Yarrowia lipolytica* (strain CLIB 122/E 150) (Yeast) (*Candida lipolytica*) | YALI0_A20130g | Q6CGD9 |
| *Candida apicola* (Yeast) | CYP52E2 | Q12573 |

TABLE 6-continued

Cytochrome P450 enzymes capable of catalyzing selective terminal alkene hydroxylation.

| Species Origin | Gene names | Accession No |
|---|---|---|
| *Macrophomina phaseolina* (strain MS6) (Charcoal rot fungus) | MPH_10814 | K2RGW0 |
| *Cyphellophora europaea* CBS 101466 | HMPREF1541_06043 | W2RTP6 |
| *Cochliobolus sativus* (strain ND90Pr/ATCC 201652) (Common root rot and spot blotch fungus) (*Bipolaris sorokiniana*) | COCSADRAFT_40532 | M2STM3 |
| *Cochliobolus sativus* (strain ND90Pr/ATCC 201652) (Common root rot and spot blotch fungus) (*Bipolaris sorokiniana*) | COCSADRAFT_148934 | M2SE93 |
| *Bipolaris victoriae* FI3 | COCVIDRAFT_89176 | W7ES92 |
| *Bipolaris zeicola* 26-R-13 | COCCADRAFT_102357 | W6Y6Y4 |
| *Cochliobolus heterostrophus* (strain C5/ATCC 48332/race O) (Southern corn leaf blight fungus) (*Bipolaris maydis*) | COCHEDRAFT_1085873 | M2TJW9 |
| *Cochliobolus heterostrophus* (strain C4/ATCC 48331/race T) (Southern corn leaf blight fungus) (*Bipolaris maydis*) | COCC4DRAFT_201005 | N4WTS2 |
| *Pseudogymnoascus destructans* (strain ATCC MYA-4855/20631-21) (Bat white-nose syndrome fungus) (*Geomyces destructans*) | GMDG_04968 | L8GCB9 |
| *Aspergillus terreus* (strain NIH 2624/FGSC A1156) | ATEG_03903 | Q0CQY1 |
| *Marssonina brunnea* f. sp. *multigermtubi* (strain MB_m1) (*Marssonina* leaf spot fungus) | MBM_06876 | K1WCN3 |
| *Penicillium marneffei* (strain ATCC 18224/CBS 334.59/QM 7333) | PMAA_093890 | B6QHD0 |
| *Neosartorya fumigata* (strain CEA10/CBS 144.89/FGSC A1163) (*Aspergillus fumigatus*) | AFUB_025410 | B0XRZ8 |
| *Candida apicola* (Yeast) | CYP52E1 | P43083 |
| *Neosartorya fumigata* (strain ATCC MYA-4609/Af293/CBS 101355/FGSC A1100) (*Aspergillus fumigatus*) | AFUA_2G09540 | Q4X1L5 |
| *Neosartorya fischeri* (strain ATCC 1020/DSM 3700/FGSC A1164/NRRL 181) (*Aspergillus fischerianus*) | NFIA_085030 | A1DGP3 |
| *Cordyceps militaris* (strain CM01) (Caterpillar fungus) | CCM_07376 | G3JQU8 |
| *Coniosporium apollinis* (strain CBS 100218) (Rock-inhabiting black yeast) | W97_02755 | R7YNR2 |
| *Penicillium chrysogenum* (strain ATCC 28089/DSM 1075/Wisconsin 54-1255) (*Penicillium notatum*) | Pc22g19240 PCH_Pc22g19240 | B6HVQ7 |
| *Penicillium digitatum* (strain Pd1/CECT 20795) (Green mold) | PDIP_65200 | K9G3N2 |
| *Penicillium digitatum* (strain PHI26/CECT 20796) (Green mold) | PDIG_30820 | K9FYP6 |
| *Penicillium roqueforti* | PROQFM164_S01g001598 | W6QDZ0 |
| *Marssonina brunnea* f. sp. *multigermtubi* (strain MB_m1) (*Marssonina* leaf spot fungus) | MBM_06372 | K1WQC3 |
| *Botryotinia fuckeliana* (strain BcDW1) (Noble rot fungus) (*Botrytis cinerea*) | BcDW1_3993 | M7U1E8 |
| *Botryotinia fuckeliana* (strain T4) (Noble rot fungus) (*Botrytis cinerea*) | BofuT4P27000003001 | G2Y6G5 |
| *Emericella nidulans* (strain FGSC A4/ATCC 38163/CBS 112.46/NRRL 194/M139) (*Aspergillus nidulans*) | AN9384.2 ANIA_09384 | Q5AQP6 |
| *Candida maltosa* (Yeast) | CYP52C2 | Q12587 |
| *Phaeosphaeria nodorum* (strain SN15/ATCC MYA-4574/FGSC 10173) (Glume blotch fungus) (*Septoria nodorum*) | SNOG_02153 | Q0V1G1 |
| *Pyrenophora tritici-repentis* (strain Pt-1C-BFP) (Wheat tan spot fungus) (*Drechslera tritici-repentis*) | PTRG_08257 | B2WF96 |
| *Pyrenophora teres* f. *teres* (strain 0-1) (Barley net blotch fungus) (*Drechslera teres* f. *teres*) | PTT_00451 | E3RCI0 |
| *Aspergillus niger* (strain ATCC 1015/CBS 113.46/FGSC A1144/LSHB Ac4/NCTC 3858a/NRRL 328/USDA 3528.7) | ASPNIDRAFT_140405 | G3YCS1 |
| *Bipolaris oryzae* ATCC 44560 | COCMIDRAFT_998 | W7A2Q6 |
| *Cochliobolus heterostrophus* (strain C4/ATCC 48331/race T) (Southern corn leaf blight fungus) (*Bipolaris maydis*) | COCC4DRAFT_169587 | N4X0M1 |
| *Cochliobolus heterostrophus* (strain C5/ATCC 48332/race O) (Southern corn leaf blight fungus) (*Bipolaris maydis*) | COCHEDRAFT_1140715 | M2U5K5 |
| *Botryosphaeria parva* (strain UCR-NP2) (Grapevine canker fungus) (*Neofusicoccum parvum*) | UCRNP2_24 | R1GXQ4 |
| *Ajellomyces capsulatus* (strain H88) (Darling's disease fungus) (*Histoplasma capsulatum*) | HCEG_07709 | F0URG7 |

TABLE 6-continued

Cytochrome P450 enzymes capable of catalyzing selective terminal alkene hydroxylation.

| Species Origin | Gene names | Accession No |
|---|---|---|
| *Bipolaris oryzae* ATCC 44560 | COCMIDRAFT_1291 | W7A267 |
| *Dactylellina haptotyla* (strain CBS 200.50) (Nematode-trapping fungus) (*Monacrosporium haptotylum*) | H072_402 | S8ARJ7 |
| *Cladophialophora carrionii* CBS 160.54 | G647_04218 | V9DES7 |
| *Exophiala dermatitidis* (strain ATCC 34100/CBS 525.76/NIH/UT8656) (Black yeast) (*Wangiella dermatitidis*) | HMPREF1120_06284 | H6C3Q7 |
| *Yarrowia lipolytica* (*Candida lipolytica*) | ALK3 | O74129 |
| *Yarrowia lipolytica* (strain CLIB 122/E 150) (Yeast) (*Candida lipolytica*) | YALI0_E23474g | F2Z6D5 |
| *Blumeria graminis* f. sp. *hordei* (strain DH14) (Barley powdery mildew) (*Oidium monilioides* f. sp. *hordei*) | BGHDH14_bgh01926 | N1JHB2 |
| *Neosartorya fischeri* (strain ATCC 1020/DSM 3700/FGSC A1164/NRRL 181) (*Aspergillus fischerianus*) | NFIA_063580 | A1D653 |
| *Dactylellina haptotyla* (strain CBS 200.50) (Nematode-trapping fungus) (*Monacrosporium haptotylum*) | H072_3894 | S8C337 |
| *Aspergillus kawachii* (strain NBRC 4308) (White koji mold) (*Aspergillus awamori* var. *kawachi*) | AKAW_03269 | G7XDZ6 |
| *Aspergillus niger* (strain ATCC 1015/CBS 113.46/FGSC A1144/LSHB Ac4/NCTC 3858a/NRRL 328/USDA 3528.7) | ASPNIDRAFT_183349 | G3Y6F0 |
| *Aspergillus oryzae* (strain 3.042) (Yellow koji mold) | Ao3042_02280 | I8IPH3 |
| *Aspergillus flavus* (strain ATCC 200026/FGSC A1120/NRRL 3357/JCM 12722/SRRC 167) | AFLA_089870 | B8NKB3 |
| *Arthroderma gypseum* (strain ATCC MYA-4604/CBS 118893) (*Microsporum gypseum*) | MGYG_08468 | E4V5T0 |
| *Arthroderma otae* (strain ATCC MYA-4605/CBS 113480) (*Microsporum canis*) | MCYG_06305 | C5FUA2 |
| *Bipolaris victoriae* FI3 | COCVIDRAFT_33397 | W7EVM0 |
| *Bipolaris oryzae* ATCC 44560 | COCMIDRAFT_22726 | W6ZD79 |
| *Byssochlamys spectabilis* (strain No. 5/NBRC 109023) (*Paecilomyces variotii*) | PVAR5_0072 | V5HQF9 |
| *Bipolaris zeicola* 26-R-13 | COCCADRAFT_21391 | W6YP58 |
| *Mycosphaerella fijiensis* (strain CIRAD86) (Black leaf streak disease fungus) (*Pseudocercospora fijiensis*) | MYCFIDRAFT_153745 | M3AEP8 |
| *Aspergillus terreus* (strain NIH 2624/FGSC A1156) | ATEG_01150 | Q0CYT4 |
| *Setosphaeria turcica* (strain 28A) (Northern leaf blight fungus) (*Exserohilum turcicum*) | SETTUDRAFT_96298 | R0JZR2 |
| *Colletotrichum graminicola* (strain M1.001/M2/FGSC 10212) (Maize anthracnose fungus) (*Glomerella graminicola*) | GLRG_01676 | E3Q5P1 |
| *Aspergillus clavatus* (strain ATCC 1007/CBS 513.65/DSM 816/NCTC 3887/NRRL 1) | ACLA_055810 | A1C9K9 |
| *Ajellomyces capsulatus* (strain G186AR/H82/ATCC MYA-2454/RMSCC 2432) (Darling's disease fungus) (*Histoplasma capsulatum*) | HCBG_07070 | C0NV90 |
| *Aspergillus oryzae* (strain ATCC 42149/RIB 40) (Yellow koji mold) | AO090124000014 | Q2U799 |
| *Aspergillus oryzae* (strain ATCC 42149/RIB 40) (Yellow koji mold) | AO090124000014 | Q2U799 |
| *Aspergillus niger* (strain CBS 513.88/FGSC A1513) | An11g04220 | A2QW84 |
| *Penicillium marneffei* (strain ATCC 18224/CBS 334.59/QM 7333) | PMAA_050330 | B6QKF3 |
| *Tuber melanosporum* (strain Mel28) (Perigord black truffle) | GSTUM_00004620001 | D5G7M1 |
| *Colletotrichum higginsianum* (strain IMI 349063) (Crucifer anthracnose fungus) | CH063_01685 | H1VAW5 |
| *Beauveria bassiana* (strain ARSEF 2860) (White muscardine disease fungus) (*Tritirachium shiotae*) | BBA_08136 | J5JHI3 |
| *Yarrowia lipolytica* (strain CLIB 122/E 150) (Yeast) (*Candida lipolytica*) | YALI0_C10054g | Q6CCE5 |
| *Botryosphaeria parva* (strain UCR-NP2) (Grapevine canker fungus) (*Neofusicoccum parvum*) | UCRNP2_3112 | R1ERB7 |
| *Setosphaeria turcica* (strain 28A) (Northern leaf blight fungus) (*Exserohilum turcicum*) | SETTUDRAFT_104406 | R0IY48 |
| *Aspergillus clavatus* (strain ATCC 1007/CBS 513.65/DSM 816/NCTC 3887/NRRL 1) | ACLA_081330 | A1CT08 |
| *Mycosphaerella fijiensis* (strain CIRAD86) (Black leaf streak disease fungus) (*Pseudocercospora fijiensis*) | MYCFIDRAFT_65755 | M3A1E6 |

TABLE 6-continued

Cytochrome P450 enzymes capable of catalyzing selective terminal alkene hydroxylation.

| Species Origin | Gene names | Accession No |
|---|---|---|
| *Aspergillus oryzae* (strain ATCC 42149/RIB 40) (Yellow koji mold) | AO090026000094 | Q2UFS5 |
| *Aspergillus oryzae* (strain 3.042) (Yellow koji mold) | Ao3042_06896 | I7ZXQ6 |
| *Aspergillus oryzae* (Yellow koji mold) | CYP584G1 | D4QC67 |
| *Aspergillus flavus* (strain ATCC 200026/FGSC A1120/NRRL 3357/JCM 12722/SRRC 167) | AFLA_138460 | B8NGX8 |
| *Candida tenuis* (strain ATCC 10573/BCRC 21748/CBS 615/JCM 9827/NBRC 10315/NRRL Y-1498/VKM Y-70) (Yeast) | CANTEDRAFT_120218 | G3B201 |
| *Aspergillus niger* (strain ATCC 1015/CBS 113.46/FGSC A1144/LSHB Ac4/NCTC 3858a/NRRL 328/USDA 3528.7) | ASPNIDRAFT_51356 | G3Y8H5 |
| *Aspergillus niger* (strain CBS 513.88/FGSC A1513) | An03g02570 | A2QGB4 |
| *Pseudogymnoascus destructans* (strain ATCC MYA-4855/20631-21) (Bat white-nose syndrome fungus) (*Geomyces destructans*) | GMDG_01087 | L8FNT2 |
| *Cladophialophora carrionii* CBS 160.54 | G647_06237 | V9D5I6 |
| *Candida albicans* (strain WO-1) (Yeast) | CAWG_05505 | C4YTL0 |
| *Coccidioides posadasii* (strain RMSCC 757/Silveira) (Valley fever fungus) | CPSG_05074 | E9D644 |
| *Coccidioides posadasii* (strain C735) (Valley fever fungus) | CPC735_058630 | C5PIZ0 |
| *Candida maltosa* (strain Xu316) (Yeast) | G210_3874 | M3J212 |
| *Metarhizium acridum* (strain CQMa 102) | MAC_00168 | E9DQZ9 |
| *Bipolaris zeicola 26-R-13* | COCCADRAFT_112912 | W6XW09 |
| *Pyronema omphalodes* (strain CBS 100304) (*Pyronema confluens*) | PCON_11087 | U4LQK1 |
| *Bipolaris victoriae* FI3 | COCVIDRAFT_39745 | W7E2W7 |
| *Botryotinia fuckeliana* (strain T4) (Noble rot fungus) (*Botrytis cinerea*) | BofuT4_P153970.1 | G2YW37 |
| *Fusarium heterosporum* | fsdH | S0ARX1 |
| *Cyphellophora europaea* CBS 101466 | HMPREF1541_04435 | W2RWT0 |
| *Metarhizium acridum* (strain CQMa 102) | MAC_07120 | E9EB72 |
| *Macrophomina phaseolina* (strain MS6) (Charcoal rot fungus) | MPH_05063 | K2R5H7 |
| *Colletotrichum graminicola* (strain M1.001/M2/FGSC 10212) (Maize anthracnose fungus) (*Glomerella graminicola*) | GLRG_01883 | E3Q8M4 |
| *Bipolaris zeicola 26-R-13* | COCCADRAFT_111835 | W6Y8G6 |
| *Cochliobolus heterostrophus* (strain C5/ATCC 48332/race O) (Southern corn leaf blight fungus) (*Bipolaris maydis*) | COCHEDRAFT_1160314 | M2SMR0 |
| *Bipolaris zeicola 26-R-13* | COCCADRAFT_101405 | W6YJB0 |
| *Cochliobolus heterostrophus* (strain C4/ATCC 48331/race T) (Southern corn leaf blight fungus) (*Bipolaris maydis*) | COCC4DRAFT_62846 | N4XCY6 |
| *Colletotrichum gloeosporioides* (strain Cg-14) (Anthracnose fungus) (*Glomerella cingulata*) | CGLO_16193 | T0L9W5 |
| *Botryotinia fuckeliana* (strain BcDW1) (Noble rot fungus) (*Botrytis cinerea*) | BcDW1_1090 | M7U9F3 |
| *Botryotinia fuckeliana* (strain T4) (Noble rot fungus) (*Botrytis cinerea*) | BofuT4P90000010001 | G2YMJ6 |
| *Sclerotinia sclerotiorum* (strain ATCC 18683/1980/Ss-1) (White mold) (*Whetzelinia sclerotiorum*) | SS1G_10037 | A7EXH2 |
| *Penicillium digitatum* (strain PHI26/CECT 20796) (Green mold) | PDIG_44570 | K9FT94 |
| *Penicillium digitatum* (strain Pd1/CECT 20795) (Green mold) | PDIP_16560 | K9GHJ2 |
| *Metarhizium anisopliae* (strain ARSEF 23/ATCC MYA-3075) | MAA_06634 | E9F2Y5 |
| *Starmerella bombicola* | | B8QHP1 |
| *Penicillium marneffei* (strain ATCC 18224/CBS 334.59/QM 7333) | PMAA_088180 | B6QDT4 |
| *Metarhizium acridum* (strain CQMa 102) | MAC_09276 | E9EHC8 |
| *Mycosphaerella pini* (strain NZE10/CBS 128990) (Red band needle blight fungus) (*Dothistroma septosporum*) | DOTSEDRAFT_74860 | N1PCY6 |
| *Aspergillus kawachii* (strain NBRC 4308) (White koji mold) (*Aspergillus awamori* var. *kawachi*) | AKAW_10068 | G7XYF8 |
| *Aspergillus niger* (strain CBS 513.88/FGSC A1513) | An13g03000 | A2R1Z6 |

TABLE 6-continued

Cytochrome P450 enzymes capable of catalyzing selective terminal alkene hydroxylation.

| Species Origin | Gene names | Accession No |
|---|---|---|
| *Aspergillus niger* (strain ATCC 1015/CBS 113.46/FGSC A1144/LSHB Ac4/NCTC 3858a/NRRL 328/USDA 3528.7) | ASPNIDRAFT_44878 | G3XQ89 |
| *Beauveria bassiana* (strain ARSEF 2860) (White muscardine disease fungus) (*Tritirachium shiotae*) | BBA_05173 | J4UM22 |
| *Beauveria bassiana* (White muscardine disease fungus) (*Tritirachium shiotae*) | | E2EAF8 |
| *Aspergillus oryzae* (strain 3.042) (Yellow koji mold) | Ao3042_05622 | I8IHV7 |
| *Aspergillus flavus* (strain ATCC 200026/FGSC A1120/NRRL 3357/JCM 12722/SRRC 167) | AFLA_045270 | B8NBF2 |
| *Aspergillus oryzae* (strain ATCC 42149/RIB 40) (Yellow koji mold) | AO090011000712 | Q2TZU9 |
| *Aspergillus oryzae* (Yellow koji mold) | CYP52G3 | D4QC12 |
| *Endocarpon pusillum* (strain Z07020/HMAS-L-300199) (Lichen-forming fungus) | EPUS_05482 | U1GCZ9 |
| *Sclerotinia sclerotiorum* (strain ATCC 18683/1980/Ss-1) (White mold) (*Whetzelinia sclerotiorum*) | SS1G_05980 | A7EKY3 |
| *Pyrenophora tritici-repentis* (strain Pt-1C-BFP) (Wheat tan spot fungus) (*Drechslera tritici-repentis*) | PTRG_06344 | B2W8N6 |
| *Candida albicans* (strain SC5314/ATCC MYA-2876) (Yeast) | ALK6 CaO19.13927 CaO19.6574 | Q5AGW4 |
| *Candida albicans* (Yeast) | ALK6 CaJ7.0170 CaO19.6574 | G1U9Z0 |
| *Trichophyton verrucosum* (strain HKI 0517) | TRV_06353 | D4DGP8 |
| *Coccidioides immitis* (strain RS) (Valley fever fungus) | CIMG_00331 | J3KGS4 |
| *Ajellomyces dermatitidis* ATCC 26199 | BDFG_02901 | T5C2N4 |
| *Ajellomyces dermatitidis* (strain ATCC 18188/CBS 674.68) (*Blastomyces dermatitidis*) | BDDG_01558 | F2T5V8 |
| *Ajellomyces dermatitidis* (strain SLH14081) (*Blastomyces dermatitidis*) | BDBG_07037 | C5JWU3 |
| *Ajellomyces dermatitidis* (strain ER-3/ATCC MYA-2586) (*Blastomyces dermatitidis*) | BDCG_07223 | C5GSH0 |
| *Coccidioides posadasii* (strain C735) (Valley fever fungus) | CPC735_073410 | C5P014 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_02045 | N4V6W7 |
| *Coccidioides immitis* (strain RS) (Valley fever fungus) | CIMG_11305 | J3KDU2 |
| *Talaromyces stipitatus* (strain ATCC 10500/CBS 375.48/QM 6759/NRRL 1006) (*Penicillium stipitatum*) | TSTA_056150 | B8MRH9 |
| *Coccidioides posadasii* (strain RMSCC 757/Silveira) (Valley fever fungus) | CPSG_06231 | E9D8S9 |
| *Uncinocarpus reesii* (strain UAMH 1704) | UREG_01634 | C4JJ27 |
| *Starmerella bombicola* | | B8QHP5 |
| *Pyrenophora tritici-repentis* (strain Pt-1C-BFP) (Wheat tan spot fungus) (*Drechslera tritici-repentis*) | PTRG_04241 | B2W1A6 |
| *Marssonina brunnea* f. sp. *multigermtubi* (strain MB_m1) (*Marssonina* leaf spot fungus) | MBM_07629 | K1XPF9 |
| *Metarhizium anisopliae* (strain ARSEF 23/ATCC MYA-3075) | MAA_00167 | E9EKL9 |
| *Macrophomina phaseolina* (strain MS6) (Charcoal rot fungus) | MPH_02135 | K2S0W5 |
| *Glarea lozoyensis* (strain ATCC 20868/MF5171) | GLAREA_00730 | S3CV81 |
| *Arthroderma otae* (strain ATCC MYA-4605/CBS 113480) (*Microsporum canis*) | MCYG_02969 | C5FKC8 |
| *Trichophyton verrucosum* (strain HKI 0517) | TRV_03431 | D4D8J5 |
| *Hypocrea atroviridis* (strain ATCC 20476/IMI 206040) (*Trichoderma atroviride*) | TRIATDRAFT_130690 | G9P640 |
| *Glarea lozoyensis* (strain ATCC 74030/MF5533) | M7I_0305 | H0ED06 |
| *Ajellomyces capsulatus* (strain NAm1/WU24) (Darling's disease fungus) (*Histoplasma capsulatum*) | HCAG_08121 | A6REQ6 |
| *Pyronema omphalodes* (strain CBS 100304) (*Pyronema confluens*) | PCON_14046 | U4LA29 |
| *Endocarpon pusillum* (strain Z07020/HMAS-L-300199) (Lichen-forming fungus) | EPUS_04540 | U1GA45 |
| *Penicillium marneffei* (strain ATCC 18224/CBS 334.59/QM 7333) | PMAA_048940 | B6QS70 |

TABLE 6-continued

Cytochrome P450 enzymes capable of catalyzing selective terminal alkene hydroxylation.

| Species Origin | Gene names | Accession No |
|---|---|---|
| *Emericella nidulans* (strain FGSC A4/ATCC 38163/CBS 112.46/NRRL 194/M139) (*Aspergillus nidulans*) | AN6057.2 ANIA_06057 | Q5B073 |
| *Botryotinia fuckeliana* (strain T4) (Noble rot fungus) (*Botrytis cinerea*) | BofuT4_P148640.1 | G2YX16 |
| *Aspergillus terreus* (strain NIH 2624/FGSC A1156) | ATEG_02893 | Q0CTU1 |
| *Aspergillus niger* (strain ATCC 1015/CBS 113.46/FGSC A1144/LSHB Ac4/NCTC 3858a/NRRL 328/USDA 3528.7) | ASPNIDRAFT_55501 | G3XTI8 |
| *Aspergillus kawachii* (strain NBRC 4308) (White koji mold) (*Aspergillus awamori* var. *kawachi*) | AKAW_10154 | G7XYN1 |
| *Beauveria bassiana* (strain ARSEF 2860) (White muscardine disease fungus) (*Tritirachium shiotae*) | BBA_02382 | J4WEG4 |
| *Sclerotinia sclerotiorum* (strain ATCC 18683/ 1980/Ss-1) (White mold) (*Whetzelinia sclerotiorum*) | SS1G_13470 | A7F790 |
| *Beauveria bassiana* (strain ARSEF 2860) (White muscardine disease fungus) (*Tritirachium shiotae*) | BBA_02428 | J5K2V9 |
| *Beauveria bassiana* (White muscardine disease fungus) (*Tritirachium shiotae*) | | E2EAF6 |
| *Cordyceps militaris* (strain CM01) (Caterpillar fungus) | CCM_04719 | G3JD19 |
| *Penicillium chrysogenum* (strain ATCC 28089/ DSM 1075/Wisconsin 54-1255) (*Penicillium notatum*) | Pc21g14130 PCH_Pc21g14130 | B6HHN6 |
| *Mycosphaerella pini* (strain NZE10/CBS 128990) (Red band needle blight fungus) (*Dothistroma septosporum*) | DOTSEDRAFT_70063 | N1PRA2 |
| *Mycosphaerella pini* (strain NZE10/CBS 128990) (Red band needle blight fungus) (*Dothistroma septosporum*) | DOTSEDRAFT_70063 | N1PRA2 |
| *Aspergillus terreus* (strain NIH 2624/FGSC A1156) | ATEG_07540 | Q0CFJ4 |
| *Arthroderma benhamiae* (strain ATCC MYA-4681/CBS 112371) (*Trichophyton mentagrophytes*) | ARB_05989 | D4AP22 |
| *Baudoinia compniacensis* (strain UAMH 10762) (Angels' share fungus) | BAUCODRAFT_63612 | M2NKX8 |
| *Candida tropicalis* (strain ATCC MYA-3404/ T1) (Yeast) | CTRG_04959 | C5MFW6 |
| *Candida tropicalis* (Yeast) | CYP52C1 | P30612 |
| *Metarhizium anisopliae* (strain ARSEF 23/ ATCC MYA-3075) | MAA_07989 | E9F6U0 |
| *Mycosphaerella graminicola* (strain CBS 115943/ IPO323) (Speckled leaf blotch fungus) (*Septoria tritici*) | CYP-29MYCGRDRAFT_76681 | F9XML6 |
| *Cladophialophora carrionii* CBS 160.54 | G647_07950 | V9D5N0 |
| *Glarea lozoyensis* (strain ATCC 20868/ MF5171) | GLAREA_09137 | S3DII6 |
| *Hypocrea virens* (strain Gv29-8/FGSC 10586) (*Gliocladium virens*) (*Trichoderma virens*) | TRIVIDRAFT_50878 | G9N4V4 |
| *Marssonina brunnea* f. sp. *multigermtubi* (strain MB_m1) (*Marssonina* leaf spot fungus) | MBM_02308 | K1X1G5 |
| *Talaromyces stipitatus* (strain ATCC 10500/ CBS 375.48/QM 6759/NRRL 1006) (*Penicillium stipitatum*) | TSTA_125560 | B8MCM6 |
| *Arthroderma benhamiae* (strain ATCC MYA-4681/CBS 112371) (*Trichophyton mentagrophytes*) | ARB_01737 | D4AZW7 |
| *Colletotrichum higginsianum* (strain IMI 349063) (Crucifer anthracnose fungus) | CH063_01286 | H1V527 |
| *Trichophyton tonsurans* (strain CBS 112818) (Scalp ringworm fungus) | TESG_03185 | F2RW94 |
| *Marssonina brunnea* f. sp. *multigermtubi* (strain MB_m1) (*Marssonina* leaf spot fungus) | MBM_09278 | K1WJW9 |
| *Aspergillus terreus* (strain NIH 2624/FGSC A1156) | ATEG_06678 | Q0CI06 |
| *Claviceps purpurea* (strain 20.1) (Ergot fungus) (*Sphacelia segetum*) | CPUR_01906 | M1VZT8 |
| *Trichophyton rubrum* (strain ATCC MYA-4607/ CBS 118892) (Athlete's foot fungus) | TERG_01394 | F2SCB2 |
| *Setosphaeria turcica* (strain 28A) (Northern leaf blight fungus) (*Exserohilum turcicum*) | SETTUDRAFT_39981 | R0ILM4 |
| *Paracoccidioides brasiliensis* (strain Pb03) | PABG_02000 | C0S2T6 |
| *Arthroderma gypseum* (strain ATCC MYA-4604/ CBS 118893) (*Microsporum gypseum*) | MGYG_08184 | E4V596 |

TABLE 6-continued

Cytochrome P450 enzymes capable of catalyzing selective terminal alkene hydroxylation.

| Species Origin | Gene names | Accession No |
|---|---|---|
| *Trichophyton equinum* (strain ATCC MYA-4606/CBS 127.97) (Horse ringworm fungus) | TEQG_06653 | F2Q0K1 |
| *Talaromyces stipitatus* (strain ATCC 10500/CBS 375.48/QM 6759/NRRL 1006) (*Penicillium stipitatum*) | TSTA_036210 | B8M882 |
| *Leptosphaeria maculans* (strain JN3/isolate v23.1.3/race Av1-4-5-6-7-8) (Blackleg fungus) (*Phoma lingam*) | LEMA_P030820.1 | E4ZWF4 |
| *Bipolaris victoriae* FI3 | COCVIDRAFT_43025 | W7E4E8 |
| *Magnaporthe oryzae* (strain Y34) (Rice blast fungus) (*Pyricularia oryzae*) | OOU_Y34scaffold00740g4 | L7HW63 |
| *Fusarium oxysporum* f. sp. *cubense* (strain race 1) (Panama disease fungus) | FOC1_g10015382 | N4TN76 |
| *Fusarium oxysporum* f. sp. *lycopersici* (strain 4287/CBS 123668/FGSC 9935/NRRL 34936) (*Fusarium vascular* wilt of tomato) | FOXG_00101 | J9MB56 |
| *Endocarpon pusillum* (strain Z07020/HMAS-L-300199) (Lichen-forming fungus) | EPUS_06065 | U1GKM5 |
| *Sphaerulina musiva* (strain SO2202) (Poplar stem canker fungus) (*Septoria musiva*) | SEPMUDRAFT_55938 | N1QLI3 |
| *Mycosphaerella graminicola* (strain CBS 115943/IPO323) (Speckled leaf blotch fungus) (*Septoria tritici*) | CYP-31.1MYCGRDRAFT_47046 | F9XH30 |
| *Penicillium oxalicum* (strain 114-2/CGMCC 5302) (*Penicillium decumbens*) | PDE_08994 | S8BFY9 |
| *Mycosphaerella graminicola* (strain CBS 115943/IPO323) (Speckled leaf blotch fungus) (*Septoria tritici*) | CYP-30MYCGRDRAFT_73230 | F9XDL6 |
| *Cladophialophora carrionii* CBS 160.54 | G647_01266 | V9DPI5 |
| *Togninia minima* (strain UCR-PA7) (Esca disease fungus) (*Phaeoacremonium aleophilum*) | UCRPA7_6516 | R8BF53 |
| *Fusarium oxysporum* (strain Fo5176) (*Fusarium vascular* wilt) | FOXB_00215 | F9F1C9 |
| *Gaeumannomyces graminis* var. *tritici* (strain R3-111a-1) (Wheat and barley take-all root rot fungus) | GGTG_11345 | J3PCX6 |
| *Cochliobolus sativus* (strain ND90Pr/ATCC 201652) (Common root rot and spot blotch fungus) (*Bipolaris sorokiniana*) | COCSADRAFT_143540 | M2R997 |
| *Neosartorya fumigata* (strain CEA10/CBS 144.89/FGSC A1163) (*Aspergillus fumigatus*) | AFUB_002090 | B0XRD5 |
| *Neosartorya fumigata* (strain ATCC MYA-4609/Af293/CBS 101355/FGSC A1100) (*Aspergillus fumigatus*) | AFUA_1G01690 | Q4WKQ1 |
| *Neosartorya fischeri* (strain ATCC 1020/DSM 3700/FGSC A1164/NRRL 181) (*Aspergillus fischerianus*) | NFIA_022940 | A1D590 |
| *Hypocrea atroviridis* (strain ATCC 20476/IMI 206040) (*Trichoderma atroviride*) | TRIATDRAFT_239723 | G9NQ55 |
| *Candida orthopsilosis* (strain 90-125) (Yeast) | CORT_0A06350 | H8WY74 |
| *Cyphellophora europaea* CBS 101466 | HMPREF1541_09254 | W2SBP3 |
| *Penicillium oxalicum* (strain 114-2/CGMCC 5302) (*Penicillium decumbens*) | PDE_02656 | S8B080 |
| Penicillium chrysogenum (strain ATCC 28089/DSM 1075/Wisconsin 54-1255) (*Penicillium notatum*) | Pc20g13950 PCH_Pc20g13950 | B6HH32 |
| *Arthroderma gypseum* (strain ATCC MYA-4604/CBS 118893) (*Microsporum gypseum*) | MGYG_07586 | E4V3K6 |
| *Hypocrea virens* (strain Gv29-8/FGSC 10586) (*Gliocladium virens*) (*Trichoderma virens*) | TRIVIDRAFT_91340 | G9MUE6 |
| *Botryotinia fuckeliana* (strain BcDW1) (Noble rot fungus) (*Botrytis cinerea*) | BcDW1_3132 | M7U3N6 |
| *Botryosphaeria parva* (strain UCR-NP2) (Grapevine canker fungus) (*Neofusicoccum parvum*) | UCRNP2_9778 | R1E711 |
| *Cochliobolus sativus* (strain ND90Pr/ATCC 201652) (Common root rot and spot blotch fungus) (*Bipolaris sorokiniana*) | COCSADRAFT_79461 | M2SNB8 |
| *Aspergillus niger* (strain CBS 513.88/FGSC A1513) | An01g00510 | A2Q7F5 |
| *Candida dubliniensis* (strain CD36/ATCC MYA-646/CBS 7987/NCPF 3949/NRRL Y-17841) (Yeast) | CD36_71370 | B9WK39 |
| *Cochliobolus heterostrophus* (strain C4/ATCC 48331/race T) (Southern corn leaf blight fungus) (*Bipolaris maydis*) | COCC4DRAFT_41710 | N4XB06 |
| *Cochliobolus heterostrophus* (strain C5/ATCC 48332/race O) (Southern corn leaf blight fungus) (*Bipolaris maydis*) | COCHEDRAFT_1208754 | M2VA93 |

TABLE 6-continued

Cytochrome P450 enzymes capable of catalyzing selective terminal alkene hydroxylation.

| Species Origin | Gene names | Accession No |
|---|---|---|
| *Aspergillus clavatus* (strain ATCC 1007/CBS 513.65/DSM 816/NCTC 3887/NRRL 1) | ACLA_032820 | A1CSC5 |
| *Hypocrea jecorina* (strain QM6a) (*Trichoderma reesei*) | TRIREDRAFT_103147 | G0R9K0 |
| *Trichophyton tonsurans* (strain CBS 112818) (Scalp ringworm fungus) | TESG_02758 | F2RVB9 |
| *Glarea lozoyensis* (strain ATCC 20868/MF5171) | GLAREA_12102 | S3D2G7 |
| *Trichophyton rubrum* (strain ATCC MYA-4607/CBS 118892) (Athlete's foot fungus) | TERG_03231 | F2SJM4 |
| *Leptosphaeria maculans* (strain JN3/isolate v23.1.3/race Av1-4-5-6-7-8) (Blackleg fungus) (*Phoma lingam*) | LEMA_P073070.1 | E5A7X3 |
| *Cyphellophora europaea* CBS 101466 | HMPREF1541_04444 | W2RWL1 |
| *Hypocrea jecorina* (strain QM6a) (*Trichoderma reesei*) | TRIREDRAFT_65036 | G0RNX6 |
| *Beauveria bassiana* (strain ARSEF 2860) (White muscardine disease fungus) (*Tritirachium shiotae*) | BBA_09022 | J5J6F5 |
| *Cordyceps militaris* (strain CM01) (Caterpillar fungus) | CCM_02084 | G3JCK3 |
| *Trichophyton rubrum* (strain ATCC MYA-4607/CBS 118892) (Athlete's foot fungus) | TERG_05441 | F2SSI7 |
| *Botryotinia fuckeliana* (strain BcDW1) (Noble rot fungus) (*Botrytis cinerea*) | BcDW1_9224 | M7U6H3 |
| *Magnaporthe oryzae* (strain P131) (Rice blast fungus) (*Pyricularia oryzae*) | OOW_P131scaffold01201g5 | L7J0M9 |
| *Magnaporthe oryzae* (strain Y34) (Rice blast fungus) (*Pyricularia oryzae*) | OOU_Y34scaffold00145g13 | L7IJZ9 |
| *Magnaporthe oryzae* (strain 70-15/ATCC MYA-4617/FGSC 8958) (Rice blast fungus) (*Pyricularia oryzae*) | MGG_09920 | G4MR75 |
| *Paracoccidioides lutzii* (strain ATCC MYA-826/Pb01) (*Paracoccidioides brasiliensis*) | PAAG_01378 | C1GS83 |
| *Bipolaris zeicola* 26-R-13 | COCCADRAFT_9928 | W6Y8S8 |
| *Verticillium dahliae* (strain VdLs.17/ATCC MYA-4575/FGSC 10137) (*Verticillium wilt*) | VDAG_04483 | G2X2F9 |
| *Trichophyton verrucosum* (strain HKI 0517) | TRV_02251 | D4D581 |
| *Arthroderma benhamiae* (strain ATCC MYA-4681/CBS 112371) (*Trichophyton mentagrophytes*) | ARB_01131 | D4AY62 |
| *Chaetomium globosum* (strain ATCC 6205/CBS 148.51/DSM 1962/NBRC 6347/NRRL 1970) (Soil fungus) | CHGG_01610 | Q2HDU4 |
| *Magnaporthe poae* (strain ATCC 64411/73-15) (Kentucky bluegrass fungus) | | M4G6C3 |
| *Hypocrea atroviridis* (strain ATCC 20476/IMI 206040) (*Trichoderma atroviride*) | TRIATDRAFT_45536 | G9NQR1 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_03064 | N4W651 |
| *Penicillium chrysogenum* (strain ATCC 28089/DSM 1075/Wisconsin 54-1255) (*Penicillium notatum*) | Pc20g11290 PCH_Pc20g11290 | B6HG66 |
| *Ophiocordyceps sinensis* (strain Co18/CGMCC 3.14243) (Yarsagumba caterpillar fungus) (*Hirsutella sinensis*) | OCS_02874 | T5AG58 |
| *Pyrenophora teres* f. *teres* (strain 0-1) (Barley net blotch fungus) (*Drechslera teres* f. *teres*) | PTT_07245 | E3RH76 |
| *Baudoinia compniacensis* (strain UAMH 10762) (Angels' share fungus) | BAUCODRAFT_71913 | M2MX22 |
| *Podospora anserina* (strain S/ATCC MYA-4624/DSM 980/FGSC 10383) (*Pleurage anserina*) | PODANS_0_160 | B2AFV1 |
| *Aspergillus terreus* (strain NIH 2624/FGSC A1156) | ATEG_05807 | Q0CKH7 |
| *Hypocrea jecorina* (strain QM6a) (*Trichoderma reesei*) | TRIREDRAFT_75713 | G0RDE9 |
| *Claviceps purpurea* (strain 20.1) (Ergot fungus) (*Sphacelia segetum*) | CPUR_06997 | M1WHP2 |
| *Aspergillus flavus* (strain ATCC 200026/FGSC A1120/NRRL 3357/JCM 12722/SRRC 167) | AFLA_128090 | B8NNJ8 |
| *Mycosphaerella fijiensis* (strain CIRAD86) (Black leaf streak disease fungus) (*Pseudocercospora fijiensis*) | MYCFIDRAFT_49209 | M3AV82 |
| *Grosmannia clavigera* (strain kw1407/UAMH 11150) (Blue stain fungus) (*Graphiocladiella clavigera*) | CMQ_2882 | F0XHG6 |
| *Lodderomyces elongisporus* (strain ATCC 11503/CBS 2605/JCM 1781/NBRC 1676/NRRL YB-4239) (Yeast) (*Saccharomyces elongisporus*) | LELG_05768 | A5H2Q3 |

TABLE 6-continued

Cytochrome P450 enzymes capable of catalyzing selective terminal alkene hydroxylation.

| Species Origin | Gene names | Accession No |
|---|---|---|
| *Candida tropicalis* (strain ATCC MYA-3404/T1) (Yeast) | CTRG_03114 | C5MAM2 |
| *Coniosporium apollinis* (strain CBS 100218) (Rock-inhabiting black yeast) | W97_03898 | R7YRY7 |
| *Candida parapsilosis* (strain CDC 317/ATCC MYA-4646) (Yeast) (*Monilia parapsilosis*) | CPAR2_206990 | G8BCR1 |
| *Aspergillus niger* (strain CBS 513.88/FGSC A1513) | An02g10700 | A5AAH7 |
| *Baudoinia compniacensis* (strain UAMH 10762) (Angels' share fungus) | BAUCODRAFT_187941 | M2MV99 |
| *Candida tropicalis* (Yeast) | CYP52B1 | P30611 |
| *Aspergillus kawachii* (strain NBRC 4308) (White koji mold) (*Aspergillus awamori* var. *kawachi*) | AKAW_04070 | G7XG31 |
| *Colletotrichum gloeosporioides* (strain Cg-14) (Anthracnose fungus) (*Glomerella cingulata*) | CGLO_15455 | T0JYY2 |
| *Colletotrichum gloeosporioides* (strain Cg-14) (Anthracnose fungus) (*Glomerella cingulata*) | CGLO_15455 | T0JYY2 |
| *Endocarpon pusillum* (strain Z07020/HMAS-L-300199) (Lichen-forming fungus) | EPUS_09448 | U1HSE1 |
| *Arthroderma gypseum* (strain ATCC MYA-4604/CBS 118893) (*Microsporum gypseum*) | MGYG_00140 | E5R368 |
| *Botryotinia fuckeliana* (strain T4) (Noble rot fungus) (*Botrytis cinerea*) | BofuT4_P052870.1 | G2XWR8 |
| *Exophiala dermatitidis* (strain ATCC 34100/CBS 525.76/NIH/UT8656) (Black yeast) (*Wangiella dermatitidis*) | HMPREF1120_00302 | H6BMQ6 |
| *Aspergillus oryzae* (Yellow koji mold) | CYP52K1 | D4QC15 |
| *Aspergillus oryzae* (strain ATCC 42149/RIB 40) (Yellow koji mold) | AO090010000548 | Q2TWI0 |
| *Neurospora tetrasperma* (strain FGSC 2508/ATCC MYA-4615/P0657) | NEUTE1DRAFT_150004 | F8N2K8 |
| *Sordaria macrospora* (strain ATCC MYA-333/DSM 997/K(L3346)/K-hell) | SMAC_04611 | F7W1Z0 |
| *Neurospora crassa* (strain ATCC 24698/74-OR23-1A/CBS 708.71/DSM 1257/FGSC 987) | NCU09115 | Q7S0G0 |
| *Eutypa lata* (strain UCR-EL1) (Grapevine dieback disease fungus) (*Eutypa armeniacae*) | UCREL1_11542 | M7T4H1 |
| *Neurospora tetrasperma* (strain FGSC 2509/P0656) | NEUTE2DRAFT_153986 | G4U5S9 |
| *Setosphaeria turcica* (strain 28A) (Northern leaf blight fungus) (*Exserohilum turcicum*) | SETTUDRAFT_164879 | R0JQZ4 |
| *Pyrenophora tritici-repentis* (strain Pt-1C-BFP) (Wheat tan spot fungus) (*Drechslera tritici-repentis*) | PTRG_11480 | B2WN31 |
| *Paracoccidioides lutzii* (strain ATCC MYA-826/Pb01) (*Paracoccidioides brasiliensis*) | PAAG_01137 | C1GRJ2 |
| *Neosartorya fischeri* (strain ATCC 1020/DSM 3700/FGSC A1164/NRRL 181) (*Aspergillus fischerianus*) | NFIA_054110 | A1DMP4 |
| *Sphaerulina musiva* (strain SO2202) (Poplar stem canker fungus) (*Septoria musiva*) | SEPMUDRAFT_149283 | M3D461 |
| *Emericella nidulans* (strain FGSC A4/ATCC 38163/CBS 112.46/NRRL 194/M139) (*Aspergillus nidulans*) | AN3917.2 ANIA_03917 | Q5B6B3 |
| *Candida orthopsilosis* (strain 90-125) (Yeast) | CORT_0H01020 | H8XAX0 |
| *Aspergillus oryzae* (strain 3.042) (Yellow koji mold) | Ao3042_10143 | I8I9N9 |
| *Aspergillus flavus* (strain ATCC 200026/FGSC A1120/NRRL 3357/JCM 12722/SRRC 167) | AFLA_074560 | B8MWJ8 |
| *Candida parapsilosis* (strain CDC 317/ATCC MYA-4646) (Yeast) (*Monilia parapsilosis*) | CPAR2_301000 | G8B912 |
| *Aspergillus oryzae* (strain ATCC 42149/RIB 40) (Yellow koji mold) | AO090005000220 | Q2UT03 |
| *Aspergillus oryzae* (Yellow koji mold) | CYP52G4 | D4QC13 |
| *Neosartorya fumigata* (strain ATCC MYA-4609/Af293/CBS 101355/FGSC A1100) (*Aspergillus fumigatus*) | AFUA_9G03090 | Q4WD06 |
| *Botryotinia fuckeliana* (strain T4) (Noble rot fungus) (*Botrytis cinerea*) | BofuT4_P109530.1 | G2Y7G7 |
| *Sclerotinia sclerotiorum* (strain ATCC 18683/1980/Ss-1) (White mold) (*Whetzelinia sclerotiorum*) | SS1G_11430 | A7F1G0 |
| *Pyronema omphalodes* (strain CBS 100304) (*Pyronema confluens*) | PCON_02181 | U4LWN1 |
| *Thielavia heterothallica* (strain ATCC 42464/BCRC 31852/DSM 1799) (*Myceliophthora thermophila*) | MYCTH_2294752 | G2Q2L5 |
| *Pestalotiopsis fici* W106-1 | PFICI_00042 | W3XJN2 |

TABLE 6-continued

Cytochrome P450 enzymes capable of catalyzing selective terminal alkene hydroxylation.

| Species Origin | Gene names | Accession No |
|---|---|---|
| *Eutypa lata* (strain UCR-EL1) (Grapevine dieback disease fungus) (*Eutypa armeniacae*) | UCREL1_5311 | M7TLT9 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_03446 | N4W590 |
| *Colletotrichum graminicola* (strain M1.001/M2/FGSC 10212) (Maize anthracnose fungus) (*Glomerella graminicola*) | GLRG_09839 | E3QV05 |
| *Trichophyton verrucosum* (strain HKI 0517) | TRV_06704 | D4DHP8 |
| *Sphaerulina musiva* (strain SO2202) (Poplar stem canker fungus) (*Septoria musiva*) | SEPMUDRAFT_39329 | M3B7G5 |
| *Nectria haematococca* (strain 77-13-4/ATCC MYA-4622/FGSC 9596/MPVI) (*Fusarium solani* subsp. *pisi*) | NECHADRAFT_31103 | C7YK50 |
| *Coniosporium apollinis* (strain CBS 100218) (Rock-inhabiting black yeast) | W97_03080 | R7YPM4 |
| *Gaeumannomyces graminis* var. *tritici* (strain R3-111a-1) (Wheat and barley take-all root rot fungus) | GGTG_12245 | J3PFH0 |
| *Fusarium pseudograminearum* (strain CS3096) (Wheat and barley crown-rot fungus) | FPSE_11595 | K3V5M1 |
| *Magnaporthe oryzae* (strain P131) (Rice blast fungus) (*Pyricularia oryzae*) | OOW_P131scaffold00556g2 | L7J9P9 |
| *Magnaporthe oryzae* (strain Y34) (Rice blast fungus) (*Pyricularia oryzae*) | OOU_Y34scaffold00501g3 | L7I9Z3 |
| *Magnaporthe oryzae* (strain 70-15/ATCC MYA-4617/FGSC 8958) (Rice blast fungus) (*Pyricularia oryzae*) | MGG_08956 | G4MW35 |
| *Thielavia terrestris* (strain ATCC 38088/NRRL 8126) (*Acremonium alabamense*) | THITE_2057357 | G2RF28 |
| *Gibberella fujikuroi* (strain CBS 195.34/IMI 58289/NRRL A-6831) (Bakanae and foot rot disease fungus) (*Fusarium fujikuroi*) | FFUJ_01480 | S0DIN1 |
| *Pyronema omphalodes* (strain CBS 100304) (*Pyronema confluens*) | PCON_09796 | U4L3P6 |
| *Gibberella moniliformis* (strain M3125/FGSC 7600) (Maize ear and stalk rot fungus) (*Fusarium verticillioides*) | FVEG_01415 | W7LF29 |
| *Magnaporthe oryzae* (strain P131) (Rice blast fungus) (*Pyricularia oryzae*) | OOW_P131scaffold01216g6 | L7IZ69 |
| *Magnaporthe oryzae* (strain 70-15/ATCC MYA-4617/FGSC 8958) (Rice blast fungus) (*Pyricularia oryzae*) | MGG_08494 | G4NAN9 |
| *Fusarium oxysporum* f. sp. *cubense* (strain race 4) (Panama disease fungus) | FOC4_g10003027 | N1RRF1 |
| *Chaetomium thermophilum* (strain DSM 1495/CBS 144.50/IMI 039719) | CTHT_0057700 | G0SCL9 |
| *Botryotinia fuckeliana* (strain BcDW1) (Noble rot fungus) (*Botrytis cinerea*) | BcDW1_5818 | M7UFT7 |
| *Verticillium alfalfae* (strain VaMs.102/ATCC MYA-4576/FGSC 10136) (*Verticillium* wilt of alfalfa) (*Verticillium albo-atrum*) | VDBG_04942 | C9SIR0 |
| *Arthroderma gypseum* (strain ATCC MYA-4604/CBS 118893) (*Microsporum gypseum*) | MGYG_09210 | E4V712 |
| *Uncinocarpus reesii* (strain UAMH 1704) | UREG_00942 | C4JF41 |
| *Bipolaris oryzae* ATCC 44560 | COCMIDRAFT_34506 | W6ZKE3 |
| *Paracoccidioides brasiliensis* (strain Pb03) | PABG_01712 | C0S297 |
| *Paracoccidioides brasiliensis* (strain Pb18) | PADG_03693 | C1G8V7 |
| *Neosartorya fumigata* (strain ATCC MYA-4609/Af293/CBS 101355/FGSC A1100) (*Aspergillus fumigatus*) | AFUA_6G08460 | Q4WMW7 |
| *Neosartorya fumigata* (strain CEA10/CBS 144.89/FGSC A1163) (*Aspergillus fumigatus*) | AFUB_074420 | B0Y7N4 |
| *Aspergillus niger* (strain ATCC 1015/CBS 113.46/FGSC A1144/LSHB Ac4/NCTC 3858a/NRRL 328/USDA 3528.7) | ASPNIDRAFT_189129 | G3XM79 |
| *Coniosporium apollinis* (strain CBS 100218) (Rock-inhabiting black yeast) | W97_05529 | R7YX00 |
| *Aspergillus niger* (strain CBS 513.88/FGSC A1513) | An11g07010 | A2QWZ5 |
| *Aspergillus niger* (strain ATCC 1015/CBS 113.46/FGSC A1144/LSHB Ac4/NCTC 3858a/NRRL 328/USDA 3528.7) | ASPNIDRAFT_56022 | G3YAT8 |
| *Neosartorya fischeri* (strain ATCC 1020/DSM 3700/FGSC A1164/NRRL 181) (*Aspergillus fischerianus*) | NFIA_049440 | A1DLD3 |

TABLE 6-continued

Cytochrome P450 enzymes capable of catalyzing selective terminal alkene hydroxylation.

| Species Origin | Gene names | Accession No |
|---|---|---|
| *Aspergillus oryzae* (strain ATCC 42149/RIB 40) (Yellow koji mold) | AO090010000075 | Q2TXN5 |
| *Aspergillus oryzae* (strain 3.042) (Yellow koji mold) | Ao3042_00404 | I8ABC4 |
| *Aspergillus oryzae* (Yellow koji mold) | CYP584E5 | D4QC66 |
| *Magnaporthe poae* (strain ATCC 64411/73-15) (Kentucky bluegrass fungus) | | M4GA78 |
| *Cladophialophora carrionii* CBS 160.54 | G647_04914 | V9DAX0 |
| *Podospora anserina* (strain S/ATCC MYA-4624/DSM 980/FGSC 10383) (*Pleurage anserina*) | PODANS_1_9520 | B2AY12 |
| *Gibberella zeae* (strain PH-1/ATCC MYA-4620/FGSC 9075/NRRL 31084) (Wheat head blight fungus) (*Fusarium graminearum*) | FG01284.1 FGSG_01284 | I1RCH0 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_05738 | N4VDA5 |
| *Neosartorya fischeri* (strain ATCC 1020/DSM 3700/FGSC A1164/NRRL 181) (*Aspergillus fischerianus*) | NFIA_113870 | A1D8Z5 |
| *Trichophyton verrucosum* (strain HKI 0517) | TRV_00955 | D4D1K4 |
| *Botryotinia fuckeliana* (strain T4) (Noble rot fungus) (*Botrytis cinerea*) | BofuT4_P140470.1 | G2YYT7 |
| *Trichophyton rubrum* (strain ATCC MYA-4607/CBS 118892) (Athlete's foot fungus) | TERG_02747 | F2SKM8 |
| *Botryotinia fuckeliana* (strain T4) (Noble rot fungus) (*Botrytis cinerea*) | BofuT4_P075800.1 | G2XNP1 |
| *Setosphaeria turcica* (strain 28A) (Northern leaf blight fungus) (*Exserohilum turcicum*) | SETTUDRAFT_159435 | R0IYM1 |
| *Bipolaris victoriae FI3* | COCVIDRAFT_96117 | W7ECV3 |
| *Bipolaris zeicola 26-R-13* | COCCADRAFT_86052 | W6YCN0 |
| *Podospora anserina* (strain S/ATCC MYA-4624/DSM 980/FGSC 10383) (*Pleurage anserina*) | PODANS_3_1920 | B2AZX1 |
| *Sporothrix schenckii* (strain ATCC 58251/de Perez 2211183) (Rose-picker's disease fungus) | HMPREF1624_01101 | U7Q4H5 |
| *Exophiala dermatitidis* (strain ATCC 34100/CBS 525.76/NIH/UT8656) (Black yeast) (*Wangiella dermatitidis*) | HMPREF1120_04188 | H6BWM7 |
| *Colletotrichum gloeosporioides* (strain Cg-14) (Anthracnose fungus) (*Glomerella cingulata*) | CGLO_16096 | T0JPF3 |
| *Arthroderma benhamiae* (strain ATCC MYA-4681/CBS 112371) (*Trichophyton mentagrophytes*) | ARB_05099 | D4ALA2 |
| *Macrophomina phaseolina* (strain MS6) (Charcoal rot fungus) | MPH_10488 | K2QR42 |
| *Trichophyton tonsurans* (strain CBS 112818) (Scalp ringworm fungus) | TESG_05856 | F2S4I4 |
| *Trichophyton equinum* (strain ATCC MYA-4606/CBS 127.97) (Horse ringworm fungus) | TEQG_04559 | F2PUI2 |
| *Arthroderma benhamiae* (strain ATCC MYA-4681/CBS 112371) (*Trichophyton mentagrophytes*) | ARB_07892 | D4AUH5 |
| *Arthroderma otae* (strain ATCC MYA-4605/CBS 113480) (*Microsporum canis*) | MCYG_08648 | C5G126 |
| *Aspergillus flavus* (strain ATCC 200026/FGSC A1120/NRRL 3357/JCM 12722/SRRC 167) | AFLA_116530 | B8NVG6 |
| *Mycosphaerella graminicola* (strain CBS 115943/IPO323) (Speckled leaf blotch fungus) (*Septoria tritici*) | CYP-28MYCGRDRAFT_111399 | F9XPH9 |
| *Penicillium chrysogenum* (strain ATCC 28089/DSM 1075/Wisconsin 54-1255) (*Penicillium notatum*) | Pc18g04990 PCH_Pc18g04990 | B6HBW9 |
| *Alternaria solani* | alt2 | Q5KTN2 |
| *Colletotrichum higginsianum* (strain IMI 349063) (Crucifer anthracnose fungus) | CH063_05380 | H1UYS7 |
| *Thielavia heterothallica* (strain ATCC 42464/BCRC 31852/DSM 1799) (*Myceliophthora thermophila*) | MYCTH_2060315 | G2QDC4 |
| *Togninia minima* (strain UCR-PA7) (Esca disease fungus) (*Phaeoacremonium aleophilum*) | UCRPA7_1480 | R8BUP2 |
| *Ophiostoma piceae* (strain UAMH 11346) (Sap stain fungus) | F503_00556 | S3C2T4 |
| *Cladophialophora carrionii* CBS 160.54 | G647_02236 | V9DGM2 |
| *Botryotinia fuckeliana* (strain BcDW1) (Noble rot fungus) (*Botrytis cinerea*) | BcDW1_141 | M7UBZ7 |
| *Mycobacterium* sp. HXN-1500 | cyp153 | Q65A64 |
| *Gordonia amicalis* NBRC 100051 = JCM 11271 | GOAMI_64_00090 | L7L6P4 |
| *Mycobacterium austroafricanum* | | B6UKY3 |
| *Mycobacterium* sp. ENV421 | ahpG | I7CD96 |
| uncultured bacterium | cyp153 | W0UDE1 |

TABLE 6-continued

Cytochrome P450 enzymes capable of catalyzing selective terminal alkene hydroxylation.

| Species Origin | Gene names | Accession No |
|---|---|---|
| uncultured bacterium | P450 | Q33DR8 |
| uncultured bacterium | P450 | Q33DR9 |
| uncultured bacterium | cyp153 | W0UDG2 |
| uncultured bacterium | cyp153 | W0UDM1 |
| uncultured bacterium | cyp153 | W0UCX8 |
| uncultured bacterium | cyp153 | W0UAP1 |
| uncultured bacterium | cyp153 | W0UCW9 |
| Polaromonas sp. (strain JS666/ATCC BAA-500) | Bpro_5301 | Q11ZY2 |
| uncultured bacterium | cyp153 | W0UDK1 |
| uncultured bacterium | cyp153 | W0UD29 |
| uncultured bacterium | cyp153 | W0UD32 |
| uncultured bacterium | cyp153 | W0UD27 |
| uncultured bacterium | cyp153 | W0UAW2 |
| uncultured bacterium | cyp153 | W0UAW6 |
| Parvibaculum sp. S13-6 | CYP153A | C7A8P8 |
| uncultured bacterium | cyp153 | W0UDM5 |
| uncultured bacterium | cyp153 | W0UD31 |
| uncultured bacterium | cyp153 | W0UDB6 |
| Parvibaculum sp. S13-5 | CYP153A | C7A8P2 |
| uncultured bacterium | P450 | Q33DS1 |
| uncultured bacterium | cyp153 | W0UDK5 |
| uncultured bacterium | cyp153 | W0UDU1 |
| Tistrella mobilis | CYP153A | C7A8Q6 |
| uncultured bacterium | cyp153 | W0UDS7 |
| Parvibaculum sp. S13-6 | CYP153A | C7A8P9 |
| uncultured bacterium | cyp153 | W0UB47 |
| Parvibaculum sp. S13-6 | CYP153A | C7A8P7 |
| gamma proteobacterium S10-1 | CYP153A | C7A8N2 |
| uncultured bacterium | cyp153 | W0UDS4 |
| uncultured bacterium | cyp153 | W0UAY8 |
| uncultured bacterium | cyp153 | W0UDB2 |
| uncultured bacterium | cyp153 | W0UB02 |
| uncultured bacterium | cyp153 | W0UDV5 |
| uncultured bacterium | cyp153 | W0UDM7 |
| uncultured bacterium | cyp153 | W0UD83 |
| uncultured bacterium | cyp153 | W0UD50 |
| Parvibaculum sp. S13-5 | CYP153A | C7A8P4 |
| Parvibaculum sp. S18-4 | CYP153A | C7A8S8 |
| Parvibaculum sp. S18-4 | CYP153A | C7A8S9 |
| uncultured bacterium | cyp153 | W0UB69 |
| Parvibaculum sp. S13-5 | CYP153A | C7A8P5 |
| uncultured bacterium | cyp153 | W0UDU6 |
| uncultured bacterium | cyp153 | W0UDD0 |
| uncultured bacterium | cyp153 | W0UDA8 |
| uncultured bacterium | cyp153 | W0UDC3 |
| uncultured bacterium | cyp153 | W0UDF5 |
| uncultured bacterium | cyp153 | W0UDD2 |
| uncultured bacterium | cyp153 | W0UD99 |
| uncultured bacterium | cyp153 | W0UB78 |
| uncultured bacterium | cyp153 | W0UDU2 |
| uncultured bacterium | cyp153 | W0UD95 |
| uncultured bacterium | cyp153 | W0UDT1 |
| uncultured bacterium | cyp153 | W0UD70 |
| uncultured bacterium | cyp153 | W0UAV3 |
| uncultured bacterium | cyp153 | W0UDJ0 |
| Parvibaculum sp. S18-4 | CYP153A | C7A8S7 |
| uncultured bacterium | cyp153 | W0UD49 |
| uncultured bacterium | cyp153 | W0UB74 |
| uncultured bacterium | cyp153 | W0UDG4 |
| uncultured bacterium | cyp153 | W0UDJ4 |
| uncultured bacterium | cyp153 | W0UDL1 |
| uncultured bacterium | cyp153 | W0UD80 |
| uncultured bacterium | cyp153 | W0UDP8 |
| uncultured bacterium | cyp153 | W0UDS6 |
| uncultured bacterium | cyp153 | W0UDC9 |
| uncultured bacterium | cyp153 | W0UDE6 |
| uncultured bacterium | cyp153 | W0UDU9 |
| uncultured bacterium | cyp153 | W0UDC0 |
| uncultured bacterium | cyp153 | W0UDW1 |
| uncultured bacterium | cyp153 | W0UDT4 |
| uncultured bacterium | cyp153 | W0UDB5 |
| uncultured bacterium | cyp153 | W0UB64 |
| uncultured bacterium | cyp153 | W0UDA3 |
| uncultured bacterium | cyp153 | W0UDR7 |
| uncultured bacterium | cyp153 | W0UB52 |

TABLE 6-continued

Cytochrome P450 enzymes capable of catalyzing selective terminal alkene hydroxylation.

| Species Origin | Gene names | Accession No |
| --- | --- | --- |
| uncultured bacterium | cyp153 | W0UDA5 |
| uncultured bacterium | cyp153 | W0UDT6 |
| *Caulobacter* sp. (strain K31) | Caul_0020 | B0T154 |
| uncultured bacterium | cyp153 | W0UCV6 |
| uncultured bacterium | cyp153 | W0UCU1 |
| uncultured bacterium | cyp153 | W0UDK0 |
| uncultured bacterium | cyp153 | W0UDI6 |
| uncultured bacterium | cyp153 | W0UAU9 |
| uncultured bacterium | cyp153 | W0UAZ2 |
| uncultured bacterium | cyp153 | W0UD75 |
| uncultured bacterium | cyp153 | W0UD14 |
| uncultured bacterium | cyp153 | W0UB97 |
| uncultured bacterium | cyp153 | W0UD23 |
| uncultured bacterium | cyp153 | W0UD18 |
| uncultured bacterium | cyp153 | W0UDQ2 |
| uncultured bacterium | cyp153 | W0UDH4 |
| uncultured bacterium | cyp153 | W0UAT6 |
| uncultured bacterium | cyp153 | W0UD79 |
| uncultured bacterium | cyp153 | W0UAN4 |
| uncultured bacterium | cyp153 | W0UDW9 |
| uncultured bacterium | cyp153 | W0UCZ3 |
| uncultured bacterium | cyp153 | W0UCZ3 |
| *Erythrobacter* sp. S11-13 | CYP153A | C7A8R4 |
| uncultured bacterium | cyp153 | W0UDK7 |
| *Parvibaculum* sp. S13-5 | CYP153A | C7A8P3 |
| uncultured bacterium | cyp153 | W0UDS2 |
| uncultured bacterium | cyp153 | W0UD84 |
| uncultured bacterium | cyp153 | W0UD90 |
| uncultured bacterium | cyp153 | W0UB38 |
| uncultured bacterium | cyp153 | W0UCW4 |
| uncultured bacterium | cyp153 | W0UB22 |
| uncultured bacterium | cyp153 | W0UDQ8 |
| uncultured Rhizobiales bacterium HF4000_48A13 | | E0XZ55 |
| uncultured Rhizobiales bacterium HF4000_48A13 | | E0XZ44 |
| uncultured bacterium | P450 | Q33DS2 |
| uncultured bacterium | P450 | Q33DS0 |
| uncultured bacterium | cyp153 | W0UDB4 |
| *Erythrobacter flavus* | | C5MKK1 |
| uncultured bacterium | cyp153 | W0UD08 |
| uncultured bacterium | cyp153 | W0UCW2 |
| *Sphingobium* sp. S13-2 | CYP153A | C7A8P1 |
| *Sphingopyxis* sp. S16-14 | CYP153A | C7A8R8 |
| uncultured bacterium | cyp153 | W0UD46 |
| *Parvibaculum* sp. S13-6 | CYP153A | C7A8P6 |
| uncultured bacterium | cyp153 | W0UDQ1 |
| uncultured bacterium | cyp153 | W0UB27 |
| uncultured bacterium | cyp153 | W0UD73 |
| uncultured bacterium | cyp153 | W0UDE2 |
| uncultured bacterium | cyp153 | W0UD17 |
| *Erythrobacter* sp. S17-1 | CYP153A | C7A8R9 |
| uncultured bacterium | cyp153 | W0UD15 |
| uncultured bacterium | cyp153 | W0UAU6 |
| *Erythrobacter flavus* | CYP153A | C7A8N4 |
| uncultured bacterium | cyp153 | W0UDD6 |
| uncultured bacterium | cyp153 | W0UDP1 |
| uncultured bacterium | cyp153 | W0UDF8 |
| uncultured bacterium | cyp153 | W0UDN8 |
| uncultured bacterium | cyp153 | W0UDD3 |
| uncultured bacterium | cyp153 | W0UDN1 |
| uncultured bacterium | cyp153 | W0UDK3 |
| uncultured bacterium | cyp153 | W0UD11 |
| uncultured bacterium | cyp153 | W0UB85 |
| uncultured bacterium | cyp153 | W0UDI2 |
| *Bradyrhizobium* sp. CCGE-LA001 | BCCGELA001_36078 | W1JJD5 |
| uncultured bacterium | cyp153 | W0UDP5 |
| uncultured bacterium | cyp153 | W0UB19 |
| uncultured bacterium | cyp153 | W0UAL6 |
| uncultured bacterium | cyp153 | W0UDN3 |
| uncultured bacterium | cyp153 | W0UD72 |
| uncultured bacterium | cyp153 | W0UCX1 |
| uncultured bacterium | cyp153 | W0UDF6 |
| uncultured bacterium | cyp153 | W0UD00 |
| uncultured bacterium | cyp153 | W0UD65 |

TABLE 6-continued

Cytochrome P450 enzymes capable of catalyzing selective terminal alkene hydroxylation.

| Species Origin | Gene names | Accession No |
|---|---|---|
| *Caulobacter* sp. AP07 | PMI01_00728 | J2H335 |
| *Parvibaculum lavamentivorans* (strain DS-1/ DSM 13023/NCIMB 13966) | Plav_1765 | A7HU01 |
| uncultured bacterium | P450 | Q33DS3 |
| uncultured bacterium | cyp153 | W0UDH8 |
| *Erythrobacter flavus* | CYP153A | C7A8R2 |
| *Erythrobacter* sp. S2-1 | CYP153A | C7A8K9 |
| *Erythrobacter citreus* | CYP153A | C7A8R1 |
| *Erythrobacter citreus* | CYP153A | C7A8R3 |
| *Erythrobacter flavus* | CYP153A | C7A8N5 |
| uncultured bacterium | cyp153 | W0UD37 |
| *Erythrobacter* sp. S14-1 | CYP153A | C7A8Q4 |
| uncultured bacterium | cyp153 | W0UDF2 |
| uncultured bacterium | cyp153 | W0UDR6 |
| uncultured bacterium | cyp153 | W0UAN1 |
| uncultured bacterium | cyp153 | W0UCX5 |
| uncultured bacterium | cyp153 | W0UD38 |
| uncultured bacterium | cyp153 | W0UDM9 |
| uncultured bacterium | cyp153 | W0UCW7 |
| uncultured bacterium | cyp153 | W0UB12 |
| uncultured bacterium | cyp153 | W0UD04 |
| uncultured bacterium | cyp153 | W0UDQ6 |
| *Sphingopyxis macrogoltabida* (*Sphingomonas macrogoltabidus*) | ahpG1 | Q5F4D9 |
| *Afipia broomeae* ATCC 49717 | HMPREF9695_03199 | K8P5Q2 |
| uncultured bacterium | cyp153 | W0UD96 |
| *Parvibaculum* sp. S18-4 | CYP153A | C7A8S5 |
| uncultured bacterium | cyp153 | W0UAN7 |
| uncultured bacterium | cyp153 | W0UCS9 |
| uncultured bacterium | cyp153 | W0UDX6 |
| uncultured bacterium | cyp153 | W0UDB7 |
| uncultured bacterium | cyp153 | W0UD56 |
| uncultured bacterium | cyp153 | W0UD44 |
| *Parvibaculum lavamentivorans* (strain DS-1/ DSM 13023/NCIMB 13966) | Plav_2128 | A7HV09 |
| *Caulobacter crescentus* (strain NA1000/ CB15N) | CCNA_00061 | B8GXF2 |
| *Caulobacter crescentus* (strain ATCC 19089/ CB15) | CC_0063 | Q9AC06 |
| *Parvibaculum lavamentivorans* (strain DS-1/ DSM 13023/NCIMB 13966) | Plav_0025 | A7HP15 |
| *Caulobacter segnis* (strain ATCC 21756/DSM 7131/JCM 7823/NBRC 15250/LMG 17158/ TK0059) (*Mycoplana segnis*) | Cseg_0011 | D5VDJ3 |
| *Novosphingobium* sp. PP1Y | PP1Y_AT31178 | F6IH26 |
| uncultured bacterium | cyp153 | W0UDC7 |
| uncultured bacterium | cyp153 | W0UDA2 |
| uncultured bacterium | cyp153 | W0UDP7 |
| *Parvibaculum* sp. S18-4 | CYP153A | C7A8S6 |
| uncultured bacterium | cyp153 | W0UAK6 |
| uncultured bacterium | cyp153 | W0UD52 |
| uncultured bacterium | cyp153 | W0UCU6 |
| uncultured bacterium | cyp153 | W0UCR4 |
| uncultured bacterium | cyp153 | W0UCS6 |
| uncultured bacterium | cyp153 | W0UDV6 |
| uncultured bacterium | cyp153 | W0UDY0 |
| uncultured bacterium | cyp153 | W0UDF0 |
| uncultured bacterium | cyp153 | W0UDF0 |
| uncultured bacterium | cyp153 | W0UAV7 |
| uncultured bacterium | cyp153 | W0UDL7 |
| *Bradyrhizobium* sp. STM 3843 | BRAS3843_1530026 | H0THQ7 |
| *Bradyrhizobium* sp. (strain ORS278) | BRADO1446 | A4YN62 |
| *Bradyrhizobium* sp. (strain BTAi1/ATCC BAA-1182) | BBta_6659 | A5EQW5 |
| *Caulobacter crescentus* OR37 | OR37_01714 | R0EKG8 |
| *Afipia broomeae* ATCC 49717 | HMPREF9695_03200 | K8P2K6 |
| *Afipia clevelandensis* ATCC 49720 | HMPREF9696_02236 | K8P5K9 |
| Bradyrhizobiaceae bacterium SG-6C | CSIRO_4275 | F7QRQ2 |
| *Novosphingobium pentaromativorans* US6-1 | ahpG3 NSU_pLA1167 | G6EL94 |
| marine gamma proteobacterium HTCC2143 | GP2143_12206 | A0YHG8 |
| *Sphingopyxis macrogoltabida* (*Sphingomonas macrogoltabidus*) | ahpG2 | Q5F4D6 |
| uncultured bacterium | cyp153 | W0UD98 |
| uncultured bacterium | cyp153 | W0UAZ7 |
| uncultured bacterium | cyp153 | W0UCU0 |

TABLE 6-continued

Cytochrome P450 enzymes capable of catalyzing selective terminal alkene hydroxylation.

| Species Origin | Gene names | Accession No |
|---|---|---|
| uncultured bacterium | cyp153 | W0UCW6 |
| *Bradyrhizobium* sp. ORS 375 | BRAO375_960079 | H0SSR8 |
| *Bradyrhizobium* sp. ORS 285 | BRAO285_1310010 | H0RSU1 |
| *Bradyrhizobium* sp. STM 3809 | BRAS3809_1790009 | H0SVY3 |
| *Rhodopseudomonas palustris* (strain BisA53) | RPE_4309 | Q07IK1 |
| *Bradyrhizobium* sp. YR681 | PMI42_06128 | J3CQJ7 |
| *Bradyrhizobium* sp. STM 3843 | BRAS3843_1530027 | H0THQ8 |
| *Rhodopseudomonas palustris* (strain BisB18) | RPC_4264 | Q20YJ8 |
| *Caulobacter* sp. (strain K31) | Caul_5296 | B0T9L7 |
| *Sphingopyxis macrogoltabida* (*Sphingomonas macrogoltabidus*) | ahpG3 | Q5F4D3 |
| *Bradyrhizobium oligotrophicum* S58 | S58_15720 | M4ZMZ3 |
| *Bradyrhizobium diazoefficiens* (strain JCM 10833/IAM 13628/NBRC 14792/USDA 110) | blr7242 | Q89E45 |
| uncultured bacterium | cyp153 | W0UAK0 |
| uncultured bacterium | cyp153 | W0UD34 |
| *Bradyrhizobium oligotrophicum* S58 | S58_15730 | M4Z3Y5 |
| *Erythrobacter litoralis* (strain HTCC2594) | ELI_14945 | Q2N5G0 |
| *Erythrobacter* sp. SD-21 | ED21_32074 | A5PDG4 |
| *Bradyrhizobium* sp. DFCI-1 | C207_05440 | U1GV14 |
| *Bradyrhizobium* sp. DFCI-1 | C207_05439 | U1HA94 |
| *Bradyrhizobium diazoefficiens* (strain JCM 10833/IAM 13628/NBRC 14792/USDA 110) | blr7243 | Q89E44 |
| *Rhodopseudomonas palustris* (strain TIE-1) | Rpal_1803 | B3Q8D0 |
| *Bradyrhizobium* sp. CCGE-LA001 | BCCGELA001_36088 | W1JKM5 |
| *Parvibaculum lavamentivorans* (strain DS-1/DSM 13023/NCIMB 13966) | Plav_1782 | A7HU17 |
| *Rhodopseudomonas palustris* (strain ATCC BAA-98/CGA009) | RPA1613 | Q6N9D6 |
| *Bradyrhizobium* sp. S23321 | S23_58660 | I0GE69 |
| *Bradyrhizobium* sp. ORS 285 | BRAO285_1310011 | H0RSU2 |
| *Bradyrhizobium* sp. ORS 375 | BRAO375_960081 | H0SSR9 |
| *Bradyrhizobium* sp. (strain BTAi1/ATCC BAA-1182) | BBta_6660 | A5EQW6 |
| *Bradyrhizobium japonicum* USDA 6 | BJ6T_79720 | G7DEP2 |
| uncultured bacterium | cyp153 | W0UDA7 |
| uncultured bacterium | cyp153 | W0UDB9 |
| *Afipia* sp. P52-10 | X566_03415 | W3RJ54 |
| *Afipia* sp. P52-10 | X566_20970 | W3RG92 |
| marine gamma proteobacterium HTCC2143 | GP2143_06774 | A0YGV8 |
| *Afipia* sp. P52-10 | X566_16815 | W3RJ04 |
| *Bradyrhizobium japonicum* USDA 6 | BJ6T_21500 | G7D7D2 |
| *Bradyrhizobium* sp. WSM471 | Bra471DRAFT_06475 | H5YKH9 |
| *Bradyrhizobium* sp. S23321 | S23_58670 | I0GE70 |
| *Rhodopseudomonas palustris* (strain DX-1) | Rpdx1_3910 | E6VIP2 |
| *Bradyrhizobium* sp. STM 3809 | BRAS3809_1790008 | H0SVY2 |
| *Bradyrhizobium* sp. (strain ORS278) | BRADO1445 | A4YN61 |
| *Rhodopseudomonas palustris* (strain HaA2) | RPB_3934 | Q2IT33 |
| *Rhodopseudomonas palustris* (strain BisB5) | RPD_3694 | Q132S4 |
| *Phenylobacterium zucineum* (strain HLK1) | p450 PHZ_c0813 | B4RGA3 |
| *Bradyrhizobium* sp. WSM1253 | Bra1253DRAFT_03743 | I2QGW7 |
| *Bradyrhizobium* sp. WSM471 | Bra471DRAFT_06476 | H5YKI0 |
| *Bradyrhizobium* sp. WSM1253 | Bra1253DRAFT_03744 | I2QGW8 |
| *Bradyrhizobium japonicum* USDA 6 | BJ6T_21490 | G7D7D1 |
| *Bradyrhizobium* sp. YR681 | PMI42_06129 | J2WD32 |
| *Afipia* sp. P52-10 | X566_20975 | W3RG20 |
| gamma proteobacterium NOR5-3 | NOR53_2355 | B8KH72 |
| *Bradyrhizobium* sp. CCGE-LA001 | BCCGELA001_12206 | W1JZ89 |
| marine gamma proteobacterium HTCC2148 | GPB2148_2599 | B7RZN8 |
| gamma proteobacterium BDW918 | DOK_00120 | I2JQ45 |
| *Congregibacter litoralis* KT71 | KT71_14444 | A4A7Y2 |
| *Bradyrhizobium diazoefficiens* (strain JCM 10833/IAM 13628/NBRC 14792/USDA 110) | blr1853 | H7C6Q5 |
| *Bradyrhizobium japonicum* | id311 | Q9AND6 |
| uncultured bacterium | cyp153 | W0UCV0 |
| uncultured bacterium | cyp153 | W0UAD7 |
| *Pseudomonas* sp. 19-rlim | | G3LGZ6 |
| *Bradyrhizobium* sp. WSM1253 | Bra1253DRAFT_06024 | I2QN59 |
| *Bradyrhizobium* sp. WSM471 | Bra471DRAFT_01541 | H5Y7S1 |
| uncultured gamma proteobacterium EB000_65A11 | | E0XZZ2 |
| marine gamma proteobacterium HTCC2148 | GPB2148_1452 | B7RXX8 |
| marine gamma proteobacterium HTCC2143 | GP2143_15156 | A0Y901 |
| *Afipia* sp. P52-10 | X566_17435 | W3RGW1 |
| gamma proteobacterium NOR5-3 | NOR53_537 | B8KPR5 |

TABLE 6-continued

Cytochrome P450 enzymes capable of catalyzing selective terminal alkene hydroxylation.

| Species Origin | Gene names | Accession No |
|---|---|---|
| *Glaciecola psychrophila* 170 | C427_3047 GPSY_3092 | K7ADG3 |
| *Marinobacter lipolyticus* SM19 | MARLIPOL_15764 | R8AWZ8 |
| gamma proteobacterium IMCC3088 | IMCC3088_2432 | F3L451 |
| uncultured bacterium | P450 | Q33DT3 |
| uncultured bacterium | P450 | Q33DS9 |
| uncultured bacterium | P450 | Q33DS8 |
| uncultured bacterium | cyp153 | W0UD71 |
| *Congregibacter litoralis* KT71 | KT71_02837 | A4A779 |
| marine gamma proteobacterium HTCC2080 | MGP2080_14441 | A0Z7J1 |
| *Marinobacter santoriniensis* NKSG1 | MSNKSG1_10343 | M7CRK4 |
| *Alcanivorax hongdengensis* | | G1C7P2 |
| *Alcanivorax* sp. DG881 | ADG881_2620 | B4WXL2 |
| uncultured bacterium | P450 | Q33DS6 |
| uncultured bacterium | cyp153 | W0UCP6 |
| uncultured bacterium | cyp153 | W0UCQ6 |
| *Ochrobactrum anthropi* | CYP153A | C7A8M0 |
| uncultured bacterium | cyp153 | W0UCN8 |
| uncultured bacterium | cyp153 | W0UCT1 |
| uncultured bacterium | cyp153 | W0UCT1 |
| uncultured bacterium | cyp153 | W0UAI3 |
| gamma proteobacterium HIMB55 | OMB55_00002070 | H3NWG4 |
| *Bradyrhizobium* sp. DFCI-1 | C207_06143 | U1H776 |
| gamma proteobacterium HIMB55 | OMB55_00014510 | H3NWP3 |
| marine gamma proteobacterium HTCC2080 | MGP2080_06587 | A0Z166 |
| *Burkholderia xenovorans* (strain LB400) | Bxe_A3593 | Q143U3 |
| *Alcanivorax* sp. P2S70 | Q670_08165 | U7G5C1 |
| *Marinobacter hydrocarbonoclasticus* ATCC 49840 | MARHY3773 | H8WA08 |
| *Marinobacter* sp. EVN1 | Q672_10645 | U7NYR4 |
| uncultured bacterium | P450 | Q33DS4 |
| uncultured bacterium | cyp153 | W0UDA1 |
| uncultured bacterium | cyp153 | W0UCR5 |
| uncultured bacterium | cyp153 | W0UD97 |
| uncultured bacterium | cyp153 | W0UD81 |
| uncultured bacterium | cyp153 | W0UCN3 |
| uncultured bacterium | cyp153 | W0UCN5 |
| uncultured bacterium | cyp153 | W0UCT3 |
| gamma proteobacterium HdN1 | ahpG HDN1F_17560 | E1VKJ7 |
| *Marinobacter adhaerens* (strain HP15) | HP15_p187g148 | E4PSB0 |
| uncultured bacterium | P450 | Q33DT0 |
| uncultured bacterium | P450 | Q33DS5 |
| uncultured bacterium | cyp153 | W0UD61 |
| uncultured bacterium | P450 | Q33DT1 |
| *Alcanivorax hongdengensis* | | B3U002 |
| uncultured bacterium | P450 | Q33DT2 |
| uncultured bacterium | P450 | Q33DS7 |
| uncultured bacterium | cyp153 | W0UCL9 |
| uncultured bacterium | cyp153 | W0UDB3 |
| *Hyphomonas neptunium* (strain ATCC 15444) | HNE_2042 | Q0C0K3 |
| *Alcanivorax dieselolei* (strain DSM 16502/ CGMCC 1.3690/B-5) | ahpG B5T_02075 | K0C9X8 |
| *Alcanivorax hongdengensis* A-11-3 | A11A3_15327 | L0WAH6 |
| *Alcanivorax dieselolei* | p450 | D0Q1H3 |
| *Alcanivorax pacificus* W11-5 | S7S_02138 | K2GI89 |
| *Marinobacter* sp. ES-1 | Q666_09590 | U7G612 |
| *Limnobacter* sp. MED105 | LMED105_04587 | A6GLB5 |
| *Marinobacter aquaeolei* (strain ATCC 700491/ DSM 11845/VT8) (*Marinobacter hydrocarbonoclasticus* (strain DSM 11845)) | Maqu_0600 | A1TY82 |
| *Marinobacter* sp. EVN1 | Q672_13925 | U7NUC4 |
| *Marinobacter* sp. EN3 | Q673_05250 | U7H5S5 |
| *Marinobacter manganoxydans* MnI7-9 | KYE_03215 | G6YPH4 |
| *Marinobacter hydrocarbonoclasticus* ATCC 49840 | ahpG2 MARHY2838 | H8WCT8 |
| *Marinobacter hydrocarbonoclasticus* (*Pseudomonas nautica*) | ahpG2 MARHY2838 | D9UAS2 |
| *Patulibacter medicamentivorans* | PAI11_40170 | H0EAZ2 |
| *Acinetobacter baumannii* WC-141 | ACINWC141_2468 | K8ZRD3 |
| *Saccharomonospora marina* XMU15 | SacmaDRAFT_5365 | H5X733 |
| *Mycobacterium marinum* (strain ATCC BAA-535/M) | cyp153A16 MMAR_3154 | B2HGN5 |
| *Mycobacterium abscessus* 3A-0930-R | p450 MA3A0930R_2169 | I9I3J4 |
| *Mycobacterium abscessus* 3A-0930-S | p450 MA3A0930S_1729 | I9I1F6 |
| *Mycobacterium abscessus* 3A-0731 | p450 MA3A0731_2042 | I9GVU0 |
| *Mycobacterium abscessus* 3A-0119-R | p450 MA3A0119R_2089 | I9FPY3 |
| *Mycobacterium abscessus* 6G-0728-R | p450 MA6G0728R_2104 | I9DR77 |

TABLE 6-continued

Cytochrome P450 enzymes capable of catalyzing selective terminal alkene hydroxylation.

| Species Origin | Gene names | Accession No |
|---|---|---|
| *Mycobacterium abscessus* subsp. *bolletii* 1S-154-0310 | p450 MM1S1540310__1492 | I9CBZ2 |
| *Mycobacterium abscessus* 6G-0728-5 | p450 MA6G0728S__5133 | I9A485 |
| *Mycobacterium abscessus* 3A-0810-R | p450 MM3A0810R__2169 | I8Q799 |
| *Mycobacterium abscessus* 3A-0122-S | p450 MA3A0122S__1691 | I8LTR4 |
| *Mycobacterium abscessus* 3A-0122-R | p450 MA3A0122R__2136 | I8L4A4 |
| *Mycobacterium abscessus* 6G-0212 | p450 MA6G0212__2171 | I8I9K7 |
| *Mycobacterium abscessus* subsp. *bolletii* 1S-153-0915 | p450 MM1S1530915__1484 | I8H4G3 |
| *Mycobacterium abscessus* subsp. *bolletii* 1S-152-0914 | p450 MM1S1520914__2142 | I8GFC6 |
| *Mycobacterium abscessus* subsp. *bolletii* 1S-151-0930 | p450 MM1S1510930__1936 | I8G1R8 |
| *Mycobacterium abscessus* 6G-1108 | p450 MA6G1108__2106 | I8G118 |
| *Mycobacterium abscessus* 6G-0125-S | p450 MA6G0125S__2116 | I8F2E6 |
| *Mycobacterium abscessus* 6G-0125-R | p450 MA6G0125R__1143 | I8EZ93 |
| *Mycobacterium abscessus* subsp. *bolletii* 2B-0307 | p450 MM2B0307__1166 | I9EQ97 |
| *Mycobacterium abscessus* subsp. *bolletii* 2B-0107 | p450 MM2B0107__1179 | I8Q7R9 |
| *Mycobacterium abscessus* subsp. *bolletii* 2B-1231 | p450 MM2B1231__1908 | I8PT86 |
| *Mycobacterium abscessus* subsp. *bolletii* 2B-0912-S | p450 MM2B0912S__1850 | I8KHB7 |
| *Mycobacterium abscessus* subsp. *bolletii* 2B-0912-R | p450 MM2B0912R__2246 | I8JU18 |
| *Mycobacterium abscessus* subsp. *bolletii* 2B-0626 | p450 MM2B0626__1842 | I8HVB7 |
| uncultured bacterium | cyp153 | W0UAF0 |
| *Parvibaculum lavamentivorans* (strain DS-1/DSM 13023/NCIMB 13966) | Plav__1951 | A7HUI3 |
| *Alcanivorax hongdengensis* | | G1C7L3 |
| *Alcanivorax* sp. DG881 | ADG881__2119 | B4X0H6 |
| *Marinobacter* sp. C1S70 | Q667__02605 | U7NVJ0 |
| marine gamma proteobacterium HTCC2143 | GP2143__06784 | A0YGW0 |
| *Alcanivorax* sp. P2S70 | Q670__00635 | U7G5B3 |
| *Marinobacter goseongensis* | p450 | T1WMH0 |
| gamma proteobacterium BDW918 | DOK__13444 | I2JHG9 |
| *Hirschia baltica* (strain ATCC 49814/DSM 5838/IFAM 1418) | Hbal__0836 | C6XQ13 |
| *Acinetobacter indicus* CIP 110367 | P253__02820 | V2UD76 |
| *Acinetobacter indicus* ANC 4215 | F956__01111 | S3N495 |
| *Acinetobacter* sp. OC4 | cyp | Q2MHE2 |
| *Acinetobacter baumannii* NIPH 527 | F921__03852 | N9HTE2 |
| *Acinetobacter* sp. CIP 102129 | F973__00680 | N8UI43 |
| *Acinetobacter* sp. NIPH 809 | F993__03507 | N8P4U1 |
| *Acinetobacter baumannii* OIFC0162 | ACIN5162__A0021 | K5DS46 |
| *Acinetobacter* sp. EB104 | nonM | Q93SX3 |
| *Dietzia cinnamea* P4 | ES5__05410 | E6J787 |
| *Acinetobacter* sp. WC-743 | ACINWC743__A0288 | L9LSK8 |
| *Acinetobacter baumannii* WC-348 | ACINWC348__A0080 | K9B8A0 |
| *Acinetobacter baumannii* WC-141 | ACINWC141__A0026 | K8ZRU7 |
| *Acinetobacter baumannii* WC-323 | ACINWC323__A0095 | K9AWS1 |
| *Gordonia malaquae* NBRC 108250 | GM1__050__00120 | M3VCF1 |
| *Rhodococcus erythropolis* SK121 | RHOER0001__0266 | C3JL15 |
| *Acinetobacter* sp. COS3 | Q674__03885 | U7GP11 |
| *Acinetobacter guillouiae* MSP4-18 | L291__2817 | S3YTQ7 |
| *Acinetobacter gyllenbergii* MTCC 11365 | L293__2966 | S3YIH4 |
| *Acinetobacter gyllenbergii* CIP 110306 | F957__03919 | S3MT86 |
| *Acinetobacter* sp. CIP 110321 | F896__03869 | R9AJ00 |
| *Acinetobacter pittii* ANC 3678 | F930__03216 | N9FYL9 |
| *Acinetobacter beijerinckii* CIP 110307 | F933__03106 | N9FFM7 |
| *Acinetobacter beijerinckii* CIP 110307 | F933__03106 | N9FFM7 |
| *Acinetobacter guillouiae* CIP 63.46 | F981__00071 | N8TRF0 |
| *Acinetobacter* sp. NIPH 236 | F992__00196 | N8PQM8 |
| *Acinetobacter radioresistens* DSM 6976 = NBRC 102413 = CIP 103788 | ACRAD__64__00110 F939__02890 | K6W366 |
| *Acinetobacter* sp. NBRC 100985 | ACT4__067__00170 | G7GIJ8 |
| *Williamsia* sp. D3 | W823__14840 | V8CZP3 |
| *Rhodococcus ruber* BKS 20-38 | G352__16177 | M2XNX0 |
| *Gordonia neofelifaecis* NRRL B-59395 | SCNU__19987 | F1YPY6 |
| *Nocardioidaceae bacterium* Broad-1 | NBCG__04744 | E9V105 |
| *Rhodococcus erythropolis* DN1 | N601__30795 | T5HW62 |
| *Rhodococcus erythropolis* (strain PR4/NBRC 100887) | RER_pREL1-02600 | Q3L9B0 |

TABLE 6-continued

Cytochrome P450 enzymes capable of catalyzing selective terminal alkene hydroxylation.

| Species Origin | Gene names | Accession No |
|---|---|---|
| *Rhodococcus erythropolis* DN1 | N601_30930 | T5HZQ2 |
| *Alcanivorax dieselolei* | | B0LCZ6 |
| uncultured bacterium | cyp153 | W0UD28 |
| uncultured bacterium | cyp153 | W0UD53 |
| uncultured bacterium | cyp153 | W0UCL1 |
| *Alcanivorax borkumensis* | ahpG1 | Q5K134 |
| *Alcanivorax* sp. 97CO-5 | Y017_09710 | W6ZMW5 |
| *Alcanivorax borkumensis* (strain SK2/ATCC 700651/DSM 11573) | p450 ABO_0201 ABO_2288 | Q0VM62 |
| *Alcanivorax borkumensis* | ahpG2 | Q5K133 |
| gamma proteobacterium HIMB55 | OMB55_00008700 | H3NSZ4 |
| *Amycolicicoccus subflavus* (strain DSM 45089/DQS3-9A1) | AS9A_4287 | F6EL57 |
| *Dietzia cinnamea* P4 | ES5_17094 | E6JDU2 |
| *Rhodococcus* sp. R04 | | G0YY52 |
| *Dietzia* sp. DQ12-45-1b | | L7QFU8 |
| *Gordonia terrae* C-6 | GTC6_22847 | R7Y2Z3 |
| *Gordonia rubripertincta* NBRC 101908 | GORBP_030_00030 | L7K246 |
| *Gordonia polyisoprenivorans* NBRC 16320 | GOPIP_035_00030 | H0RD32 |
| *Gordonia amicalis* NBRC 100051 = JCM 11271 | GOAMI_32_00650 | L7L3E0 |
| *Nocardia cyriacigeorgica* (strain GUH-2) | NOCYR_1539 | H6R8V9 |
| *Mycobacterium gilvum* (strain PYR-GCK) (*Mycobacterium flavescens* (strain ATCC 700033/PYR-GCK)) | Mflv_4592 | A4TFM0 |
| *Acinetobacter* sp. ANC 3862 | F900_00467 | N9M6H3 |
| *Rhodococcus erythropolis* (strain PR4/NBRC 100887) | RER_pREL1-02830 | Q3L987 |
| *Mycobacterium rhodesiae* (strain NBB3) | MycrhN_5185 | G8RXP7 |
| *Rhodococcus wratislaviensis* IFP 2016 | Rwratislav_02222 | L2TWM7 |
| *Nocardioides* sp. CF8 | CF8_1774 | R7XZ06 |
| *Rhodococcus* sp. AW25M09 | RHODMAR_4781 | L8DQ69 |
| *Mycobacterium* sp. (strain MCS) | Mmcs_3218 | Q1B709 |
| *Mycobacterium* sp. (strain JLS) | Mjls_3229 | A3Q1I0 |
| *Mycobacterium* sp. (strain KMS) | Mkms_3280 | A1UI16 |
| *Mycobacterium intracellulare* MOTT-02 | OCO_23030 | H8J7G3 |
| *Mycobacterium abscessus* subsp. *bolletii* str. GO 06 | linC MYCMA_1074 | I6ZDN8 |
| *Mycobacterium abscessus* (strain ATCC 19977/DSM 44196) | MAB_2048c | B1MP79 |
| *Mycobacterium abscessus* V06705 | M879_18655 | T0B128 |
| *Mycobacterium abscessus* M94 | S7W_02670 | I0PWL5 |
| *Mycobacterium avium* subsp. *hominissuis* 10-4249 | O971_10910 | V7M646 |
| *Mycobacterium parascrofulaceum* ATCC BAA-614 | HMPREF0591_1257 | D5P513 |
| *Rhodococcus* sp. AW25M09 | RHODMAR_0629 | L8DBR6 |
| *Nocardia asteroides* NBRC 15531 | NCAST_16_00270 | U5E995 |
| *Aeromicrobium marinum* DSM 15272 | HMPREF0063_10876 | E2SA86 |
| *Mycobacterium abscessus* MAB_091912_2446 | L833_0535 | V6ZS84 |
| *Mycobacterium abscessus* MAB_082312_2258 | L830_0536 | V6ZGT1 |
| *Mycobacterium abscessus* 47J26 | MAB47J26_13072 | G6X6X6 |
| *Nocardioides* sp. CF8 | CF8_1685 | R7XZ92 |
| *Gordonia polyisoprenivorans* NBRC 16320 | GOPIP_007_00470 | H0R8L5 |
| *Gordonia araii* NBRC 100433 | GOARA_078_00570 | G7H6Y3 |
| marine gamma proteobacterium HTCC2080 | MGP2080_13483 | A0Z5X9 |
| *Gordonia paraffinivorans* NBRC 108238 | GP2_063_00030 | M3V7L0 |
| *Planctomyces maris* DSM 8797 | PM8797T_18726 | A6CH25 |
| *Amycolicicoccus subflavus* (strain DSM 45089/DQS3-9A1) | AS9A_2813 | F6EJ28 |
| *Candidatus Microthrix parvicella* RN1 | BN381_420018 | R4Z0X4 |
| *Gordonia paraffinivorans* NBRC 108238 | GP2_036_00650 | M3TVA1 |
| *Nocardioides* sp. CF8 | CF8_2601 | R7XVN2 |
| *Mycobacterium chubuense* (strain NBB4) | Mycch_5830 | D2K2F1 |
| *Gordonia polyisoprenivorans* (strain DSM 44266/VH2) | GPOL_c44990 | H6MXH6 |
| *Aeromicrobium marinum* DSM 15272 | HMPREF0063_10264 | E2S8A7 |
| *Gordonia rubripertincta* NBRC 101908 | GORBP_109_00410 | L7KEM4 |
| *Gordonia namibiensis* NBRC 108229 | GONAM_02_01570 | K6XIG5 |
| *Gordonia* sp. KTR9 | KTR9_5380 | J9STN3 |
| *Gordonia terrae* NBRC 100016 | GOTRE_050_00060 | H5UDF7 |
| *Gordonia alkanivorans* NBRC 16433 | GOALK_030_00300 | F9VS44 |
| *Gordonia alkanivorans* | goaBAC | B3IX64 |
| *Gordonia* sp. TF6 | aoxA | A9CMS7 |
| *Alcanivorax borkumensis* (strain SK2/ATCC 700651/DSM 11573) | | Q6RCE3 |
| *Gordonia malaquae* NBRC 108250 | GM1_011_00750 | M3UVQ9 |

TABLE 6-continued

Cytochrome P450 enzymes capable of catalyzing selective terminal alkene hydroxylation.

| Species Origin | Gene names | Accession No |
|---|---|---|
| alpha proteobacterium JLT2015 | C725_0051 | M2TQQ4 |
| Oceanicola batsensis HTCC2597 | OB2597_05915 | A3TT18 |
| Sphingobium baderi LL03 | L485_17855 | T0HGM2 |
| Erythrobacter litoralis (strain HTCC2594) | ELI_12445 | Q2N6W0 |
| Erythrobacter sp. SD-21 | ED21_18817 | A5P986 |
| Novosphingobium nitrogenifigens DSM 19370 | Y88_2850 | F1Z4F0 |
| Sphingopyxis macrogoltabida (Sphingomonas macrogoltabidus) | ahpG5 | Q5F4D8 |
| Sphingopyxis alaskensis (strain DSM 13593/LMG 18877/RB2256) (Sphingomonas alaskensis) | Sala_2865 | Q1GP52 |
| Sphingopyxis macrogoltabida (Sphingomonas macrogoltabidus) | ahpG4 | Q5F4D1 |
| Novosphingobium aromaticivorans (strain DSM 12444) | Saro_0220 | Q2GBV5 |
| Dickeya dadantii (strain Ech586) | Dd586_1369 | D2BW78 |
| Sphingopyxis sp. MC1 | EBMC1_05939 | N9UVB0 |
| Dietzia sp. D5 | | W0C650 |
| Sphingobium indicum B90A | SIDU_06697 | I5BFE4 |
| Sphingobium chinhatense IP26 | M527_09955 | W1KG42 |
| Sphingobium sp. HDIP04 | L286_21540 | T0G3B9 |
| Erythrobacter sp. NAP1 | NAP1_13673 | A3WFL2 |
| Dickeya dadantii (strain 3937) (Erwinia chrysanthemi (strain 3937)) | Dda3937_03358 | E0SIQ2 |
| Sphingomonas sanxanigenens DSM 19645 = NX02 | NX02_10200 | W0AB84 |
| Sphingopyxis sp. MC1 | EBMC1_03994 | N9WE44 |
| Dickeya sp. D s0432-1 | A544_2711 | U6Z9W7 |
| Novosphingobium aromaticivorans (strain DSM 12444) | Saro_1821 | Q2G7B2 |
| Erythrobacter litoralis (strain HTCC2594) | ELI_09815 | Q2N8D6 |
| Parvibaculum lavamentivorans (strain DS-1/DSM 13023/NCIMB 13966) | Plav_0029 | A7HP19 |
| Novosphingobium pentaromativorans US6-1 | NSU_3817 | G6EHJ6 |

In some embodiments, the disclosure provide methods for synthesizing olefinic alcohol products as described above, wherein the enzyme is selected from AlkB, AlkB P1, and AlkB1 AB. In some embodiments, the enzyme is selected from CYP153 M. sp; CYP153A M. aq; CYP153A M. aq. (G307A); Cyp153A M. aq. (G307A)-CPR$_{BM3}$; Cyp153A P.sp.-CPR$_{BM3}$; CYP153A13N2; CYP153A13N3; CYP153A13P2; and CYP153A7. In some embodiments, the enzyme is selected from CYP52A13 and CYP52A3.

In a related aspect, the disclosure provides a whole cell catalyst comprising an enzyme capable of selectively hydroxylating one terminal carbon of an unsaturated or saturated hydrocarbon substrate. In some embodiments, the cell is a microbial cell. In some embodiments, the enzyme is selected from the group consisting of a non-heme diiron monooxygenase, a long-chain alkane hydroxylase, a cytochrome P450, and combinations thereof. In some embodiments, the enzyme is selected from Table 4, Table 5, Table 6, or a variant thereof having at least 90% identity thereto.

TABLE 6

Exemplary strains suitable for the present disclosure.

| Species | Plasmid Genotype (or relevant gene deletions) | Reference |
|---|---|---|
| E. coli K12 GEc137 | pGEc47J contains alkBFGKL alkST | Grant et al. Enzyme Microb. Technol. 2011 |
| E. coli W3110 | pBT10 contains alkBFG alkST | Schrewe et al. Adv. Synth. Cat. 2011 |
| E. coli W3110 | pBTL10 contains alkBFGL alkST | Julsing et al. Adv. Synth. Cat. 2011 |
| E. coli BL21(DE3) | pET-28a(+)-LadA contains LadA | Dong et al. Appl. Microbiol. Biotechnol. 2012 |
| E. coli BL21(DE3) | pET-28a(+)-CYP153A6 operon | Gudimichi et al. Appl. Microbiol. Biotechnol. 2012 |
| E. coli JM109 | pJOE-CYP153A$_{M.aq.}$(G307A)-CPR$_{BM3}$ | Scheps et al. Microb. Biotechnol. 2013 |
| E. coli HMS174 | pET-28(+)-CYP153A$_{M.aq.}$(G307A)-CPR$_{BM3}$ | |
| E. coli HMS174 | pColaDuet-1-CYP153A$_{M.aq.}$(G307A)-CPR$_{BM3}$, alkL | |
| E. coli HMS174 | pET-28(+)-CYP153A$_{P. sp.}$-CPR$_{BM3}$ | Malca el al. Chem. Comm. 2012 |

TABLE 6-continued

Exemplary strains suitable for the present disclosure.

| Species | Plasmid Genotype (or relevant gene deletions) | Reference |
|---|---|---|
| C. tropicalis DP522 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A13 | Lu et al. J. Am. Chem. Soc. 2010 |
| C. tropicalis DP526 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A12 | |
| C. tropicalis DP428 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A17 | |

The methods of the disclosure allow for the production of terminal alcohols with controlled regioselectivity, while disfavoring the formation of unwanted species such as epoxides or elimination products. The stereochemistry of an olefinic alcohol product will depend on factors including the structure of the particular olefinic substrate used in a particular reaction, as well as the identity of the enzyme. The methods of the disclosure can be conducted with enzymes that are selective for particular substrates (e.g., cis or Z alkenes vs. trans or E alkenes), as well as with enzymes that demonstrate terminal selectivity (e.g., hydroxylation of one end of an asymmetric alkene vs. the other end of the asymmetric alkene).

In certain instances, a hydroxylase enzyme will exhibit catalytic efficiency with one isomer of an internal alkene (e.g., the cis or Z isomer of an internal alkene) that is greater than the catalytic efficiency exhibited with the other isomer of the same internal alkene (e.g., the trans or E isomer of an internal alkene). In some embodiments, the disclosure provides methods wherein the catalytic efficiency of the hydroxylase enzyme is at least about 2-fold greater with one isomer of an internal alkene than with the other isomer of the internal alkene. The catalytic efficiency exhibited by a hydroxylase with one isomer of an internal alkene can be, for example, at least about 4-fold, at least about 5-fold, at least about 6-fold, at least about 7-fold, at least about 8-fold, at least about 9-fold, at least about 10-fold, at least about 25-fold, at least about 50-fold, at least about 100-fold, or at least about 500-fold greater than the catalytic efficiency exhibited by the hydroxylase with the other isomer of the internal alkene.

A particular enzyme can therefore produce Z product over E product from a mixture of Z and E isomeric substrates or enrich the Z product over the E product. In certain embodiments, the disclosure provides methods for preparing olefinic alcohol products wherein the Z:E (cis:trans) isomeric ratio of the olefinic alcohol product is different from the Z:E (cis:trans) isomeric ratio of the olefinic substrate. The Z:E isomeric ratio of the olefinic alcohol product can be, for example, around 2 times greater than the Z:E isomeric ratio of the olefinic substrate. The Z:E isomeric ratio of the olefinic alcohol product can be, for example, around 1.25 times, 1.5 times, 2 times, 2.5 times, 3 times, 4 times, 5 times, 10 times, 20 times, 30 times, or 40 times greater than the Z:E isomeric ratio of the olefinic substrate.

In some embodiments, the disclosure provides methods for preparing olefinic alcohol products wherein the E:Z (trans:cis) isomeric ratio of the olefinic alcohol product is different from the E:Z (trans:cis) isomeric ratio of the olefinic substrate. The E:Z isomeric ratio of the olefinic alcohol product can be, for example, around 2 times greater than the E:Z isomeric ratio of the olefinic substrate. The E:Z isomeric ratio of the olefinic alcohol product can be, for example, around 1.25 times, 1.5 times, 2 times, 2.5 times, 3 times, 4 times, 5 times, 10 times, 20 times, 30 times, or 40 times greater than the E:Z isomeric ratio of the olefinic substrate.

In some embodiments, the Z:E isomeric ratio of the olefinic alcohol is about 1.25 times greater than the Z:E isomeric ratio of the olefinic substrate. In some embodiments, the E:Z isomeric ratio of the olefinic alcohol is about 1.25 times greater than the E:Z isomeric ratio of the olefinic substrate.

In certain instances, the biohydroxylation reactions in the methods of the disclosure have the potential to form a mixture of two or more products from the same substrate. When an olefinic substrate is asymmetric, for example, hydroxylation of one end/terminus of the substrate leads to one product while hydroxylation of the other end/terminus of the substrate leads to a different product. A reaction could therefore result in a mixture of two olefinic alcohol products. The terminal isomer ratio of an asymmetric olefinic alcohol product can range from about 1:99 to about 99:1. The terminal isomer ratio can be, for example, from about 1:99 to about 1:75, or from about 1:75 to about 1:50, or from about 1:50 to about 1:25, or from about 99:1 to about 75:1, or from about 75:1 to about 50:1, or from about 50:1 to about 25:1. The terminal isomer ratio can be from about 1:80 to about 1:20, or from about 1:60 to about 1:40, or from about 80:1 to about 20:1 or from about 60:1 to about 40:1. The terminal isomer ratio can be about 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, or about 1:95. The terminal isomer ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

The distribution of a product mixture can be expressed as a regioselectivity percentage ("regioselectivity %"). Taking the reaction in FIG. 3 as a non-limiting example, for instance, the regioselectivity of (Z)-5-hexadecene hydroxylation can be calculated using the formula: regioselectivity %=[($\chi_{11}$)/($\chi_{11}$+$\chi_5$)]×100%, wherein $\chi_{11}$ is the mole fraction for (Z)-11-hexadecen-1-ol and wherein $\chi_5$ is the mole fraction for (Z)-5-hexadecen-1-ol. In general, the regioselectivity % with respect to terminal alcohol isomers ranges from about 1% to about 99%. The regioselectivity % can be from about 1% to about 99%, or from about 20% to about 80%, or from about 40% to about 60%, or from about 1% to about 25%, or from about 25% to about 50%, or from about 50% to about 75%. The regioselectivity % can be at least about 5% 10%, 15%, 20%, 25%, 30%, 35%, 40%, 45%, 50%, 55%, 60%, 65%, 70%, 75%, 80%, 85%, 90%, or 95%.

In some embodiments, the regioselectivity % is at least about 60%. In some embodiments, the regioselectivity % is at least about 60% and the Z:E isomeric ratio of the olefinic alcohol is about 1.25 times greater than the Z:E isomeric ratio of the olefinic substrate.

In certain instances, varying levels of olefin epoxidation will occur during the biohydroxylation reactions used in the methods of the disclosure. See, e.g., Scheme 7. Epoxidation of terminal alkenes, in particular, can occur when certain hydroxylase enzymes are used. It is often desirable to minimize such epoxidation or avoid the formation of epoxides altogether. Typically, methods of the disclosure are conducted with hydroxylase enzymes that produce product mixtures with alcohol product:epoxide ratios of at least 1:1. The alcohol product:epoxide ratio can range from about 1:1 to about 99:1. The alcohol:epoxide ratio can be, for example, from about 99:1 to about 75:1, or from about 75:1 to about 50:1, or from about 50:1 to about 25:1. The alcohol:epoxide ratio can be from about 80:1 to about 20:1 or from about 60:1 to about 40:1. The alcohol:epoxide ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

In some embodiments, methods are conducted using an enzyme that produces an olefinic alcohol product:epoxide product ratio of greater than 1:1. In some embodiments, the enzyme produces an olefinic alcohol product:epoxide product ratio of greater than 2:1.

The distribution of a product mixture can be expressed as a percent selectivity for hydroxylation vs. epoxidation. Taking the reaction in Scheme 7a as a non-limiting example, the percent selectivity for hydroxylation vs. epoxidation of a terminal alkene can be calculated using the formula: selectivity %=[($\chi_H$)/($\chi_H$+$\chi_E$)]×100%, wherein $\chi_H$ is the mole fraction for the hydroxylation product (i.e., the terminal olefinic alcohol) and wherein $\chi_E$ is the mole fraction for the epoxidation product (i.e., the terminal epoxide). In general, the percent selectivity for hydroxylation vs. epoxidation ranges from about 1% to about 99%. The percent selectivity for hydroxylation vs. epoxidation can be from about 1% to about 99%, or from about 20% to about 80%, or from about 40% to about 60%, or from about 1% to about 25%, or from about 25% to about 50%, or from about 50% to about 75%. The percent selectivity for hydroxylation vs. epoxidation can be about 5% 10%, 15%, 20%, 25%, 30%, 35%, 40%, 45%, 50%, 55%, 60%, 65%, 70%, 75%, 80%, 85%, 90%, or 95%.

When halogen-substituted substrates are used in the methods of the disclosure, varying levels of dehalogenation can occur during hydroxylation. Dehalogenation typically results in the formation of aldehyde byproduct. Preferably, dehalogenation is minimized or avoided during the hydroxylation reactions. Typically, methods of the disclosure are conducted with hydroxylase enzymes that produce product mixtures with alcohol:aldehyde ratios of at least 1:1. The alcohol:aldehyde ratio of the product can range from about 1:1 to about 99:1. The alcohol:aldehyde ratio can be, for example, from about 99:1 to about 75:1, or from about 75:1 to about 50:1, or from about 50:1 to about 25:1. The alcohol:aldehyde ratio can be from about 80:1 to about 20:1 or from about 60:1 to about 40:1. The alcohol:aldehyde ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

The distribution of a product mixture can be expressed as a percent selectivity for hydroxylation vs. dehalogenation. The percent selectivity for hydroxylation vs. dehalogenation of a halogen-substituted substrate can be calculated using the formula: selectivity %=[($\chi_H$)/($\chi_H$+$\chi_A$)]×100%, wherein $\chi_H$ is the mole fraction for the hydroxylation product and wherein $\chi_A$ is the mole fraction for the aldehyde product. In general, the percent selectivity for hydroxylation vs. dehalogenation ranges from about 1% to about 99%. The percent selectivity for hydroxylation vs. dehalogenation can be from about 1% to about 99%, or from about 20% to about 80%, or from about 40% to about 60%, or from about 1% to about 25%, or from about 25% to about 50%, or from about 50% to about 75%. The percent selectivity for hydroxylation vs. dehalogenation can be about 5% 10%, 15%, 20%, 25%, 30%, 35%, 40%, 45%, 50%, 55%, 60%, 65%, 70%, 75%, 80%, 85%, 90%, or 95%.

Biohydroxylation of Subterminal Carbon

In some embodiments, biohydroxylation can occur on an subterminal carbon as shown in Scheme 8. Accordingly, in some embodiments, the disclosure provides for isomers of a sex pheromone which include an subterminal alcohol functional group, an subterminal acetyl, or an subterminal ketone, provided, however, that the subterminal ketone is not located on the same carbon that forms a double bond with an adjacent carbon.

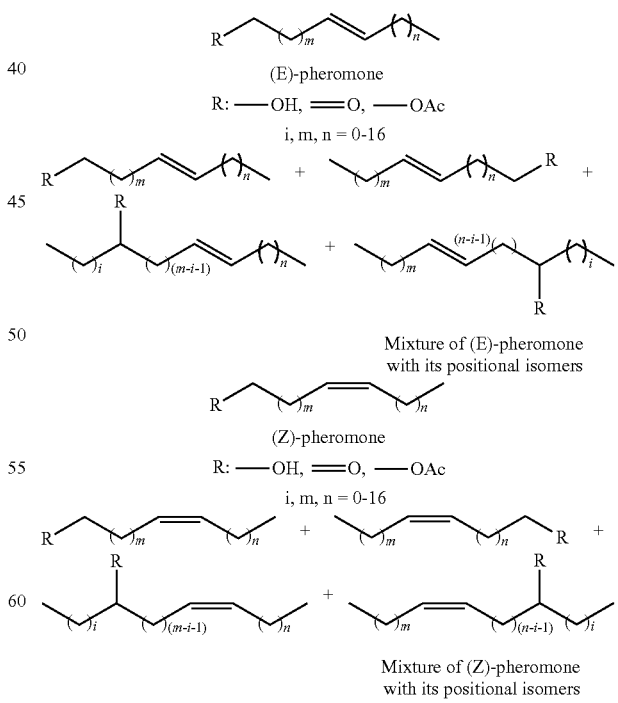

Scheme 8

In some embodiments, for example, n is 0, m is 1, i is 3; or n is 1, m is 1, and i is 2; or n is 2, m is 1, and i is 1; or n is 0, m is 2, i is 2; or n is 1, m is 2, and i is 1; or n is 0, m is 3, i is 1; and positional isomers thereof.

In some embodiments, for example, n is 0, m is 1, and i is 4; or n is 1, m is 1; and i is 3; or n is 2, m is 1, and i is 2; or n is 3, m is 1, and i is 1; n is 0, m is 2, i is 3; or n is 1, m is 2, and i is 2; or n is 2, m is 2, and i is 1; n is 0, nm is 3, i is 2; or n is 1, m is 3, and i is 1; n is 0, m is 4, i is 1; and positional isomers thereof.

In some embodiments, for example, n is 0, m is 1, and i is 5; or n is 1, m is 1, and i is 4; or n is 2, m is 1, and i is 3; or n is 3, m is 1, i is 2; or n is 4, m is 1, and i is 1; or n is 0, m is 2, and i is 4; or n is 1, m is 2, and i is 3; or n is 2, m is 2, and i is 2; or n is 3, m is 2; and i is 1; or n is 0, m is 3, and i is 3; or n is 1, n is 3 and i is 2; or n is 2, m is 3, and i is 1; or n is 0, m is 4, and i is 2; or n is 1, m is 4 and i is 1; or n is 0, m is 5, and i is 1; and positional isomers thereof.

In some embodiments, for example, n is 0, m is 1 and i is 6; or n is 1, m is 1, and i is 5; or n is 2, m is 1, and i is 4; or n is 3, m is 1, and i is 3; or n is 4, m is 1; and i is 2; or n is 5, m is 1, and i is 1; or n is 0, m is 2 and i is 5; or n is 1, m is 2, i and is 4; or n is 2, m is 2, and i is 3; or n is 3, m is 2, and i is 2; or n is 4, m is 2, and i is 1; or n is 0, m is 3 and i is 4; or n is 1, m is 3, i is 3; or n is 2, m is 3, and i is 2; or n is 3, m is 3, and i is 1; or n is 0, m is 4 and i is 3; or n is 1, m is 4, i is 2; or n is 2, m is 4, and i is 1; or n is 0, m is 5 and i is 2; or n is 1, m is 5, i is 1; or n is 0, m is 6, and i is 1; and positional isomers thereof.

In some embodiments, for example, n is 0, m is 1, and i is 7; or n is 1 and m is 1, and i is 6; or n is 2, m is 1, and i is 5; or n is 3, m is 1, and i is 4; or n is 4, m is 1, and i is 3; or n is 5, m is 1, and i is 2; or n is 6, m is 1; and i is 1; n is 0, m is 2, and i is 6; or n is 1 and m is 2, and i is 5; or n is 2, m is 2, and i is 4; or n is 3, m is 2, and i is 3; or n is 4, m is 2, and i is 2; or n is 5, m is 2, and i is 1; n is 0, m is 3, and i is 5; or n is 1, and m is 3, and i is 4; or n is 2, m is 3, and i is 3; or n is 3, m is 3, and i is 2; or n is 4, m is 3, and i is 1; n is 0, m is 4, and i is 4; or n is 1 and m is 4, and i is 3; or n is 2, m is 4, and i is 2; or n is 3, m is 4, and i is 1; n is 0, m is 5, and i is 3; or n is 1 and m is 5, and i is 2; or n is 2, m is 5, and i is 1; n is 0, m is 6, and i is 2; or n is 1 and m is 6, and i is 1; n is 0, m is 7, and i is 1; and positional isomers thereof.

In some embodiments, for example, n is 0, m is 1; and i is 8; or n is 1, m is 1, and i is 7; or n is 2, m is 1, i is 6; or n is 3, m is 1, i is 5; or n is 4, m is 1, i is 4; or n is 5, m is 1, i is 3; or n is 6, m is 1, i is 2 or n is 7, m is 1, and i is 1; n is 0, m is 2; and i is 7; or n is 1, m is 2, and i is 6; or n is 2, m is 2, i is 5; or n is 3, m is 2, i is 4; or n is 4, m is 2, i is 3; or n is 5, m is 2, i is 2; or n is 6, m is 2, i is 1; n is 0, m is 3; and i is 6; or n is 1, m is 3, and i is 5; or n is 2, m is 3, i is 4; or n is 3, m is 3, i is 3; or n is 4, m is 3, i is 2; or n is 5, m is 3, i is 1; n is 0, m is 4; and i is 5; or n is 1, m is 4, and i is 4; or n is 2, m is 4, i is 3; or n is 3, m is 4, i is 2; or n is 4, m is 4, i is 1; n is 0, m is 5; and i is 4; or n is 1, m is 5, and i is 3; or n is 2, m is 5, i is 2; or n is 3, m is 5, i is 1; n is 0, m is 6; and i is 3; or n is 1, m is 6, and i is 2; or n is 2, m is 6, i is 1; n is 0, m is 7; and i is 2; or n is 1, m is 7, and i is 1; or n is 0, m is 8, i is 1; and positional isomers thereof.

In some embodiments, for example, n is 0, m is 1, and i is 9; or n is 1, m is 1, i is 8; or n is 2, m is 1, and i is 7; or n is 3, m is 1, and i is 6; or n is 4, m is 1, and i is 5; or n is 5, m is 1, and i is 4; or n is 6, m is 1, and i is 3; or n is 7, m is 1, and i is 2; or n is 8, m is 1 and i is 1; n is 0, m is 2, and i is 8; or n is 1, m is 2, i is 7; or n is 2, m is 2, and i is 6; or n is 3, m is 2, and i is 5; or n is 4, m is 2, and i is 4; or n is 5, m is 2, and i is 3; or n is 6, m is 2, and i is 2; or n is 7, m is 2, and i is 1; n is 0, m is 3, and i is 7; or n is 1, m is 3, i is 6; or n is 2, m is 3, and i is 5; or n is 3, m is 3, and i is 4; or n is 4, m is 3, and i is 3; or n is 5, m is 3, and i is 2; or n is 6, m is 3, and i is 1; n is 0, m is 4, and i is 6; or n is 1, m is 4, i is 5; or n is 2, m is 4, and i is 4; or n is 3, m is 4, and i is 3; or n is 4, m is 4, and i is 2; or n is 5, m is 4, and i is 1; n is 0, m is 5, and i is 5; or n is 1, m is 5, i is 4; or n is 2, m is 5, and i is 3; or n is 3, m is 5, and i is 2; or n is 4, m is 5, and i is 1; n is 0, m is 6, and i is 4; or n is 1, m is 6, i is 3; or n is 2, m is 6, and i is 2; or n is 3, m is 6, and i is 1; n is 0, m is 7, and i is 3; or n is 1, m is 7, i is 2; or n is 2, m is 7, and i is 1; n is 0, m is 8, and i is 2; or n is 1, m is 8, i is 1; n is 0, n is 9, and i is 1; and positional isomers thereof.

In some embodiments, for example, n is 0, m is 1, and i is 10; or n is 1, m is 1, and i is 9; or n is 2, m is 1, and i is 8; or n is 3, m is 1, and i is 7; or n is 4, m is 1, and i is 6; or n is 5, n is 1, i is 5; or n is 6, m is 1, and i is 4; or n is 7, m is 1 and i is 3; or n is 8, m is 1, i is 2; or n is 9, m is 1, and i is 1; or n is 0, m is 2, and i is 9; or n is 1, m is 2, and i is 8; or n is 2, m is 2, and i is 7; or n is 3, m is 2, and i is 6; or n is 4, m is 2, and i is 5; or n is 5, m is 2, i is 4; or n is 6, m is 2, and i is 3; or n is 7, m is 2 and i is 2; or n is 8, m is 2, i is 1; n is 0, m is 3, and i is 8; or n is 1, m is 3, and i is 7; or n is 2, m is 3, and i is 6; or n is 3, m is 3, and i is 5; or n is 4, m is 3, and i is 4; or n is 5, m is 3, i is 3; or n is 6, m is 3, and i is 2; or n is 7, m is 3 and i is 1; n is 0, m is 4, and i is 7; or n is 1, m is 4, and i is 6; or n is 2, m is 4, and i is 5; or n is 3, m is 4, and i is 4; or n is 4, m is 4, and i is 3; or n is 5, m is 4, i is 2; or n is 6, m is 4, and i is 1; n is 0, m is 5, and i is 6; or n is 1, m is 5, and i is 5; or n is 2, m is 5, and i is 4; or n is 3, m is 5, and i is 3; or n is 4, m is 5, and i is 2; or n is 5, m is 5, i is 1; n is 0, m is 6, and i is 5; or n is 1, m is 6, and i is 4; or n is 2, m is 6, and i is 3; or n is 3, m is 6, and i is 2; or n is 4, m is 6, and i is 1; n is 0, m is 7, and i is 4; or n is 1, m is 7, and i is 3; or n is 2, m is 7, and i is 2; or n is 3, m is 7, and i is 1; n is 0, m is 8, and i is 3; or n is 1, m is 8, and i is 2; or n is 2, m is 8, and i is 1; n is 0, m is 7, and i is 4; or n is 1, m is 7, and i is 3; or n is 2, m is 7, and i is 2; or n is 3, m is 7, and i is 1; n is 0, m is 9, and i is 2; or n is 1, m is 9, and i is 1; or n is 0, m is 10, and i is 1; and positional isomers thereof.

In some embodiments, for example, n is 0, m is 1, and i is 11; or n is 1, m is 1, and i is 10; or n is 2, m is 1, and i is 9; or n is 3, m is 1, and i is 8; or n is 4, m is 1, and i is 7; or n is 5, m is 1, and i is 6; or n is 6, m is 1 and i is 5; or n is 7, m is 1 and i is 4; or n is 8, m is 1, and i is 3; or n is 9, m is 1, and i is 2; or n is 10, m is 1 and i is 1; n is 0, m is 2, and i is 10; or n is 1, m is 2, and i is 9; or n is 2, m is 2, and i is 8; or n is 3, m is 2, and i is 7; or n is 4, m is 2, and i is 6; or n is 5, m is 2, and i is 5; or n is 6, m is 2 and i is 4; or n is 7, m is 2 and i is 3; or n is 8, m is 2, and i is 2; or n is 9, m is 2 and i is 1; n is 0, m is 3, and i is 9; or n is 1, m is 3, and i is 8; or n is 2, m is 3, and i is 7; or n is 3, m is 3, and i is 6; or n is 4, m is 3, and i is 5; or n is 5, m is 3, and i is 4; or n is 6, m is 3 and i is 3; or n is 7, m is 3 and i is 2; or n is 8, m is 3, and i is 1; n is 0, m is 4, and i is 8; or n is 1, m is 4, and i is 7; or n is 2, m is 4, and i is 6; or n is 3, m is 4, and i is 5; or n is 4, m is 4, and i is 4; or n is 5, m is 4, and i is 3; or n is 6, m is 4 and i is 2; or n is 7, m is 4 and i is 1; n is 0, m is 5, and i is 7; or n is 1, m is 5, and i is 6; or n is 2, m is 5 and i is 5; or n is 3, m is 5, and i is 4; or n is 4, m is 5, and i is 3; or n is 5, m is 5, and i is 2; or n is 6, m is 5 and i is 1; n is 0, m is 6, and i is 6; or n is 1, m is 6, and i is 5; or n is 2, m is 6 and i is 4; or n is 3, m is 6, and i is 3; or n is 4, m is 6, and i is 2; or n is 5, m is 6, and i is 1; n is 0, m is 7, and i is 5; or n is 1, m is 7, and i is 4; or n is 2, m is 7 and i is 3; or n is 3, m is 7, and i is 2; or n is 4, m is 7, and i is 1; n is 0, m is 8, and i is 4; or n is 1, m is 8, and i is 3; or n is 2, m is 8 and i is 2; or n is 3, m is 8, and i is 1; n is 0, m is 9, and i is 3; or n is 1, m is 9, and i is 2; or n is 2, m is 9 and i is 1; n is 0, m is 10, and i is 2; or n is 1, m is 10, and i is 1; or n is 0, m is 11 and i is 1; and positional isomers thereof.

In some embodiments, for example, n is 0, m is 1, and i is 12; or n is 1, m is 1, and i is 11; or n is 2, m is 1, and i is 10; or n is 3, m is 1, and i is 9; or n is 4, m is 1, and i is 8; or n is 5, m is 1, and i is 7; or n is 6, m is 1, and i is 6; or n is 7, m is 1, and i is 5; or n is 8, m is 1, and i is 4; or n is 9, m is 1, and i is 3; or n is 10, m is 1, and i is 2; or n is 11, m is 1 and i is 1; n is 0, m is 2, and i is 11; or n is 1, m is 2, and i is 10; or n is 2, m is 2, and i is 9; or n is 3, m is 2, and i is 8; or n is 4, m is 2, and i is 7; or n is 5, m is 2, and i is 6; or n is 6, m is 2, and i is 5; or n is 7, m is 2, and i is 4; or n is 8, m is 2, and i is 3; or n is 9, m is 2, and i is 2; or n is 10, m is 2, and i is 1; n is 0, m is 2, and i is 11; or n is 1, m is 2, and i is 10; or n is 2, m is 2, and i is 9; or n is 3, m is 2, and i is 8; or n is 4, m is 2, and i is 7; or n is 5, m is 2, and i is 6; or n is 6, m is 2, and i is 5; or n is 7, m is 2, and i is 4; or n is 8, m is 2, and i is 3; or n is 9, m is 2, and i is 2; or n is 10, m is 2, and i is 1; n is 0, m is 3, and i is 10; or n is 1, m is 3, and i is 9; or n is 2, m is 3, and i is 8; or n is 3, m is 3, and i is 7; or n is 4, m is 3, and i is 6, or n is 5, m is 3, and i is 5; or n is 6, m is 3, and i is 4; or n is 7, m is 3, and i is 3; or n is 8, m is 3, and i is 2; or n is 9, m is 3, and i is 1; n is 0, m is 4, and i is 9; or n is 1, m is 4, and i is 8; or n is 2, m is 4, and i is 7; or n is 3, m is 4, and i is 6; or n is 4, m is 4, and i is 5, or n is 5, m is 4, and i is 4; or n is 6, m is 4, and i is 3; or n is 7, m is 4, and i is 2; or n is 8, m is 4, and i is 1; n is 0, m is 5, and i is 8; or n is 1, m is 5, and i is 7; or n is 2, m is 5, and i is 6; or n is 3, m is 5, and i is 7; or n is 4, m is 5, and i is 4, or n is 5, m is 5, and i is 3; or n is 6, m is 5, and i is 2; or n is 7, m is 5, and i is 1; n is 0, m is 6, and i is 7; or n is 1, m is 6, and i is 6; or n is 2, m is 6, and i is 5; or n is 3, m is 6, and i is 4; or n is 4, m is 6, and i is 3, or n is 5, m is 6, and i is 2; or n is 6, m is 6, and i is 1; n is 0, m is 7, and i is 6; or n is 1, m is 7, and i is 5; or n is 2, m is 7, and i is 4; or n is 3, m is 7, and i is 3; or n is 4, m is 7, and i is 2, or n is 5, m is 7, and i is 1; n is 0, m is 8, and i is 5; or n is 1, m is 8, and i is 4; or n is 2, m is 8, and i is 3; or n is 3, m is 8, and i is 2; or n is 4, m is 8, and i is 1; n is 0, m is 9, and i is 4; or n is 1, m is 9, and i is 3; or n is 2, m is 9, and i is 2; or n is 3, m is 8, and i is 1; n is 0, m is 10, and i is 3; or n is 1, m is 10, and i is 2; or n is 2, m is 10, and i is 1; n is 0, m is 11, and i is 2; or n is 1, m is 11, and i is 1; or n is 0, m is 12, and i is 1; and positional isomers thereof.

In some embodiments, for example, n is 0, m is 1, and i is 13; or n is 1, m is 1, and i is 12; or n is 2, m is 1, and i is 11; or n is 3, m is 1, and i is 10; or n is 4, m is 1, and i is 9; or n is 5, m is 1, and i is 8; or n is 6, m is 1, and i is 7; or n is 8, m is 1, and i is 5; or n is 9, m is 1, and i is 4; or n is 10, m is 1, and i is 3; or n is 11, m is 1, and i is 2; or n is 12, m is 1, and i is 1; n is 0, m is 2, and i is 12; or n is 1, m is 2, and i is 11; or n is 2, m is 2, and i is 10; or n is 3, m is 2, and i is 9; or n is 4, m is 2, and i is 8; or n is 5, m is 2, and i is 7; or n is 6, m is 2, and i is 6; or n is 7, m is 2, and i is 5, n is 8, m is 2, and i is 4; or n is 9, m is 2, and i is 3; or n is 10, m is 2, and i is 2; or n is 11, m is 2, and i is 1; n is 0, m is 3, and i is 11; or n is 1, m is 3, and i is 10; or n is 2, m is 3, and i is 9; or n is 3, m is 3, and i is 8; or n is 4, m is 3, and i is 7; or n is 5, m is 3, and i is 6; or n is 6, m is 3, and i is 5; or n is 7, m is 3, and i is 4; or n is 8, m is 3, and i is 3; or n is 9, m is 3, and i is 2; or n is 10, m is 3, and i is 1; n is 0, m is 4, and i is 10; or n is 1, m is 4, and i is 9; or n is 2, m is 4, and i is 8; or n is 3, m is 4, and i is 7; or n is 4, m is 4, and i is 6; or n is 5, m is 4, and i is 5; or n is 6, m is 4, and i is 4; or n is 7, m is 4, and i is 3; or n is 8, m is 4, and i is 2; or n is 9, m is 4, and i is 1; n is 0, m is 5, and i is 9; or n is 1, m is 5, and i is 8; or n is 2, m is 5, and i is 7; or n is 3, m is 5, and i is 6; or n is 4, m is 5, and i is 5; or n is 5, m is 5, and i is 4; or n is 6, m is 5, and i is 3; or n is 7, m is 5, and i is 2; or n is 8, m is 5, and i is 1; n is 0, m is 6, and i is 8; or n is 1, m is 6, and i is 7; or n is 2, m is 6, and i is 6; or n is 3, m is 6, and i is 5; or n is 4, m is 6, and i is 4; or n is 5, m is 6, and i is 3; or n is 6, m is 6, and i is 2; or n is 7, m is 6, and i is 1; n is 0, m is 7, and i is 7; or n is 1, m is 7, and i is 6; or n is 2, m is 7, and i is 5; or n is 3, m is 7, and i is 4; or n is 4, m is 7, and i is 3; or n is 5, m is 7, and i is 2; or n is 6, m is 7, and i is 1; n is 0, m is 8, and i is 6; or n is 1, m is 8, and i is 5; or n is 2, m is 8, and i is 4; or n is 3, m is 8, and i is 3; or n is 4, m is 8, and i is 2; or n is 5, m is 8, and i is 1; n is 0, m is 9, and i is 5; or n is 1, m is 9, and i is 4; or n is 2, m is 9, and i is 3; or n is 3, m is 9, and i is 2; or n is 4, m is 9, and i is 1; n is 0, m is 10, and i is 4; or n is 1, m is 10, and i is 3; or n is 2, m is 10, and i is 2; or n is 3, m is 10, and i is 1; n is 0, m is 11, and i is 3; or n is 1, m is 11, and i is 2; or n is 2, m is 11, and i is 1; n is 0, m is 12, and i is 2; or n is 1, m is 12, and i is 1; or n is 0, m is 13, and i is 1; and positional isomers thereof.

In some embodiments, for example, n is 0, m is 1, and i is 14; or n is 1, m is 1, and i is 13; or n is 2, m is 1, and i is 12; or n is 3, m is 1, or i is 11; or n is 4, m is 1, and i is 10; or n is 5, m is 1, and i is 9; or n is 6, m is 1, and i is 8; or n is 7, m is 1, and i is 7; or n is 8, m is 1, and i is 6; or n is 9, m is 1, and i is 5; or n is 10, m is 1, and i is 4; or n is 11, m is 1 and i is 3; or n is 12, m is 1, and i is 2; or n is 13 and m is 1, and i is 1; n is 0, m is 2, and i is 13; or n is 1, m is 2, and i is 12; or n is 2, m is 2, and i is 11; or n is 3, m is 2, or i is 10; or n is 4, m is 2, and i is 9; or n is 5, m is 2, and i is 8; or n is 6, m is 2, and i is 7; or n is 7, m is 2, and i is 6; or n is 8, m is 2, and i is 5; or n is 9, m is 2, and i is 4; or n is 10, m is 2, and i is 3; or n is 11, m is 2 and i is 2; n is 12, m is 2 and i is 1; or n is 0, m is 3, and i is 12; or n is 1, m is 3, and i is 11; or n is 2, m is 3, and i is 10; or n is 3, m is 3, or i is 9; or n is 4, m is 3, and i is 8; or n is 5, m is 3, and i is 7; or n is 6, m is 3, and i is 6; or n is 7, m is 3, and i is 5; or n is 8, m is 3, and i is 4; or n is 9, m is 3, and i is 3; or n is 10, m is 3, and i is 2; or n is 11, m is 3 and i is 1; n is 0, m is 4, and i is 11; or n is 1, m is 4, and i is 10; or n is 2, m is 4, and i is 9; or n is 3, m is 4, or i is 8; or n is 4, m is 4, and i is 7; or n is 5, m is 4, and i is 6; or n is 6, m is 4, and i is 5; or n is 7, m is 4, and i is 4; or n is 8, m is 4, and i is 3; or n is 9, m is 4, and i is 2; or n is 10, m is 4, and i is 1; n is 0, m is 5, and i is 10; or n is 1, m is 5, and i is 9; or n is 2, m is 5, and i is 8; or n is 3, m is 5, or i is 7; or n is 4, m is 5, and i is 6; or n is 5, m is 5, and i is 5; or n is 6, m is 5, and i is 4; or n is 7, m is 5, and i is 3; or n is 8, m is 5, and i is 2; or n is 9, m is 5, and i is 1; n is 0, m is 6, and i is 9; or n is 1, m is 6, and i is 8; or n is 2, m is 6, and i is 7; or n is 3, m is 6, or i is 6; or n is 4, m is 6, and i is 5; or n is 5, m is 6, and i is 4; or n is 6, m is 6, and i is 3; or n is 7, m is 6, and i is 2; or n is 8, m is 6, and i is 1; n is 0, m is 7, and i is 8; or n is 1, m is 7, and i is 7; or n is 2, m is 7, and i is 6; or n is 3, m is 7, or i is 5; or n is 4, m is 7, and i is 4; or n is 5, m is 7, and i is 3; or n is 6, m is 7, and i is 2; or n is 7, m is 7, and i is 1; n is 0, m is 8, and i is 7; or n is 1, m is 8, and i is 6; or n is 2, m is 8, and i is 5; or n is 3, m is 8, or i is 4; or n is 4, m is 8, and i is 3; or n is 5, m is 8, and i is 2; or n is 6, m is 8, and i is 1; n is 0, m is 9, and i is 6; or n is 1, m is 9, and i is 5; or n is 2, m is 9, and i is 4; or n is 3, m is 9, or i is 3; or n is 4, m is 9, and i is 2; or n is 5, m is 9, and i is 1; n is 0, m is 10, and i is 5; or n is 1, m is 10, and i is 4; or n is 2, m is 10, and i is 3; or n is 3, m is 10, or i is 2; or n is 4, m is 10, and i is 1; n is 0, m is 11, and i is 4; or n is 1, m is 11, and i is 3; or n is 2, m is 11, and i is 2; or n is 3, m is 11, or i is 1; n is 0, m is 12, and i is 3; or n is 1, m is 12, and i is 2; or n is 2, m is 12, and i is 1; n is 0, m is 13, and i is 2; or n is 1, m is 13, and i is 1; n is 0, m is 14, and i is 1;

In some embodiments, for example, n is 0, m is 1, and i is 15; or n is 1, m is 1, and i is 14; or n is 2, m is 1 and i is 13; or n is 3, m is 1, and i is 12; or n is 4, m is 1, and i is 11; or n is 5, m is 1, and i is 10; or n is 6, m is 1 and i is 9; or n is 7, m is 1, and i is 8; or n is 9, m is 1, and i is 6; or n is 10, m is 1, and i is 5; or n is 11, m is 1, and i is 4; or n is 12, m is 1, and i is 3; or n is 13, m is 1, and i is 2; or n is 14, m is 1, and i is 1; n is 0, m is 2, and i is 14; or n is 1, m is 2, and i is 13; or n is 2, m is 2 and i is 12; or n is 3, m is 2, and i is 11; or n is 4, m is 2, and i is 10; or n is 5, m is 2, and i is 9; or n is 6, m is 2 and i is 8; or n is 7, m is 2, and i is 7; or n is 9, m is 2, and i is 5; or n is 10, m is 2, and i is 4; or n is 11, m is 2, and i is 3; or n is 12, m is 2, and i is 2; or n is 13, m is 1, and i is 1; n is 0, m is 3, and i is 13; or n is 1, m is 3, and i is 12; or n is 2, m is 3 and i is 11; or n is 3, m is 3, and i is 10; or n is 4, m is 3, and i is 9; or n is 5, m is 3, and i is 8; or n is 6, m is 3 and i is 7; or n is 7, m is 3, and i is 6; or n is 9, m is 3, and i is 4; or n is 10, m is 3, and i is 3; or n is 11, m is 3, and i is 2; or n is 12, m is 3, and i is 1; n is 0, m is 4, and i is 12; or n is 1, m is 4, and i is 11; or n is 2, m is 4 and i is 10; or n is 3, m is 4, and i is 9; or n is 4, m is 4, and i is 8; or n is 5, m is 4, and i is 7; or n is 6, m is 4 and i is 6; or n is 7, m is 4, and i is 5; or n is 8, m is 4, and i is 4; or n is 9, m is 4, and i is 3; or n is 10, m is 4, and i is 2; or n is 11, m is 4, and i is 1; n is 0, m is 5, and i is 11; or n is 1, m is 5, and i is 10; or n is 2, m is 5 and i is 9; or n is 3, m is 5, and i is 8; or n is 4, m is 5, and i is 7; or n is 5, m is 5, and i is 6; or n is 6, m is 5 and i is 5; or n is 7, m is 5, and i is 4; or n is 8, m is 5, and i is 3; or n is 9, m is 5, and i is 2; or n is 10, m is 5, and i is 1; n is 0, m is 6, and i is 10; or n is 1, m is 6, and i is 9; or n is 2, m is 6 and i is 8; or n is 3, m is 6, and i is 7; or n is 4, m is 6, and i is 6; or n is 5, m is 6, and i is 5; or n is 6, m is 6 and i is 4; or n is 7, m is 6, and i is 3; or n is 8, m is 6, and i is 2; or n is 9, m is 6, and i is 1; n is 0, m is 7, and i is 9; or n is 1, m is 7, and i is 8; or n is 2, m is 7 and i is 7; or n is 3, m is 7, and i is 6; or n is 4, m is 7, and i is 5; or n is 5, m is 7, and i is 4; or n is 6, m is 7 and i is 3; or n is 7, m is 7, and i is 2; or n is 8, m is 7, and i is 1; n is 0, m is 8, and i is 8; or n is 1, m is 8, and i is 7; or n is 2, m is 8 and i is 6; or n is 3, m is 8, and i is 5; or n is 4, m is 8, and i is 4; or n is 5, m is 8, and i is 3; or n is 6, m is 8 and i is 2; or n is 7, m is 8, and i is 1; n is 0, m is 9, and i is 7; or n is 1, m is 9, and i is 6; or n is 2, m is 9 and i is 5; or n is 3, m is 9, and i is 4; or n is 4, m is 9, and i is 3; or n is 5, m is 9, and i is 2; or n is 6, m is 9 and i is 1; n is 0, m is 10, and i is 6; or n is 1, m is 10, and i is 5; or n is 2, m is 10 and i is 4; or n is 3, m is 10, and i is 3; or n is 4, m is 10, and i is 2; or n is 5, m is 10, and i is 1; n is 0, m is 11, and i is 5; or n is 1, m is 11, and i is 4; or n is 2, m is 11 and i is 3; or n is 3, m is 11, and i is 2; or n is 4, m is 11, and i is 1; n is 0, m is 12, and i is 4; or n is 1, m is 12, and i is 3; or n is 2, m is 12 and i is 2; or n is 3, m is 12, and i is 1; n is 0, m is 13, and i is 3; or n is 1, m is 13, and i is 2; or n is 2, m is 13 and i is 1; n is 0, m is 14, and i is 2; or n is 1, m is 14, and i is 1; n is 0, m is 15, and i is 1; and positional isomers thereof.

In some embodiments, for example, n is 0, m is 1, and i is 16, or n is 1, m is 1, and i is 15; or n is 2, m is 1, and i is 14; or n is 3, m is 1, and i is 13; or n is 4, m is 1, and i is 12; or n is 5, m is 1 and i is 11; or n is 6, m is 1, and i is 10; or n is 7, m is 1, and i is 9; or n is 8, m is 1, and i is 8; or n is 9, m is 1, and i is 7; or n is 10, m is 1, and i is 6; or n is 11, m is 1, and i is 5; or n is 12, m is 1; and i is 4; or n is 13, m is 1, and i is 3; or n is 14, m is 1, and i is 2; or n is 15, m is 1 and i is 1; n is 0, m is 2, and i is 15, or n is 1, m is 2, and i is 14; or n is 2, m is 2, and i is 13; or n is 3, m is 2, and i is 12; or n is 4, m is 2, and i is 11; or n is 5, m is 2 and i is 10; or n is 6, m is 2, and i is 9; or n is 7, m is 2, and i is 8; or n is 8, m is 2, and i is 7; or n is 9, m is 2, and i is 6; or n is 10, m is 2, and i is 5; or n is 11, m is 2, and i is 4; or n is 12, m is 2; and i is 3; or n is 13, m is 2, and i is 2; or n is 14, m is 1, and i is 1; n is 0, m is 3, and i is 14, or n is 1, m is 3, and i is 13; or n is 2, m is 3, and i is 12; or n is 3, m is 3, and i is 11; or n is 4, m is 3, and i is 10; or n is 5, m is 3 and i is 9; or n is 6, m is 3, and i is 8; or n is 7, m is 3, and i is 7; or n is 8, m is 3, and i is 6; or n is 9, m is 3, and i is 5; or n is 10, m is 3, and i is 4; or n is 11, m is 3, and i is 3; or n is 12, m is 3; and i is 2; or n is 13, m is 3, and i is 1; n is 0, m is 4, and i is 13, or n is 1, m is 4, and i is 12; or n is 2, m is 4, and i is 11; or n is 3, m is 4, and i is 10; or n is 4, m is 4, and i is 9; or n is 5, m is 4 and i is 8; or n is 6, m is 4, and i is 7; or n is 7, m is 4, and i is 6; or n is 8, m is 4, and i is 5; or n is 9, m is 4, and i is 4; or n is 10, m is 4, and i is 3; or n is 11, m is 4, and i is 2; or n is 12, m is 4; and i is 1; n is 0, m is 5, and i is 12, or n is 1, m is 5, and i is 11; or n is 2, m is 5, and i is 10; or n is 3, m is 5, and i is 9; or n is 4, m is 5, and i is 8; or n is 5, m is 5 and i is 7; or n is 6, m is 5, and i is 6; or n is 7, m is 5, and i is 5; or n is 8, m is 5, and i is 4; or n is 9, m is 5, and i is 3; or n is 10, m is 5, and i is 2; or n is 11, m is 5, and i is 1; n is 0, m is 6, and i is 11, or n is 1, m is 6, and i is 10; or n is 2, m is 6, and i is 9; or n is 3, m is 6, and i is 8; or n is 4, m is 6, and i is 7; or n is 5, m is 6 and i is 6; or n is 6, m is 6, and i is 5; or n is 7, m is 6, and i is 4; or n is 8, m is 6, and i is 3; or n is 9, m is 6, and i is 2; or n is 10, m is 6, and i is 1; n is 0, m is 7, and i is 10, or n is 1, m is 7, and i is 9; or n is 2, m is 7, and i is 8; or n is 3, m is 7, and i is 7; or n is 4, m is 7, and i is 6; or n is 5, m is 7 and i is 5; or n is 6, m is 7, and i is 4; or n is 7, m is 7, and i is 3; or n is 8, m is 7, and i is 2; or n is 9, m is 7, and i is 1; n is 0, m is 8, and i is 9, or n is 1, m is 8, and i is 8; or n is 2, m is 8, and i is 7; or n is 3, m is 8, and i is 6; or n is 4, m is 8, and i is 5; or n is 5, m is 8 and i is 4; or n is 6, m is 8, and i is 3; or n is 7, m is 8, and i is 2; or n is 8, m is 8, and i is 1; n is 0, m is 9, and i is 8, or n is 1, m is 9, and i is 7; or n is 2, m is 9, and i is 6; or n is 3, m is 9, and i is 5; or n is 4, m is 9, and i is 4; or n is 5, m is 9 and i is 3; or n is 6, m is 9, and i is 2; or n is 7, m is 9, and i is 1; n is 0, m is 10, and i is 7, or n is 1, m is 10, and i is 6; or n is 2, m is 10, and i is 5; or n is 3, m is 10, and i is 4; or n is 4, m is 10, and i is 3; or n is 5, m is 10 and i is 2; or n is 6, m is 10, and i is 1; n is 0, m is 11, and i is 6, or n is 1, m is 11, and i is 5; or n is 2, m is 11, and i is 4; or n is 3, m is 11, and i is 3; or n is 4, m is 11, and i is 2; or n is 5, m is 11 and i is 1; n is 0, m is 12, and i is 5; or n is 1, m is 12, and i is 4; or n is 2, m is 12, and i is 3; or n is 3, m is 12, and i is 2; or n is 4, m is 12, and i is 1; n is 0, m is 13, and i is 4, or n is 1, m is 13, and i is 3; or n is 2, m is 13, and i is 2; or n is 3, m is 13, and i is 1; n is 0, m is 14, and i is 3, or n is 1, m is 14, and i is 2; or n is 2, m is 14, and i is 1; n is 0, m is 15, and i is 2, or n is 1, m is 15, and i is 1; or n is 0, m is 16, and i is 1; or positional isomers thereof.

Accordingly, some embodiments of the disclosure provide methods for preparing an olefinic alcohol product as described above, wherein the olefinic substrate is a metathesis product, and wherein the method includes: a) cross-metathesizing a first terminal olefin and a second different terminal olefin in the presence of a metathesis catalyst to form the metathesis product; and b) incubating the metathesis product with an enzyme capable of hydroxylating an subterminal carbon of the metathesis product to form an olefinic alcohol product.

In some embodiments, the first terminal olefin has the formula $(CH_2=CH)(CH_2)_mH$, the second different terminal olefin has the formula $(CH_2=CH)(CH_2)_nH$, the metathesis product has the formula $H(CH_2)_m(CH=CH)(CH_2)_nH$, the olefinic alcohol product has the formula $H(CH_2)_iCHOH(CH_2)_{m-i-1}(CH=CH)(CH_2)_nH$ or $H(CH_2)_m(CH=CH)(CH_2)_{n-i-1}CHOH(CH_2)_iH$, and m, n and i are different integers between 1 and 17. In some embodiments, m, n, and i are different integers between 1 and 9.

The methods of the disclosure can also be conducted such that the biohydroxylation step is conducted prior to the metathesis step and/or other synthetic transformation steps. Accordingly, some embodiments of the disclosure provide methods wherein the olefinic substrate is a first terminal olefin, and wherein the method includes: a) incubating the first terminal olefin with an enzyme capable of hydroxylating an subterminal carbon of the terminal olefin to form an alkenol; and b) metathesizing the alkenol and a second terminal olefin in the presence of a metathesis catalyst to form the olefinic alcohol product.

The alcohol can be protected with a suitable protecting group if necessary. In some embodiments, the methods of the disclosure include: a) incubating the first terminal olefin with an enzyme capable of selectively hydroxylating an subterminal carbon of the terminal olefin to form an alkenol; b) protecting the alkenol to form a protected alkenol; c) metathesizing the protected alkenol and a second terminal olefin in the presence of a metathesis catalyst to form a protected olefinic alcohol product; and d) deprotecting the protected olefinic alcohol product to form the olefinic alcohol product.

Any suitable alcohol protecting group can be used in the methods of the disclosure. Such protecting groups are well known to one of ordinary skill in the art, including those that are disclosed in *Protective Groups in Organic Synthesis*, 4th edition, T. W. Greene and P. G. M. Wuts, John Wiley & Sons, New York, 2006, which is incorporated herein by reference in its entirety. In some embodiments, the α,ω-alkenol is protected via esterification and the should alkenol is protected via esterification with an acid selected from the group consisting of formate and acetate.

Synthesis of Terminal Alkenals

As indicated above, the alcohol moiety generated via hydroxylation can be further modified to generate alkenals or acetate esters.

Oxidation of Fatty Alcohols

Oxidation of fatty alcohols is often achieved via selective oxidation via pyridinium chlorochromate (PCC) (Scheme 9).

Scheme 9

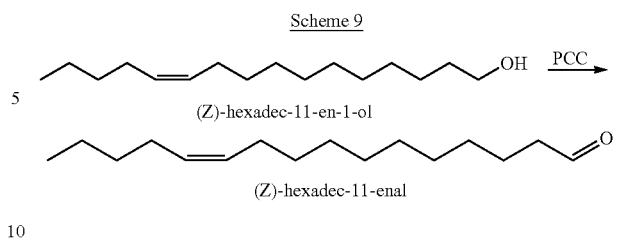

(Z)-hexadec-11-en-1-ol (Z)-hexadec-11-enal

Alternatively, TEMPO (TEMPO=2,2,6,6-tetramethylpiperidinyl-N-oxyl) and related catalyst systems can be used to selectively oxidize alcohols to aldehydes. These methods are described in Ryland and Stahl (2014), herein incorporated by reference in its entirety.

Bio-Oxidation of Terminal Alcohols

Many insect pheromones are fatty aldehydes or comprise a fatty aldehyde component. As such, the conversion of the fatty alcohol produced via terminal hydroxylation to the fatty aldehyde is required to produce certain pheromones. The conversion of a fatty alcohol to a fatty aldehyde is known to be catalyzed by alcohol dehydrogenases (ADH) and alcohol oxidases (AOX). Additionally, the conversion of a length $C_n$ fatty acid to a $C_{n-1}$ fatty aldehyde is catalyzed by plant α-dioxygenases (α-DOX) (Scheme 10).

Scheme 10

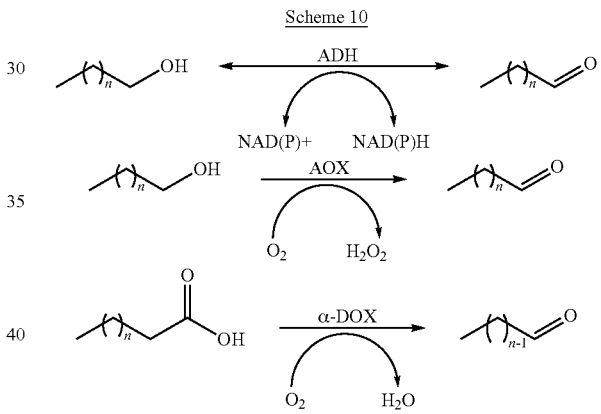

The present disclosure describes enzymes that oxidize fatty alcohols to fatty aldehydes.

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some member of these four groups are better suited than others as candidates for evaluation.

Short chain alcohol oxidases (including but not limited to those currently classified as EC 1.1.3.13, Table 7) catalyze the oxidation of lower chain length alcohol substrates in the range of C1-C8 carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of C6 to C11 when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 8) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979), *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported KM in the 10-50 µM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 7

Alcohol oxidase enzymes capable of oxidizing short chain alcohols (EC 1.1.3.13)

| Organism | Gene names | Accession No. |
| --- | --- | --- |
| *Komagataella pastoris* (strain ATCC 76273/CBS 7435/CECT 11047/NRRL Y-11430/Wegner 21-1) (Yeast) (*Pichia pastoris*) | AOX1 PP7435_Chr4-0130 | F2QY27 |
| *Komagataella pastoris* (strain GS115/ATCC 20864) (Yeast) (*Pichia pastoris*) | AOX1 PAS_chr4_0821 | P04842 |
| *Komagataella pastoris* (strain ATCC 76273/CBS 7435/CECT 11047/NRRL Y-11430/Wegner 21-1) (Yeast) (*Pichia pastoris*) | AOX2 PP7435_Chr4-0863 | F2R038 |
| *Komagataella pastoris* (strain GS115/ATCC 20864) (Yeast) (*Pichia pastoris*) | AOX2 PAS_chr4_0152 | C4R702 |
| *Candida boidinii* (Yeast) | AOD1 | Q00922 |
| *Pichia angusta* (Yeast) (*Hansenula polymorpha*) | MOX | P04841 |
| *Thanatephorus cucumeris* (strain AG1-IB/isolate 7/3/14) (Lettuce bottom rot fungus) (*Rhizoctonia solani*) | AOD1 BN14_10802 | M5CC52 |
| *Thanatephorus cucumeris* (strain AG1-IB/isolate 7/3/14) (Lettuce bottom rot fungus) (*Rhizoctonia solani*) | MOX BN14_12214 | M5CF32 |
| *Thanatephorus cucumeris* (strain AG1-IB/isolate 7/3/14) (Lettuce bottom rot fungus) (*Rhizoctonia solani*) | AOD1 BN14_10691 | M5CAV1 |
| *Thanatephorus cucumeris* (strain AG1-IB/isolate 7/3/14) (Lettuce bottom rot fungus) (*Rhizoctonia solani*) | AOD1 BN14_09479 | M5C7F4 |
| *Thanatephorus cucumeris* (strain AG1-IB/isolate 7/3/14) (Lettuce bottom rot fungus) (*Rhizoctonia solani*) | AOD1 BN14_10803 | M5CB66 |
| *Thanatephorus cucumeris* (strain AG1-IB/isolate 7/3/14) (Lettuce bottom rot fungus) (*Rhizoctonia solani*) | AOD1 BN14_09900 | M5C9N9 |
| *Thanatephorus cucumeris* (strain AG1-IB/isolate 7/3/14) (Lettuce bottom rot fungus) (*Rhizoctonia solani*) | AOD1 BN14_08302 | M5C2L8 |

TABLE 7-continued

Alcohol oxidase enzymes capable of oxidizing short chain alcohols (EC 1.1.3.13)

| Organism | Gene names | Accession No. |
|---|---|---|
| *Thanatephorus cucumeris* (strain AG1-IB/ isolate 7/3/14) (Lettuce bottom rot fungus) (*Rhizoctonia solani*) | MOX BN14_09408 | M5C784 |
| *Thanatephorus cucumeris* (strain AG1-IB/ isolate 7/3/14) (Lettuce bottom rot fungus) (*Rhizoctonia solani*) | MOX BN14_09478 | M5C8F8 |
| *Thanatephorus cucumeris* (strain AG1-IB/ isolate 7/3/14) (Lettuce bottom rot fungus) (*Rhizoctonia solani*) | AOD1 BN14_11356 | M5CH40 |
| *Ogataea henricii* | AOD1 | A5LGF0 |
| *Candida methanosorbosa* | AOD1 | A5LGE5 |
| *Candida methanolovescens* | AOD1 | A5LGE4 |
| *Candida succiphila* | AOD1 | A5LGE6 |
| *Aspergillus niger* (strain CBS 513.88/FGSC A1513) | An15g02200 | A2R501 |
| *Aspergillus niger* (strain CBS 513.88/FGSC A1513) | An18g05480 | A2RB46 |
| *Moniliophthora perniciosa* (Witches'-broom disease fungus) (*Marasmius perniciosus*) | | I7CMK2 |
| *Candida cariosilignicola* | AOD1 | A5LGE3 |
| *Candida pignaliae* | AOD1 | A5LGE1 |
| *Candida pignaliae* | AOD2 | A5LGE2 |
| *Candida sonorensis* | AOD1 | A5LGD9 |
| *Candida sonorensis* | AOD2 | A5LGE0 |
| *Pichia naganishii* | AOD1 | A5LGF2 |
| *Ogataea minuta* | AOD1 | A5LGF1 |
| *Ogataea philodendri* | AOD1 | A5LGF3 |
| *Ogataea wickerhamii* | AOD1 | A5LGE8 |
| *Kuraishia capsulata* | AOD1 | A5LGE7 |
| *Talaromyces stipitatus* (strain ATCC 10500/ CBS 375.48/QM 6759/NRRL 1006) (*Penicillium stipitatum*) | TSTA_021940 | B8MHF8 |
| *Talaromyces stipitatus* (strain ATCC 10500/ CBS 375.48/QM 6759/NRRL 1006) (*Penicillium stipitatum*) | TSTA_065150 | B8LTH7 |
| *Talaromyces stipitatus* (strain ATCC 10500/ CBS 375.48/QM 6759/NRRL 1006) (*Penicillium stipitatum*) | TSTA_065150 | B8LTH8 |
| *Talaromyces stipitatus* (strain ATCC 10500/ CBS 375.48/QM 6759/NRRL 1006) (*Penicillium stipitatum*) | TSTA_000410 | B8MSB1 |
| *Ogataea glucozyma* | AOD1 | A5LGE9 |
| *Ogataea parapolymorpha* (strain DL-1/ATCC 26012/NRRL Y-7560) (Yeast) (*Hansenula polymorpha*) | HPODL_03886 | W1QCJ3 |
| *Gloeophyllum trabeum* (Brown rot fungus) | AOX | A8DPS4 |
| *Pichia angusta* (Yeast) (*Hansenula polymorpha*) | mox1 | A6PZG8 |
| *Pichia trehalophila* | AOD1 | A5LGF4 |
| *Pichia angusta* (Yeast) (*Hansenula polymorpha*) | mox1 | A6PZG9 |
| *Pichia angusta* (Yeast) (*Hansenula polymorpha*) | mox1 | A6PZG7 |
| *Ixodes scapularis* (Black-legged tick) (Deer tick) | IscW_ISCW017898 | B7PIZ7 |

TABLE 8

Alcohol oxidase enzymes capable of oxidizing long chain alcohols including fatty alcohols (EC 1.1.3.20)

| Organism | Gene names | Accession No. |
|---|---|---|
| *Lotus japonicus* (*Lotus corniculatus* var. *japonicus*) | FAO1 | B5WWZ8 |
| *Arabidopsis thaliana* (Mouse-ear cress) | FAO1 At1g03990 F21M11.7 | Q9ZWB9 |
| *Lotus japonicus* (*Lotus corniculatus* var. *japonicus*) | FAO2 | B5WWZ9 |
| *Arabidopsis thaliana* (Mouse-ear cress) | FAO3 At3g23410 MLM24.14 MLM24.23 | Q9LW56 |
| *Arabidopsis thaliana* (Mouse-ear cress) | FAO4A At4g19380 T5K18.160 | O65709 |
| *Arabidopsis thaliana* (Mouse-ear cress) | FAO4B At4g28570 T5F17.20 | Q94BP3 |
| *Microbotryum violaceum* (strain p1A1 Lamole) (Anther smut fungus) (*Ustilago violacea*) | MVLG_06864 | U5HIL4 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Ajellomyces dermatitidis* ATCC 26199 | BDFG_03507 | T5BNQ0 |
| *Gibberella zeae* (strain PH-1/ATCC MYA-4620/FGSC 9075/NRRL 31084) (Wheat head blight fungus) (*Fusarium graminearum*) | FG06918.1 FGSG_06918 | I1RS14 |
| *Pichia sorbitophila* (strain ATCC MYA-4447/BCRC 22081/CBS 7064/ NBRC 10061/NRRL Y-12695) (Hybrid yeast) | Piso0_004410 GNLVRS01_PISO0K16268g GNLVRS01_PISO0L16269g | G8Y5E1 |
| *Emericella nidulans* (strain FGSC A4/ ATCC 38163/CBS 112.46/NRRL 194/ M139) (*Aspergillus nidulans*) | AN0623.2 ANIA_00623 | Q5BFQ7 |
| *Pyrenophora tritici-repentis* (strain Pt-1C-BFP) (Wheat tan spot fungus) (*Drechslera tritici-repentis*) | PTRG_10154 | B2WJW5 |
| *Paracoccidioides lutzii* (strain ATCC MYA-826/Pb01) (*Paracoccidioides brasiliensis*) | PAAG_09117 | C1HEC6 |
| *Candida parapsilosis* (strain CDC 317/ ATCC MYA-4646) (Yeast) (*Monilia parapsilosis*) | CPAR2_204420 | G8BG15 |
| *Pseudozyma brasiliensis* (strain GHG001) (Yeast) | PSEUBRA_SCAF2g03010 | V5GPS6 |
| *Candida parapsilosis* (strain CDC 317/ ATCC MYA-4646) (Yeast) (*Monilia parapsilosis*) | CPAR2_204430 | G8BG16 |
| *Sclerotinia borealis* F-4157 | SBOR_5750 | W9CDE2 |
| *Sordaria macrospora* (strain ATCC MYA-333/DSM 997/K(L3346)/K-hell) | SMAC_06361 | F7W6K4 |
| *Sordaria macrospora* (strain ATCC MYA-333/DSM 997/K(L3346)/K-hell) | SMAC_01933 | F7VSA1 |
| *Meyerozyma guilliermondii* (strain ATCC 6260/CBS 566/DSM 6381/ JCM 1539/NBRC 10279/NRRL Y-324) (Yeast) (*Candida guilliermondii*) | PGUG_03467 | A5DJL6 |
| *Trichophyton rubrum* CBS 202.88 | H107_00669 | A0A023ATC5 |
| *Arthrobotrys oligospora* (strain ATCC 24927/CBS 115.81/DSM 1491) (Nematode-trapping fungus) (*Didymozoophaga oligospora*) | AOL_s00097g516 | G1XJI9 |
| *Scheffersomyces stipitis* (strain ATCC 58785/CBS 6054/NBRC 10063/ NRRL Y-11545) (Yeast) (*Pichia stipitis*) | FAO1 PICST_90828 | A3LYX9 |
| *Scheffersomyces stipitis* (strain ATCC 58785/CBS 6054/NBRC 10063/ NRRL Y-11545) (Yeast) (*Pichia stipitis*) | FAO2 PICST_32359 | A3LW61 |
| *Aspergillus oryzae* (strain 3.042) (Yellow koji mold) | Ao3042_09114 | I8TL25 |
| *Fusarium oxysporum* (strain Fo5176) (*Fusarium* vascular wilt) | FOXB_17532 | F9GFU8 |
| *Rhizopus delemar* (strain RA 99-880/ ATCC MYA-4621/FGSC 9543/ NRRL 43880) (Mucormycosis agent) (*Rhizopus arrhizus* var. *delemar*) | RO3G_08271 | I1C536 |
| *Rhizopus delemar* (strain RA 99-880/ ATCC MYA-4621/FGSC 9543/ NRRL 43880) (Mucormycosis agent) (*Rhizopus arrhizus* var. *delemar*) | RO3G_00154 | I1BGX0 |
| *Fusarium oxysporum* (strain Fo5176) (*Fusarium* vascular wilt) | FOXB_07532 | F9FMA2 |
| *Penicillium roqueforti* | PROQFM164_S02g001772 | W6QPY1 |
| *Aspergillus clavatus* (strain ATCC 1007/ CBS 513.65/DSM 816/NCTC 3887/ NRRL 1) | ACLA_018400 | A1CNB5 |
| *Arthroderma otae* (strain ATCC MYA-4605/CBS 113480) (*Microsporum canis*) | MCYG_08732 | C5G1B0 |
| *Trichophyton tonsurans* (strain CBS 112818) (Scalp ringworm fungus) | TESG_07214 | F2S8I2 |
| *Colletotrichum higginsianum* (strain IMI 349063) (Crucifer anthracnose fungus) | CH063_13441 | H1VUE7 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Ajellomyces capsulatus* (strain H143) (Darling's disease fungus) (*Histoplasma capsulatum*) | HCDG_07658 | C6HN77 |
| *Trichophyton rubrum* (strain ATCC MYA-4607/CBS 118892) (Athlete's foot fungus) | TERG_08235 | F2T096 |
| *Cochliobolus heterostrophus* (strain C5/ATCC 48332/race O) (Southern corn leaf blight fungus) (*Bipolaris maydis*) | COCHEDRAFT_1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (Valley fever fungus) | CPC735_000380 | C5P005 |
| *Magnaporthe oryzae* (strain P131) (Rice blast fungus) (*Pyricularia oryzae*) | OOW_P131scaffold01214g15 | L7IZ92 |
| *Neurospora tetrasperma* (strain FGSC 2508/ATCC MYA-4615/P0657) | NEUTE1DRAFT_82541 | F8MKD1 |
| *Hypocrea virens* (strain Gv29-8/FGSC 10586) (*Gliocladium virens*) (*Trichoderma virens*) | TRIVIDRAFT_54537 | G9MMY7 |
| *Hypocrea virens* (strain Gv29-8/FGSC 10586) (*Gliocladium virens*) (*Trichoderma virens*) | TRIVIDRAFT_53801 | G9MT89 |
| *Aspergillus niger* (strain CBS 513.88/FGSC A1513) | An01g09620 | A2Q9Z3 |
| *Verticillium dahliae* (strain VdLs.17/ATCC MYA-4575/FGSC 10137) (*Verticillium* wilt) | VDAG_05780 | G2X6J8 |
| *Ustilago maydis* (strain 521/FGSC 9021) (Corn smut fungus) | UM02023.1 | Q4PCZ0 |
| *Fusarium oxysporum* f. sp. *lycopersici* MN25 | FOWG_13006 | W9LNI9 |
| *Fusarium oxysporum* f. sp. *lycopersici* MN25 | FOWG_02542 | W9N9Z1 |
| *Candida tropicalis* (Yeast) | FAO1 | Q6QIR6 |
| *Magnaporthe oryzae* (strain 70-15/ATCC MYA-4617/FGSC 8958) (Rice blast fungus) (*Pyricularia oryzae*) | MGG_11317 | G4MVK1 |
| *Candida tropicalis* (Yeast) | faot | Q9P8D9 |
| *Candida tropicalis* (Yeast) | FAO2a | Q6QIR5 |
| *Phaeosphaeria nodorum* (strain SN15/ATCC MYA-4574/FGSC 10173) (Glume blotch fungus) (*Septoria nodorum*) | SNOG_02371 | Q0V0U3 |
| *Candida tropicalis* (Yeast) | FAO2b | Q6QIR4 |
| *Pestalotiopsis fici* W106-1 | PFICI_11209 | W3WU04 |
| *Magnaporthe oryzae* (strain Y34) (Rice blast fungus) (*Pyricularia oryzae*) | OOU_Y34scaffold00240g57 | L7IFT5 |
| *Pseudogymnoascus destructans* (strain ATCC MYA-4855/20631-21) (Bat white-nose syndrome fungus) (*Geomyces destructans*) | GMDG_01756 | L8G0G6 |
| *Pseudogymnoascus destructans* (strain ATCC MYA-4855/20631-21) (Bat white-nose syndrome fungus) (*Geomyces destructans*) | GMDG_04950 | L8GCY2 |
| *Mycosphaerella fijiensis* (strain CIRAD86) (Black leaf streak disease fungus) (*Pseudocercospora fijiensis*) | MYCFIDRAFT_52380 | M2Z831 |
| *Bipolaris oryzae* ATCC 44560 | COCMIDRAFT_84580 | W7A0I8 |
| *Cladophialophora psammophila* CBS 110553 | A1O5_08147 | W9WTM9 |
| *Fusarium oxysporum* f. sp. *melonis* 26406 | FOMG_05173 | X0AEE6 |
| *Fusarium oxysporum* f. sp. *melonis* 26406 | FOMG_17829 | W9ZBB7 |
| *Cyphellophora europaea* CBS 101466 | HMPREF1541_02174 | W252S5 |
| *Aspergillus kawachii* (strain NBRC 4308) (White koji mold) (*Aspergillus awamori* var. kawachi) | AKAW_00147 | G7X626 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Aspergillus terreus* (strain NIH 2624/FGSC A1156) | ATEG_05086 | Q0CMJ8 |
| *Coccidioides immitis* (strain RS) (Valley fever fungus) | CIMG_02987 | J3KAI8 |
| *Ajellomyces dermatitidis* (strain ER-3/ATCC MYA-2586) (*Blastomyces dermatitidis*) | BDCG_04701 | C5GLS5 |
| *Fusarium oxysporum* f. sp. *cubense* (strain race 1) (Panama disease fungus) | FOC1_g10013865 | N4U732 |
| *Rhodotorula glutinis* (strain ATCC 204091/IIP 30/MTCC 1151) (Yeast) | RTG_00643 | G0SVU8 |
| *Aspergillus niger* (strain ATCC 1015/CBS 113.46/FGSC A1144/LSHB Ac4/NCTC 3858a/NRRL 328/USDA 3528.7) | ASPNIDRAFT_35778 | G3XTM6 |
| *Candida cloacae* | fao1 | Q9P8D8 |
| *Candida cloacae* | fao2 | Q9P8D7 |
| *Fusarium oxysporum* f. sp. *cubense* (strain race 1) (Panama disease fungus) | FOC1_g10006358 | N4TUH3 |
| *Candida albicans* (strain SC5314/ATCC MYA-2876) (Yeast) | FAO1 CaO19.13562 orf19.13562 | Q59RS8 |
| *Candida albicans* (strain SC5314/ATCC MYA-2876) (Yeast) | FAO1 CaO19.6143 orf19.6143 | Q59RP0 |
| *Chaetomium thermophilum* (strain DSM 1495/CBS 144.50/IMI 039719) | CTHT_0018560 | G0S2U9 |
| *Mucor circinelloides* f. *circinelloides* (strain 1006PhL) (Mucormycosis agent) (*Calyptromyces circinelloides*) | HMPREF1544_05296 | S2JDN0 |
| *Mucor circinelloides* f. *circinelloides* (strain 1006PhL) (Mucormycosis agent) (*Calyptromyces circinelloides*) | HMPREF1544_05295 | S2JYP5 |
| *Mucor circinelloides* f. *circinelloides* (strain 1006PhL) (Mucormycosis agent) (*Calyptromyces circinelloides*) | HMPREF1544_06348 | S2JVK9 |
| *Botryotinia fuckeliana* (strain BcDW1) (Noble rot fungus) (*Botrytis cinerea*) | BcDW1_6807 | M7UD26 |
| *Podospora anserina* (strain S/ATCC MYA-4624/DSM 980/FGSC 10383) (*Pleurage anserina*) | PODANS_5_13040 | B2AFD8 |
| *Neosartorya fumigata* (strain ATCC MYA-4609/Af293/CBS 101355/FGSC A1100) (*Aspergillus fumigatus*) | AFUA_1G17110 | Q4WR91 |
| *Fusarium oxysporum* f. sp. *vasinfectum* 25433 | FOTG_00686 | X0MEE6 |
| *Fusarium oxysporum* f. sp. *vasinfectum* 25433 | FOTG_12485 | X0LE98 |
| *Trichophyton interdigitale* H6 | H101_06625 | A0A022U717 |
| *Beauveria bassiana* (strain ARSEF 2860) (White muscardine disease fungus) (*Tritirachium shiotae*) | BBA_04100 | J4UNY3 |
| *Fusarium oxysporum* f. sp. *radicis-lycopersici* 26381 | FOCG_00843 | X0GQ62 |
| *Fusarium oxysporum* f. sp. *radicis-lycopersici* 26381 | FOCG_15170 | X0F4T1 |
| *Neurospora tetrasperma* (strain FGSC 2509/P0656) | NEUTE2DRAFT_88670 | G4UNN6 |
| *Pseudozyma hubeiensis* (strain SY62) (Yeast) | PHSY_000086 | R9NVU1 |
| *Lodderomyces elongisporus* (strain ATCC 11503/CBS 2605/JCM 1781/NBRC 1676/NRRL YB-4239) (Yeast) (*Saccharomyces elongisporus*) | LELG_03289 | A5E102 |
| *Malassezia globosa* (strain ATCC MYA-4612/CBS 7966) (Dandruff-associated fungus) | MGL_3855 | A8QAY8 |
| *Byssochlamys spectabilis* (strain No. 5/NBRC 109023) (*Paecilomyces variotii*) | PVAR5_7014 | V5GBL6 |
| *Ajellomyces capsulatus* (strain H88) (Darling's disease fungus) (*Histoplasma capsulatum*) | HCEG_03274 | F0UF47 |
| *Trichosporon asahii* var. *asahii* (strain ATCC 90039/CBS 2479/JCM 2466/KCTC 7840/NCYC 2677/UAMH 7654) (Yeast) | A1Q1_03669 | J6FBP4 |

TABLE 8-continued

Alcohol oxidase enzymes capable of oxidizing long chain alcohols including fatty alcohols (EC 1.1.3.20)

| Organism | Gene names | Accession No. |
| --- | --- | --- |
| *Penicillium oxalicum* (strain 114-2/ CGMCC 5302) (*Penicillium decumbens*) | PDE_00027 | S7Z8U8 |
| *Fusarium oxysporum* f. sp. *conglutinans* race 2 54008 | FOPG_02304 | X0IBE3 |
| *Fusarium oxysporum* f. sp. *conglutinans* race 2 54008 | FOPG_13066 | X0H540 |
| *Fusarium oxysporum* f. sp. *raphani* 54005 | FOQG_00704 | X0D1G8 |
| *Fusarium oxysporum* f. sp. *raphani* 54005 | FOQG_10402 | X0C482 |
| *Metarhizium acridum* (strain CQMa 102) | MAC_03115 | E9DZR7 |
| *Arthroderma benhamiae* (strain ATCC MYA-4681/CBS 112371) (*Trichophyton mentagrophytes*) | ARB_02250 | D4B1C1 |
| *Fusarium oxysporum* f. sp. *cubense* tropical race 4 54006 | FOIG_12161 | X0JFI6 |
| *Fusarium oxysporum* f. sp. *cubense* tropical race 4 54006 | FOIG_12751 | X0JDU5 |
| *Cochliobolus heterostrophus* (strain C4/ ATCC 48331/race T) (Southern corn leaf blight fungus) (*Bipolaris maydis*) | COCC4DRAFT_52836 | N4WZZ0 |
| *Trichosporon asahii* var. *asahii* (strain CBS 8904) (Yeast) | A1Q2_00631 | K1VZW1 |
| *Mycosphaerella graminicola* (strain CBS 115943/IPO323) (Speckled leaf blotch fungus) (*Septoria tritici*) | MYCGRDRAFT_37086 | F9X375 |
| *Botryotinia fuckeliana* (strain T4) (Noble rot fungus) (*Botrytis cinerea*) | BofuT4_P072020.1 | G2XQ18 |
| *Metarhizium anisopliae* (strain ARSEF 23/ATCC MYA-3075) | MAA_05783 | E9F0I4 |
| *Cladophialophora carrionii* CBS 160.54 | G647_05801 | V9DAR1 |
| *Coccidioides posadasii* (strain RMSCC 757/Silveira) (Valley fever fungus) | CPSG_09174 | E9DH75 |
| *Rhodosporidium toruloides* (strain NP11) (Yeast) (*Rhodotorula gracilis*) | RHTO_06879 | M7X159 |
| *Puccinia graminis* f. sp. *tritici* (strain CRL 75-36-700-3/race SCCL) (Black stem rust fungus) | PGTG_10521 | E3KIL8 |
| *Trichophyton rubrum* CBS 288.86 | H103_00624 | A0A022WG28 |
| *Colletotrichum fioriniae* PJ7 | CFIO01_08202 | A0A010RKZ4 |
| *Trichophyton rubrum* CBS 289.86 | H104_00611 | A0A022XB46 |
| *Cladophialophora yegresii* CBS 114405 | A1O7_02579 | W9WC55 |
| *Colletotrichum orbiculare* (strain 104-T/ ATCC 96160/CBS 514.97/LARS 414/ MAFF 240422) (Cucumber anthracnose fungus) (*Colletotrichum lagenarium*) | Cob_10151 | N4VFP3 |
| *Drechslerella stenobrocha* 248 | DRE_03459 | W7IDL6 |
| *Neosartorya fumigata* (strain CEA10/ CBS 144.89/FGSC A1163) (*Aspergillus fumigatus*) | AFUB_016500 | B0XP90 |
| *Thielavia terrestris* (strain ATCC 38088/ NRRL 8126) (*Acremonium alabamense*) | THITE_2117674 | G2R8H9 |
| *Gibberella fujikuroi* (strain CBS 195.34/ IMI 58289/NRRL A-6831) (Bakanae and foot rot disease fungus) (*Fusarium fujikuroi*) | FFUJ_02948 | S0DZP7 |
| *Gibberella fujikuroi* (strain CBS 195.34/ IMI 58289/NRRL A-6831) (Bakanae and foot rot disease fungus) (*Fusarium fujikuroi*) | FFUJ_12030 | S0EMC6 |
| *Aspergillus flavus* (strain ATCC 200026/ FGSC A1120/NRRL 3357/JCM 12722/SRRC 167) | AFLA_109870 | B8N941 |
| *Togninia minima* (strain UCR-PA7) (Esca disease fungus) (*Phaeoacremonium aleophilum*) | UCRPA7_1719 | R8BTZ6 |
| *Ajellomyces dermatitidis* (strain ATCC 18188/CBS 674.68) (*Blastomyces dermatitidis*) | BDDG_09783 | F2TUC0 |
| *Macrophomina phaseolina* (strain MS6) (Charcoal rot fungus) | MPH_10582 | K2RHA5 |

TABLE 8-continued

Alcohol oxidase enzymes capable of oxidizing long chain alcohols including fatty alcohols (EC 1.1.3.20)

| Organism | Gene names | Accession No. |
| --- | --- | --- |
| *Neurospora crassa* (strain ATCC 24698/ 74-OR23-1A/CBS 708.71/DSM 1257/ FGSC 987) | NCU08977 | Q7S2Z2 |
| *Neosartorya fischeri* (strain ATCC 1020/ DSM 3700/FGSC A1164/NRRL 181) (*Aspergillus fischerianus*) | NFIA_008260 | A1D156 |
| *Fusarium pseudograminearum* (strain CS3096) (Wheat and barley crown-rot fungus) | FPSE_11742 | K3U9J5 |
| *Spathaspora passalidarum* (strain NRRL Y-27907/11-Y1) | SPAPADRAFT_54193 | G3AJP0 |
| *Spathaspora passalidarum* (strain NRRL Y-27907/11-Y1) | SPAPADRAFT_67198 | G3ANX7 |
| *Trichophyton verrucosum* (strain HKI 0517) | TRV_07960 | D4DL86 |
| *Arthroderma gypseum* (strain ATCC MYA-4604/CBS 118893) (*Microsporum gypseum*) | MGYG_07264 | E4V2J0 |
| *Hypocrea jecorina* (strain QM6a) (*Trichoderma reesei*) | TRIREDRAFT_43893 | G0R7P8 |
| *Trichophyton rubrum* MR1448 | H110_00629 | A0A022Z1G4 |
| *Aspergillus ruber* CBS 135680 | EURHEDRAFT_512125 | A0A017SPR0 |
| *Glarea lozoyensis* (strain ATCC 20868/ MF5171) | GLAREA_04397 | S3D6C1 |
| *Setosphaeria turcica* (strain 28A) (Northern leaf blight fungus) (*Exserohilum turcicum*) | SETTUDRAFT_20639 | R0K6H8 |
| *Paracoccidioides brasiliensis* (strain Pb18) | PADG_06552 | C1GH16 |
| *Fusarium oxysporum* Fo47 | FOZG_13577 | W9JPG9 |
| *Fusarium oxysporum* Fo47 | FOZG_05344 | W9KPH3 |
| *Trichophyton rubrum* MR1459 | H113_00628 | A0A022ZY09 |
| *Penicillium marneffei* (strain ATCC 18224/CBS 334.59/QM 7333) | PMAA_075740 | B6QBY3 |
| *Sphaerulina musiva* (strain SO2202) (Poplar stem canker fungus) (*Septoria musiva*) | SEPMUDRAFT_154026 | M3DAK6 |
| *Gibberella moniliformis* (strain M3125/ FGSC 7600) (Maize ear and stalk rot fungus) (*Fusarium verticillioides*) | FVEG_10526 | W7N4P8 |
| *Gibberella moniliformis* (strain M3125/ FGSC 7600) (Maize ear and stalk rot fungus) (*Fusarium verticillioides*) | FVEG_08281 | W7MVR9 |
| *Pseudozyma antarctica* (strain T-34) (Yeast) (*Candida antarctica*) | PANT_22d00298 | M9MGF2 |
| *Paracoccidioides brasiliensis* (strain Pb03) | PABG_07795 | C0SJD4 |
| *Rhizophagus irregularis* (strain DAOM 181602/DAOM 197198/MUCL 43194) (Arbuscular mycorrhizal fungus) (*Glomus intraradices*) | GLOINDRAFT_82554 | U9TF61 |
| *Penicillium chrysogenum* (strain ATCC 28089/DSM 1075/Wisconsin 54- 1255) (*Penicillium notatum*) | Pc21g23700 PCH_Pc21g23700 | B6HJ58 |
| *Baudoinia compniacensis* (strain UAMH 10762) (Angels' share fungus) | BAUCODRAFT_274597 | M2M6Z5 |
| *Hypocrea atroviridis* (strain ATCC 20476/IMI 206040) (*Trichoderma atroviride*) | TRIATDRAFT_280929 | G9NJ32 |
| *Colletotrichum gloeosporioides* (strain Cg-14) (Anthracnose fungus) (*Glomerella cingulata*) | CGLO_06642 | T0LPH0 |
| *Cordyceps militaris* (strain CM01) (Caterpillar fungus) | CCM_02665 | G3JB34 |
| *Pyronema omphalodes* (strain CBS 100304) (*Pyronema confluens*) | PCON_13062 | U4LKE9 |
| *Colletotrichum graminicola* (strain M1.001/M2/FGSC 10212) (Maize anthracnose fungus) (*Glomerella graminicola*) | GLRG_08499 | E3QR67 |
| *Glarea lozoyensis* (strain ATCC 74030/ MF5533) | M7I_2117 | H0EHX4 |
| *Fusarium oxysporum* f. sp. *cubense* (strain race 4) (Panama disease fungus) | FOC4_g10002493 | N1S969 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Fusarium oxysporum* f. sp. *cubense* (strain race 4) (Panama disease fungus) | FOC4_g10011461 | N1RT80 |
| *Cochliobolus sativus* (strain ND90Pr/ ATCC 201652) (Common root rot and spot blotch fungus) (*Bipolaris sorokiniana*) | COCSADRAFT_295770 | M2TBE4 |
| *Mixia osmundae* (strain CBS 9802/ IAM 14324/JCM 22182/KY 12970) | Mo05571 E5Q_05571 | G7E7S3 |
| *Mycosphaerella pini* (strain NZE10/ CBS 128990) (Red band needle blight fungus) (*Dothistroma septosporum*) | DOTSEDRAFT_69651 | N1PXR0 |
| *Grosmannia clavigera* (strain kw1407/ UAMH 11150) (Blue stain fungus) (*Graphiocladiella clavigera*) | CMQ_1113 | F0XC64 |
| *Fusarium oxysporum* FOSC 3-a | FOYG_03004 | W9IUE5 |
| *Fusarium oxysporum* FOSC 3-a | FOYG_16040 | W9HNP0 |
| *Fusarium oxysporum* FOSC 3-a | FOYG_17058 | W9HB31 |
| *Nectria haematococca* (strain 77-13-4/ ATCC MYA-4622/FGSC 9596/ MPVI) (*Fusarium solani* subsp. *pisi*) | NECHADRAFT_37686 | C7YQL1 |
| *Nectria haematococca* (strain 77-13-4/ ATCC MYA-4622/FGSC 9596/ MPVI) (*Fusarium solani* subsp. *pisi*) | NECHADRAFT_77262 | C7ZJI0 |
| *Tuber melanosporum* (strain Mel28) (Perigord black truffle) | GSTUM_00010376001 | D5GLS0 |
| *Ajellomyces dermatitidis* (strain SLH14081) (*Blastomyces dermatitidis*) | BDBG_07633 | C5JYI9 |
| *Chaetomium globosum* (strain ATCC 6205/CBS 148.51/DSM 1962/NBRC 6347/NRRL 1970) (Soil fungus) | CHGG_09885 | Q2GQ69 |
| *Candida tenuis* (strain ATCC 10573/ BCRC 21748/CBS 615/JCM 9827/ NBRC 10315/NRRL Y-1498/VKM Y-70) (Yeast) | CANTEDRAFT_108652 | G3B9Z1 |
| *Trichophyton rubrum* CBS 100081 | H102_00622 | A0A022VKY4 |
| *Pyrenophora teres* f. *teres* (strain 0-1) (Barley net blotch fungus) (*Drechslera teres* f. *teres*) | PTT_09421 | E3RLZ3 |
| *Colletotrichum gloeosporioides* (strain Nara gc5) (Anthracnose fungus) (*Glomerella cingulata*) | CGGC5_4608 | L2GB29 |
| *Gibberella zeae* (Wheat head blight fungus) (*Fusarium graminearum*) | FG05_06918 | A0A016PCS4 |
| *Trichophyton soudanense* CBS 452.61 | H105_00612 | A0A022Y6A6 |
| *Sclerotinia sclerotiorum* (strain ATCC 18683/1980/Ss-1) (White mold) (*Whetzelinia sclerotiorum*) | SS1G_07437 | A7EQ37 |
| *Fusarium oxysporum* f. sp. *pisi* HDV247 | FOVG_14401 | W9NWU8 |
| *Fusarium oxysporum* f. sp. *pisi* HDV247 | FOVG_02874 | W9Q5V3 |
| *Ustilago hordei* (strain Uh4875-4) (Barley covered smut fungus) | UHOR_03009 | I2G1Z4 |
| *Sporisorium reilianum* (strain SRZ2) (Maize head smut fungus) | sr12985 | E6ZYF7 |
| *Bipolaris zeicola* 26-R-13 | COCCADRAFT_81154 | W6YIP8 |
| *Melampsora larici-populina* (strain 98AG31/pathotype 3-4-7) (Poplar leaf rust fungus) | MELLADRAFT_78490 | F4RUZ8 |
| *Fusarium oxysporum* f. sp. *lycopersici* (strain 4287/CBS 123668/FGSC 9935/ NRRL 34936) (*Fusarium* vascular wilt of tomato) | FOXG_01901 | J9MG95 |
| *Fusarium oxysporum* f. sp. *lycopersici* (strain 4287/CBS 123668/FGSC 9935/ NRRL 34936) (*Fusarium* vascular wilt of tomato) | FOXG_11941 | J9N9S4 |
| *Bipolaris victoriae* FI3 | COCVIDRAFT_39053 | W7EMJ8 |
| *Debaryomyces hansenii* (strain ATCC 36239/CBS 767/JCM 1990/NBRC 0083/IGC 2968) (Yeast) (*Torulaspora hansenii*) | DEHA2E04268g | Q6BQL4 |
| *Clavispora lusitaniae* (strain ATCC 42720) (Yeast) (*Candida lusitaniae*) | CLUG_01505 | C4XZX3 |
| *Candida albicans* (strain WO-1) (Yeast) | CAWG_02023 | C4YME4 |
| *Trichophyton rubrum* MR850 | H100_00625 | A0A022U0Q2 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Candida dubliniensis* (strain CD36/ATCC MYA-646/CBS 7987/NCPF 3949/NRRL Y-17841) (Yeast) | CD36_32890 | B9WMC7 |
| *Starmerella bombicola* | AOX1 | A0A024FB95 |
| *Thielavia heterothallica* (strain ATCC 42464/BCRC 31852/DSM 1799) (*Myceliophthora thermophila*) | MYCTH_103590 | G2QJL7 |
| *Claviceps purpurea* (strain 20.1) (Ergot fungus) (*Sphacelia segetum*) | CPUR_07614 | M1WFI4 |
| *Aspergillus oryzae* (strain ATCC 42149/RIB 40) (Yellow koji mold) | AO090023000571 | Q2UH61 |
| *Dictyostelium discoideum* (Slime mold) | DDB_0184181 DDB_G0292042 | Q54DT6 |
| *Triticum urartu* (Red wild einkorn) (*Crithodium urartu*) | TRIUR3_22733 | M7YME5 |
| *Solanum tuberosum* (Potato) | PGSC0003DMG400017211 | M1BG07 |
| *Oryza sativa* subsp. *japonica* (Rice) | OSJNBb0044B19.5 LOC_Os10g33540 | Q8W5P8 |
| *Oryza sativa* subsp. *japonica* (Rice) | OJ1234_B11.20 Os02g0621800 | Q6K9N5 |
| *Oryza sativa* subsp. *japonica* (Rice) | OSJNBa0001K12.5 LOC_Os10g33520 | Q8W5P3 |
| *Zea mays* (Maize) | ZEAMMB73_809149 | C0P3J6 |
| *Citrus clementina* | CICLE_v10011111mg | V4S9P4 |
| *Citrus clementina* | CICLE_v10018992mg | V4U4C9 |
| *Citrus clementina* | CICLE_v10004405mg | V4S9D3 |
| *Citrus clementina* | CICLE_v10004403mg | V4RZZ6 |
| *Morus notabilis* | L484_011703 | W9RIK0 |
| *Morus notabilis* | L484_005930 | W9RET7 |
| *Medicago truncatula* (Barrel medic) (*Medicago tribuloides*) | MTR_1g075650 | G7I4U3 |
| *Arabidopsis thaliana* (Mouse-ear cress) | | Q8LDP0 |
| *Medicago truncatula* (Barrel medic) (*Medicago tribuloides*) | MTR_4g081080 | G7JF07 |
| *Simmondsia chinensis* (Jojoba) (*Buxus chinensis*) | | L7VFV2 |
| *Prunus persica* (Peach) (*Amygdalus persica*) | PRUPE_ppa018458mg | M5VXL1 |
| *Aphanomyces astaci* | H257_07411 | W4GI89 |
| *Aphanomyces astaci* | H257_07412 | W4GI44 |
| *Aphanomyces astaci* | H257_07411 | W4GKE3 |
| *Aphanomyces astaci* | H257_07411 | W4GK29 |
| *Aphanomyces astaci* | H257_07411 | W4GJ79 |
| *Aphanomyces astaci* | H257_07411 | W4GI38 |
| *Phaeodactylum tricornutum* (strain CCAP 1055/1) | PHATRDRAFT_48204 | B7G6C1 |
| *Hordeum vulgare* var. *distichum* (Two-rowed barley) | | F2E4R4 |
| *Hordeum vulgare* var. *distichum* (Two-rowed barley) | | F2DZG1 |
| *Hordeum vulgare* var. *distichum* (Two-rowed barley) | | M0YPG7 |
| *Hordeum vulgare* var. *distichum* (Two-rowed barley) | | M0YPG6 |
| *Hordeum vulgare* var. *distichum* (Two-rowed barley) | | F2CUY4 |
| *Ricinus communis* (Castor bean) | RCOM_0867830 | B9S1S3 |
| *Brassica rapa* subsp. *pekinensis* (Chinese cabbage) (*Brassica pekinensis*) | BRA014947 | M4DEM5 |
| *Ricinus communis* (Castor bean) | RCOM_0258730 | B9SV13 |
| *Brassica rapa* subsp. *pekinensis* (Chinese cabbage) (*Brassica pekinensis*) | BRA001912 | M4CCI2 |
| *Brassica rapa* subsp. *pekinensis* (Chinese cabbage) (*Brassica pekinensis*) | BRA012548 | M4D7T8 |
| *Brassica rapa* subsp. *pekinensis* (Chinese cabbage) (*Brassica pekinensis*) | BRA024190 | M4E5Y6 |
| *Brassica rapa* subsp. *pekinensis* (Chinese cabbage) (*Brassica pekinensis*) | BRA015283 | M4DFL0 |
| *Ricinus communis* (Castor bean) | RCOM_1168730 | B9SS54 |
| *Zea mays* (Maize) | | C4J691 |
| *Oryza glaberrima* (African rice) | | I1P2B7 |
| *Zea mays* (Maize) | | B6SXM3 |
| *Zea mays* (Maize) | | C0HFU4 |
| *Aegilops tauschii* (Tausch's goatgrass) (*Aegilops squarrosa*) | F775_19577 | R7W4J3 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Solanum habrochaites* (Wild tomato) (*Lycopersicon hirsutum*) | | R9R6T0 |
| *Physcomitrella patens* subsp. *patens* (Moss) | PHYPADRAFT_124285 | A9S535 |
| *Physcomitrella patens* subsp. *patens* (Moss) | PHYPADRAFT_113581 | A9RG13 |
| *Physcomitrella patens* subsp. *patens* (Moss) | PHYPADRAFT_182504 | A9S9A5 |
| *Solanum pennellii* (Tomato) (*Lycopersicon pennellii*) | | R9R6Q1 |
| *Vitis vinifera* (Grape) | VIT_02s0087g00630 | F6HJ27 |
| *Vitis vinifera* (Grape) | VIT_07s0005g03780 | F6HZM3 |
| *Vitis vinifera* (Grape) | VIT_05s0049g01400 | F6H8T4 |
| *Vitis vinifera* (Grape) | VITISV_019349 | A5AH38 |
| *Capsella rubella* | CARUB_v10013046mg | R0HIT3 |
| *Capsella rubella* | CARUB_v10004212mg | R0GUX4 |
| *Capsella rubella* | CARUB_v10004208mg | R0F3X6 |
| *Capsella rubella* | CARUB_v10012453mg | R0ILD0 |
| *Capsella rubella* | CARUB_v10004208mg | R0GUX1 |
| *Eutrema salsugineum* (Saltwater cress) (*Sisymbrium salsugineum*) | EUTSA_v10024496mg | V4MD54 |
| *Eutrema salsugineum* (Saltwater cress) (*Sisymbrium salsugineum*) | EUTSA_v10020141mg | V4NM59 |
| *Eutrema salsugineum* (Saltwater cress) (*Sisymbrium salsugineum*) | EUTSA_v10024496mg | V4LUR9 |
| *Eutrema salsugineum* (Saltwater cress) (*Sisymbrium salsugineum*) | EUTSA_v10024528mg | V4P767 |
| *Eutrema salsugineum* (Saltwater cress) (*Sisymbrium salsugineum*) | EUTSA_v10006882mg | V4L2P6 |
| *Selaginella moellendorffii* (Spikemoss) | SELMODRAFT_87684 | D8R6Z6 |
| *Selaginella moellendorffii* (Spikemoss) | SELMODRAFT_87621 | D8R6Z5 |
| *Selaginella moellendorffii* (Spikemoss) | SELMODRAFT_74601 | D8QN81 |
| *Selaginella moellendorffii* (Spikemoss) | SELMODRAFT_73531 | D8QN82 |
| *Sorghum bicolor* (Sorghum) (*Sorghum vulgare*) | Sb04g026390 SORBIDRAFT_04g026390 | C5XXS4 |
| *Sorghum bicolor* (Sorghum) (*Sorghum vulgare*) | Sb04g026370 SORBIDRAFT_04g026370 | C5XXS1 |
| *Sorghum bicolor* (Sorghum) (*Sorghum vulgare*) | Sb01g019470 SORBIDRAFT_01g019470 | C5WYH6 |
| *Sorghum bicolor* (Sorghum) (*Sorghum vulgare*) | Sb01g019480 SORBIDRAFT_01g019480 | C5WYH7 |
| *Sorghum bicolor* (Sorghum) (*Sorghum vulgare*) | Sb01g019460 SORBIDRAFT_01g019460 | C5WYH5 |
| *Solanum pimpinellifolium* (Currant tomato) (*Lycopersicon pimpinellifolium*) | | R9R6J2 |
| *Phaseolus vulgaris* (Kidney bean) (French bean) | PHAVU_007G124200g | V7BGM7 |
| *Phaseolus vulgaris* (Kidney bean) (French bean) | PHAVU_011G136600g | V7AI35 |
| *Phaseolus vulgaris* (Kidney bean) (French bean) | PHAVU_001G162800g | V7D063 |
| *Solanum tuberosum* (Potato) | PGSC0003DMG400024294 | M1C923 |
| *Solanum tuberosum* (Potato) | PGSC0003DMG400018458 | M1BKV4 |
| *Solanum tuberosum* (Potato) | PGSC0003DMG400018458 | M1BKV3 |
| *Glycine max* (Soybean) (*Glycine hispida*) | | K7LK61 |
| *Glycine max* (Soybean) (*Glycine hispida*) | | K7KXQ9 |
| *Populus trichocarpa* (Western balsam poplar) (*Populus balsamifera* subsp. *trichocarpa*) | POPTR_0008s16920g | B9HKS3 |
| *Picea sitchensis* (Sitka spruce) (*Pinus sitchensis*) | | B8LQ84 |
| *Populus trichocarpa* (Western balsam poplar) (*Populus balsamifera* subsp. *trichocarpa*) | POPTR_0004s24310g | U5GKQ5 |
| *Populus trichocarpa* (Western balsam poplar) (*Populus balsamifera* subsp. *trichocarpa*) | POPTR_0010s07980g | B9HSG9 |
| *Glycine max* (Soybean) (*Glycine hispida*) | | I1N9S7 |
| *Glycine max* (Soybean) (*Glycine hispida*) | | I1LSK5 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Setaria italica* (Foxtail millet) (*Panicum italicum*) | Si034362m.g | K4A658 |
| *Solanum lycopersicum* (Tomato) (*Lycopersicon esculentum*) | Solyc09g072610.2 | K4CUT7 |
| *Setaria italica* (Foxtail millet) (*Panicum italicum*) | Si016380m.g | K3YQ38 |
| *Solanum lycopersicum* (Tomato) (*Lycopersicon esculentum*) | | R9R6I9 |
| *Solanum lycopersicum* (Tomato) (*Lycopersicon esculentum*) | Solyc09g090350.2 | K4CW61 |
| *Solanum lycopersicum* (Tomato) (*Lycopersicon esculentum*) | Solyc08g005630.2 | K4CI54 |
| *Solanum lycopersicum* (Tomato) (*Lycopersicon esculentum*) | Solyc08g075240.2 | K4CMP1 |
| *Setaria italica* (Foxtail millet) (*Panicum italicum*) | Si034359m.g | K4A655 |
| *Setaria italica* (Foxtail millet) (*Panicum italicum*) | Si034354m.g | K4A650 |
| *Mimulus guttatus* (Spotted monkey flower) (Yellow monkey flower) | MIMGU_mgv1a001896mg | A0A022PU07 |
| *Mimulus guttatus* (Spotted monkey flower) (Yellow monkey flower) | MIMGU_mgv1a022390mg | A0A022RAV4 |
| *Mimulus guttatus* (Spotted monkey flower) (Yellow monkey flower) | MIMGU_mgv1a001868mg | A0A022S2E6 |
| *Mimulus guttatus* (Spotted monkey flower) (Yellow monkey flower) | MIMGU_mgv1a001883mg | A0A022S275 |
| *Mimulus guttatus* (Spotted monkey flower) (Yellow monkey flower) | MIMGU_mgv1a001761mg | A0A022QNF0 |
| *Musa acuminata* subsp. *malaccensis* (Wild banana) (*Musa malaccensis*) | | M0SNA8 |
| *Musa acuminata* subsp. *malaccensis* (Wild banana) (*Musa malaccensis*) | | M0RUT7 |
| *Musa acuminata* subsp. *malaccensis* (Wild banana) (*Musa malaccensis*) | | M0RUK3 |
| *Saprolegnia diclina* VS20 | SDRG_1901 | T0RG89 |
| *Brachypodium distachyon* (Purple false brome) (*Trachynia distachya*) | BRADI3G49085 | I1IBP7 |
| *Brachypodium distachyon* (Purple false brome) (*Trachynia distachya*) | BRADI3G28677 | I1I4N2 |
| *Brachypodium distachyon* (Purple false brome) (*Trachynia distachya*) | BRADI3G28657 | I1I4N0 |
| *Oryza sativa* subsp. *indica* (Rice) | OsI_34012 | B8BHG0 |
| *Oryza sativa* subsp. *indica* (Rice) | OsI_08118 | B8AFT8 |
| *Oryza sativa* subsp. *indica* (Rice) | OsI_34008 | A2Z8H1 |
| *Oryza sativa* subsp. *indica* (Rice) | OsI_34014 | B8BHG1 |
| *Oryza sativa* subsp. *japonica* (Rice) | LOC_Os10g33460 | Q7XDG3 |
| *Oryza sativa* subsp. *japonica* (Rice) | Os10g0474800 | Q0IX12 |
| *Oryza sativa* subsp. *japonica* (Rice) | Os10g0474966 | C7J7R1 |
| *Oryza sativa* subsp. *japonica* (Rice) | OSJNBa0001K12.13 | Q8W5N7 |
| *Oryza sativa* subsp. *japonica* (Rice) | OsJ_31873 | B9G683 |
| *Oryza sativa* subsp. *japonica* (Rice) | OsJ_31875 | B9G684 |
| *Oryza sativa* subsp. *japonica* (Rice) | OSJNBa0001K12.3 | Q8W5P5 |
| *Arabidopsis lyrata* subsp. *lyrata* (Lyre-leaved rock-cress) | ARALYDRAFT_470376 | D7KDA3 |
| *Arabidopsis lyrata* subsp. *lyrata* (Lyre-leaved rock-cress) | ARALYDRAFT_479855 | D7L3B6 |
| *Arabidopsis lyrata* subsp. *lyrata* (Lyre-leaved rock-cress) | ARALYDRAFT_491906 | D7MDA9 |
| *Arabidopsis lyrata* subsp. *lyrata* (Lyre-leaved rock-cress) | ARALYDRAFT_914728 | D7MGS9 |

In some embodiments, an alcohol dehydrogenase (ADH, Table 9) is used to catalyze the conversion of a fatty alcohol to a fatty aldehyde. A number of ADHs identified from alkanotrophic organisms, *Pseudomonas fluorescens* NRRL B-1244 (Hou et al. 1983), *Pseudomonas butanovora* ATCC 43655 (Vangnai and Arp 2001), and *Acinetobacter* sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-ω-fatty acids has been observed (Lu et al. 2010). Recently, two ADHs were characterized from *Geobacillus thermodenitrificans* NG80-2, an organism that degrades Cis to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 9

Exemplary alcohol dehydrogenase enzymes.

| Organisms | Gene Name | Accession No. |
| --- | --- | --- |
| *Bactrocera oleae* (Olive fruit fly) (*Dacus oleae*) | ADH | Q9NAR7 |
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affinidisjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticornis* (Fruit fly) (*Idiomyia picticornis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyrus malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus* sp. (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699/H16/ DSM 428/Stanier 337) (*Ralstonia eutropha*) | adh, H16_A0757 | Q0KDL6 |
| *Mycobacterium tuberculosis* (strain CDC 1551/ Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618/ H37Rv) | adh, Rv1530 | P9WQC3 |
| *Staphylococcus aureus* (strain N315) | adh, SA0562 | Q7A742 |
| *Staphylococcus aureus* (strain bovine RF122/ ET3-1) | adh, SAB0557 | Q2YSX0 |
| *Sulfolobus acidocaldarius* (strain ATCC 33909/ DSM 639/JCM 8929/NBRC 15157/NCIMB 11770) | adh, Saci_2057 | Q4J781 |

TABLE 9-continued

Exemplary alcohol dehydrogenase enzymes.

| Organisms | Gene Name | Accession No. |
|---|---|---|
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |
| *Staphylococcus aureus* (strain Mu50/ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984/RP62A) | adh, SERP0257 | Q5HRD6 |
| *Sulfolobus solfataricus* (strain ATCC 35092/DSM 1617/JCM 11322/P2) | adh, SSO2536 | P39462 |
| *Sulfolobus tokodaii* (strain DSM 16993/JCM 10545/NBRC 100140/7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |
| *Ceratitis cosyra* (Mango fruit fly) (*Trypeta cosyra*) | ADH1 | Q70UN9 |
| *Gallus gallus* (Chicken) | ADH1 | P23991 |
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adh1 | P23236 |
| *Drosophila montana* (Fruit fly) | Adh1 | P48586 |
| *Drosophila mettleri* (Fruit fly) | Adh1 | P22246 |
| *Drosophila mulleri* (Fruit fly) | Adh1 | P07161 |
| *Drosophila navojoa* (Fruit fly) | Adh1 | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (Petunia) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508/S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972/ATCC 24843) (Fission yeast) | adh1, adh, SPCC13B11.01 | P00332 |
| *Drosophila lacicola* (Fruit fly) | Adh1, Adh-1 | Q27404 |
| *Mus musculus* (Mouse) | Adh1, Adh-1 | P00329 |
| *Peromyscus maniculatus* (North American deer mouse) | ADH1, ADH-1 | P41680 |
| *Rattus norvegicus* (Rat) | Adh1, Adh-1 | P06757 |
| *Drosophila virilis* (Fruit fly) | Adh1, Adh-1, GJ18208 | B4M8Y0 |
| *Scheffersomyces stipitis* (strain ATCC 58785/CBS 6054/NBRC 10063/NRRL Y-11545) (Yeast) (*Pichia stipitis*) | ADH1, ADH2, PICST_68558 | O00097 |
| *Aspergillus flavus* (strain ATCC 200026/FGSC A1120/NRRL 3357/JCM 12722/SRRC 167) | adh1, AFLA_048690 | P41747 |
| *Neurospora crassa* (strain ATCC 24698/74-OR23-1A/CBS 708.71/DSM 1257/FGSC 987) | adh-1, B17C10.210, NCU01754 | Q9P6C8 |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |

TABLE 9-continued

Exemplary alcohol dehydrogenase enzymes.

| Organisms | Gene Name | Accession No. |
|---|---|---|
| *Drosophila mojavensis* (Fruit fly) | Adh1, GI17644 | P09370 |
| *Kluyveromyces lactis* (strain ATCC 8585/CBS 2359/DSM 70799/NBRC 1267/NRRL Y-1140/ WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (Hamadryas baboon) | ADH1B | P14139 |
| *Homo sapiens* (Human) | ADH1B, ADH2 | P00325 |
| *Homo sapiens* (Human) | ADH1C, ADH3 | P00326 |
| *Papio hamadryas* (Hamadryas baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q70UP5 |
| *Ceratitis rosa* (Natal fruit fly) (*Pterandrus rosa*) | ADH2 | Q70UP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |
| *Scheffersomyces stipitis* (strain ATCC 58785/ CBS 6054/NBRC 10063/NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508/ S288c) (Baker's yeast) | ADH2, ADR2, YMR303C, YM9952.05C | P00331 |
| *Candida albicans* (strain SC5314/ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC_Os11g10510 | Q0ITW7 |
| *Drosophila mojavensis* (Fruit fly) | Adh2, GI17643 | P09369 |
| *Kluyveromyces lactis* (strain ATCC 8585/CBS 2359/DSM 70799/NBRC 1267/NRRL Y-1140/ WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585/CBS 2359/DSM 70799/NBRC 1267/NRRL Y-1140/ WM37) (Yeast) (*Candida sphaerica*) | ADH3, KLLA0B09064g | P49384 |
| *Saccharomyces cerevisiae* (strain ATCC 204508/ S288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585/CBS 2359/DSM 70799/NBRC 1267/NRRL Y-1140/ WM37) (Yeast) (*Candida sphaerica*) | ADH4, KLLA0F13530g | P49385 |
| *Schizosaccharomyces pombe* (strain 972/ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508/ | ADH4, ZRG5, | P10127 |

TABLE 9-continued

Exemplary alcohol dehydrogenase enzymes.

| Organisms | Gene Name | Accession No. |
|---|---|---|
| S288c) (Baker's yeast) | YGL256W, NRC465 | |
| *Saccharomyces pastorianus* (Lager yeast) (*Saccharomyces cerevisiae* x *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |
| *Mus musculus* (Mouse) | Adh5, Adh-2, Adh2 | P28474 |
| *Rattus norvegicus* (Rat) | Adh5, Adh-2, Adh2 | P12711 |
| *Oryctolagus cuniculus* (Rabbit) | ADH5, ADH3 | O19053 |
| *Homo sapiens* (Human) | ADH5, ADHX, FDH | P11766 |
| *Dictyostelium discoideum* (Slime mold) | adh5, DDB_G0281865 | Q54TC2 |
| *Saccharomyces cerevisiae* (strain ATCC 204508/ S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551/ Oshkosh) | adhA, MT1911 | P9WQC0 |
| *Rhizobium meliloti* (strain 1021) (*Ensifer meliloti*) (*Sinorhizobium meliloti*) | adhA, RA0704, SMa1296 | O31186 |
| *Mycobacterium tuberculosis* (strain ATCC 25618/ H37Rv) | adhA, Rv1862 | P9WQC1 |
| *Zymomonas mobilis* subsp. *mobilis* (strain ATCC 31821/ZM4/CP4) | adhA, ZMO1236 | P20368 |
| *Mycobacterium bovis* (strain ATCC BAA-935/ AF2122/97) | adhB, Mb0784c | Q7U1B9 |
| *Mycobacterium tuberculosis* (strain CDC 1551/ Oshkosh) | adhB, MT0786 | P9WQC6 |
| *Mycobacterium tuberculosis* (strain ATCC 25618/ H37Rv) | adhB, Rv0761c, MTCY369.06c | P9WQC7 |
| *Zymomonas mobilis* subsp. *mobilis* (strain ATCC 31821/ZM4/CP4) | adhB, ZMO1596 | P0DJA2 |
| *Zymomonas mobilis* subsp. *mobilis* (strain ATCC 10988/DSM 424/LMG 404/NCIMB 8938/ NRRL B-806/ZM1) | adhB, Zmob_1541 | F8DVL8 |
| *Mycobacterium tuberculosis* (strain CDC 1551/ Oshkosh) | adhD, MT3171 | P9WQB8 |
| *Mycobacterium tuberculosis* (strain ATCC 25618/ H37Rv) | adhD, Rv3086 | P9WQB9 |
| *Clostridium acetobutylicum* (strain ATCC 824/ DSM 792/JCM 1419/LMG 5710/VKM B-1787) | adhE, aad, CA_P0162 | P33744 |
| *Escherichia coli* (strain K12) | adhE, ana, b1241, JW1228 | P0A9Q7 |
| *Escherichia coli* O157:H7 | adhE, Z2016, ECs1741 | P0A9Q8 |
| *Rhodobacter sphaeroides* (strain ATCC 17023/ 2.4.1/NCIB 8253/DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (*Bacillus stearothermophilus*) | adhT | P12311 |
| *Emericella nidulans* (strain FGSC A4/ATCC 38163/CBS 112.46/NRRL 194/M139) (*Aspergillus nidulans*) | alcA, AN8979 | P08843 |
| *Emericella nidulans* (strain FGSC A4/ATCC 38163/CBS 112.46/NRRL 194/M139) (*Aspergillus nidulans*) | alc, AN3741 | P54202 |
| *Emericella nidulans* (strain FGSC A4/ATCC | alcC, adh3, | P07754 |

TABLE 9-continued

Exemplary alcohol dehydrogenase enzymes.

| Organisms | Gene Name | Accession No. |
|---|---|---|
| 38163/CBS 112.46/NRRL 194/M139) (*Aspergillus nidulans*) | AN2286 | |
| *Arabidopsis thaliana* (Mouse-ear cress) | At1g22430, F12K8.22 | Q9SK86 |
| *Arabidopsis thaliana* (Mouse-ear cress) | At1g22440, F12K8.21 | Q9SK87 |
| *Arabidopsis thaliana* (Mouse-ear cress) | At1g32780, F6N18.16 | A1L4Y2 |
| *Arabidopsis thaliana* (Mouse-ear cress) | At1g64710, F13O11.3 | Q8VZ49 |
| *Arabidopsis thaliana* (Mouse-ear cress) | At4g22110, F1N20.210 | Q0V7W6 |
| *Arabidopsis thaliana* (Mouse-ear cress) | At5g24760, T4C12_30 | Q8LEB2 |
| *Arabidopsis thaliana* (Mouse-ear cress) | At5g42250, K5J14.5 | Q9FH04 |
| *Zea mays* (Maize) | FDH | P93629 |
| *Drosophila melanogaster* (Fruit fly) | Fdh, gfd, ODH, CG6598 | P46415 |
| *Bacillus subtilis* (strain 168) | gbsB, BSU31050 | P71017 |
| *Caenorhabditis elegans* | H24K24.3 | Q17335 |
| *Oryza sativa* subsp. *japonica* (Rice) | Os02g0815500, LOC_Os02g57040, OsJ_008550, P0643F09.4 | Q0DWH1 |
| *Mycobacterium tuberculosis* (strain ATCC 25618/ H37Rv) | Rv1895 | O07737 |
| *Caenorhabditis elegans* | sodh-1, K12G11.3 | Q17334 |
| *Caenorhabditis elegans* | sodh-2, K12G11.4 | O45687 |
| *Pseudomonas* sp. | terPD | P33010 |
| *Escherichia coli* (strain K12) | yiaY, b3589, JW5648 | P37686 |
| *Moraxella* sp. (strain TAE123) | | P81786 |
| *Alligator mississippiensis* (American alligator) | | P80222 |
| *Catharanthus roseus* (Madagascar periwinkle) (*Vinca rosea*) | | P85440 |
| *Gadus morhua* subsp. *callarias* (Baltic cod) (*Gadus callarias*) | | P26325 |
| *Naja naja* (Indian cobra) | | P80512 |
| *Pisum sativum* (Garden pea) | | P12886 |
| *Pelophylax perezi* (Perez's frog) (*Rana perezi*) | | P22797 |
| *Saara hardwickii* (Indian spiny-tailed lizard) (*Uromastyx hardwickii*) | | P25405 |
| *Saara hardwickii* (Indian spiny-tailed lizard) (*Uromastyx hardwickii*) | | P25406 |
| *Equus caballus* (Horse) | | P00327 |
| *Equus caballus* (Horse) | | P00328 |
| *Geobacillus stearothermophilus* (*Bacillus stearothermophilus*) | | P42328 |
| *Gadus morhua* (Atlantic cod) | | P81600 |
| *Gadus morhua* (Atlantic cod) | | P81601 |
| *Myxine glutinosa* (Atlantic hagfish) | | P80360 |
| *Octopus vulgaris* (Common octopus) | | P81431 |
| *Pisum sativum* (Garden pea) | | P80572 |
| *Saara hardwickii* (Indian spiny-tailed lizard) (*Uromastyx hardwickii*) | | P80467 |
| *Scyliorhinus canicula* (Small-spotted catshark) (*Squalus canicula*) | | P86884 |
| *Sparus aurata* (Gilthead sea bream) | | P79896 |

In some embodiments, an α-dioxygenase is used to catalyze the conversion of a fatty acid to a fatty aldehyde (Hamberg et al. 2005). Alpha-dioxygenases catalyze the conversion of a $C_n$ fatty acid to a $C_{n-1}$ aldehyde and may serve as an alternative to both ADH and AOX for fatty aldehyde production if a fatty acid is used as a biotransformation substrate. Due to the chain shortening of the dioxygenase reaction, this route requires a different synthesis pathway compared to the ADH and AOX routes. Biotransformations of *E. coli* cells expressing a rice α-dioxygenase exhibited conversion of C10, C12, C14 and C16 fatty acids to the corresponding $C_{n-1}$ aldehydes. With the addition of the detergent Triton X 100, 3.7 mM of pentadecanal (0.8 g/L) was obtained after 3 hours from hexadecanoic acid with 74% conversion (Kaehne et al. 2011). Exemplary α-dioxygenases are shown in Table 10.

TABLE 10

Exemplary alpha-dioxygenases

| Entry | Organism | Gene names |
|---|---|---|
| Q9SGH6 | *Arabidopsis thaliana* (Mouse-ear cress) | DOX1 DIOX1 PADOX-1 PIOX At3g01420 T13O15.6 |

TABLE 10-continued

Exemplary alpha-dioxygenases

| Entry | Organism | Gene names |
|---|---|---|
| Q9C9U3 | *Arabidopsis thaliana* (Mouse-ear cress) | DOX2 DIOX2 At1g73680 F25P22.10 |
| P14550 | *Homo sapiens* (Human) | AKR1A1 ALDR1 ALR |
| Q69EZ9 | *Solanum lycopersicum* (Tomato) (*Lycopersicon esculentum*) | LOC543896 |
| Q5WM33 | *Solanum lycopersicum* (Tomato) (*Lycopersicon esculentum*) | alpha-DOX2 |
| Q69F00 | *Solanum lycopersicum* (Tomato) (*Lycopersicon esculentum*) | |
| D7LAG3 | *Arabidopsis lyrata* subsp. *lyrata* (Lyre-leaved rock-cress) | ALPHA-DOX1 ARALYDRAFT_317048 |
| D8LJL3 | *Ectocarpus siliculosus* (Brown alga) | DOX Esi_0026_0091 |
| E3U9P5 | *Nicotiana attenuata* (Coyote tobacco) | adox2 |

An enzyme's total turnover number (or TTN) refers to the maximum number of molecules of a substrate that the enzyme can convert before becoming inactivated. In general, the TTN for the hydroxylases and other enzymes used in the methods of the disclosure range from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more.

When whole cells expressing a hydroxylase are used to carry out a hydroxylation reaction, the turnover can be expressed as the amount of substrate that is converted to product by a given amount of cellular material. In general, in vivo hydroxylation reactions exhibit turnovers from at least about 0.01 to at least about 10 mmol·$g_{cdw}^{-1}$, wherein gnaw is the mass of cell dry weight in grams. When whole cells expressing a hydroxylase are used to carry out a hydroxylation reaction, the activity can further be expressed as a specific productivity, e.g., concentration of product formed by a given concentration of cellular material per unit time, e.g., in g/L of product per g/L of cellular material per hour (g·$g_{cdw}^{-1}$ h$^{-1}$). In general, in vivo hydroxylation reactions exhibit specific productivities from at least about 0.01 to at least about 0.5 g·$g_{cdw}^{-1}$ h$^{-1}$, wherein gnaw is the mass of cell dry weight in grams.

The TTN for heme enzymes, in particular, typically ranges from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more. In certain embodiments, the variant or chimeric heme enzymes of the present disclosure have higher TTNs compared to the wild-type sequences. In some instances, the variant or chimeric heme enzymes have TTNs greater than about 100 (e.g., at least about 100, 150, 200, 250, 300, 325, 350, 400, 450, 500, or more) in carrying out in vitro hydroxylation reactions. In other instances, the variant or chimeric heme enzymes have TTNs greater than about 1000 (e.g., at least about 1000, 2500, 5000, 10,000, 25,000, 50,000, 75,000, 100,000, or more) in carrying out in vivo whole cell hydroxylation reactions.

When whole cells expressing a heme enzyme are used to carry out a hydroxylation reaction, the turnover can be expressed as the amount of substrate that is converted to product by a given amount of cellular material. In general, in vivo hydroxylation reactions exhibit turnovers from at least about 0.01 to at least about 10 mmol·$g_{cdw}^{-1}$, wherein gnaw is the mass of cell dry weight in grams. For example, the turnover can be from about 0.1 to about 10 mmol·$g_{cdw}^{-1}$, or from about 1 to about 10 mmol·$g_{cdw}^{-1}$, or from about 5 to about 10 mmol·$g_{cdw}^{-1}$, or from about 0.01 to about 1 mmol·$g_{cdw}^{-1}$, or from about 0.01 to about 0.1 mmol·$g_{cdw}^{-1}$, or from about 0.1 to about 1 mmol·$g_{cdw}^{-1}$, or greater than 1 mmol·$g_{cdw}^{-1}$. The turnover can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or about 10 mmol·$g_{cdw}^{-1}$.

When whole cells expressing a heme enzyme are used to carry out a hydroxylation reaction, the activity can further be expressed as a specific productivity, e.g., concentration of product formed by a given concentration of cellular material per unit time, e.g., in g/L of product per g/L of cellular material per hour (g·$g_{cdw}^{-1}$ h$^{-1}$). In general, in vivo hydroxylation reactions exhibit specific productivities from at least about 0.01 to at least about 0.5 g·$g_{cdw}^{-1}$ h$^{-1}$, wherein gnaw is the mass of cell dry weight in grams. For example, the specific productivity can be from about 0.01 to about 0.1 g·$g_{cdw}^{-1}$ h$^{-1}$, or from about 0.1 to about 0.5 g·$g_{cdw}^{-1}$ h$^{-1}$, or greater than 0.5 g·$g_{cdw}^{-1}$ h$^{-1}$. The specific productivity can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, or about 0.5 g·$g_{cdw}^{-1}$ h$^{-1}$.

In certain embodiments, mutations can be introduced into the target gene using standard cloning techniques (e.g., site-directed mutagenesis) or by gene synthesis to produce the hydroxylases (e.g., cytochrome P450 variants) of the present disclosure. The mutated gene can be expressed in a host cell (e.g., bacterial cell) using an expression vector under the control of an inducible promoter or by means of chromosomal integration under the control of a constitutive promoter. Hydroxylation activity can be screened in vivo or in vitro by following product formation by GC or HPLC as described herein.

The expression vector comprising a nucleic acid sequence that encodes a heme enzyme of the disclosure can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme enzyme that is operably linked to a promoter, wherein the promoter comprises a viral, bacterial, archaeal, fungal, insect, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

It is to be understood that affinity tags may be added to the N- and/or C-terminus of a heme enzyme expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

The host cell can be a bacterial cell, an archaeal cell, a fungal cell, a yeast cell, an insect cell, or a mammalian cell.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus, Metallosphera sedula, Thermococcus litoralis, Methanobacterium thermoautotrophicum, Methanococcus jannaschii, Pyrococcus abyssi, Sulfolobus solfataricus, Pyrococcus woesei, Sulfolobus shibatae*, and variants thereof. Fungal host cells include, but are not limited to, yeast cells from the genera *Saccharomyces* (e.g., *S. cerevisiae*), *Pichia* (*P. Pastoris*), *Candida* (*C. tropicalis*), *Kluyveromyces* (e.g., *K. lactis*), *Hansenula* and *Yarrowia*, and filamentous fungal cells from the genera *Aspergillus, Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NS0 hybridoma cells, baby hamster kidney (BHK) cells, MDCK cells, NIH-3T3 fibroblast cells, and any other immortalized cell line derived from a mammalian cell.

In certain embodiments, the present disclosure provides heme enzymes such as the P450 variants described herein that are active hydroxylation catalysts inside living cells. As a non-limiting example, bacterial cells (e.g., *E. coli*) can be used as whole cell catalysts for the in vivo hydroxylation reactions of the present disclosure. In some embodiments, whole cell catalysts containing P450 enzymes with the equivalent C400X mutation are found to significantly enhance the total turnover number (TTN) compared to in vitro reactions using isolated P450 enzymes.

Biohydroxylation Reaction Conditions

The methods of the disclosure include forming reaction mixtures that contain the hydroxylases described herein. The hydroxylases can be, for example, purified prior to addition to a reaction mixture or secreted by a cell present in the reaction mixture. The reaction mixture can contain a cell lysate including the enzyme, as well as other proteins and other cellular materials. Alternatively, a hydroxylase can catalyze the reaction within a cell expressing the hydroxylase. Any suitable amount of hydroxylase can be used in the methods of the disclosure. In general, hydroxylation reaction mixtures contain from about 0.01 weight % (wt %) to about 100 wt % hydroxylase with respect to the hydrocarbon substrate. The reaction mixtures can contain, for example, from about 0.01 wt % to about 0.1 wt % hydroxylase, or from about 0.1 wt % to about 1 wt % hydroxylase, or from about 1 wt % to about 10 wt % hydroxylase, or from about 10 wt % to about 100 wt % hydroxylase. The reaction mixtures can contain from about 0.05 wt % to about 5 wt % hydroxylase, or from about 0.05 wt % to about 0.5 wt % hydroxylase. The reaction mixtures can contain about 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, or about 3 wt % hydroxylase. One of skill in the art will understand how to convert wt % values to mol % values with respect to the hydroxylase and/or substrate concentrations set forth herein.

If the hydroxylase catalyses the reaction within a cell expressing the hydroxylase then any suitable amount of cells can be used in the methods of the disclosure. In general, hydroxylation whole-cell reaction mixtures contain from about 1 weight % to about 10,000 wt % of cells on a cell dry weight basis with respect to the hydrocarbon substrate. The whole-cell reaction mixtures can contain, for example, from about 1 wt % to about 10 wt % cells, or from about 10 wt % to about 100 wt % cells, or from about 100 wt % to about 1000 wt % cells, or from about 1000 wt % cells to about 2500 wt % cells, or from about 2500 wt % cells to about 5000 wt % cells, or from about 5000 wt % cells to about 7500 wt % cells, or from about 7500 wt % cells to about 10000 wt % cells with respect to the hydrocarbon substrate. The whole-cell reaction mixtures can contain from about 2 wt % to about 1000 wt % cells, or from about 5 wt % to about 500 wt % cells with respect to the hydrocarbon substrate. The whole-cell reaction mixtures can contain about 5, 10, 20, 30, 40, 50, 60, 70, 80, 90, 100, 200, 300, 400, 500, 600, 700, 800, 900, or about 1000 wt % cells with respect to the hydrocarbon substrate.

The concentration of a saturated or unsaturated hydrocarbon substrate is typically in the range of from about 100 μM to about 1 M. The concentration can be, for example, from about 100 μM to about 1 mM, or about from 1 mM to about 100 mM, or from about 100 mM to about 500 mM, or from about 500 mM to 1 M. The concentration can be from about 500 μM to about 500 mM, 500 μM to about 50 mM, or from about 1 mM to about 50 mM, or from about 15 mM to about 45 mM, or from about 15 mM to about 30 mM. The concentration of the saturated or unsaturated hydrocarbon substrate can be, for example, about 100, 200, 300, 400, 500, 600, 700, 800, or 900 μM. The concentration of the saturated or unsaturated hydrocarbon substrate can be about 1, 5, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guandinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N,N-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl) phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 μM to about 1 M. For example, a buffer, a cosolvent, a salt, a denaturant, a detergent, a chelator, a sugar, or a reducing agent can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M. Cosolvents, in particular, can be included in the reaction mixtures in amounts ranging from about 1% v/v to about 75% v/v, or higher. A co-solvent can be included in the reaction mixture, for example, in an amount of about 5, 10, 20, 30, 40, or 50% (v/v).

Reactions are conducted under conditions sufficient to catalyze the formation of a hydroxylation product. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 3 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours, or about 96 hours, or about 120 hours, or about 144 hours, or about 168 hours, or about 192 hours. In general, reactions are conducted under aerobic conditions. In some embodiments, the solvent forms a second phase, and the hydroxylation occurs in the aqueous phase. In some embodiments, the hydroxylases is located in the aqueous layer whereas the substrates and/or products occur in an organic layer. Other reaction conditions may be employed in the methods of the disclosure, depending on the identity of a particular hydroxylase, or olefinic substrate.

Reactions can be conducted in vivo with intact cells expressing a hydroxylase of the disclosure. The in vivo reactions can be conducted with any of the host cells used for expression of the hydroxylases, as described herein. A suspension of cells can be formed in a suitable medium supplemented with nutrients (such as mineral micronutrients, glucose and other fuel sources, and the like). Hydroxylation yields from reactions in vivo can be controlled, in part, by controlling the cell density in the reaction mixtures. Cellular suspensions exhibiting optical densities ranging from about 0.1 to about 50 at 600 nm can be used for hydroxylation reactions. Other densities can be useful, depending on the cell type, specific hydroxylases, or other factors.

Pheromones, Precursors, Positional Isomers, and Analogs Comprising More than One C=C Double Bond In some embodiments, an olefinic product described herein can have more than one carbon-carbon (C=C) double bond. In some embodiments, such olefinic products can be used to synthetically derive pheromones with more than one double bond.

In some embodiments, conjugated and unconjugated alkenes can be biohydroxylated to generate corresponding conjugated and unconjugated alkenols as illustrated in Scheme 11 below.

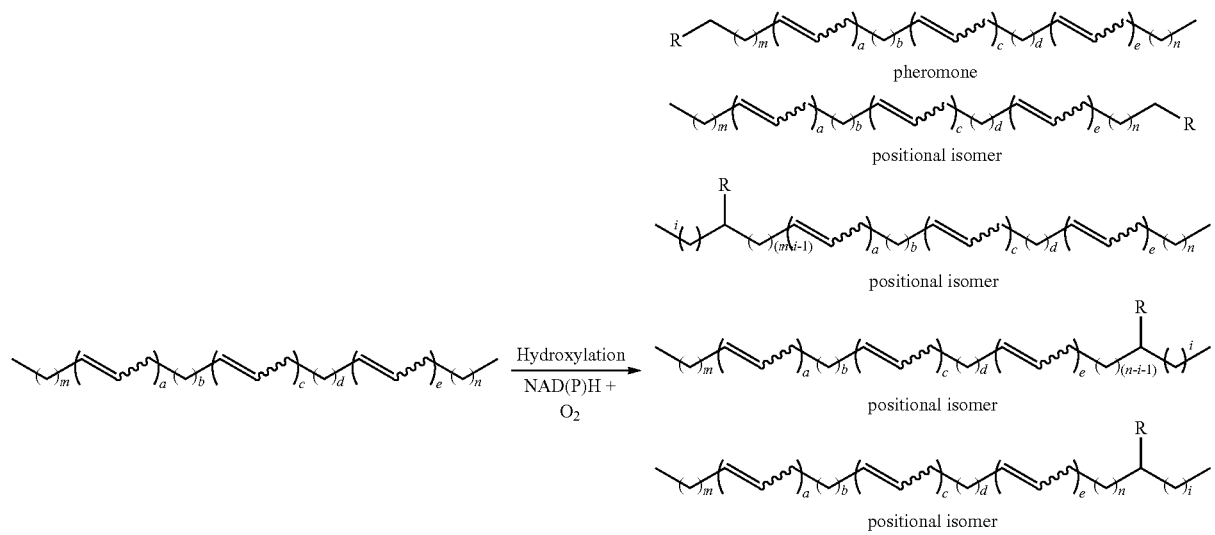

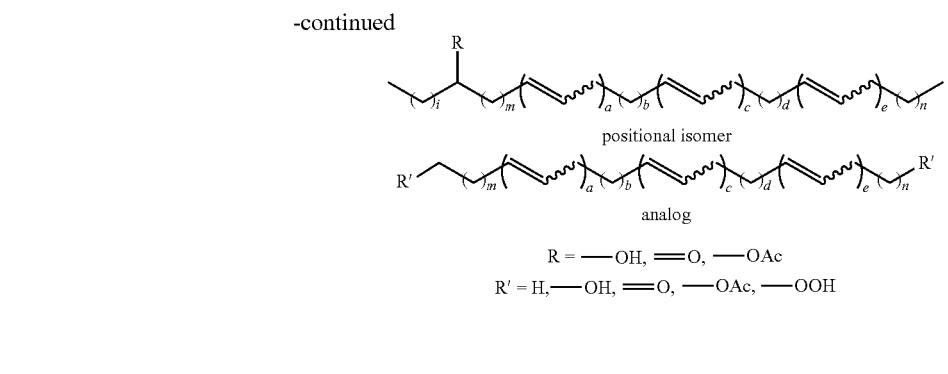

positional isomer analog

R = —OH, =O, —OAc
R' = H, —OH, =O, —OAc, —OOH m, n = 0-15
a, c, e = 0-3
b, d = 0-10

In some embodiments, biohydroxylation occurs on the terminal carbon an m-end of a carbon-carbon double bond in an unsaturated hydrocarbon substrate to produce first synthetically derived insect pheromone having a chemical structure corresponding to the chemical structure of a naturally occurring insect pheromone produced by the target insect. In some embodiments, biohydroxylation occurs on a terminal carbon of an n-end of the carbon-carbon double bond in the unsaturated hydrocarbon substrate a positional isomer of said first synthetically derived insect pheromone. In some embodiments, biohydroxylation occurs on a subterminal carbon on the m-end or the n-end of the carbon-carbon double bond in the unsaturated hydrocarbon substrate thereby forming an i-end, wherein the i-end comprises a terminal carbon of the unsaturated hydrocarbon substrate. In some embodiments, biohydroxylation and subsequent oxidation produces a pheromone or precursor that is over-oxidized, e.g., by hydroxylation of both terminal carbons (i.e., the m-end and the n-end of the carbon-carbon double bond in the unsaturated hydrocarbon substrate) and/or oxidation to a carboxylic acid.

The substrate, the pheromone, the positional isomer, and the analog can have any suitable combination of subscripts a, b, c, d, e, i, m, and n. In some embodiments, a, c, and e are independently integers from 0 to 1, provided that at least one of a, c, or e is 1. In some embodiments, m and n are integers independently selected from 1 to 15. In some embodiments, m, n, and i are integers independently selected from 1 to 15. In some embodiments, b and d are integers independently selected from 1 to 10. In some embodiments, the sum of a, b, c, d, e, m, and n is an integer that results in a total number of carbons from 6 to 20. In some embodiments, the sum of a, b, c, d, e, i, m, and n is an integer that results in a total number of carbons from 6 to 20. In some embodiments, each R is independently —OH, =O, or —OAc. In some embodiments, each R' is independently —OH, =O, —OAc, or —OOH.

Pheromone Compositions

In some embodiments, the present disclosure provides for a pheromone and its positional isomer. For example, in some embodiments, the present disclosure provides for the synthesis of (E/Z)-hexadecen-1-al. Depending on the synthetic route and starting material, embodiments described herein, a variety of isomers of Z-hexadecen-1-al can be synthesized. Accordingly, a pheromone composition prepared as described herein can include a mixture of two or more of the following isomers: Z-hexadec-2-en-1-al, Z-hexadec-3-en-1-al, Z-hexadec-4-en-1-al, Z-hexadec-5-en-1-al, Z-hexadec-6-en-1-al, Z-hexadec-7-en-1-al, Z-hexadec-8-en-1-al, Z-hexadec-9-en-1-al, Z-hexadec-10-en-1-al, Z-hexadec-11-en-1-al, Z-hexadec-12-en-1-al, Z-hexadec-13-en-1-al, Z-hexadec-14-en-1-al, and Z-hexadec-15-en-1-al. Thus, in some embodiments, a pheromone composition as described herein can include at least one isomer of a natural pheromone or a mixture of isomers.

In some embodiments, the isomer is a positional isomer. The positional isomer produced using the methodology disclosed herein occurs via biohydroxylation of a location on the carbon skeleton which is different from location required to produce the natural pheromone for an insect. Accordingly, in some embodiments, a pheromone composition as described herein can include a natural pheromone produced by an insect and least one positional isomer of the natural pheromone. In some embodiments, the positional isomer is not produced by the insect whose behavior is modified by the pheromone composition. Thus, in some embodiments, the pheromone composition can include a first insect pheromone having a chemical structure of an insect sex pheromone produced by a member of the order Lepidoptera and a positional isomer of said first insect pheromone. In one such embodiment, the positional isomer is not produced by a member of the order Lepidoptera.

Mixtures of a pheromone with its positional isomer, as disclosed herein, can be used modulate the behavior of Lepidopteran species in a controllable or tunable manner. Although positional isomers of a pheromone, which are contained in various compositions of the disclosure, may not be emitted by a female Lepidoptera, its presence in mixtures with the authentic pheromone elicits a mating response from male Lepidoptera. The mating response of the male insects differ with different ratios of the positional isomer to the authentic pheromone, which indicates that the use of pheromones in mixtures of its positional isomers enables modulation of a male insect response that cannot be obtained with pure pheromone alone. For example, mixtures of (Z)-5-hexadecenal with the natural (Z)-11hexadecenal are able to elicit a mating response from H. zea males, even though (Z)-11-hexadecenal is emitted by the female Lepidoptera. The addition of (Z)-9-hexadecenal to mixtures of (Z)-5-hexadecenal and (Z)-11-hexadecenal may also act an as insect pheromone attractant. Accordingly, embodiments of the disclosure provide for mixtures of a natural pheromone with its positional isomer to elicit altered insect responses. The elicited response can be tuned depending on the ratio of the positional isomer to the natural pheromone. Thus, the amount of the positional isomer present in the mixture can be used to attenuate the mating response of an insect, e.g., male Lepidoptera, thereby eliciting a response which would not be possible with the natural pheromone.

In an exemplary embodiment, the pheromone compositions can include at least one synthetically derived natural pheromone and its synthetically derived positional isomer.

In some embodiments, the pheromone composition includes Z-11-hexadecenal and it positional isomer Z-5-hexadecenal. In some embodiments, the pheromone composition includes a synthetically derived natural blend of Z-11-hexadecenal/Z-9-hexadecenal and the synthetically derived positional isomer of Z-11-hexadecenal—Z-5-hexadecenal, which is not produced by the target insect. In a further embodiment, the pheromone composition can also include the synthetically derived positional isomer of Z-9-hexadecenal—Z-7-hexadecenal, which is not produced by the target insect.

Thus, in some such embodiments, the pheromone composition can include compounds selected from the group consisting of Z-11-hexadecenal, Z-5-hexadecenal, Z-9-hexadecenal, Z-7-hexadecenal and combinations thereof. In other exemplary embodiments, the pheromone composition can include at least one of following combinations of synthetically derived natural pheromones and its positional isomer: Z-11-hexadecenal and Z-5-hexadecenal, or Z-9-hexadecenal and Z-7-hexadecenal.

In some embodiments, the pheromone composition includes a mixture of Z-11-hexadecenal and Z-5-hexadecenal. In some such embodiments, the percent of Z-11-hexadecenal to the percent of Z-5-hexadecenal in the composition is about 99.9% to about 0.1%, about 99.8% to about 0.2%, about 99.7% to about 0.3%, about 99.6% to about 0.4%, about 99.5% to about 0.5%, about 99.4% to about 0.6%, about 99.3% to about 0.7%, about 99.2% to about 0.8%, or about 99.1% to about 0.9%, including all values and subranges in between. In other embodiments, the ratio of Z-11-hexadecenal to Z-5-hexadecenal in the composition is about 99% to about 1.0%, 98% to about 2.0%, about 97% to about 3.0%, about 96% to about 4.0%, about 94% to about 6.0%, about 93% to about 7.0%, about 92% to about 8.0%, about 91% to about 9%, about 90% to about 10%, about 85% to about 15%, about 80% to about 20%, about 75% to about 25%, about 70% to about 30%, about 65% to about 35%, about 60% to about 40%, about 55% to about 45%, about 50% to about 50%, including all values and subranges in between.

In some such embodiments, the percent of Z-5-hexadecenal to the percent of Z-11-hexadecenal in the composition is about 99.9% to about 0.1%, about 99.8% to about 0.2%, about 99.7% to about 0.3%, about 99.6% to about 0.4%, about 99.5% to about 0.5%, about 99.4% to about 0.6%, about 99.3% to about 0.7%, about 99.2% to about 0.8%, or about 99.1% to about 0.9%, include all values and subranges in between. In some such embodiments, the percent of Z-5-hexadecenal to the percent of Z-11-hexadecenal in the composition is about 99% to about 1.0%, about 98% to about 2.0%, about 97% to about 3.0%, about 96% to about 4.0%, about 94% to about 6.0%, about 93% to about 7.0%, about 92% to about 8.0%, about 91% to about 9%, about 90% to about 10%, about 85% to about 15%, about 80% to about 20%, about 75% to about 25%, about 70% to about 30%, about 65% to about 35%, about 60% to about 40%, about 55% to about 45%, about 50% to about 50%, including all values and subranges in between.

In some embodiments, Z-11-hexadecenal is present in the composition at a percent of from about 99% mol to about 1 mol %, about 95 mol % to about 5 mol %, about 90 mol % to about 10 mol %, about 85 mol % to about 15 mol %, about 80 mol % to about 20 mol %, about 75 mol % to about 25 mol %, about 70 mol % to about 30 mol %, about 65 mol % to about 35 mol %, about 60 mol % to about 40 mol %, about 55 mol % to about 45 mol %, including all values and subranges in between. In some embodiments, Z-11-hexadecenal is present in the composition at a percent of about 97 mol % or less.

In some embodiments, the Z-11-hexadecenal is present in the composition in an amount of from about 99.9% w/w to about 0.1% w/w, about 99% to about 1% w/w, about 98% w/w to about 2% w/w, about 97% w/w to about 3% w/w, about 96% w/w to about 4% w/w, about 95% w/w to about 5% w/w, about 90% w/w to about 10% w/w, about 80% w/w to about 20% w/w, about 70% w/w to about 30% w/w, about 60% w/w to about 40% w/w, or about 50% w/w. In some embodiments, Z-11-hexadecenal is present in the composition at a percent of about 97% or less.

In some embodiments, Z-5-hexadecenal is present at a percent of from about 99.9 mol % to about 0.1 mol %, about 99 mol % to about 1 mol %, about 95 mol % to about 5 mol %, about 90 mol % to about 10 mol %, about 85 mol % to about 15 mol %, about 80 mol % to about 20 mol %, about 75 mol % to about 25 mol %, about 70 mol % to about 30 mol %, about 65 mol % to about 35 mol %, about 60 mol % to about 40 mol %, about 55 mol % to about 45 mol %, including all values and subranges in between. In other embodiments, Z-5-hexadecenal is present in the composition at percent of about 100 mol % or less, about 50 mol % or less, or about 5 mol % or less.

In some embodiments, the Z-5-hexadecenal is present in the composition in an amount of from about 99.9% w/w to about 0.1% w/w, 99% w/w to about 1% w/w, about 98% w/w to about 2% w/w, about 97% w/w to about 3% w/w, about 96% w/w to about 4% w/w, about 95% w/w to about 5% w/w, about 90% w/w to about 10% w/w, about 80% w/w to about 20% w/w, about 70% w/w to about 30% w/w, about 60% w/w to about 40% w/w, or about 50% w/w. In other embodiments, Z-5-hexadecenal is present in the composition in an amount about 100% w/w or less, about 50% w/w or less, about 5% w/w or less, or about 0.5% or less.

In some embodiments, the Z-9-hexadecenal is present in the composition at a percent of from about 99.9 mol % to about 0.1 mol %, about 99 mol % to about 1 mol %, about 95 mol % to about 5 mol %, about 90 mol % to about 10 mol %, about 85 mol % to about 15 mol %, about 80 mol % to about 20 mol %, about 75 mol % to about 25 mol %, about 70 mol % to about 30 mol %, about 65 mol % to about 35 mol %, about 60 mol % to about 40 mol %, about 55 mol % to about 45 mol %, including all values and subranges in between. In some embodiments, Z-9-hexadecenal is present in the composition at less than or equal to about 50 mol %, less than or equal to about 40 mol %, less than or equal to about 30 mol %, less than or equal to about 25 mol %, less than or equal to about 20 mol %, less than or equal to about 15 mol %, or less than or equal to about 10 mol %. In some embodiments, Z-9-hexadecenal is present at less than or equal to about 10 mol %, less than or equal to about 9 mol %, less than or equal to about 8 mol %, less than or equal to about 7 mol %, less than or equal to about 6 mol %, less than or equal to about 5 mol %, less than or equal to about 4 mol %, less than or equal to about 3 mol %, less than or equal to about 2 mol %, or less than or equal to 1 mol %. In some embodiments, the Z-9-hexadecenal is present at about 3 mol % or less, about 2.5 mol %, at about 2 mol %, at about 1.5 mol %, at about 1 mol %, or at about 0.5 mol % or less.

In some embodiments, the Z-9-hexadecenal is present in the composition in an about amount of from about 99.9% w/w to about 0.1% w/w, about 99% w/w to about 1% w/w, about 98% to about 2% w/w, about 97% w/w to about 3% w/w, about 96% w/w to about 4% w/w, about 95% w/w to about 5% w/w, about 90% w/w to about 10% w/w, about 80% w/w to about 20% w/w, about 70% to about 30% w/w, about 60% to about 40% w/w, or about 50% w/w. In some embodiments, the Z-9-hexadecenal is present in the composition in an amount of 3% w/w or less.

In some embodiments, the Z-7-hexadecenal is present at a percent of from about 99.9 mol % to about 0.1 mol %, about 99 mol % to about 1 mol %, about 95 mol % to about 5 mol %, about 90 mol % to about 10 mol %, about 85 mol % to about 15 mol %, about 80 mol % to about 20 mol %, about 75 mol % to about 25 mol %, about 70 mol % to about 30 mol %, about 65 mol % to about 35 mol %, about 60 mol % to about 40 mol %, about 55 mol % to about 45 mol %, including all values and subranges in between. In some embodiments, Z-9-hexadecenal is preset less than or equal to about 50 mol %, less than or equal to about 40 mol %, less than or equal to about 30 mol %, less than or equal to about 25 mol %, less than or equal to about 20 mol %, less than or equal to about 15 mol %, or less than or equal to about 10 mol %. In some embodiments, Z-7-hexadecenal is preset less than or equal to about 10 mol %, less than or equal to about 9 mol %, less than or equal to about 8 mol %, less than or equal to about 7 mol %, less than or equal to about 6 mol %, less than or equal to about 5 mol %, less than or equal to about 4 mol %, less than or equal to about 3 mol %, less than or equal to about 2 mol %, or less than or equal to 1 mol %. In some embodiments, the Z-7-hexadecenal is present at about 3 mol %, about 2.5 mol %, at about 2 mol %, at about 1.5 mol %, at about 1 mol %, or at about 0.5 mol % or less.

In some embodiments, the Z-7-hexadecenal is present in the composition in an amount of from about 99.9% w/w to about 0.1% w/w, about 99% w/w to about 1% w/w, about 98% w/w to about 2% w/w, about 97% w/w to about 3% w/w, about 96% w/w to about 4% w/w, about 95% w/w to about 5% w/w, about 90% w/w to about 10% w/w, about 80% w/w to about 20% w/w, about 70% w/w to about 30% w/w, about 60% w/w to about 40% w/w, or about 50% w/w.

In some embodiments, the pheromone composition comprises about 97% Z-11-hexadecenal and about 3% Z-9-hexadecenal. In further embodiments, Z-5-hexadecenal is added to the composition comprising 97/3 Z-11-hexadecenal to Z-9-hexadecenal such that the Z-5-hexadecenal constitutes about 0.5 mol %, about 1 mol %, about 5 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol % or about 99 mol %, of the resulting composition.

By varying the ratio of the synthetically derived sex pheromone to its positional isomer, embodiments described herein create a tunable pheromone composition which can be used to modulate the response of the target insect species. In some embodiments, the ratio of the sex pheromone to the positional isomer can varied by selecting and/or engineering the biocatalyst. The insect that is "attracted" to the compositions taught herein may, or may not, physically contact a locus containing said pheromone composition. That is, in some aspects, the compositions taught herein are able to attract a given insect within a close proximity to a locus containing the disclosed pheromone compositions, but do not entice said insect to physically contact the locus. However, in other aspects, the compositions taught herein do entice and/or attract an insect to physically come into contact with a locus containing said pheromone compositions. In this way, inter alia, the pheromone compositions taught herein are highly "tunable" and are able to modulate the behavior (e.g., degree of attracting an insect) of an insect to a high degree, which is not associated with pheromone compositions of the prior art (i.e., compositions including only the natural pheromone). Accordingly, the pheromone compositions of the present disclosure are able to modulate the degree to which an insect is attracted along a continuous scale, depending upon, among other things, the ratio of natural pheromone to its positional isomer.

Agricultural Compositions

As described above, a variety of pheromones can be synthesized according to the MBO or MBE method. Further, utilization of the aforementioned synthesis methods can produce positional isomers of said pheromones via biohydroxylation of an alternative location of the carbon skeleton. The pheromone and its positional isomer, prepared according to these methods, can be formulated for use in compositions which modify the behavior of insects, e.g., by applying the pheromone composition to a locus thereby attracting a target insect. Pheromone compositions can contain at least one pheromone and optionally adjuvants and other compounds provided that such compounds do not substantially interfere with the activity of the composition.

In some embodiments, the agricultural compositions of the present disclosure may include, but are not limited to: wetters, compatibilizing agents (also referred to as "compatibility agents"), antifoam agents, cleaning agents, sequestering agents, drift reduction agents, neutralizing agents and buffers, corrosion inhibitors, dyes, odorants, spreading agents (also referred to as "spreaders"), penetration aids (also referred to as "penetrants"), sticking agents (also referred to as "stickers" or "binders"), dispersing agents, thickening agents (also referred to as "thickeners"), stabilizers, emulsifiers, freezing point depressants, antimicrobial agents, and the like.

Carriers

In some embodiments, a pheromone composition can include a carrier. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, China clay, mineral earths such as silicas, silica gels, silicates, attaclay, limestone, chalk, loess, clay, dolomite, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; waxes, such as beeswax, lanolin, shellac wax, carnauba wax, fruit wax (such as bayberry or sugar cane wax) candelilla wax, other waxes such as microcrystalline, ozocerite, ceresin, or montan; salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamateand mixtures thereof. Baits or feeding stimulants can also be added to the carrier.

Synergist

In some embodiments, the pheromone composition is combined with an active chemical agent such that a synergistic effect results. The synergistic effect obtained by the taught methods can be quantified according to Colby's formula (i.e. (E)=X+Y−(X*Y/100). See Colby, R. S., "Calculating Synergistic and Antagonistic Responses of Herbicide Combinations", 1967 Weeds, vol. 15, pp. 20-22, incorporated herein by reference in its entirety. Thus, by "synergistic" is intended a component which, by virtue of its presence, increases the desired effect by more than an additive amount. The pheromone compositions and adjuvants of the present methods can synergistically increase the effectiveness of agricultural active compounds and also agricultural auxiliary compounds.

Thus, in some embodiments, a pheromone composition can be formulated with a synergist. The term, "synergist," as used herein, refers to a substance that can be used with a pheromone for reducing the amount of the pheromone dose or enhancing the effectiveness of the pheromone for attracting at least one species of insect. The synergist may or may not be an independent attractant of an insect in the absence of a pheromone.

In some embodiments, the synergist is a volatile phytochemical that attracts at least one species of Lepidoptera. The term, "phytochemical," as used herein, means a compound occurring naturally in a plant species. In a particular embodiment, the synergist is selected from the group comprising β-caryophyllene, iso-caryophyllene, α-humulene, inalool, Z3-hexenol/yl acetate, β-farnesene, benzaldehyde, phenylacetaldehyde, and combinations thereof.

The pheromone composition can contain the pheromone and the synergist in a mixed or otherwise combined form, or it may contain the pheromone and the synergist independently in a non-mixed form.

Insecticide

The pheromone composition can include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, neonicotinoids, diamides, avermectin and derivatives, spinosad and derivatives, azadirachtin, pyridalyl, and mixtures thereof.

In another embodiment, the insecticides are one or more biological insecticides known to one skilled in the art. Examples of the biological insecticides include, but are not limited to, azadirachtin (neem oil), toxins from natural pyrethrins, Bacillus thuringiencis and Beauveria bassiana, viruses (e.g., CYD-X™, CYD-X HP™, Germstar™ Madex H P™ and Spod-X™), peptides (Spear-T™, Spear-P™, and Spear-C™)

In another embodiment, the insecticides are insecticides that target the nerve and muscle. Examples include acetylcholinesterase (AChE) inhibitors, such as carbamates (e.g., methomyl and thiodicarb) and organophosphates (e.g., chlorpyrifos) GABA-gated chloride channel antagonists, such as cyclodiene organochlorines (e.g., endosulfan) and phenylpyrazoles (e.g., fipronil), sodium channel modulators, such as pyrethrins and pyrethroids (e.g., cypermethrin and λ-cyhalothrin), nicotinic acetylcholine receptor (nAChR) agonists, such as neonicotinoids (e.g., acetamiprid, tiaclorid, thiamethoxam), nicotinic acetylcholine receptor (nAChR) allosteric modulators, such as spinosyns (e.g., spinose and spinetoram), chloride channel activators, such as avermectins and milbemycins (e.g., abamectin, emamectin benzoate), Nicotinic acetylcholine receptor (nAChR) blockers, such as bensultap and cartap, voltage dependent sodium channel blockers, such as indoxacarb and metaflumizone, ryanodine receptor modulator, such as diamides (e.g. dhlorantraniliprole and flubendiamide). In another embodiment, the insecticides are insecticides that target respiration. Examples include chemicals that uncouple oxidative phosphorylation via disruption of the proton gradient, such as chlorfenapyr, and mitochondrial complex I electron transport inhibitors.

In another embodiment, the insecticides are insecticides that target midgut. Examples include microbial disruptors of insect midgut membranes, such as Bacillus thuringiensis and Bacillus sphaericus.

In another embodiment, the insecticides are insecticides that target growth and development. Examples include juvenile hormone mimics, such as juvenile hormone analogues (e.g. fenoxycarb), inhibitors of chitin biosynthesis, Type 0, such as benzoylureas (e.g., flufenoxuron, lufenuron, and novaluron), and ecdysone receptor agonists, such as diacylhydrazines (e.g., methoxyfenozide and tebufenozide)

Stabilizer

According to another embodiment of the disclosure, the pheromone composition may include one or more additives that enhance the stability of the composition. Examples of additives include, but are not limited to, fatty acids and vegetable oils, such as for example olive oil, soybean oil, corn oil, safflower oil, canola oil, and combinations thereof.

Filler

According to another embodiment of the disclosure, the pheromone composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

Solvent

According to another embodiment, the pheromone compositions of the present disclosure can include one or more solvents. Compositions containing solvents are desirable when a user is to employ liquid compositions which may be applied by brushing, dipping, rolling, spraying, or otherwise applying the liquid compositions to substrates on which the user wishes to provide a pheromone coating (e.g., a lure). In some embodiments, the solvent(s) to be used is/are selected so as to solubilize, or substantially solubilize, the one or more ingredients of the pheromone composition. Examples of solvents include, but are not limited to, water, aqueous solvent (e.g., mixture of water and ethanol), ethanol, methanol, chlorinated hydrocarbons, petroleum solvents, turpentine, xylene, and any combinations thereof.

In some embodiments, the pheromone compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization when the formulation is emulsified into water. Alcohols are sometimes used as co-solvents to increase solvent power.

Solubilizing Agent

In some embodiments, the pheromone compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Binder

According to another embodiment of the disclosure, the pheromone composition may include one or more binders. Binders can be used to promote association of the pheromone composition with the surface of the material on which said composition is coated. In some embodiments, the binder can be used to promote association of another additive (e.g., insecticide, insect growth regulators, and the like) to the pheromone composition and/or the surface of a material. For example, a binder can include a synthetic or natural resin typically used in paints and coatings. These may be modified to cause the coated surface to be friable enough to allow insects to bite off and ingest the components of the composition (e.g., insecticide, insect growth regulators, and the like), while still maintaining the structural integrity of the coating.

Non-limiting examples of binders include polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the binder also acts a filler and/or a thickener. Examples of such binders include, but are not limited to, one or more of shellac, acrylics, epoxies, alkyds, polyurethanes, linseed oil, tung oil, and any combinations thereof.

Surface-Active Agents

In some embodiments, the pheromone compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the pheromone compositions comprise surfactants. Surfactants are sometimes used, either alone or with other additives, such as mineral or vegetable oils as adjuvants to spray-tank mixes to improve the biological performance of the pheromone on the target. The surface-active agents can be anionic, cationic, or nonionic in character, and can be employed as emulsifying agents, wetting agents, suspending agents, or for other purposes. In some embodiments, the surfactants are non-ionics such as: alky ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acids with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Wetting Agents

In some embodiments, the pheromone compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the pheromone compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

Dispersing Agent

In some embodiments, the pheromone compositions of the present disclosure comprise dispersing agents. A dispersing agent is a substance which adsorbs onto the surface of particles and helps to preserve the state of dispersion of the particles and prevents them from reaggregating. In some embodiments, dispersing agents are added to pheromone compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylated phosphate esters are also used. In some embodiments, such as alkylarylethylene oxide condensates and EO-PO block copolymers are sometimes combined with anionics as dispersing agents for suspension concentrates.

Polymeric Surfactant

In some embodiments, the pheromone compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in pheromone compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

Emulsifying Agent

In some embodiments, the pheromone compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

Gelling Agent

In some embodiments, the pheromone compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the pheromone compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenam; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

Anti-Foam Agent

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the nonsilicone anti-foam agents are water-insoluble oils, such as octanol and nonanol, or silica. In both cases, the function of the anti-foam agent is to displace the surfactant from the air-water interface.

Preservative

In some embodiments, the pheromone compositions comprise a preservative.

Additional Active Agent

According to another embodiment of the disclosure, the pheromone composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the disclosure, the pheromone composition may include one or more insect growth regulators ("IGRs"). IGRs may be used to alter the growth of the insect and produce deformed insects. Examples of insect growth regulators include, for example, dimilin.

According to another embodiment of the disclosure, the attractant-composition may include one or more insect sterilants that sterilize the trapped insects or otherwise block their reproductive capacity, thereby reducing the population in the following generation. In some situations allowing the sterilized insects to survive and compete with non-trapped insects for mates is more effective than killing them outright.

Sprayable Compositions

In some embodiments, the pheromone compositions disclosed herein can be formulated as a sprayable composition (i.e., a sprayable pheromone composition). An aqueous solvent can be used in the sprayable composition, e.g., water or a mixture of water and an alcohol, glycol, ketone, or other water-miscible solvent. In some embodiments, the water content of such mixture is at least about 10%, at least about 20%, at least about 30%, at least about 40%, 50%, at least about 60%, at least about 70%, at least about 80%, or at least about 90%. In some embodiments, the sprayable composition is concentrate, i.e. a concentrated suspension of the pheromone, and other additives (e.g., a waxy substance, a stabilizer, and the like) in the aqueous solvent, and can be diluted to the final use concentration by addition of solvent (e.g., water).

In some embodiments, the a waxy substance can be used as a carrier for the pheromone and its positional isomer in the sprayable composition. The waxy substance can be, e.g., a biodegradable wax, such as bees wax, carnauba wax and the like, candelilla wax (hydrocarbon wax), montan wax, shellac and similar waxes, saturated or unsaturated fatty acids, such as lauric, palmitic, oleic or stearic acid, fatty acid amides and esters, hydroxylic fatty acid esters, such as hydroxyethyl or hydroxypropyl fatty acid esters, fatty alcohols, and low molecular weight polyesters such as polyalkylene succinates.

In some embodiments, a stabilizer can be used with the sprayable pheromone compositions. The stabilizer can be used to regulate the particle size of concentrate and/or to allow the preparation of a stable suspension of the pheromone composition. In some embodiments, the stabilizer is selected from hydroxylic and/or ethoxylated polymers. Examples include ethylene oxide and propylene oxide copolymer, polyalcohols, including starch, maltodextrin and other soluble carbohydrates or their ethers or esters, cellulose ethers, gelatin, polyacrylic acid and salts and partial esters thereof and the like. In other embodiments, the stabilizer can include polyvinyl alcohols and copolymers thereof, such as partly hydrolyzed polyvinyl acetate. The stabilizer may be used at a level sufficient to regulate particle size and/or to prepare a stable suspension, e.g., between 0.1% and 15% of the aqueous solution.

In some embodiments, a binder can be used with the sprayable pheromone compositions. In some embodiments, the binder can act to further stabilize the dispersion and/or improve the adhesion of the sprayed dispersion to the target locus (e.g., trap, lure, plant, and the like). The binder can be polysaccharide, such as an alginate, cellulose derivative (acetate, alkyl, carboxymethyl, hydroxyalkyl), starch or starch derivative, dextrin, gum (arabic, guar, locust bean, tragacanth, carrageenan, and the like), sucrose, and the like. The binder can also be a non-carbohydrate, water-soluble polymer such as polyvinyl pyrrolidone, or an acidic polymer such as polyacrylic acid or polymethacrylic acid, in acid and/or salt form, or mixtures of such polymers.

Microencapsulated Pheromones

In some embodiments, the pheromone compositions disclosed herein can be formulated as a microencapsulated pheromone, such as disclosed in Ill'lchev, A L et al., *J. Econ. Entomol.* 2006; 99(6):2048-54; and Stelinki, L L et al., *J. Econ. Entomol.* 2007; 100(4):1360-9. Microencapsulated pheromones (MECs) are small droplets of pheromone enclosed within polymer capsules. The capsules control the release rate of the pheromone into the surrounding environment, and are small enough to be applied in the same method as used to spray insecticides. The effective field longevity of the microencapsulated pheromone formulations can range from a few days to slightly more than a week, depending on inter alia climatic conditions, capsule size and chemical properties.

Slow-Release Formulation

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices. Alternatively, the pheromone composition can be formulated as a slow release sprayable.

In certain embodiments, the pheromone composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof. Examples of celluloses include, but are not limited to, methylcellulose, ethyl cellulose, cellulose acetate, cellulose acetate-butyrate, cellulose acetate-propionate, cellulose propionate, and combinations thereof.

Other agents which can be used in slow-release or sustained-release formulations include fatty acid esters (such as a sebacate, laurate, palmitate, stearate or arachidate ester) or a fatty alcohols (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol).

Administration of Pheromone Composition

Lures

The pheromone compositions of the present disclosure may be coated on or sprayed on a lure, or the lure may be otherwise impregnated with a pheromone composition.

Traps

The pheromone compositions of the disclosure may be used in traps, such as those commonly used to attract any insect species, e.g., insects of the order Lepidoptera. Such traps are well known to one skilled in the art, and are commonly used in many states and countries in insect eradication programs. In one embodiment, the trap includes one or more septa, containers, or storage receptacles for holding the pheromone composition. Thus, in some embodiments, the present disclosure provides a trap loaded with at least one pheromone composition. Thus, the pheromone compositions of the present disclosure can be used in traps for example to attract insects as part of a strategy for insect monitoring, mass trapping, mating disruption, or lure/attract and kill for example by incorporating a toxic substance into the trap to kill insects caught.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of an insecticide. The insecticide may be an insecticide known to one skilled in the art. The insecticide may be mixed with the attractant-composition or may be separately present in a trap. Mixtures may perform the dual function of attracting and killing the insect.

Such traps may take any suitable form, and killing traps need not necessarily incorporate toxic substances, the insects being optionally killed by other means, such as drowning or electrocution. Alternatively, the traps can contaminate the insect with a fungus or virus that kills the insect later. Even where the insects are not killed, the trap can serve to remove the male insects from the locale of the female insects, to prevent breeding.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the disclosure can be colored brightly, to provide additional attraction for the insects.

In some embodiments, the pheromone traps containing the composition may be combined with other kinds of trapping mechanisms. For example, in addition to the pheromone composition, the trap may include one or more florescent lights, one or more sticky substrates and/or one or more colored surfaces for attracting moths. In other embodiments, the pheromone trap containing the composition may not have other kinds of trapping mechanisms.

The trap may be set at any time of the year in a field. Those of skill in the art can readily determine an appropriate amount of the compositions to use in a particular trap, and can also determine an appropriate density of traps/acre of crop field to be protected.

The trap can be positioned in an area infested (or potentially infested) with insects. Generally, the trap is placed on or close to a tree or plant. The aroma of the pheromone attracts the insects to the trap. The insects can then be caught, immobilized and/or killed within the trap, for example, by the killing agent present in the trap.

Traps may also be placed within an orchard to overwhelm the pheromones emitted by the females, so that the males simply cannot locate the females. In this respect, a trap need be nothing more than a simple apparatus, for example, a protected wickable to dispense pheromone.

The traps of the present disclosure may be provided in made-up form, where the compound of the disclosure has already been applied. In such an instance, depending on the half-life of the compound, the compound may be exposed, or may be sealed in conventional manner, such as is standard with other aromatic dispensers, the seal only being removed once the trap is in place.

Alternatively, the traps may be sold separately, and the compound of the disclosure provided in dispensable format so that an amount may be applied to trap, once the trap is in place. Thus, the present disclosure may provide the compound in a sachet or other dispenser.

Dispenser

Pheromone compositions can be used in conjunction with a dispenser for release of the composition in a particular environment. Any suitable dispenser known in the art can be used. Examples of such dispensers include but are not limited to, aerosol emitters, hand-applied dispensers, bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

In another embodiment, a device may be used that contaminates the male insects with a powder containing the pheromone substance itself. The contaminated males then fly off and provide a source of mating disruption by permeating the atmosphere with the pheromone substance, or by attracting other males to the contaminated males, rather than to real females.

Behavior Modification

Pheromone compositions prepared according to the methods disclosed herein can be used to control or modulate the behavior of insects. In some embodiments, the behavior of the target insect can be modulated in a tunable manner inter alia by varying the ratio of the pheromone to the positional isomer in the composition such that the insect is attracted to a particular locus but does not contact said locus or such the insect in fact contacts said locus. Thus, in some embodiments, the pheromones can be used to attract insects away from vulnerable crop areas. Accordingly, the disclosure also provides a method for attracting insects to a locus. The method includes administering to a the locus an effective amount of the pheromone composition.

The method of mating disruption may include periodically monitoring the total number or quantity of the trapped insects. The monitoring may be performed by counting the number of insects trapped for a predetermined period of time such as, for example, daily, Weekly, bi-Weekly, monthly, once-in-three months, or any other time periods selected by the monitor. Such monitoring of the trapped insects may help estimate the population of insects for that particular period, and thereby help determine a particular type and/or dosage of pest control in an integrated pest management system. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

Mating Disruption

Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle.

In many insect species of interest to agriculture, such as those in the order Lepidoptera, females emit an airborne trail of a specific chemical blend constituting that species' sex pheromone. This aerial trail is referred to as a pheromone plume. Males of that species use the information contained in the pheromone plume to locate the emitting female (known as a "calling" female). Mating disruption exploits the male insects' natural response to follow the plume by introducing a synthetic pheromone into the insects' habitat, which is designed to mimic the sex pheromone produced by the female insect. Thus, in some embodiments, the synthetic pheromone utilized in mating disruption is a synthetically derived pheromone composition comprising a pheromone having a chemical structure of a sex pheromone and a positional isomer thereof which is not produced by the target insect.

The general effect of mating disruption is to confuse the male insects by masking the natural pheromone plumes, causing the males to follow "false pheromone trails" at the expense of finding mates, and affecting the males' ability to respond to "calling" females. Consequently, the male population experiences a reduced probability of successfully locating and mating with females, which leads to the eventual cessation of breeding and collapse of the insect infestation Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

In some embodiments, a wick or trap may be adapted to emit a pheromone for a period at least equivalent to the breeding season(s) of the midge, thus causing mating disruption. If the midge has an extended breeding season, or repeated breeding season, the present disclosure provides a wick or trap capable of emitting pheromone for a period of time, especially about two weeks, and generally between about 1 and 4 weeks and up to 6 weeks, which may be rotated or replaced by subsequent similar traps. A plurality of traps containing the pheromone composition may be placed in a locus, e.g., adjacent to a crop field. The locations of the traps, and the height of the traps from ground may be selected in accordance with methods known to one skilled in the art.

Alternatively, the pheromone composition may be dispensed from formulations such as microcapsules or twist-ties, such as are commonly used for disruption of the mating of insect pests.

A variety of pheromones, including those set forth in Table 1 can be prepared according to the methods and formulations as described above. For example, the methods can be used to synthesize a corn earworm (*H. zea*) sex pheromone blend, which is generally understood in the art to entail a mixture of (Z)-hexadeca-9-en-1-al (3%) and (Z)-hexadeca-11-en-1-al (97%). However, as disclosed herein, the pheromone blend can be doped with (Z)-hexadeca-5-en-1-al to tunably elicit a response in the male corn earworms. Thus, the corn earworm sex pheromone can be used in conjunction with a sustained pheromone release device having a polymer container containing a mixture of the sex pheromone and a fatty acid ester (such as a sebacate, laurate, palmitate, stearate or arachidate ester) or a fatty alcohol (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol). The polymer container can be a tube, an ampule, or a bag made of a polyolefin or an olefin component-containing copolymer. Sex pheromones of other pest insects, such as, but not limited to, the cotton bollworm (*Helicoverpa armigera*), fall army worm (*Spodoptera frugiperda*), oriental fruit moth (*Grapholita molesta*), peach twig borer (*Anarsia lineatella*), diamondback moth (*Plutella xylostella*), soybean looper (*Chrysodeixis includes*) and leaf roller (Tortricidae) can be used in this type of sustained pheromone release device.

As will be apparent to one of skill in the art, the amount of a pheromone or pheromone composition used for a particular application can vary depending on several factors such as the type and level of insect infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

EXAMPLES

The present disclosure will be described in greater detail by way of specific examples. The following examples are offered for illustrative purposes, and are not intended to limit the disclosure in any manner. Those of skill in the art will readily recognize a variety of noncritical parameters which can be changed or modified to yield essentially the same results.

Example 1: Hydroxylation of (Z)-5-Hexadecene by Cytochromes P450 of the CYP52 Family The purpose of this example is to illustrate the biocatalytic hydroxylation of (Z)-5-hexadecene by members of the CYP52 family.

Two P450 cytochromes of the CYP52 family were integrated into the *P. pastoris* CBS7435 Mut$^s$ genome along with their corresponding cytochrome P450 reductases (CPR). Biotransformations were performed with these strains to determine whether these P450s hydroxylate (Z)-5-hexadecene. Strains and oligonucleotides disclosed in this example are listed in Tables 11 and 12.

TABLE 11

Genotypes of strains used in Example 1.

| Strain No. | Genotype |
|---|---|
| SPV048 | *P. pastoris* CBS7435 mut$^s$ pPpT4_SmiI_cmRED_cmCYP52A3 |
| SPV051 | *P. pastoris* CBS7435 mut$^s$ pPpT4_SmiI_ctRED_ctCYP52A13 |

TABLE 12

Oligonucleotide sequences used in Example 1.

| Primer | Sequence | Description | SEQ ID NO. |
|---|---|---|---|
| OPV 0042 | ATGACGGTTCATGACATCATCGC | CYP52A13 forward primer | 1 |

TABLE 12-continued

Oligonucleotide sequences used in Example 1.

| Primer | Sequence | Description | SEQ ID NO. |
|---|---|---|---|
| OPV 0043 | CTGACATCCTCTTGAGCGGC | CYP52A13/ A3 reverse primer | 2 |
| OPV 0044 | ATGGCTATTGAGCAGATTATCGAAG | CYP52A3 forward primer | 3 |

Gene sequences for *C. tropicalis* CYP52A13 (Accession No. AAO73953.1), *C. tropicalis* CPR (Accession No. P37201.1), *C. maltosa* CYP52A3 (Accession No. P24458.1), as well as the *C. maltosa* CPR (Accession No. P50126.1), were ordered as synthetic genes (DNA 2.0, Menlo Park, Calif., USA), and cloned into the pT4_S vector using EcoRI/NotI restriction sites for directional cloning. The plasmid containing the expression cassettes for CYP52A3/CPR and CYP52A13/CPR under the control of an AOX promoter and terminator were linearized using the restriction enzyme SmiI and purified. Next, 500 ng of the linearized DNA sequences for expressing CYP52A3/CPR (SEQ ID NO:4) and CYP52A13/CPR (SEQ ID NO:5) were used to transform *P. pastoris* CBS7435 Mut$^s$. The parent strain and the generation of the pT4 S plasmid used to generate the subsequent constructs are described by Gudiminchi et al. (*Biotechnology Journal*, 2013, 8(1), 146-52).

Colony PCR of the obtained *P. pastoris* strains was performed to verify the P450 enzymes CYP52A3 and CYP52A13 were present using the Failsafe™ PCR Kit (EPICENTRE® Biotechnologies, Madison, Wis; Catalog #FS99060) using Premix D and primers shown in Table 21 according to the manufactures recommendations.

Shake flask cultivations of the strains SPV048 and SPV051 were started from single colonies derived from an YBD agar plate (10 g/L Bacto™ yeast extract, 20 g/L Bacto™ peptone, 20 g/L D (+) glucose, 15 g/L agar) containing 100 mg/L Zeocin™. A volume of 45 mL of BMD1 medium (BMD1(1 L): 10 g/L D (+) glucose autoclaved, 200 mL 10×PPB (10×PPB: 30.0 g/L K$_2$HPO$_4$, 118 g/L KH$_2$PO$_4$, pH 6.0, autoclaved), 100 mL 10×YNB (10× YNB: 134 g/L Difco™ yeast nitrogen base without amino acids, autoclaved), 2 mL 500×buffer B (buffer B:10 mg/50 mL d-Biotin, filter sterilized), add autoclaved H$_2$O to 1 L) was inoculated with a single colony and incubated for approximately 63 h at 28° C. to 30° C. and 130 rpm in a 250 mL baffled Erlenmeyer flask. After the initial 63 h incubation 5 mL of BMM10 medium (BMM10 (1 L): 50 mL methanol, 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500×buffer B (buffer B:10 mg/50 mL d-Biotin, filter sterilized), add autoclaved H$_2$O to 1 L) was added. The cultivations were incubated for 12 h at 28° C. to 30° C., 130 rpm. After 12 hours incubation 0.4 mL of methanol was added to induce expression of the P450 enzymes and their corresponding CPR's and incubated for 12 h at 28° C. to 30° C., 130 rpm. Thereafter, 0.4 mL of methanol was added every 12 h and incubated at 28° C. to 30° C., 130 rpm. Cells were harvested after induction for approximately 72 h to 80 h and a total cultivation time of approximately 132 h to 143 h.

As control a volume of 45 mL of BMD1 medium (BMD1 (1 L): 10 g/L D (+) glucose autoclaved, 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500×buffer B (buffer B:10 mg/50 mL d-Biotin, filter sterilized), add autoclaved H$_2$O to 1 L) was inoculated with a single colony of strain SPV051 incubated for approximately 63 h at 28° C. to 30° C. and 130 rpm in a 250 mL baffled Erlenmeyer flask. After the initial 63 h incubation 5 mL of BMM10 medium without methanol (BMM10 without methanol (1 L): 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500×buffer B (buffer B:10 mg/50 mL d-Biotin, filter sterilized), add autoclaved H$_2$O to 1 L) was added. The cultivations were incubated for additional 60 h to 68 h at 28° C. to 30° C., 130 rpm. Cells were harvested after a total cultivation time of approximately 132 h to 143 h.

Cultivations were harvested in 50 mL Falcon tubes via centrifugation at 3000×rcf for 5 min at 4° C. The supernatant was discarded. The pellet was resuspended in 5 mL 100 mM PPB (mix stock solutions: 80.2 mL of 1M K$_2$HPO$_4$ (174.18 g/L) with 19.8 mL of 1M KH$_2$PO$_4$ (136.09 g/L) autoclaved, add autoclaved H$_2$O to 1 L and adjust pH 7.4), containing 20% glycerol, pH 7.4 and centrifuged again at 3000×rcf for 5 min at 4° C. (washing step). The supernatant was discarded and the Falcon tube was carefully patted on a Kimwipe to remove excess buffer. Each pellet was weighed to determine the cell wet weight (cww) of the cultures. The washed pellet was resuspended in bioconversion buffer (100 mM PPB (mix stock solutions: 80.2 mL of 1M K$_2$HPO$_4$ (174.18 g/L) with 19.8 mL of 1M KH$_2$PO$_4$ (136.09 g/L) autoclaved, add autoclaved H$_2$O to 1 L and adjust to pH 7.4), 20% glycerol, 0.2% Emulgen 913 (Kao Chemicals, Japan), pH 7.4) targeting a final cell density of ~200 g cww/L.

1 ml of the resuspended cultivation (200 g cww/L) was dispensed in a 50 mL Falcon tube. 125 µL neat substrate was added to each culture to initiate the bioconversion reactions. The bioconversion reactions were incubated at 30° C. and 200 rpm for 40 h to 48 h. The samples were stored at -80° C. until extraction and analysis of the respective product formation.

250 µL of 3 M HCl was added to each of the frozen samples. After addition of HCl samples were extracted twice with 1×1 mL or 2×2 mL diethyl ether. 10 µL of 10 mg/mL 1-Heptanol or 10 µL of 10 mg/mL 1-Tetradecanol was added to the sample as internal standard. Upon addition of diethyl ether and internal standard the sample was vortexed for 5 min. The entire sample was transferred to new reaction tubes and centrifuged for 10 min/8000×rcf at room temperature. The organic upper phase was transferred to a glass vial and air dried. The sample was resuspended to a final volume of 100 µL to 150 µL using Methyl Tertiary Butyl Ether (MTBE) or resuspended to a final volume of 200 µL using Tetrahydrofuran (THF) and analyzed via gas chromatography (GC).

An Agilent 6890 equipped with an FID detector and a J&W DB-23 column (length: 30 m, I.D. 25 mm, film 25 µm) was used to analyze the samples using the following program: Split ratio of 1:10. 240° C. for the injector inlet: 240° C. for the detector. H$_2$ at 40.0 mL/min, Air at 450 mL/min, Makeup flow (He) at 45 mL/min. Carrier He at 1.1 ml/min and 13 psi. 45° C. oven for 0.5 min; 5° C./min gradient to 50° C. then hold at 50° C. for 0.5 min; 30° C./min gradient to 220° C., then hold at 220° C. for 3.33 min. Analysis was performed in triplicate using authentic standards (obtained from Sigma-Aldrich or Bedoukian Research).

Figure 2:
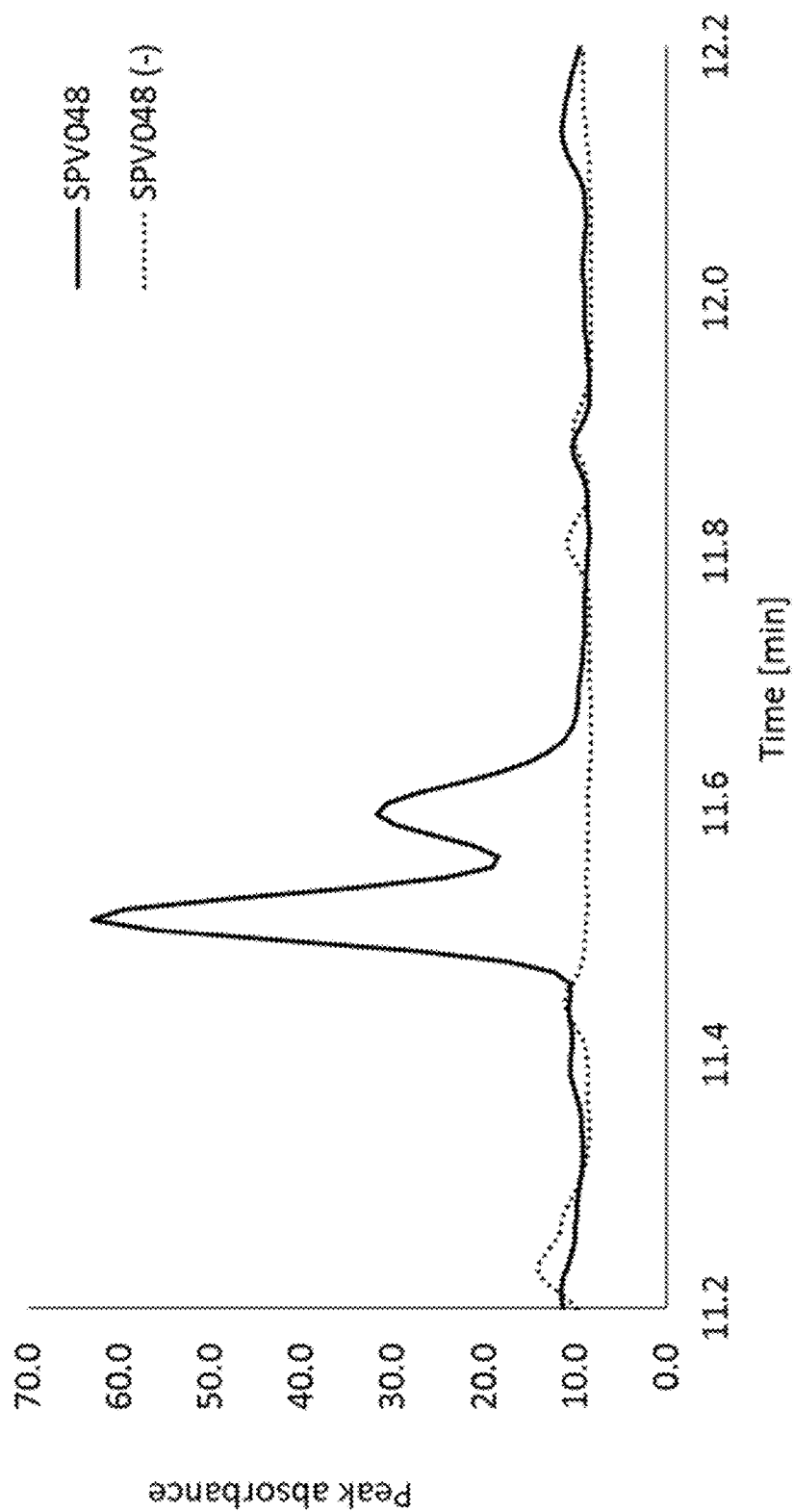
FIG. 2 shows the bioconversion reaction of (Z)-5-hexadecene using induced strain SPV048. (Z)-5-hexedecen-1-ol elutes at 11.5 min while (Z)-11-hexadecen-1-ol elutes at 11.6 min.

Results are shown in Table 13 and FIG. 2. Surprisingly, the CYP52 enzymes exhibit selectivity for one end of the (Z)-5-hexadecene substrate over the other: The SPV048 bioconversion produced 66.8% (Z)-5-hexadecen-1-ol and 33.2% (Z)-11-hexadecen-1-ol while the SPV051 bioconversion produced 27.6% (Z)-5-hexadecen-1-ol and 74.4% (Z)-11-hexadecen-1-ol.

TABLE 13

Results for bioconversions.

| Strain | Enzyme | Induced (Y/N) | Substrate | Products | Selectivity [%] |
|---|---|---|---|---|---|
| SPV048 | CYP52A3 | N | (Z)-5-hexadecene | n.d. | n/a |
| SPV048 | CYP52A3 | Y | (Z)-5-hexadecene | (Z)-5-hexadecen-1-ol | 66.8 ± 7.6 |
|  |  |  |  | (Z)-11-hexadecen-1-ol | 33.2 ± 1.0 |
| SPV051 | CYP52A13 | N | (Z)-5-hexadecene | n.d. | n/a |
| SPV051 | CYP52A13 | Y | (Z)-5-hexadecene | (Z)-5-hexadecen-1-ol, | 27.6 ± 4.3 |
|  |  |  |  | (Z)-11-hexadecen-1-ol | 74.4 ± 2.2 |

The results indicate that the biohydroxylation catalyst can functionalize an unsaturated hydrocarbon substrate on different termini to generate a mixture which includes a pheromone having a chemical structure corresponding to that of a natural insect pheromone produced by a given target member of the order Lepidoptera and a positional isomer of said sex pheromone, which is not naturally produced by said target insect.

Example 2. Synthesis of (Z)-11-Hexadecenol Carried Out According to Scheme 12

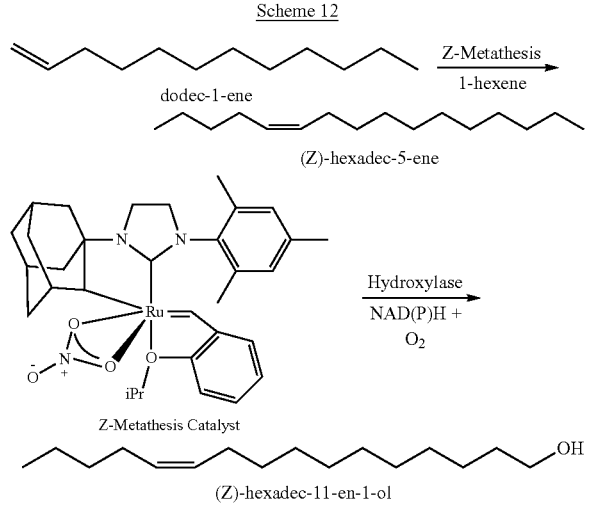

Z-5-Hexadecene:

The cross metathesis reactions of 1-hexene and dodec-1-ene is carried out in a 250 mL three-necked round-bottomed flask fitted with a condenser, thermometer and septum. The dodec-1-ene (20 mL) is transferred to the reaction flask along with 4 mole equivalent of 1-hexene and the mixture is heated to the desired reaction temperature (ranging from 30 to 100° C.) using an oil bath on a controlled hotplate magnetic stirrer. Thereafter 0.5 mol % of the catalyst is added to the flask and the reaction mixture is continuously stirred with a magnetic stirrer bar until the formation of the primary metathesis products is completed. The progress of the reaction is monitored by GC/FID. The sample is prepared for GC analysis by diluting an aliquot (0.3 mL) of the sample, taken at various reaction time intervals, with 0.3 mL toluene and quenched with 2 drops of tert-butyl hydrogen peroxide prior to analysis. Once dodec-1-ene is completely consumed, the reaction is quenched with tert-butyl hydrogen peroxide and filtered through a plug of silica using hexane as eluent. The hexane filtrate is concentrated and the Z-5-hexadecene is isolated by distillation.

Z-11-Hexadecen-1-ol:

Z-5-Hexadecene is subjected to biohydroxylation according to the process disclosed in Example 1 to generate Z-11-hexadecen-1-ol. The product is isolated by extraction of the fermentation broth with organic solvent, concentrate and silica-gel chromatography.

Example 3. Synthesis of (Z)-11-Hexadecenol Carried Out According to Scheme 13

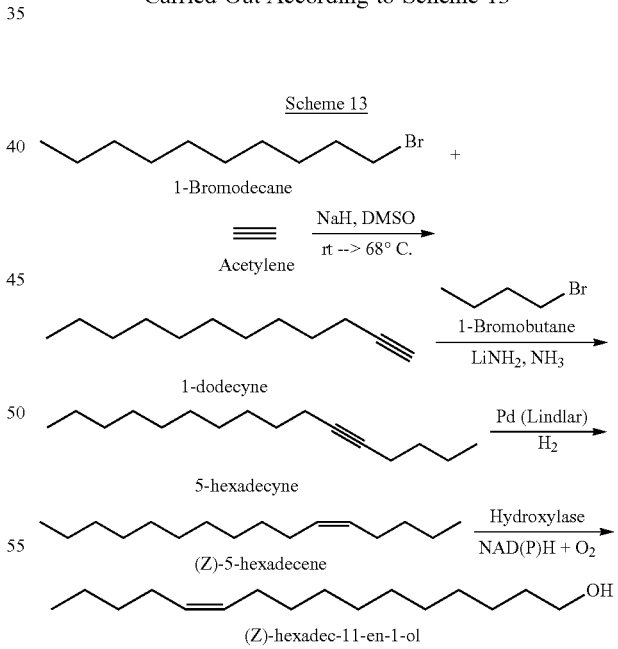

1-Dodecyne:

The synthesis of 1-dodecyne is carried out according to the protocol described in Oprean, Ioan et al. Studia Universitatis Babes-Bolyai, *Chemia*, 2006, 51, 33.

5-Hexadecyne:

To a −78° C. solution of 1-dodecyne (5 mmol) in THF (20 mL), 2.5M n-BuLi (5 mmol) in hexane is added dropwise via a syringe. A solution of 1-bromobutane (5 mmol) and TBAI (0.2 mmol) dissolve in THF is then dropwise added to the reaction mixture. The reaction mixture is allowed to warm to room temperature and then heat at 70° C. for 24 hours. The reaction is quenched with 5 mL of 1M NH₄Cl and extract with hexanes (3×). The organic fractions are combined, dry with anhydrous MgSO₄ and concentrate under reduced pressure. The resulting residue is purified by silica gel flash chromatography using 60:1/hexane:ethyl acetate as mobile phase. Fractions containing the desired product are pulled and concentrate. 5-Hexadecyne is further purified by distillation.

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford the desired product, Z-5-hexadecene, which can be further purified by distillation.

Z-11-Hexadecen-1-ol:

Z-5-hexadecene is then subject to biohydroxylation according to the process disclosed in Example 1 to generate Z-11-hexadecen-1-ol. The product is isolated by extraction of the fermentation broth with ethyl acetate and further purified by distillation.

Example 4. Synthesis of (Z)-11-Hexadecenol Carried Out According to Scheme 14

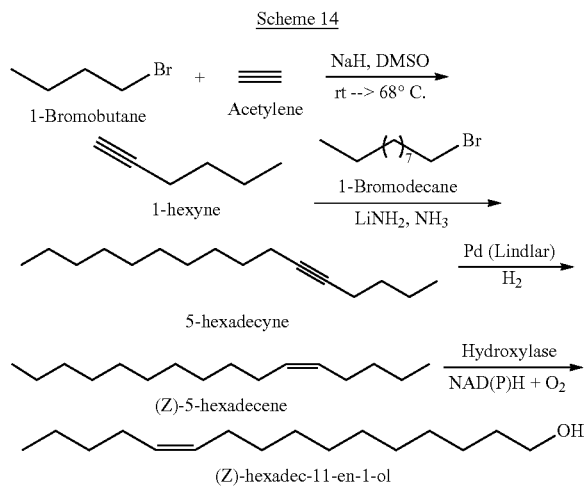

Scheme 14

1-Hexyne:

The synthesis of 1-hexyne is carried out according to the protocol described in Oprean, Joan et al. Studia Universitatis Babes-Bolyai, *Chemia*, 2006, 51, 33.

5-Hexadecyne:

To a −78° C. solution of 1-hexyne (5 mmol) in THF (20 mL), 2.5M n-BuLi (5 mmol) in hexane is added dropwise via a syringe. A solution of 1-bromodecane (5 mmol) and n-Bu₄NI (TBAI) (0.2 mmol) dissolve in THF is then dropwise added to the reaction mixture. The reaction mixture is allowed to warm to room temperature and then heat at 70° C. for 24 hours. The reaction is quenched with 5 mL of 1M NH₄Cl and extract with hexanes (3×). The organic fractions are combined, dry with anhydrous MgSO₄ and concentrate under reduced pressure. The resulting residue is purified by silica gel flash chromatography using 60:1/hexane:ethyl acetate as mobile phase. Fractions containing the desired product are pulled and concentrate.

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford Z-5-hexadecene, which can be further purified by distillation.

Z-11-Hexadecen-1-ol:

Z-5-Hexadecene is then subjected to biohydroxylation according to the process disclosed in Example 1 to generate Z-11-hexadecen-1-ol. The product is isolated by extraction of the fermentation broth with organic solvent and further purified by distillation.

Example 5. Synthesis of (Z)-11-Hexadecenol Carried Out According to Scheme 15

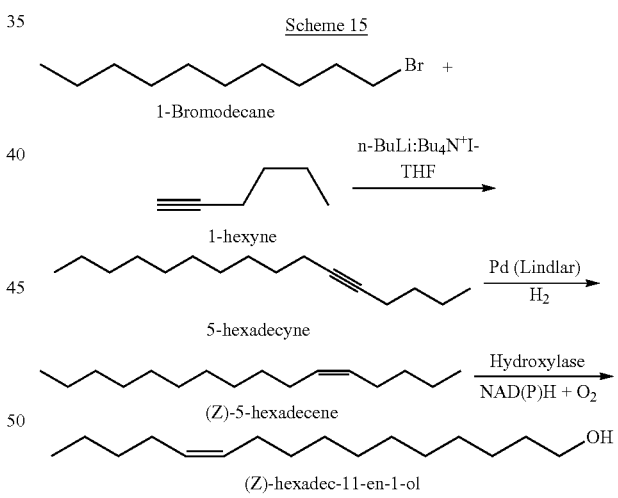

Scheme 15

5-Hexadecyne:

To a −78° C. solution of 1-hexyne (0.383 g, 4.67 mmol) in THF (20 mL), 2.5 M n-BuLi (1.87 mL, 4.67 mmol) in hexane is added dropwise via a syringe. A solution of 1-bromodecane (4.67 mmol) and n-Bu₄NI (TBAI, 57 mg, 0.16 mmol) dissolved in THF is then dropwise added to the reaction mixture. The reaction mixture is allowed to warm to room temperature and then heat at 70° C. for 24 hours. The reaction is quenched with 5 mL of 1M NH₄Cl and extract with hexanes (3×). The organic fractions are combined, dried with anhydrous MgSO₄, and concentrated under reduced pressure. The resulting residue is purified by silica gel flash chromatography using 60:1 hexane:ethyl acetate as the mobile phase. Fractions containing the desired product, 5-hexadecyne, are pooled and concentrated.

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford the desired product, Z-5-hexadecene.

Z-11-Hexadecen-1-ol:

Z-5-Hexadecene is then subjected to biohydroxylation according to the process disclosed in Example 1 to generate Z-11-hexadecen-1-ol. The product is isolated by extraction of the fermentation broth with organic solvent and purified by distillation.

Example 6. Synthesis of (Z)-11-Hexadecenol Carried Out According to Scheme 16

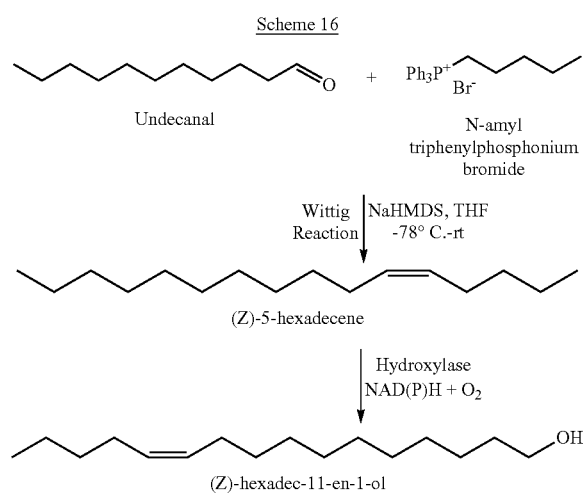

Z-5-Hexadecene:

Into an oven-dried three-neck RBF, N-amyl triphenylphosphnium bromide (13.98 g, 33.83 mmol) is dissolved in anhydrous toluene (30 mL). The mixture is allowed to stir via a magnetic stir bar at ambient temperature until complete dissolution of the alkyl phosphonium bromide salt is achieved. A solution of 6.57 g of potassium bis(trimethylsilyl)amide (KHMDS) in anhydrous toluene (30 mL) is then dropwise added to the reaction mixture. Upon complete addition of KHMDS solution to the reaction mixture, the reaction solution is allowed to stir for another 15 minutes, and is then cooled to −78° C. in an acetone and dry ice bath.

A solution of undecanal (4.59 mL, 22.28 mmol) in toluene (40 mL) is then drop-wise added to the reaction mixture via an addition funnel. The reaction is stirred at −78° C. for 20 minutes, then allowed to warm at room temperature with stirring for another 30 minutes. The reaction is terminated by addition of methanol (40 mL) and then concentrated under reduced pressure. The resulting residue is triturated with hexanes and white precipitate, triphenyl phosphine oxide, is removed by filtration. The process is repeated until triphenyl phosphine oxide is no longer precipitated out of the solution. The remnant triphenyl phosphine oxide is removed by passing the crude reaction product through a short bed of silica using hexane as a mobile phase. Z-5-hexadecane is obtained as a colorless oil.

Z-11-hexadecen-1-ol:

Z-5-Hexadecene is subjected to biohydroxylation according to the process disclosed in Example 1 to generate Z-11-hexadecen-1-ol. The product is isolated by extraction of the fermentation broth with organic solvent and purified by distillation.

Example 7. The Use of Mixtures of (Z)-11-Hexadecenal and (Z)-5-Hexadecenal for Pest Control of Insects with Mating Response to (Z)-11-Hexadecenal As proof of principal that a synthetically derived pheromone composition comprised of a synthetically derived sex pheromone and a positional isomer can be used to modulate the behavior of a target insect (*H. zea*), the Z-5-hexadecene was subject to biohydroxylation and oxidation as described above. A mixture of Z-hexadec-11-enal and Z-hexadec-5-enal was produced as shown below.

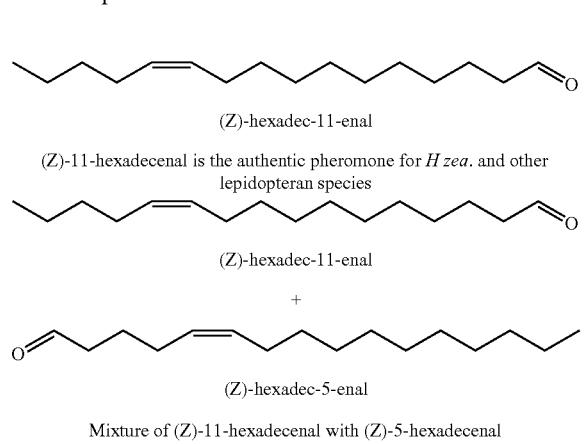

Example 8. Wind Tunnel Studies Using Positional Isomer Z-5-Hexadecenal

Four separate experiments were conducted with the moth *Helicoverpa zea* and its respective pheromone components (Z-11-hexadecenal, Z-9-hexadecenal). Further, the addition of Z-5-hexadecenal, the positional isomer of the natural insect Z-11-hexadecenal pheromone, was also added to the Z-11 and Z-9 blends and tested. Upwind flight and lure location of male moths were compared for: natural ratios of pheromone (97% Z-11-hexadecenal with 3% of Z-9-hexadecenal) with and without addition of the Z-5-hexadecenal positional isomer at various ratios.

Methods

Moths (4-6 day-old males in second half of scotophase) were flown in a glass wind tunnel (120×30×30 cm). A fan pushed air into the wind tunnel at 0.4 m sec$^{-1}$ and a second fan exhausted air at a similar rate. To provide visual cues for navigation, the floor was covered with light colored construction paper on which small (2-5 cm) circles were drawn with marker (Experiment 1) or light colored circles that were cut from light colored construction paper were placed on the floor (Experiments 2-4). Lures were made with Soxhlet-extracted, grey-rubber septa from West. Compounds were added to the septa in 50 μL of hexane and lures were dried in a fume hood for 1 h before use. Our lures (Experiments 1 and 2) were loaded with 5 μg of the pheromone (Z-11-hexadecenal with 3% of Z-9-hexadecenal) and this treatment was compared to lures with 50, 5 or 0.5% added Z-5-hexadecenal.

Conditions in the wind tunnel (27° C., 50% relative humidity) were similar to the air in the room during bioassays and to conditions under which moths were kept before assays were run.

A moth in a release cage was held on a platform 20 cm above the floor for 15 s in the plume of pheromone and then released by turning open end of the cage toward upwind. The lure was at the same height as the moth and 90 cm upwind. Moths were given 5 min to locate the lure. Data collected were: 1) whether or not a moth contacted the pheromone lure, 2) whether or not a moth nearly contacted the lure (hovering downwind within 10 cm of the lure without contact: "close but no contact"), and 3) time until contact. Flights were recorded on video and data were collected from videos.

We ran 2 experiments:
1) 3 treatments: 2.5 μg (50%), 0.25 μg (5%), or no (0%; positive control) Z-5-hexadecenal.
2) 3 treatments: 0.25 μg (5%), 0.025 μg (0.5%), or no Z-5-hexadecenal.

Over the course of the 4 experiments, occasionally lures with no pheromone (50 uL clean hexane) were included as negative controls (n=35). Conditions in the wind tunnel were the same for all experiments.

Experiment 8.1: Natural Ratios of Pheromone (Z-11-Hexadecenal with 3% of Z-9-Hexadecenal) with and without Addition of the Z-5-Hexadecenal Positional Isomer This experiment was performed to evaluate the response of the moths to pheromone coated lures with and without high concentrations of the Z-5-hexadecenal positional isomer With the treatments, the moths flew upwind, although relatively few moths located the pheromone lure, and there were no significant differences between numbers of moths that flew close to the lure but did not make contact (4, 6, and 5 respectively); however, significantly more moths contacted the lure (43%) with the natural pheromone blend (0% added Z5-hexadecacenal) than with 5% added Z5-hexadecacenal (Table 15; 11%; $\chi_2$=9.07, P<0.01) or 50% added Z11-hexadecacenal (Table 15; 14%; $\chi_2$=8.04, P<0.01). There were no significant differences among treatments in any experiment in latency (time from the start of the bioassay and contact with the lure).

TABLE 15

Expanded Wind Tunnel Experiments with 0%, 5%, and 50% Z-5-hexadecenal

| Treatment | n | # contacting lure | % contact | Close but no contact | time until contact (s) |
|---|---|---|---|---|---|
| 0% Z5 | 37 | 16 | 43 | 4 | 109 |
| 5% Z5 | 35 | 4 | 11 | 6 | 72 |
| 50% Z5 | 37 | 5 | 14 | 5 | 135 |

Z-5 = Z-5-hexadecenal

To the surprise of the inventors, the results from Experiment 8.1 indicate that the number of *Helicoverpa zea* moths finding the pheromone composition that includes the Z-5-hexadecenal positional isomer was significantly reduced relative to the natural pheromone blend. The moth is unexpectedly responsive to pheromone compositions including the Z-5-hexadecenal positional isomer despite the structural difference compared to Z-11-hexadecenal as the moth species flew upwind to interact with a plume in the presence and absence of the Z-5-hexadecenal positional isomer. That is, the natural pheromone blend elicited an flew upwind flight and contact response, whereas, in the presence of the Z-5-hexadecenal positional isomer, the moths flew upwind but did not contact the lures.

Experiment 8.2 Natural Ratios of Pheromone (Z-11-Hexadecenal with 3% of Z-9-Hexadecenal) with and without Addition of the Z-5-Hexadecenal Positional Isomer This experiment was performed to assess the response of the target moth to lower concentrations of the Z-5-hexadecenal in the natural pheromone blend.

There were no significant differences between treatments in number of moths that flew close to the lure but did not make contact (Table 16; $\chi_2$=3.98, P>0.05). Significantly more moths contacted the lure with 0% Z5-hexadecenal (38%) than with 5% added Z5-hexadecacenal (Table 16; 17%; $\chi_2$=4.11, P<0.05), but there was no difference in numbers contacting the lures with 0 or 0.5% Z5-hexadecacenal (38 and 44% respectively; $\chi_2$=0.33, P>0.05).

TABLE 16

Expanded Wind Tunnel Experiments with 0%, 0.5%, and 5% Z-5-hexadecenal

| Treatment | n | # contacting lure | % contact | Close but no contact | time until contact (s) |
|---|---|---|---|---|---|
| 0% Z5 | 37 | 14 | 38 | 5 | 140 |
| 0.5% Z5 | 36 | 16 | 44 | 3 | 127 |
| 5% Z5 | 36 | 6 | 17 | 9 | 113 |

Z-5 = Z-5-hexadecenal

The results of Experiment 8.2 indicate that while normal upwind flight seems to occur when the Z-5-hexadecenal positional isomer is included in the composition, contact with the lure is reduced. Furthermore, the results indicate that the amount of the Z-5-hexadecenal positional isomer can be varied to modulate attraction and landing as more moths landed on the lure in the presence of 0% or only 0.5% Z-5 hexadecenal compared to 5% Z-5 hexadecenal, whereas more moths came close to but did not contact the lure coated with 5% Z-5 hexadecenal compared to 0% or only 0.5% Z-5 hexadecenal. Thus, the pheromone compositions described herein can be used to elicit a tunable response in a target insect by inter alia varying the ratio of the positional isomer to the natural pheromone to thereby modulate attraction and/or landing.

Conclusions from 8.1-8.2

Across all treatments, nearly all moths flew upwind and most interacted with the plume in some way. Thus, the Z-5-hexadecedenal positional isomer triggers a similar upwind flight response in male moths. In general, contact was lower for treatments with added Z-5-hexadecenal.

These results indicate that the presence of the Z-5-hexadecenal positional isomer in the natural pheromone blend reduced the number of moths contacting the lures while still maintaining upwind orientation similar to the physiological responses to the natural pheromone blend alone.

The moths therefore can respond to the Z-5-hexadecenal positional isomer, which indicates that a positional isomer has valuable applications in modulating insect behavior. Thus, the presence of the positional isomer can be used to elicit a tunable response from target insects. That is, the amount of the he Z-5-hexadecenal positional isomer in the pheromone composition can be varied to either cause the moths to fly toward the lure but not land or to land on the lure.

Some moths flew upwind when an unbaited lure was present (15 of 35) but none of these exhibited plume-oriented flight or lure contact.

Thus, a surprising and unexpected result of including the Z-5-hexadecenal positional isomer in the pheromone composition was that the number of moths finding the lures was reduced while upwind orientation was maintained relative to the natural pheromone blend (i.e., in the absence of Z-5-hexadecenal). Although the number of moths finding the lures was reduced, the ability to attract the moth species using a pheromone composition containing a positional isomer indicates that the compositions taught herein can be used to modify insect behavior. Further, because the response elicited was dependent on the relative amount of the Z-5-hexadecenal positional isomer, these results indicate the response of the targeted insects can be tuned, e.g., to attract a target insect or to cause the target insect to land, by varying the amount of the positional isomer.

Prophetic Example 9. Mixtures of (Z)-9-Tetradecenal and (Z)-5-Tetradecenal to Modulate the Behavior of Insects with Mating Response to (Z)-9-Tetradecenal As shown below, Z-9-tetradecenal is a naturally produced sex pheromone for various lepidopteran species. Using the biohydroxylation methodology disclosed herein, a pheromone composition comprising Z-9-tetradecenal and its positional isomer Z-5-tetradecenal can be prepared as shown below.

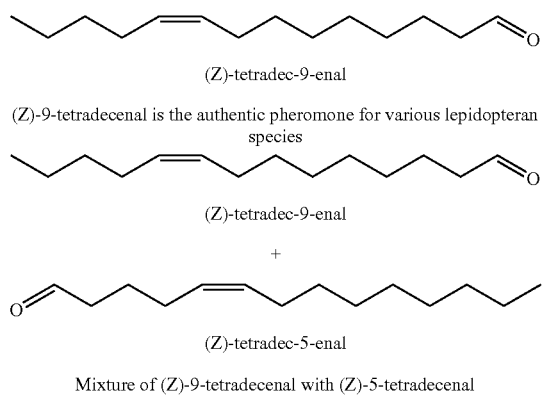

(Z)-tetradec-9-enal (Z)-9-tetradecenal is the authentic pheromone for various lepidopteran species (Z)-tetradec-9-enal

+

(Z)-tetradec-5-enal

Mixture of (Z)-9-tetradecenal with (Z)-5-tetradecenal

Wind tunnel experiments will be performed as described above using pheromone compositions comprising synthetically derived sex pheromone and a positional isomer. The inventors expect the positional isomer Z-5-tetradecenal to elicit an upwind flight response.

Prophetic Example 10. Mixtures of (Z)-9-Tetradecenyl Acetate and (Z)-5-Tetradecenyl Acetate for Pest Control of Insects to Modulate the Behavior of Insects with Mating Response to (Z)-9-Tetradecenyl Acetate The blend of sex pheromones produced by female *Spodoptera frugiperda* (Fall armyworm) includes an 96.4/3.6 mixture of Z-9-tetradecenyl acetate and Z-7 dodecenyl acetate.

The Z-9-tetradecenyl acetate sex pheromone produced by female *Spodoptera frugiperda* (Fall armyworm) is shown below. Using the biohydroxylation methodology disclosed herein, a pheromone composition comprising Z-9-tetradecenyl acetate and its positional isomer Z-5-tetradecenyl acetate can be prepared as shown below.

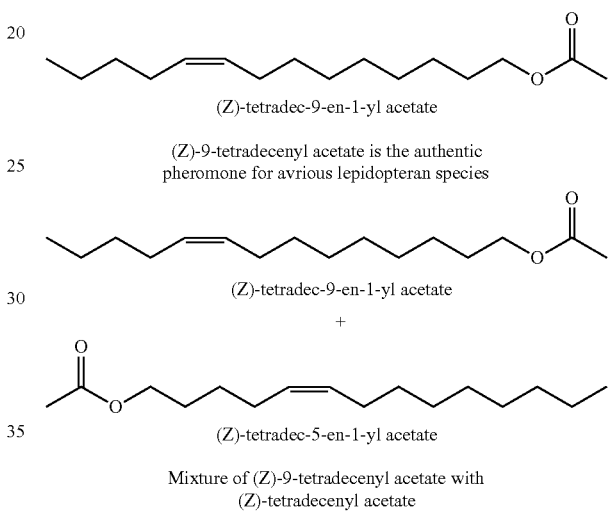

(Z)-tetradec-9-en-1-yl acetate (Z)-9-tetradecenyl acetate is the authentic pheromone for avrious lepidopteran species (Z)-tetradec-9-en-1-yl acetate

+

(Z)-tetradec-5-en-1-yl acetate

Mixture of (Z)-9-tetradecenyl acetate with (Z)-tetradecenyl acetate

Wind tunnel experiments will be performed as described above using pheromone compositions comprising the synthetically derived sex pheromone and a positional isomer. The inventors expect the positional isomer Z-5-tetradecenyl acetate in a composition with Z-9-tetradecenyl acetate to elicit response physiological response.

Prophetic Example 11. Pheromone Compositions

Any of the pheromones listed in Table 1 above can be synthesized as described herein to produce a pheromone composition comprising synthetically derived mixture of a natural pheromone and a positional isomer.

Wind tunnel experiments can be performed using a pheromone composition comprising synthetically derived mixture of a natural pheromone and a positional isomer to modulate the behavior of the target insect.

Prophetic Example 12. Synthesis of a Positional Isomer with a Subterminal Functional Group Based on the inventors' unexpected and first reported discovery that enzyme catalysts can be used to hydroxylate an unsaturated hydrocarbon substrate, thereby creating olefins with a terminal alcohol, the inventor propose using different biohydroxylation catalysts to hydroxylate carbon atoms within the carbon skeleton (i.e., subterminal carbons). A variety of P450 enzyme are known to catalyze hydroxylation of subterminal carbons to produce secondary alcohols. See, e.g., Greer et al., Plant Physiology. 2007; 143(3):653-667. It is also possible that the hydroxylase enzymes disclosed herein catalyze the formation of subterminal hydroxyl groups in low yields. Further, it is also possible to engineer an enzyme to selectively catalyze hydroxylation of an subterminal carbon.

As shown below, the hydroxyl group can be inserted on an subterminal carbon of an unsaturated hydrocarbon substrate to produce an olefinic alcohol. Subsequent oxidation, acetylation, or esterification can generate a positional isomer of a sex pheromone naturally produced by an insect species.

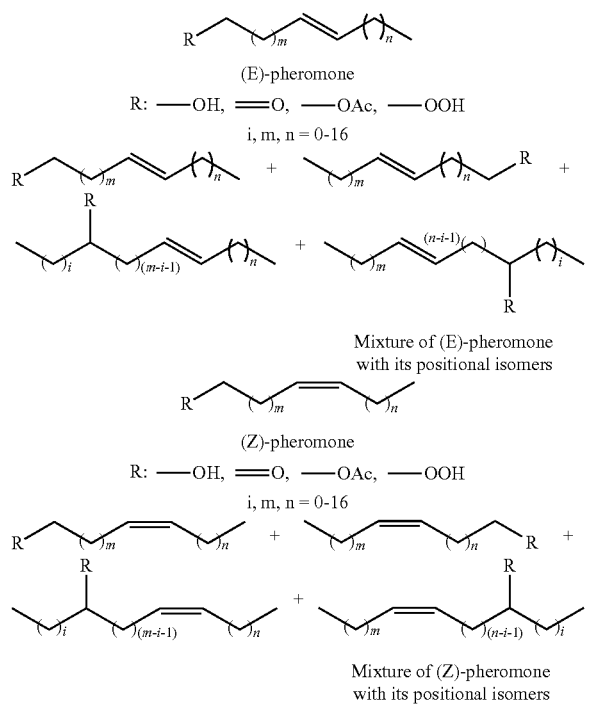

Based on the wind tunnel results discussed above with terminally functionalized positional isomer thereof, the inventors expect that isomers with a subterminal hydroxy group will similarly modulate the behavior of an insect.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

LIST OF REFERENCES

S. H. Malca, D. Scheps, L. Kuhnel, E. Venegas-Venegas, A. Seifert, B. M. Nestl, B. Hauer, Bacterial CYP153A monooxygenases for the synthesis of omega-hydroxylated fatty acids. *Chemical Communications* 48, 5115-5117 (2012)10.1039/c2cc18103 g).

D. Weissbart, J. P. Salaun, F. Durst, P. Pflieger, C. Mioskowski, Regioselectivity of a plant lauric acid omega hydroxylase. Omega hydroxylation of cis and trans unsaturated lauric acid analogs and epoxygenation of the terminal olefin by plant cytochrome P-450. *Biochimica et Biophysica Acta, Lipids and Lipid Metabolism* 1124, 135-142 (1992); published online Epub//(10.1016/0005-2760(92)90089-E).

M. Bordeaux, A. Galarneau, J. Drone, Catalytic, Mild, and Selective Oxyfunctionalization of Linear Alkanes: Current Challenges. *Angew. Chem.-Int. Edit.* 51, 10712-10723 (2012)10.1002/anie.201203280).

Y. R. Ji, G. N. Mao, Y. Y. Wang, M. Bartlam, Structural insights into diversity and n-alkane biodegradation mechanisms of alkane hydroxylases. *Front. Microbiol.* 4, (2013); published online EpubMar (10.3389/fmicb.2013.00058).

E. G. Funhoff, U. Bauer, I. Garcia-Rubio, B. Witholt, J. B. van Beilen, CYP153A6, a soluble P450 oxygenase catalyzing terminal-alkane hydroxylation. *J. Bacteriol.* 188, 5220-5227 (2006); published online EpubJul (10.1128/jb.00286-06).

D. Scheps, S. H. Malca, H. Hoffmann, B. M. Nestl, B. Hauer, Regioselective omega-hydroxylation of medium-chain n-alkanes and primary alcohols by CYP153 enzymes from *Mycobacterium marinum* and *Polaromonas* sp strain J5666. *Org. Biomol. Chem.* 9, 6727-6733 (2011)10.1039/c1ob05565h).

J. B. Vanbeilen, J. Kingma, B. Witholt, Substrate-specificity of the alkane hydroxylase system of *Pseudomonas-oleovorans* GPO1. *Enzyme Microb. Technol.* 16, 904-911 (1994); published online EpubOct (10.1016/0141-0229(94)90066-3).

T. Fujii, T. Narikawa, K. Takeda, J. Kato, Biotransformation of various alkanes using the *Escherichia coli* expressing an alkane hydroxylase system from *Gordonia* sp TF6. *Biosci. Biotechnol. Biochem.* 68, 2171-2177 (2004); published online EpubOct (10.1271/bbb.68.2171).

L. Feng, W. Wang, J. S. Cheng, Y. Ren, G. Zhao, C. X. Gao, Y. Tang, X. Q. Liu, W. Q. Han, X. Peng, R. L. Liu, L. Wang, Genome and proteome of long-chain alkane degrading *Geobacillus thermodenitrificans* NG80-2 isolated from a deep-subsurface oil reservoir. *Proc. Natl. Acad. Sci. U S. A.* 104, 5602-5607 (2007); published online EpubMar (10.1073/pnas.0609650104).

U. Scheller, T. Zimmer, E. Kargel, W. H. Schunck, Characterization of the n-alkane and fatty acid hydroxylating cytochrome P450 forms 52A3 and 52A4. *Arch. Biochem. Biophys.* 328, 245-254 (1996); published online EpubApr (10.1006/abbi.1996.0170).

D. Kim, M. J. Cryle, J. J. De Voss, P. R. O. de Montellano, Functional expression and characterization of cytochrome P450 52A21 from *Candida albicans*. *Arch. Biochem. Biophys.* 464, 213-220 (2007); published online Epub-Aug (10.1016/j.abb.2007.02.032).

J. B. van Beilen, E. G. Funhoff, Expanding the alkane oxygenase toolbox: new enzymes and applications. *Curr. Opin. Biotechnol.* 16, 308-314 (2005); published online EpubJun (10.1016/j.copbio.2005.04.005).

T. H. M. Smits, M. A. Seeger, B. Witholt, J. B. van Beilen, New alkane-responsive expression vectors for *Escherichia coli* and *Pseudomonas*. *Plasmid* 46, 16-24 (2001); published online EpubJul (10.1006/plas.2001.1522).

T. H. M. Smits, B. Witholt, J. B. van Beilen, Functional characterization of genes involved in alkane oxidation by *Pseudomonas aeruginosa*. *Antonie Van Leeuwenhoek* 84, 193-200 (2003)10.1023/a:1026000622765).

C. Grant, J. M. Woodley, F. Baganz, Whole-cell bio-oxidation of n-dodecane using the alkane hydroxylase system of *P-putida* GPo1 expressed in E-coil. *Enzyme Microb. Technol.* 48, 480-486 (2011); published online EpubMay (10.1016/j.enzmictec.2011.01.008).

S. Cornelissen, M. K. Julsing, J. Volmer, O. Riechert, A. Schmid, B. Buhler, Whole-cell-based CYP153A6-catalyzed (S)-limonene hydroxylation efficiency depends on host background and profits from monoterpene uptake via AlkL. *Biotechnology and Bioengineering* 110, 1282-1292 (2013); published online EpubMay (10.1002/bit.24801).

M. K. Julsing, M. Schrewe, S. Cornelissen, I. Hermann, A. Schmid, B. Buhler, Outer Membrane Protein AlkL Boosts Biocatalytic Oxyfunctionalization of Hydrophobic Substrates in *Escherichia coli*. *Appl. Environ. Microbiol.* 78, 5724-5733 (2012); published online EpubAug (10.1128/aem.00949-12).

D. Scheps, S. H. Malca, S. M. Richter, K. Marisch, B. M. Nestl, B. Hauer, Synthesis of omega-hydroxy dodecanoic acid based on an engineered CYP153A fusion construct. *Microb. Biotechnol.* 6, 694-707 (2013); published online EpubNov (10.1111/1751-7915.12073).

M. Schrewe, A. O. Magnusson, C. Willrodt, B. Buhler, A. Schmid, Kinetic Analysis of Terminal and Unactivated C?H Bond Oxyfunctionalization in Fatty Acid Methyl Esters by Monooxygenase-Based Whole-Cell Biocatalysis. *Advanced Synthesis & Catalysis* 353, 3485-3495 (2011); published online EpubDec (10.1002/adsc.201100440).

D. L. Craft, K. M. Madduri, M. Eshoo, C. R. Wilson, Identification and characterization of the CYP52 family of *Candida tropicalis* ATCC 20336, important for the conversion of fatty acids and Alkanes to alpha,omega-dicarboxylic acids. *Appl. Environ. Microbiol.* 69, 5983-5991 (2003); published online EpubOct (10.1128/aem.69.10.5983-5991.2003).

U. Scheller, T. Zimmer, D. Becher, F. Schauer, W. H. Schunck, Oxygenation cascade in conversion of n-alkanes to alpha,omega-dioic acids catalyzed by cytochrome p450 52A3. *J. Biol. Chem.* 273, 32528-32534 (1998); published online EpubDec (10.1074/jbc.273.49.32528).

W. Seghezzi, C. Meili, R. Ruffiner, R. Kuenzi, D. Sanglard, A. Fiechter, Identification and characterization of additional members of the cytochrome-p450 multigene family CYP52 of *Candida-tropicalis*. *DNA Cell Biol.* 11, 767-780 (1992); published online EpubDec (10.1089/dna.1992.11.767).

T. Zimmer, M. Ohkuma, A. Ohta, M. Takagi, W. H. Schunck, The CYP52 multigene family of *Candida maltosa* encodes functionally diverse n-alkane-inducible cytochromes P450. *Biochem. Biophys. Res. Commun.* 224, 784-789 (1996); published online EpubJul (10.1006/bbrc.1996.1100).

W.-H. Lu, J. E. Ness, W.-C. Xie, X.-Y. Zhang, J. Minshull, R. A. Gross, Biosynthesis of Monomers for Plastics from Renewable Oils. *J. Am. Chem. Soc.* 132, 15451-15455 (2010)10.1021/ja107707v).

E. G. Funhoff, J. Salzmann, U. Bauer, B. Witholt, J. B. van Beilen, Hydroxylation and epoxidation reactions catalyzed by CYP153 enzymes. *Enzyme and Microbial Technology* 40, 806-812 (2007); published online EpubMar (10.1016/j.enzmictec.2006.06.014).

R. K. Gudiminchi, C. Randall, D. J. Opperman, O. A. Olaofe, S. T. L. Harrison, J. Albertyn, M. S. Smit, Whole-cell hydroxylation of n-octane by *Escherichia coli* strains expressing the CYP153A6 operon. *Appl. Microbiol. Biotechnol.* 96, 1507-1516 (2012); published online EpubDec (10.1007/s00253-012-3984-5).

Y. P. Dong, J. Yan, H. Q. Du, M. Chen, T. Ma, L. Feng, Engineering of LadA for enhanced hexadecane oxidation using random- and site-directed mutagenesis. *Appl. Microbiol. Biotechnol.* 94, 1019-1029 (2012); published online EpubMay (10.1007/s00253-012-4035-y).

Banthorpe D (1976) Purification and properties of alcohol oxidase from *Tanacetum vulgare*. Phytochemistry 15:391-394. doi: 10.1016/S0031-9422(00)86829-6

Bronner S M, Herbert M B, Patel P R, et al. (2014) Ru-based Z-selective metathesis catalysts with modified cyclometalated carbene ligands. Chem Sci 5:4091-4098. doi: 10.1039/C4SC01541J Buck M, Chong J M (2001) Alkylation of 1-alkynes in THF. Tetrahedron Lett 42:5825-5827. doi: http://dx.doi.org/10.1016/S0040-4039(01)01131-5

Cannon J S, Grubbs R H (2013) Alkene Chemoselectivity in Ruthenium-Catalyzed Z-Selective Olefin Metathesis. Angew Chemie, Int Ed 52:9001-9004. doi: 10.1002/anie.201302724

Cappaert L, Larroche C (2004) Oxidation of a mixture of 2-(R) and 2-(S)-heptanol to 2-heptanone by *Saccharomyces cerevisiae* in a biphasic system. Biocatal Biotransformation 22:291-296. doi: 10.1080/10242420400011992

Cardemil E (1978) Alcohol-oxidizing enzymes from various organisms. Comp Biochem Physiol B 60:1-7. doi: 10.1016/0305-0491(78)90019-6

Cheng Q, Liu H T, Bombelli P, et al. (2004) Functional identification of AtFao3, a membrane bound long chain alcohol oxidase in *Arabidopsis thaliana*. FEBS Lett 574:62-68. doi: 10.1016/j.febslet.2004.07.086

Cheng Q, Sanglard D, Vanhanen S, et al. (2005) *Candida* yeast long chain fatty alcohol oxidase is a c-type haemoprotein and plays an important role in long chain fatty acid metabolism. Biochim Biophys Acta—Mol Cell Biol Lipids 1735:192-203. doi: 10.1016/j.bbalip.2005.06.006

Dienys G, Jarmalavičius S, Budriene S, et al. (2003) Alcohol oxidase from the yeast *Pichia pastoris*—A potential catalyst for organic synthesis. J. Mol. Catal. B Enzym. pp 47-49

Duff S J B, Murray W D (1988) Production and application of methylotrophic yeast *pichia-pastoris*. Biotechnol Bioeng 31:44-49. doi: 10.1002/bit.260310108

Eirich L D, Craft D L, Steinberg L, et al. (2004) Cloning and characterization of three fatty alcohol oxidase genes from *Candida tropicalis* strain ATCC 20336. Appl Environ Microbiol 70:4872-4879. doi: 10.1128/aem.70.8.4872-4879.2004

Endo K, Grubbs R H (2011) Chelated ruthenium catalysts for Z-selective olefin metathesis. J Am Chem Soc 133:8525-8527. doi: 10.1021/ja202818v Ernst M, Kaup B, Muller M, et al. (2005) Enantioselective reduction of carbonyl compounds by whole-cell biotransformation, combining a formate dehydrogenase and a (R)-specific alcohol dehydrogenase. Appl Microbiol Biotechnol 66:629-634. doi: 10.1007/s00253-004-1765-5

Gabelman A, Luzio G A (1997) Enzymatic oxidation of alcohols to aldehydes in a continuous reaction system using *Candida boidinii*.

Goswami P, Chinnadayyala S S R, Chakraborty M, et al. (2013) An overview on alcohol oxidases and their potential applications. Appl Microbiol Biotechnol 97:4259-4275. doi: 10.1007/s00253-013-4842-9

Grubbs R H (2012) Synthesis of large and small molecules using olefin metathesis catalysts. PMSE Prepr No pp. given.

Hamberg M, Ponce de Leon I, Rodriguez M J, Castresana C (2005) α-Dioxygenases. Biochem Biophys Res Commun 338:169-174. doi: http://dx.doi.org/10.1016/j.bbrc.2005.08.117

Hartung J, Dornan P K, Grubbs R H (2014) Enantioselective Olefin Metathesis with Cyclometalated Ruthenium Complexes. J Am Chem Soc 136:13029-13037. doi: 10.1021/ja506611k Hartung J, Grubbs R H (2013) Highly Z-selective and enantioselective ring-opening/cross-metathesis catalyzed by a resolved stereogenic-at-Ru complex. J Am Chem Soc 135:10183-10185. doi: 10.1021/ja4046422

Herbert M B, Marx V M, Pederson R L, Grubbs R H (2013) Concise syntheses of insect pheromones using Z-selective cross metathesis. Angew Chem Int Ed Engl 52:310-314. doi: 10.1002/anie.201206079

Hommel R, Ratledge C (1990) Evidence for two fatty alcohol oxidases in the biosurfactant-producing yeast Candida (Torulopsis) bombicola. FEMS Microbiol Lett 58:183-186.

Hommel R K, Lassner D, Weiss J, Kleber H P (1994) The inducible microsomal fatty alcohol oxidase of Candida (Torulopsis) apicola. Appl Microbiol Biotechnol 40:729-734. doi: 10.1007/s002530050057

Hou C T, Patel R N, Laskin A I, et al. (1983) Thermostable NAD-linked secondary alcohol-dehydrogenase from propane-grown pseudomonas-fluorescens NRRL-B-1244. Appl Environ Microbiol 46:98-105.

Kaehne F, Buchhaupt M, Schrader J (2011) A recombinant alpha-dioxygenase from rice to produce fatty aldehydes using E. coli. Appl Microbiol Biotechnol 90:989-995. doi: 10.1007/s00253-011-3165-y Karra-Chaabouni M, Pulvin S, Meziani A, et al. (2003) Biooxidation of n-Hexanol by Alcohol Oxidase and Catalase in Biphasic and Micellar Systems Without Solvent. Biotechnol Bioeng 81:27-32. doi: 10.1002/bit.10452

Keitz B K, Endo K, Patel P R, et al. (2012a) Improved ruthenium catalysts for Z-selective olefin metathesis. J Am Chem Soc 134:693-699. doi: 10.1021/ja210225e Keitz B K, Fedorov A, Grubbs R H (2012b) Cis-selective ring-opening metathesis polymerization with ruthenium catalysts. J Am Chem Soc 134:2040-2043. doi: 10.1021/ja211676y Kemp G D, Dickinson F M, Ratledge C (1988) INDUCIBLE LONG-CHAIN ALCOHOL OXIDASE FROM ALKANE-GROWN CANDIDA-TROPICALIS. Appl Microbiol Biotechnol 29:370-374.

Kemp G D, Dickinson F M, Ratledge C (1991) ACTIVITY AND SUBSTRATE-SPECIFICITY OF THE FATTY ALCOHOL OXIDASE OF CANDIDA-TROPICALIS IN ORGANIC-SOLVENTS. Appl Microbiol Biotechnol 34:441-445.

Kemp G D, Dickinson F M, Ratledge C (1990) Light sensitivity of then-alkane-induced fatty alcohol oxidase from Candida tropicalis and Yarrowia lipolytica. Appl Microbiol Biotechnol 32:461-464. doi: 10.1007/BF00903783

Khan R K, Torker S, Hoveyda A H (2013) Readily accessible and easily modifiable Ru-based catalysts for efficient and Z-selective ring-opening metathesis polymerization and ring-opening/cross-metathesis. J Am Chem Soc 135: 10258-10261. doi: 10.1021/ja404208a Kumar A K, Goswami P (2006) Functional characterization of alcohol oxidases from Aspergillus terreus MTCC 6324. Appl Microbiol Biotechnol 72:906-911. doi: 10.1007/s00253-006-0381-y Liu X Q, Dong Y P, Zhang J, et al. (2009) Two novel metal-independent long-chain alkyl alcohol dehydrogenases from Geobacillus thermodenitrificans NG80-2. Microbiology-Sgm 155:2078-2085. doi: 10.1099/mic.0.027201-0

Lu W-H, Ness J E, Xie W-C, et al. (2010) Biosynthesis of Monomers for Plastics from Renewable Oils. J Am Chem Soc 132:15451-15455. doi: 10.1021/ja107707v Marx V M, Herbert M B, Keitz B K, Grubbs R H (2013) Stereoselective access to Z and E macrocycles by ruthenium-catalyzed Z-selective ring-closing metathesis and ethenolysis. J Am Chem Soc 135:94-97. doi: 10.1021/ja311241q Mauersberger S, Drechsler H, Oehme G, Muller H G (1992) SUBSTRATE-SPECIFICITY AND STEREOSELECTIVITY OF FATTY ALCOHOL OXIDASE FROM THE YEAST CANDIDA-MALTOSA. Appl Microbiol Biotechnol 37:66-73.

Moreau, R. A., Huang A H (1979) Oxidation of fatty alcohol in the cotyledons of jojoba seedlings. Arch Biochem Biophys 194:422-430. doi: 10.1016/0003-9861(79)90636-2

Murray W D, Duff S J B (1990) Biooxidation of aliphatic and aromatic high-molecular-weight alcohols by pichia-pastoris alcohol oxidase. Appl Microbiol Biotechnol 33:202-205.

Oprean I, Botar A A, Gansca L, Vasian I (2006) Synthesis of cis-7,8-epoxyoctadecane, species-specific component of the sex pheromone of nun moth Lymantria monacha (Lepidoptera, Limantriidae). Stud Univ Babes-Bolyai, Chem 51:33-38.

Ozimek P, Veenhuis M, Van Der Klei I J (2005) Alcohol oxidase: A complex peroxisomal, oligomeric flavoprotein. FEMS Yeast Res 5:975-983. doi: 10.1016/j.femsyr.2005.06.005

Pederson R L, Grubbs R H (2002) Metathesis syntheses of pheromones or their components. US Pat Appl Publ 63 pp., Cont.-in-part of U.S. Pat. No. 6,215,019.

Richard L. Pederson et al. Adv. Synth. Catal. 2002, 344, 728

M. Jordaan et al. J. Mol. Catal. A: Chem. 2006, 254, 145

Presecki A V, Makovsek K, Vasic-Racki D (2012) Coenzyme Regeneration in Hexanol Oxidation Catalyzed by Alcohol Dehydrogenase. Appl Biochem Biotechnol 167: 595-611. doi: 10.1007/s12010-012-9712-x Pribisko M A, Ahmed T S, Grubbs R H (2014) Z-Selective ruthenium metathesis catalysts: Comparison of nitrate and nitrite X-type ligands. Polyhedron Ahead of Print. doi: 10.1016/j.poly.2014.06.055

Quigley B L, Grubbs R H (2014) Ruthenium-catalysed Z-selective cross metathesis of allylic-substituted olefins. Chem Sci 5:501-506. doi: 10.1039/c3sc52806e Rosebrugh L E, Herbert M B, Marx V M, et al. (2013) Highly active ruthenium metathesis catalysts exhibiting unprecedented activity and Z-selectivity. J Am Chem Soc 135:1276-1279. doi: 10.1021/ja311916m Ryland B L, Stahl S S (2014) Practical Aerobic Oxidations of Alcohols and Amines with Homogeneous Copper/TEMPO and Related Catalyst Systems. Angew Chemie Int Ed 53:8824-8838. doi: 10.1002/anie.201403110

Sato S, Sato F, Gotoh H, Yamada Y (2013) Selective Dehydration of Alkanediols into Unsaturated Alcohols over Rare Earth Oxide Catalysts. ACS Catal 3:721-734. doi: 10.1021/cs300781v Savitha J, Ratledge C (1991) Alcohol oxidase of Aspergillus flavipes grown on hexadecanol. FEMS Microbiol Lett 80:221-224. doi: 10.1111/j.1574-6968.1991.tb04665.x Schroer K, Mackfeld U, Tana I A W, et al. (2007) Continuous asymmetric ketone reduction processes with recombinant *Escherichia coli*. J Biotechnol 132:438-444. doi: 10.1016/j.jbiotec.2007.08.003

Shahane S, Bruneau C, Fischmeister C (2013) Z Selectivity: Recent Advances in one of the Current Major Challenges of Olefin Metathesis. ChemCatChem 5:3436-3459. doi: 10.1002/cctc.201300688

Smith A B, Beauchamp T J, LaMarche M J, et al. (2000) Evolution of a Gram-Scale Synthesis of (+)-Discodermolide. J Am Chem Soc 122:8654-8664. doi: 10.1021/ja0015287

Sugimoto K, Matsui K, Iijima Y, et al. (2014) Intake and transformation to a glycoside of (Z)-3-hexenol from infested neighbors reveals a mode of plant odor reception and defense. Proc Natl Acad Sci 111:7144-7149. doi: 10.1073/pnas.1320660111

Tani A, Sakai Y, Ishige T, Kato N (2000) Thermostable NADP(+)-dependent medium-chain alcohol dehydrogenase from *Acinetobacter* sp strain M-1: Purification and characterization and gene expression in *Escherichia coli*. Appl Environ Microbiol 66:5231-5235. doi: 10.1128/aem.66.12.5231-5235.2000

Van der Klei I J, Harder W, Veenhuis M (1991) Biosynthesis and assembly of alcohol oxidase, a peroxisomal matrix protein in methylotrophic yeasts: a review. Yeast 7:195-209. doi: 10.1002/yea.320070302

Vangnai A S, Arp D J (2001) An inducible 1-butanol dehydrogenase, a quinohaemoprotein, is involved in the oxidation of butane by "*Pseudomonas butanovora*." Microbiology-Uk 147:745-756.

Vanhanen S, West M, Kroon J T, et al. (2000) A consensus sequence for long-chain fatty-acid alcohol oxidases from *Candida* identifies a family of genes involved in lipid omega-oxidation in yeast with homologues in plants and bacteria. J Biol Chem 275:4445-4452. doi: 10.1074/jbc.275.6.4445

Zhao S, Lin Z, Ma W, et al. (2008) Cloning and characterization of long-chain fatty alcohol oxidase LjFAO1 in *Lotus japonicus*. Biotechnol Prog 24:773-779. doi: 10.1021/bp0703533

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

---

What we claim is:

1. An insect pheromone composition for modifying the behavior of a target member of the order Lepidoptera, comprising:
    a) a first synthetically derived insect pheromone, having a chemical structure corresponding to that of a natural insect pheromone produced by a given target member of the order Lepidoptera; and
    b) a positional isomer of said first synthetically derived insect pheromone, wherein said positional isomer is not naturally produced by the target member of the order Lepidoptera, wherein the first synthetically derived insect pheromone is Z-11-hexadecenal and the positional isomer is Z-5-hexadecenal.

2. An insect pheromone composition for modifying the behavior of a target member of the order Lepidoptera, comprising:
    a) a first synthetically derived insect pheromone, having a chemical structure corresponding to that of a natural insect pheromone produced by a given target member of the order Lepidoptera;
    b) a positional isomer of said first synthetically derived insect pheromone, wherein said positional isomer is not naturally produced by the target member of the order Lepidoptera,
    c) a second synthetically derived insect pheromone, having a chemical structure corresponding to that of a natural insect pheromone produced by a given target member of the order Lepidoptera; and
    d) optionally, a positional isomer of said second synthetically derived insect pheromone, wherein said positional isomer is not naturally produced by the target member of the order Lepidoptera,
wherein the first synthetically derived insect pheromone is Z-11-hexadecenal and the positional isomer of the first synthetically derived insect pheromone is Z-5-hexadecenal, and wherein the second synthetically derived insect pheromone is Z-9-hexadecenal and if the positional isomer of the second synthetically derived insect pheromone is present it is Z-7-hexadecenal.

3. An insect pheromone composition for modifying the behavior of male *Helicoverpa* sp., comprising:
    a) Z-11-hexadecenal and Z-5-hexadecenal; and
    b) an agriculturally acceptable adjuvant or carrier.

4. The insect pheromone composition of claim 3, wherein the Z-11-hexadecenal is present in the composition in a ratio of from about 99% to about 1%, relative to the Z-5-hexadecenal, which is present in the composition in a ratio of from about 1% to about 99%.

5. The insect pheromone composition of claim 3, wherein the Z-11-hexadecenal is present in the composition in an amount of from about 99% to about 1% w/w and the Z-5-hexadecenal is present in the composition in an amount of from about 99% to about 1% w/w.

6. The insect pheromone composition of claim 3, further comprising: Z-9-hexadecenal.

7. The insect pheromone composition of claim 3, further comprising: Z-9-hexadecenal and Z-7-hexadecenal.

8. The insect pheromone composition of claim 7, wherein the Z-11-hexadecenal is present in the composition in an amount of from about 99% to about 1% w/w, the Z-5-hexadecenal is present in the composition in an amount of from about 99% to about 1% w/w, the Z-9-hexadecenal is present in the composition in an amount of from about 99% to about 1% w/w, and the Z-7-hexadecenal is present in the composition in an amount of from about 99% to about 1% w/w.

* * * * *